(12) United States Patent
Ye et al.

(10) Patent No.: US 7,727,978 B2
(45) Date of Patent: Jun. 1, 2010

(54) CYCLIC 11-BETA HYDROXYSTEROID DEHYDROGENASE TYPE I INHIBITORS

(75) Inventors: Xiang-Yang Ye, Princeton, NJ (US); Jeffrey A. Robl, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 63 days.

(21) Appl. No.: 11/843,015

(22) Filed: Aug. 22, 2007

(65) Prior Publication Data

US 2008/0234249 A1    Sep. 25, 2008

Related U.S. Application Data

(60) Provisional application No. 60/840,071, filed on Aug. 24, 2006.

(51) Int. Cl.
*A61K 31/397* (2006.01)
*C07D 206/00* (2006.01)

(52) U.S. Cl. ............... 514/210.17; 514/336; 546/268.1; 548/953; 548/530

(58) Field of Classification Search ........... 548/953, 548/530; 546/268.1; 514/210.17, 336
See application file for complete search history.

(56) References Cited

U.S. PATENT DOCUMENTS

| | | | |
|---|---|---|---|
| 3,083,204 | A | 3/1963 | Klavehn et al. |
| 4,691,051 | A | 9/1987 | Georgiev et al. |
| 6,242,615 | B1 | 6/2001 | Pelleter et al. |
| 6,740,647 | B1 | 5/2004 | Baucke et al. |
| 2003/0114460 | A1 | 6/2003 | Hughes et al. |
| 2004/0072830 | A1 | 4/2004 | Okada et al. |
| 2004/0209858 | A1 | 10/2004 | Bennani et al. |
| 2005/0070720 | A1 | 3/2005 | Balkovec et al. |
| 2005/0277647 | A1 | 12/2005 | Link et al. |
| 2006/0079506 | A1 | 4/2006 | Linders et al. |
| 2006/0094699 | A1 | 5/2006 | Kampen et al. |
| 2006/0111348 | A1 | 5/2006 | Kampen et al. |
| 2006/0111366 | A1 | 5/2006 | Andersen et al. |
| 2006/0148871 | A1 | 7/2006 | Rohde et al. |
| 2006/0149070 | A1 | 7/2006 | Rohde et al. |
| 2009/0124609 | A1 | 5/2009 | Albrecht et al. |
| 2009/0124612 | A1 | 5/2009 | Albrecht et al. |

FOREIGN PATENT DOCUMENTS

| | | |
|---|---|---|
| EP | 0130882 B1 | 1/1985 |
| EP | 0699438 | 3/1996 |
| JP | 2002-356458 | 12/2002 |
| WO | WO 92/18132 | 10/1992 |
| WO | WO 95/09634 | 4/1995 |
| WO | WO 97/33859 | 9/1997 |
| WO | WO 98/05336 | 2/1998 |
| WO | WO 98/25923 | 6/1998 |
| WO | WO 98/43946 | 10/1998 |
| WO | WO 99/09984 | 3/1999 |
| WO | WO 99/31075 | 6/1999 |
| WO | WO 99/37668 | 7/1999 |
| WO | WO 01/60818 | 8/2001 |
| WO | WO 02/076973 | 10/2002 |
| WO | WO 03/063845 | 8/2003 |
| WO | WO 03/065983 | 8/2003 |
| WO | WO 2004/056745 | 7/2004 |
| WO | WO 2004/065351 | 8/2004 |
| WO | WO 2004/089415 | 10/2004 |
| WO | WO 2004/089416 | 10/2004 |
| WO | WO 2004/089470 | 10/2004 |
| WO | WO 2004/089896 | 10/2004 |
| WO | WO 2006/069787 | 7/2006 |
| WO | WO 2006/074244 | 7/2006 |
| WO | WO 2007/038452 | 4/2007 |
| WO | WO 2007/047625 | 4/2007 |
| WO | WO 2007/068330 | 6/2007 |

OTHER PUBLICATIONS

Kampen et al., 2004, CAS: 141: 360694.*
Mao et al., 2004, CAS: 141: 207043.*
Balkovec et al., 2003, CAS: 139: 180065.*
Dooley et al., 2003, CAS: 139: 164792.*
Georgiev et al., 1988, CAS: 108: 6426.*
Fleming et al., 1982, CAS: 97: 109824.*
Baiocchi et al., 1974, CAS: 81: 25277.*
Zoidis et al., 2005, CAS: 142: 481759.*
Bhattacharyya, K.C., Current Science, No. 11, pp. 312-313 (1952).

* cited by examiner

*Primary Examiner*—Rei-tsang Shiao
(74) *Attorney, Agent, or Firm*—Terence J. Bogie

(57) ABSTRACT

Novel compounds are provided which are 11-beta-hydroxysteroid dehydrogenase type I inhibitors. 11-Beta-hydroxysteroid dehydrogenase type I inhibitors are useful in treating, preventing, or slowing the progression of diseases requiring 11-beta-hydroxysteroid dehydrogenase type I inhibitor therapy. These novel compounds have the structure:

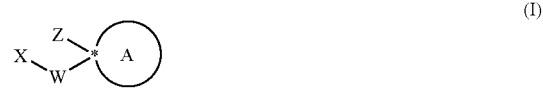

(I)

enantiomers, diastereomers, solvates, or salts thereof, wherein A, W, X and Z are defined herein.

27 Claims, No Drawings

CYCLIC 11-BETA HYDROXYSTEROID DEHYDROGENASE TYPE I INHIBITORS

CROSS-REFERENCES TO RELATED APPLICATION

This application claims priority benefit under Title 35 §119(e) of U.S. provisional Application No. 60/840,071, filed Aug. 24, 2006, the contents of which are herein incorporated by reference in its entirety.

BACKGROUND OF THE INVENTION

The steroid hormone cortisol is a key regulator of many physiological processes. However, an excess of cortisol, as occurs in Cushing's Disease, provokes severe metabolic abnormalities including: type 2 diabetes, cardiovascular disease, obesity, and osteoporosis. Many patients with these diseases, however, do not show significant increases in plasma cortisol levels. In addition to plasma cortisol, individual tissues can regulate their glucocorticoid tone via the in situ conversion of inactive cortisone to the active hormone cortisol. Indeed, the normally high plasma concentration of cortisone provides a ready supply of precursor for conversion to cortisol via the intracellular enzyme 11-beta-hydroxysteroid dehydrogenase type I (11beta-HSD1).

11beta-HSD1 is a member of the short chain dehydrogenase superfamily of enzymes. By catalyzing the conversion of cortisone to cortisol, 11beta-HSD1 controls the intracellular glucocorticoid tone according to its expression and activity levels. In this manner, 11beta-HSD1 can determine the overall metabolic status of the organ. 11beta-HSD1 is expressed at high levels in the liver and at lower levels in many metabolically active tissues including the adipose, the CNS, the pancreas, and the pituitary. Taking the example of the liver, it is predicted that high levels of 11beta-HSD1 activity will stimulate gluconeogenesis and overall glucose output. Conversely, reduction of 11beta-HSD1 activity will downregulate gluconeogenesis resulting in lower plasma glucose levels.

Various studies have been conducted that support this hypothesis. For example, transgenic mice expressing 2× the normal level of 11beta-HSD1 in only the adipose tissue show abdominal obesity, hyperglycemia, and insulin resistance. (H. Masuzaki, J. Paterson, H. Shinyama, N. M. Morton, J. J. Mullins, J. R. Seckl, J. S. Flier, "A Transgenic Model of Visceral Obesity and the Metabolic Syndrome", *Science*, 294:2166-2170 (2001). Conversely, when the 11beta-HSD1 gene is ablated by homologous recombination, the resulting mice are resistant to diet induced obesity and the accompanying dysregulation of glucose metabolism (N. M. Morton, J. M. Paterson, H. Masuzaki, M. C. Holmes, B. Staels, C. Fievet, B. R. Walker, J. S. Flier, J. J. Mullings, J. R. Seckl, "Novel Adipose Tissue-Mediated Resistance to Diet-induced Visceral Obesity in 11β-Hydroxysteroid Dehydrogenase Type 1-Deficient Mice", *Diabetes*, 53:931-938 (2004). In addition, treatment of genetic mouse models of obesity and diabetes (ob/ob, db/db and KKAy mice) with a specific inhibitor of 11beta-HSD1 causes a decrease in glucose output from the liver and an overall increase in insulin sensitivity (P. Alberts, C. Nilsson, G. Selen, L. O. M. Engblom, N. H. M. Edling, S. Norling, G. Klingstrom, C. Larsson, M. Forsgren, M. Ashkzari, C. E. Nilsson, M. Fiedler, E. Bergqvist, B. Ohman, E. Bjorkstrand, L. B. Abrahmsen, "Selective Inhibition of 11β-Hydroxysteroid Dehydrogenase Type I Improves Hepatic Insuling Sensitivity in Hyperglycemic Mice Strains", *Endocrinology*, 144:4755-4762 (2003)). Furthermore, inhibitors of 11beta-HSD1 have been shown to be effective in treating metabolic syndrome and atherosclerosis in high fat fed mice (Hermanowski-Vosatka et al., *J. Exp. Med.*, 202(4):517-527 (2002)). Based in part on these studies, it is believed that local control of cortisol levels is important in metabolic diseases in these model systems. In addition, the results of these studies also suggest that inhibition of 11beta-HSD1 will be a viable strategy for treating metabolic diseases such as type 2 diabetes, obesity, and the metabolic syndrome.

Lending further support to this idea are the results of a series of preliminary clinical studies. For example, several reports have shown that adipose tissue from obese individuals has elevated levels of 11beta-HSD1 activity. In addition, studies with carbenoxolone, a natural product derived from licorice that inhibits both 11beta-HSD1 and 11beta-HSD2 (converts cortisol to cortisone in kidney) have shown promising results. A seven day, double blind, placebo controlled, cross over study with carbenoxolone in mildly overweight individuals with type 2 diabetes showed that patients treated with the inhibitor, but not the placebo group, displayed a decrease in hepatic glucose production (R. C. Andrews, O. Rooyackers, B. R. Walker, *J. Clin. Endocrinol. Metab.*, 88:285-291 (2003)). This observation is consistent with the inhibition of 11beta-HSD1 in the liver. The results of these preclinical and early clinical studies strongly support the concept that treatment with a potent and selective inhibitor of 11beta-HSD1 will be an efficacious therapy in patients afflicted with type 2 diabetes, obesity, and the metabolic syndrome.

SUMMARY OF THE INVENTION

In accordance with the present invention, compounds are provided that have the general structure of formula I:

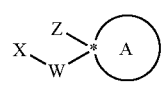

(I)

wherein m, A, X, W and Z are defined below.

The compounds of the present invention inhibit the activity of the enzyme 11-beta-hydroxysteroid dehydrogenase type I. Consequently, the compounds of the present invention may be used in the treatment of multiple diseases or disorders associated with 11-beta-hydroxysteroid dehydrogenase type I, such as diabetes and related conditions, microvascular complications associated with diabetes, the macrovascular complications associated with diabetes, cardiovascular diseases, Metabolic Syndrome and its component conditions, inflammatory diseases and other maladies. Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae (acute coronary syndrome, myocardial infarction, angina pectoris, peripheral vascular disease, intermitant claudication), abnormal heart function, myocardial ischemia, stroke, Metabolic Syndrome, hypertension, obesity, dislipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma and inflammatory diseases, such as, rheumatoid arthritis, Cushing's Disease, Alzheimer's Disease and osteoarthritis.

The present invention provides for compounds of formula I, pharmaceutical compositions employing such compounds, and for methods of using such compounds. In particular, the present invention provides a pharmaceutical composition comprising a therapeutically effective amount of a compound of formula I, alone or in combination with a pharmaceutically acceptable carrier.

Further, in accordance with the present invention, a method is provided for preventing, inhibiting, or treating the progression or onset of diseases or disorders associated with the activity of the enzyme 11-beta-hydroxysteroid dehydrogenase type I, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s).

Further, the present invention provides a method for preventing, inhibiting, or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

DESCRIPTION OF THE INVENTION

In accordance with the present invention, compounds of formula I are provided

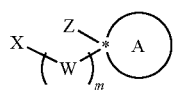

(I)

enantiomers, diastereomers, solvates, or salts thereof wherein:

A is a 5- to 20-membered non-aromatic bi-, tri- or polycyclic ring system optionally containing 1-3 heteroatoms selected from N, O, S, S(O) and S(O)$_2$, which may be optionally substituted with one or more $R_4$'s;

X is —C(=O)OH, —C(=O)C(=O)OH, —C(=O)NR$_9$R$_9$, tetrazolyl, or —C(=O)NHS(O)$_2$R$_9$;

W is absent, (—CR$_{8a}$R$_{8b}$—)$_m$, (—CR$_{8a}$R$_{8b}$—)$_m$—O—, (—CR$_{8a}$R$_{8b}$—)$_m$—N(R$_{14}$)—, C$_{3-6}$ cycloalkyl, alkenyl or alkynyl, wherein the cycloalkyl or alkenyl may be optionally substituted with one or more $R_{8a}$'s;

m is 1-3;

Z is —CN, C$_{3-10}$ alkyl, cycloalkyl, aryl, arylalkyl, heterocyclyl or heterocyclylalkyl, all of which may be optionally substituted with one or more $R_4$'s, and the heterocyclyl and heterocyclylalkyl contain 1-4 heteroatoms selected from N, O, and S;

provided that W and Z, or when W is absent, X and Z, are attached to the same carbon on Ring A;

$R_4$, at each occurrence, is independently selected from hydrogen, alkyl, aryl, alkenyl, alkynyl, cycloalkyl, heterocyclyl, halo, =O, —NH$_2$, —CN, —NO$_2$, —C(=O)OH, —C(=O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O) OR$_8$ or —NR$_9$S(O)$_2$R$_8$, wherein the alkyl, aryl, alkenyl, alkynyl, cycloalkyl, or heterocyclyl may be optionally substituted with one or more $R_5$'s;

$R_5$, at each occurrence, is independently selected from hydrogen, alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O) NR$_9$S(O)$_2$R$_9$, —S(O)$_2$NR$_9$C(=O)OR$_9$, —S(O)$_2$NR$_9$C (=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S (O)$_2$R$_{10}$, —O—S(O)$_2$R$_{10}$, —NR$_9$C(=O)OR$_8$ or —NR$_9$S (O)$_2$R$_8$;

$R_8$, at each occurrence, is independently alkyl, aryl or heterocyclyl;

$R_{8a}$, at each occurrence, is independently hydrogen, alkyl or aryl;

$R_{8b}$, at each occurrence, is independently hydrogen, —C(=O)OH, alkyl, —OH, halo, —CN, —OR$_{10}$, —C(=O) R$_{10}$ or —C(=O)NR$_9$R$_9$, wherein the alkyl may be optionally substituted with one or more $R_{9a}$'s; or $R_{8a}$ and $R_{8b}$ are taken together with the carbon to which both are attached to form a 3- to 7-membered ring, which may optionally contain 1-4 heteroatoms selected from N, O, and S and be optionally substituted with 0-3 $R_{9a}$;

$R_9$, at each occurrence, is independently hydrogen, alkyl, alkoxy, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-5 $R_{9a}$, and the heterocyclyl or heterocyclylalkyl contain 1-4 heteroatoms selected from N, O, and S; or two $R_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more $R_{9a}$'s;

$R_{9a}$, at each occurrence, is independently selected from alkyl, haloalkyl, aryl, alkenyl, alkynyl, cycloalkyl, cycloalkylalkyl, heterocyclyl, heterocyclylalkyl, halo, =O, —NH$_2$, —CN, —NO$_2$, —C(=O)OH, —C(=O)OR$_{14}$, —OCF$_3$, —OR$_{10}$, —OH, —OCF$_3$, —SH, —SR$_{14}$, —C(=O)$_2$ NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —OS(O)$_2$R$_{14}$, —NR$_{14}$C(=O) OR$_{10}$, —NR$_{14}$S(O)$_2$R$_8$, —C(=O)R$_{10}$, —OC(=O) NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_{10}$, at each occurrence, is independently selected from alkyl, cycloalkyl, alkenyl, alkynyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

R$_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —C(=NR$_{15}$)NR$_{15}$R$_{15}$, —NHC(=NR$_{15}$)NR$_{15}$R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl;

R$_{15}$, at each occurrence, is independently selected from hydrogen, alkyl, cycloalkyl, aryl or arylalkyl; and provided that:

(i) when W is absent, Z is phenyl, X is —C(=O)OH, lower alkyl or tetrazolyl, A is not bicyclo(2,2,1)heptanyl, bicyclo(2,2,1)heptenyl, bicyclo(2,2,2)octanyl, or bicyclo(2,2,2)octenyl;

(ii) when W is absent, Z is optionally substituted phenyl, or heterocyclyl, X is —C(=O)OH or —C(=O)NR$_9$R$_9$ and R$_9$ is hydrogen or lower alkyl, A is not 8-azabicyclo(3.2.1)octanyl;

(iii) the compound is not a compound of the following structure:

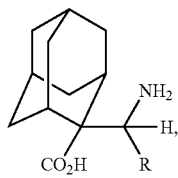

wherein R is optionally substituted phenyl;

(iv) the compound is not a compound of the following structure:

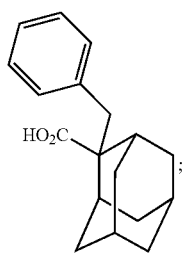

(v) the compound is not a compound of the following structure:

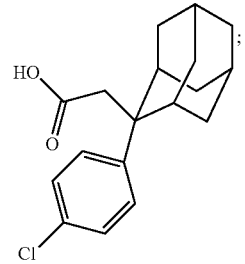

(vi) the compound is not a compound of the following structure:

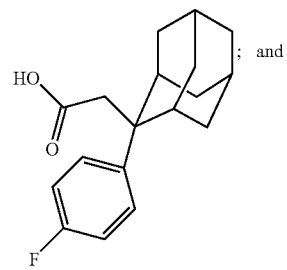
; and (vii) the compound is not a compound of the following structure:

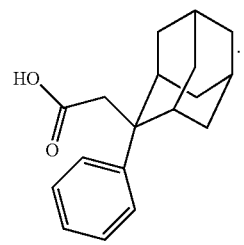

In another embodiment, compounds of formula I are those in which A is a 5- to 20-membered non-aromatic bi-, tri- or polycyclic ring system optionally containing 1-3 heteroatoms selected from N, O, S, S(O) and S(O)$_2$, which is substituted with at least one R$_4$.

In another embodiment, compounds of formula I are those in which:

A is a 6- to 15-membered non-aromatic bi-, tri- or polycyclic ring system optionally containing 1-3 heteroatoms selected from N, O, S, S(O) and S(O)$_2$, which may be optionally substituted with one or more R$_4$'s;

X is —C(=O)OH, —C(=O)C(=O)OH, —C(=O)NR$_9$R$_9$, or tetrazolyl;

W is absent, (—CR$_{8a}$R$_{8b}$—)$_m$, (—CR$_{8a}$R$_{8b}$—)$_m$—O—, (—CR$_{8a}$R$_{8b}$—)$_m$—N(R$_{14}$)—, or alkenyl, wherein the alkenyl may be optionally substituted with one or more R$_{8a}$'s;

m is 1-3;

Z is CN, C$_{3-10}$ alkyl, cycloalkyl, aryl, arylalkyl, heterocyclyl or heterocyclylalkyl, all of which may be optionally substituted with one or more R$_4$'s, and the heterocyclyl and heterocyclylalkyl contain 1-4 heteroatoms selected from N, O, and S;

provided that W and Z, or when W is absent, X and Z, are attached to the same carbon on Ring A;

$R_4$, at each occurrence, is independently selected from hydrogen, alkyl, aryl, alkenyl, alkynyl, cycloalkyl, heterocyclyl, halo, =O, —$NH_2$, —CN, —$NO_2$, —C(=O)OH, —C(=O)$OR_{10}$, —$OR_{10}$, —OH, —$OCF_3$, —SH, —$SR_{10}$, —C(=O)$NR_9R_9$, —$NR_9R_9$, —S(O)$_2NR_9R_9$, —$NR_9$S(O)$_2CF_3$, —C(=O)$NR_9$S(O)$_2R_9$, —S(O)$_2NR_9$C(=O)$R_9$, —S(O)$_2NR_9$C(=O)$NR_9R_9$, —C(=O)$NR_9$S(O)$_2CF_3$, —C(=O)$R_{10}$, —$NR_9$C(=O)$R_{10}$, —OC(=O)$R_{10}$, —S(=O)$R_{10}$, —S(O)$_2R_{10}$, —O—S(O)$_2R_{10}$, —$NR_9$C(=O)$OR_8$ or —$NR_9$S(O$_2$)$R_8$, wherein the alkyl, aryl, alkenyl, alkynyl, cycloalkyl, or heterocyclyl may be optionally substituted with one or more $R_5$'s;

$R_5$, at each occurrence, is independently selected from hydrogen, alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)$OR_{10}$, —$OCF_3$, —$OR_{10}$, —OH, —SH, —$SR_{10}$, —C(=O)$NR_9R_9$, —$NR_9R_9$, —S(O)$_2NR_9R_9$, —$NR_9$S(O)$_2CF_3$, —C(=O)$NR_9$S(O)$_2R_9$, —S(O)$_2NR_9$C(=O)$OR_9$, —S(O)$_2NR_9$C(=O)$NR_9R_9$, —C(=O)$NR_9$S(O)$_2CF_3$, —C(=O)$R_{10}$, —$NR_9$C(=O)$R_{10}$, —OC(=O)$R_{10}$, —S(=O)$R_{10}$, —S(O)$_2R_{10}$, —O—S(O)$_2R_{10}$, —$NR_9$C(=O)$OR_8$ or —$NR_9$S(O$_2$)$R_8$;

$R_8$, at each occurrence, is independently alkyl, aryl or heterocyclyl;

$R_{8a}$, at each occurrence, is independently hydrogen, alkyl or aryl;

$R_{8b}$, at each occurrence, is independently hydrogen, —C(=O)OH, alkyl, —OH, halo, —CN, —$OR_{10}$, —C(=O)$R_{10}$ or —C(=O)$NR_9R_9$, wherein the alkyl may be optionally substituted with one or more $R_{9a}$'s; or $R_{8a}$ and $R_{8b}$ are taken together with the carbon to which both are attached to form a 3- to 7-membered ring, which may optionally contain 1-4 heteroatoms selected from N, O, and S and be optionally substituted with 0-3 $R_{9a}$;

$R_9$, at each occurrence, is independently hydrogen, alkyl, alkoxy, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-5 $R_{9a}$, and the heterocyclyl or heterocyclylalkyl contain 1-4 heteroatoms selected from N, O, and S; or two $R_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more $R_{9a}$'s;

$R_{9a}$, at each occurrence, is independently selected from alkyl, haloalkyl, aryl, alkenyl, alkynyl, cycloalkyl, cycloalkylalkyl, heterocyclyl, heterocyclylalkyl, halo, =O, —$NH_2$, —CN, —$NO_2$, —C(=O)OH, —C(=O)$OR_{14}$, —$OCF_3$, —$OR_{10}$, —OH, —SH, —$SR_{14}$, —C(=O)$NR_{14}R_{14}$, —$NR_{14}R_{14}$, —S(O)$_2NR_{14}R_{14}$, —$NR_{14}$S(O)$_2CF_3$, —C(=O)$NR_{14}$S(O)$_2R_{10}$, —S(O)$_2NR_{14}$C(=O)$OR_{10}$, —S(O)$_2NR_{14}$C(=O)$NR_{14}R_{14}$, —C(=O)$NR_{14}$S(O)$_2R_{14}$, —C(=O)$R_{14}$, —$NR_{14}$C(=O)$R_{14}$, —OC(=O)$R_{14}$, —S(=O)$R_{14}$, —S(O)$_2R_{14}$, —OS(O)$_2R_{14}$, —$NR_{14}$C(=O)$OR_{10}$, —$NR_{14}$S(O$_2$)$R_8$, —C(=O)$R_{10}$, —OC(=O)$NR_{14}R_{14}$, —$NR_{14}$C(=O)$NR_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_{10}$, at each occurrence, is independently selected from alkyl, cycloalkyl, alkenyl, alkynyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —C(=O)$NR_{14}R_{14}$, —$NR_{14}R_{14}$, —S(O)$_2NR_{14}R_{14}$, —$NR_{14}$S(O)$_2CF_3$, —C(=O)$NR_{14}$S(O)$_2R_{14}$, —S(O)$_2NR_{14}$C(=O)$OR_{14}$, —S(O)$_2NR_{14}$C(=O)$NR_{14}R_{14}$, —C(=O)$NR_{14}$S(O)$_2CF_3$, —C(=O)$R_{14}$, —$NR_{14}$C(=O)$R_{14}$, —OC(=O)$R_{14}$, —S(=O)$R_{14}$, —S(O)$_2R_{14}$, —$NR_{14}$C(=O)$OR_8$, —$NR_{14}$S(O$_2$)$R_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)$OR_{15}$, —$OCF_3$, —$OR_{15}$, —OH, —SH, —$SR_{15}$, —C(=O)$NR_{15}R_{15}$, —$NR_{15}R_{15}$, —S(O)$_2NR_{15}R_{15}$, —$NR_{15}$S(O)$_2CF_3$, —C(=O)$NR_{15}$S(O)$_2R_{15}$, —S(O)$_2NR_{15}$C(=O)$OR_{15}$, —S(O)$_2NR_{15}$C(=O)$NR_{15}R_{15}$, —C(=O)$NR_{15}$S(O)$_2CF_3$, —C(=O)$R_{15}$, —$NR_{15}$C(=O)$R_{15}$, —OC(=O)$R_{15}$, —S(=O)$R_{15}$, —S(O)$_2R_{15}$, —$NR_{15}$C(=O)$OR_8$, —$NR_{15}$S(O$_2$)$R_8$ or arylalkyl; and $R_{15}$, at each occurrence, is independently selected from hydrogen, alkyl, cycloalkyl, aryl or arylalkyl.

In yet another embodiment, compounds of formula I are those in which:

A is a 7- to 14-membered non-aromatic bi-, tri- or polycyclic ring system optionally containing 1-3 heteroatoms selected from N, O, S, S(O) and S(O)$_2$, which may be optionally substituted with one or more $R_4$'s;

X is —C(=O)OH, —C(=O)$NR_9R_9$, or tetrazolyl;

W is absent, (—$CR_{8a}R_{8b}$—)$_m$, (—$CR_{8a}R_{8b}$—)$_m$—O— or alkenyl, wherein the alkenyl may be optionally substituted with one or more $R_{8a}$'s;

m is 1-2;

Z is CN, $C_{3-10}$ alkyl, cycloalkyl, aryl, arylalkyl, heterocyclyl or heterocyclylalkyl, all of which may be optionally substituted with one or more $R_4$'s, and the heterocyclyl and heterocyclylalkyl contain 1-4 heteroatoms selected from N, O, and S;

provided that W and Z, or when W is absent, X and Z, are attached to the same carbon on Ring A;

$R_4$, at each occurrence, is independently selected from hydrogen, alkyl, aryl, alkenyl, alkynyl, cycloalkyl, heterocyclyl, halo, =O, —$NH_2$, —CN, —$NO_2$, —C(=O)OH, —C(=O)$OR_{10}$, —$OR_{10}$, —OH, —$OCF_3$, —SH, —$SR_{10}$, —C(=O)$NR_9R_9$, —$NR_9R_9$, —S(O)$_2NR_9R_9$, —$NR_9$S(O)$_2CF_3$, —C(=O)$NR_9$S(O)$_2R_9$, —S(O)$_2NR_9$C(=O)$OR_9$, —S(O)$_2NR_9$C(=O)$NR_9R_9$, —C(=O)$NR_9$S(O)$_2CF_3$, —C(=O)$R_{10}$, —$NR_9$C(=O)$R_{10}$, —OC(=O)$R_{10}$, —S(=O)$R_{10}$, —S(O)$_2R_{10}$, —O—S(O)$_2R_{10}$, —$NR_9$C(=O)$OR_8$ or —$NR_9$S(O$_2$)$R_8$, wherein the alkyl, aryl, alkenyl, alkynyl, cycloalkyl, or heterocyclyl may be optionally substituted with one or more $R_5$'s;

$R_5$, at each occurrence, is independently selected from hydrogen, alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)$OR_{10}$, —$OCF_3$, —$OR_{10}$, —OH, —SH, —$SR_{10}$, —C(=O)$NR_9R_9$, —$NR_9R_9$, —S(O)$_2NR_9R_9$, —$NR_9$S(O)$_2CF_3$, —C(=O)$NR_9$S(O)$_2R_9$, —S(O)$_2NR_9$C(=O)$OR_9$, —S(O)$_2NR_9$C (=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

R$_8$, at each occurrence, is independently alkyl, aryl or heterocyclyl;

R$_{8a}$, at each occurrence, is independently hydrogen, alkyl or aryl;

R$_{8b}$, at each occurrence, is independently hydrogen, —C(=O)OH, alkyl, —OH, halo, —CN, —OR$_{10}$, —C(=O)R$_{10}$ or —C(=O)NR$_9$R$_9$, wherein the alkyl may be optionally substituted with one or more R$_{9a}$'s; or R$_{8a}$ and R$_{8b}$ are taken together with the carbon to which both are attached to form a 3- to 7-membered ring, which may optionally contain 1-4 heteroatoms selected from N, O, and S and be optionally substituted with 0-3 R$_{9a}$;

R$_9$, at each occurrence, is independently hydrogen, alkyl, alkoxy, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-5 R$_{9a}$, and the heterocyclyl or heterocyclylalkyl contain 1-4 heteroatoms selected from N, O, and S; or two R$_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more R$_{9a}$'s;

R$_{9a}$, at each occurrence, is independently selected from alkyl, haloalkyl, aryl, alkenyl, alkynyl, cycloalkyl, cycloalkylalkyl, heterocyclyl, heterocyclylalkyl, halo, =O, —NH$_2$, —CN, —NO$_2$, —C(=O)OH, —C(=O)OR$_{14}$, —OCF$_3$, —OR$_{10}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —C(=O)R$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_{10}$, at each occurrence, is independently selected from alkyl, cycloalkyl, alkenyl, alkynyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

R$_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl, aryl or arylalkyl.

In another embodiment, compounds of formula I are those in which:

A is a 7- to 14-membered non-aromatic bi-, tri- or polycyclic ring system optionally containing 1-3 heteroatoms selected from N, O, S, S(O) and S(O)$_2$, which may be optionally substituted with one or more R$_4$'s;

X is —C(=O)OH, —C(=O)NR$_9$R$_9$, or tetrazolyl;

W is absent, (—CR$_{8a}$R$_{8b}$—)$_m$, (—CR$_{8a}$R$_{8b}$)$_m$—O— or alkenyl, wherein the alkenyl may be optionally substituted with one or more R$_{8a}$'s;

m is 1-2;

Z is cycloalkyl, aryl, arylalkyl, heterocyclyl or heterocyclylalkyl, all of which may be optionally substituted with one or more R$_4$'s, and the heterocyclyl and heterocyclylalkyl contain 1-4 heteroatoms selected from N, O, and S;

provided that W and Z, or when W is absent, X and Z, are attached to the same carbon on Ring A;

R$_4$, at each occurrence, is independently selected from hydrogen, alkyl, aryl, alkenyl, alkynyl, cycloalkyl, heterocyclyl, halo, =O, —NH$_2$, —CN, —NO$_2$, —C(=O)OH, —C(=O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$, wherein the alkyl, aryl, alkenyl, alkynyl, cycloalkyl, or heterocyclyl may be optionally substituted with one or more R$_5$'s;

R$_5$, at each occurrence, is independently selected from hydrogen, alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

R$_8$, at each occurrence, is independently alkyl, aryl or heterocyclyl;

R$_{8a}$, at each occurrence, is independently hydrogen, alkyl or aryl;

R$_{8b}$, at each occurrence, is independently hydrogen, —C(=O)OH, alkyl, —OH, halo, —CN, —OR$_{10}$, —C(=O)R$_{10}$ or —C(=O)NR$_9$R$_9$, wherein the alkyl may be optionally substituted with one or more R$_{9a}$'s; or R$_{8a}$ and R$_{8b}$ are taken together with the carbon to which both are attached to form a 3- to 7-membered ring, which may optionally contain 1-4 heteroatoms selected from N, O, and S and be optionally substituted with 0-3 R$_{9a}$;

R$_9$, at each occurrence, is independently hydrogen, alkyl, alkoxy, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-5 R$_{9a}$, and the heterocyclyl or heterocyclylalkyl contain 1-4 heteroatoms selected from N, O, and S; or two $R_9$'s together with the nitrogen to which they are attached form a unsaturated, saturated or partially saturated cyclic ring system containing from 2-10 carbon atoms and from 0-4 additional heteroatoms selected from N, O, S, S(O) and $S(O)_2$, wherein said ring system may be optionally substituted or fused with one or more $R_{9a}$'s;

$R_{9a}$, at each occurrence, is independently selected from alkyl, haloalkyl, aryl, alkenyl, alkynyl, cycloalkyl, cycloalkylalkyl, heterocyclyl, heterocyclylalkyl, halo, =O, —$NH_2$, —CN, —$NO_2$, —C(=O)OH, —C(=O)$OR_{14}$, —$OCF_3$, —$OR_{10}$, —OH, —SH, —$SR_{14}$, —C(=O)$NR_{14}R_{14}$, —$NR_{14}R_{14}$, —S(O)$_2NR_{14}R_{14}$, —$NR_{14}S(O)_2CF_3$, —C(=O)$NR_{14}S(O)_2R_{10}$, —S(O)$_2NR_{14}$C(=O)$OR_{10}$, —S(O)$_2NR_{14}$C(=O)$NR_{14}R_{14}$, —C(=O)$NR_{14}S(O)_2R_{14}$, —C(=O)$R_{14}$, —$NR_{14}$C(=O)$R_{14}$, —OC(=O)$R_{14}$, —S(=O)$R_{14}$, —S(O)$_2R_{14}$, —OS(O)$_2R_{14}$, —$NR_{14}$C(=O)$OR_{10}$, —$NR_{14}S(O_2)R_8$, —C(=O)$R_{10}$, —OC(=O)$NR_{14}R_{14}$, —$NR_{14}$C(=O)$NR_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_{10}$, at each occurrence, is independently selected from alkyl, cycloalkyl, alkenyl, alkynyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —C(=O)$NR_{14}R_{14}$, —$NR_{14}R_{14}$, —S(O)$_2NR_{14}R_{14}$, —$NR_{14}S(O)_2CF_3$, —C(=O)$NR_{14}S(O)_2R_{14}$, —S(O)$_2NR_{14}$C(=O)$OR_{14}$, —S(O)$_2NR_{14}$C(=O)$NR_{14}R_{14}$, —C(=O)$NR_{14}S(O)_2CF_3$, —C(=O)$R_{14}$, —$NR_{14}$C(=O)$R_{14}$, —OC(=O)$R_{14}$, —S(=O)$R_{14}$, —S(O)$_2R_{14}$, —$NR_{14}$C(=O)$OR_8$, —$NR_{14}S(O_2)R_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)$OR_{15}$, —$OCF_3$, —$OR_{15}$, —OH, —SH, —$SR_{15}$, —C(=O)$NR_{15}R_{15}$, —$NR_{15}R_{15}$, —S(O)$_2NR_{15}R_{15}$, —$NR_{15}S(O)_2CF_3$, —C(=O)$NR_{15}S(O)_2R_{15}$, —S(O)$_2NR_{15}$C(=O)$OR_{15}$, —S(O)$_2NR_{15}$C(=O)$NR_{15}R_{15}$, —C(=O)$NR_{15}S(O)_2CF_3$, —C(=O)$R_{15}$, —$NR_{15}$C(=O)$R_{15}$, —OC(=O)$R_{15}$, —S(=O)$R_{15}$, —S(O)$_2R_{15}$, —$NR_{15}$C(=O)$OR_8$, —$NR_{15}S(O_2)R_8$ or arylalkyl; and $R_{15}$, at each occurrence, is independently selected from hydrogen, alkyl, cycloalkyl, aryl or arylalkyl.

In still yet another embodiment, compounds of formula I are those in which:

A is a 7- to 14-membered non-aromatic bi-, tri- or polycyclic ring system optionally containing 1-3 heteroatoms selected from N, O, S, S(O) and $S(O)_2$, which may be optionally substituted with one or more $R_4$'s;

X is —C(=O)OH, —C(=O)$NR_9R_9$, or tetrazolyl;

W is absent, —($CR_{8a}R_{8b}$—)$_m$, —($CR_{8a}R_{8b}$)$_m$—O— or alkenyl, wherein the alkenyl may be optionally substituted with one or more $R_{8a}$'s;

m is 1-2;

Z is aryl, arylalkyl, heterocyclyl or heterocyclylalkyl, all of which may be optionally substituted with one or more $R_4$'s, and the heterocyclyl and heterocyclylalkyl contain 1-4 heteroatoms selected from N, O, and S;

provided that W and Z, or when W is absent, X and Z, are attached to the same carbon on Ring A;

$R_4$, at each occurrence, is independently selected from hydrogen, alkyl, aryl, alkenyl, alkynyl, cycloalkyl, heterocyclyl, halo, =O, —$NH_2$, —CN, —$NO_2$, —C(=O)OH, —C(=O)$OR_{10}$, —$OR_{10}$, —OH, —$OCF_3$, —SH, —$SR_{10}$, —C(=O)$NR_9R_9$, —$NR_9R_9$, —S(O)$_2NR_9R_9$, —$NR_9S(O)_2CF_3$, —C(=O)$NR_9S(O)_2R_9$, —S(O)$_2NR_9$C(=O)$OR_9$, —S(O)$_2NR_9$C(=O)$NR_9R_9$, —C(=O)$NR_9S(O)_2CF_3$, —C(=O)$R_{10}$, —$NR_9$C(=O)$R_{10}$, —OC(=O)$R_{10}$, —S(=O)$R_{10}$, —S(O)$_2R_{10}$, —O—S(O)$_2R_{10}$, —$NR_9$C(=O)$OR_8$ or —$NR_9S(O)_2R_8$, wherein the alkyl, aryl, alkenyl, alkynyl, cycloalkyl, or heterocyclyl may be optionally substituted with one or more $R_5$'s;

$R_5$, at each occurrence, is independently selected from hydrogen, alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)$OR_{10}$, —$OCF_3$, —$OR_{10}$, —OH, —SH, —$SR_{10}$, —C(=O)$NR_9R_9$, —$NR_9R_9$, —S(O)$_2NR_9R_9$, —$NR_9S(O)_2CF_3$, —C(=O)$NR_9S(O)_2R_9$, —S(O)$_2NR_9$C(=O)$OR_9$, —S(O)$_2NR_9$C(=O)$NR_9R_9$, —C(=O)$NR_9S(O)_2CF_3$, —C(=O)$R_{10}$, —$NR_9$C(=O)$R_{10}$, —OC(=O)$R_{10}$, —S(=O)$R_{10}$, —S(O)$_2R_{10}$, —O—S(O)$_2R_{10}$, —$NR_9$C(=O)$OR_8$ or —$NR_9S(O_2)R_8$;

$R_8$, at each occurrence, is independently alkyl, aryl or heterocyclyl;

$R_{8a}$, at each occurrence, is independently hydrogen, alkyl or aryl;

$R_{8b}$, at each occurrence, is independently hydrogen, —C(=O)OH, alkyl, —OH, halo, —CN, —$OR_{10}$, —C(=O)$R_{10}$ or —C(=O)$NR_9R_9$, wherein the alkyl may be optionally substituted with one or more $R_{9a}$'s; or $R_{8a}$ and $R_{8b}$ are taken together with the carbon to which both are attached to form a 3- to 7-membered ring, which may optionally contain 1-4 heteroatoms selected from N, O, and S and be optionally substituted with 0-3 $R_{9a}$;

$R_9$, at each occurrence, is independently hydrogen, alkyl, alkoxy, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-5 $R_{9a}$, and the heterocyclyl or heterocyclylalkyl contain 1-4 heteroatoms selected from N, O, and S; or two $R_9$'s together with the nitrogen to which they are attached form a unsaturated, saturated or partially saturated cyclic ring system containing from 2-10 carbon atoms and from 0-4 additional heteroatoms selected from N, O, S, S(O) and $S(O)_2$, wherein said ring system may be optionally substituted or fused with one or more $R_{9a}$'s;

$R_{9a}$, at each occurrence, is independently selected from alkyl, haloalkyl, aryl, alkenyl, alkynyl, cycloalkyl, cycloalkylalkyl, heterocyclyl, heterocyclylalkyl, halo, =O, —$NH_2$, —CN, —$NO_2$, —C(=O)OH, —C(=O)$OR_{14}$, —$OCF_3$, —$OR_{10}$, —OH, —SH, —$SR_{14}$, —C(=O)$NR_{14}R_{14}$, —$NR_{14}R_{14}$, —S(O)$_2NR_{14}R_{14}$, —$NR_{14}S(O)_2CF_3$, —C(=O)$NR_{14}S(O)_2R_{10}$, —S(O)$_2NR_{14}$C(=O)$OR_{10}$, —S(O)$_2NR_{14}$C(=O)$NR_{14}R_{14}$, —C(=O)$NR_{14}S(O)_2R_{14}$, —C(=O)$R_{14}$, —$NR_{14}$C(=O)$R_{14}$, —OC(=O)$R_{14}$, —S(=O)$R_{14}$, —S(O)$_2R_{14}$, —OS(O)$_2R_{14}$, —$NR_{14}$C(=O)$OR_{10}$, —$NR_{14}S(O_2)R_8$, —C(=O)$R_{10}$, —OC(=O)$NR_{14}R_{14}$, —$NR_{14}$C(=O)$NR_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_{10}$, at each occurrence, is independently selected from alkyl, cycloalkyl, alkenyl, alkynyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —C(=O)$NR_{14}R_{14}$, —$NR_{14}R_{14}$, —S(O)$_2NR_{14}R_{14}$, —$NR_{14}S(O)_2CF_3$, —C(=O)$NR_{14}S(O)_2R_{14}$, —S(O)$_2NR_{14}C$(=O)$OR_{14}$, —S(O)$_2NR_{14}C$(=O)$NR_{14}R_{14}$, —C(=O)$NR_{14}S(O)_2CF_3$, —C(=O)$R_{14}$, —$NR_{14}C$(=O)$R_{14}$, —OC(=O)$R_{14}$, —S(=O)$R_{14}$, —S(O)$_2R_{14}$, —$NR_{14}C$(=O)$OR_8$, —$NR_{14}S(O_2)R_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)$OR_{15}$, —$OCF_3$, —$OR_{15}$, —OH, —SH, —$SR_{15}$, —C(=O)$NR_{15}R_{15}$, —$NR_{15}R_{15}$, —S(O)$_2NR_{15}R_{15}$, —$NR_{15}S(O)_2CF_3$, —C(=O)$NR_{15}S(O)_2R_{15}$, —S(O)$_2NR_{15}C$(=O)$OR_{15}$, —S(O)$_2NR_{15}C$(=O)$NR_{15}R_{15}$, —C(=O)$NR_{15}S(O)_2CF_3$, —C(=O)$R_{15}$, —$NR_{15}C$(=O)$R_{15}$, —OC(=O)$R_{15}$, —S(=O)$R_{15}$, —S(O)$_2R_{15}$, —$NR_{15}C$(=O)$OR_8$, —$NR_{15}S(O_2)R_8$ or arylalkyl; and $R_{15}$, at each occurrence, is independently selected from hydrogen, alkyl, cycloalkyl, aryl or arylalkyl.

In one embodiment, compounds of formula I are those in which:

A is a 7- to 14-membered non-aromatic bi-, tri- or polycyclic ring system optionally containing 1-3 heteroatoms selected from N, O, S, S(O) and S(O)$_2$, which may be optionally substituted with one or more $R_4$'s;

X is —C(=O)OH, —C(=O)$NR_9R_9$, or tetrazolyl;

W is absent, (—$CR_{8a}R_{8b}$—)$_m$, —(—$CR_{8a}R_{8b}$)$_m$—O— or alkenyl, wherein the alkenyl may be optionally substituted with one or more $R_{8a}$'s;

m is 1-2;

Z is aryl, arylalkyl or heterocyclylalkyl, all of which may be optionally substituted with one or more $R_4$'s, and the heterocyclylalkyl contain 1-4 heteroatoms selected from N, O, and S;

provided that W and Z, or when W is absent, X and Z, are attached to the same carbon on Ring A;

$R_4$, at each occurrence, is independently selected from hydrogen, alkyl, aryl, alkenyl, cycloalkyl, heterocyclyl, halo, =O, —$NH_2$, —CN, —$NO_2$, —C(=O)OH, —C(=O)$OR_{10}$, —$OR_{10}$, —OH, —$OCF_3$, —SH, —$SR_{10}$, —C(=O)$NR_9R_9$, —$NR_9R_9$, —S(O)$_2NR_9R_9$, —$NR_9S(O)_2CF_3$, —C(=O)$NR_9S(O)_2R_9$, —S(O)$_2NR_9C$(=O)$OR_9$, —S(O)$_2NR_9C$(=O)$NR_9R_9$, —C(=O)$NR_9S(O)_2CF_3$, —C(=O)$R_{10}$, —$NR_9C$(=O)$R_{10}$, —OC(=O)$R_{10}$, —S(=O)$R_{10}$, —S(O)$_2R_{10}$, —O—S(O)$_2R_{10}$, —$NR_9C$(=O)$OR_8$ or —$NR_9S(O_2)R_8$, wherein the alkyl, aryl, alkenyl, cycloalkyl, or heterocyclyl may be optionally substituted with one or more $R_5$'s;

$R_5$, at each occurrence, is independently selected from hydrogen, alkyl, haloalkyl, aryl, alkenyl, cycloalkyl, cycloalkylalkyl, heterocyclyl, heterocyclylalkyl, halo, —$NH_2$, —CN, —$NO_2$, —C(=O)OH, —C(=O)$OR_{10}$, —$OCF_3$, —$OR_{10}$, —OH, —SH, —$SR_{10}$, —C(=O)$NR_9R_9$, —$NR_9R_9$, —S(O)$_2NR_9R_9$, —$NR_9S(O)_2CF_3$, —C(=O)$NR_9S(O)_2R_9$, —S(O)$_2NR_9C$(=O)$OR_9$, —S(O)$_2NR_9C$(=O)$NR_9R_9$, —C(=O)$NR_9S(O)_2CF_3$, —C(=O)$R_{10}$, —$NR_9C$(=O)$R_{10}$, —OC(=O)$R_{10}$, —S(=O)$R_{10}$, —S(O)$_2R_{10}$, —O—S(O)$_2R_{10}$, —$NR_9C$(=O)$OR_8$ or —$NR_9S(O_2)R_8$;

$R_8$, at each occurrence, is independently alkyl, aryl or heterocyclyl;

$R_{8a}$, at each occurrence, is independently hydrogen, alkyl or aryl;

$R_{8b}$, at each occurrence, is independently hydrogen, —C(=O)OH, alkyl, —OH, halo, —CN, —$OR_{10}$, —C(=O)$R_{10}$ or —C(=O)$NR_9R_9$, wherein the alkyl may be optionally substituted with one or more $R_{9a}$'s; or $R_{8a}$ and $R_{8b}$ are taken together with the carbon to which both are attached to form a 3- to 7-membered ring, which may optionally contain 1-4 heteroatoms selected from N, O, and S and be optionally substituted with 0-3 $R_{9a}$;

$R_9$, at each occurrence, is independently hydrogen, alkyl, alkoxy, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-5 $R_{9a}$, and the heterocyclyl or heterocyclylalkyl contain 1-4 heteroatoms selected from N, O, and S; or two $R_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more $R_{9a}$'s;

$R_{9a}$, at each occurrence, is independently selected from alkyl, haloalkyl, aryl, alkenyl, cycloalkyl, cycloalkylalkyl, heterocyclyl, heterocyclylalkyl, halo, =O, —$NH_2$, —CN, —$NO_2$, —C(=O)OH, —C(=O)$OR_{14}$, —$OCF_3$, —$OR_{10}$, —OH, —SH, —$SR_{14}$, —C(=O)$NR_{14}R_{14}$, —$NR_{14}R_{14}$, —S(O)$_2NR_{14}R_{14}$, —$NR_{14}S(O)_2CF_3$, —C(=O)$NR_{14}S(O)_2R_{10}$, —S(O)$_2NR_{14}C$(=O)$OR_{10}$, —S(O)$_2NR_{14}C$(=O)$NR_{14}R_{14}$, —C(=O)$NR_{14}S(O)_2R_{14}$, —C(=O)$R_{14}$, —$NR_{14}C$(=O)$R_{14}$, —OC(=O)$R_{14}$, —S(=O)$R_{14}$, —S(O)$_2R_{14}$, —OS(O)$_2R_{14}$, —$NR_{14}C$(=O)$OR_{10}$, —$NR_{14}S(O_2)R_8$, —C(=O)$R_{10}$, —OC(=O)$NR_{14}R_{14}$, —$NR_{14}C$(=O)$NR_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_{10}$, at each occurrence, is independently selected from alkyl, cycloalkyl, alkenyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, cycloalkyl, cycloalkylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —C(=O)$NR_{14}R_{14}$, —$NR_{14}R_{14}$, —S(O)$_2NR_{14}R_{14}$, —$NR_{14}S(O)_2CF_3$, —C(=O)$NR_{14}S(O)_2R_{14}$, —S(O)$_2NR_{14}C$(=O)$OR_{14}$, —S(O)$_2NR_{14}C$(=O)$NR_{14}R_{14}$, —C(=O)$NR_{14}S(O)_2CF_3$, —C(=O)$R_{14}$, —$NR_{14}C$(=O)$R_{14}$, —OC(=O)$R_{14}$, —S(=O)$R_{14}$, —S(O)$_2R_{14}$, —$NR_{14}C$(=O)$OR_8$, —$NR_{14}S(O_2)R_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, cycloalkyl, cycloalkylalkyl, heterocyclyl, heterocyclylalkyl, halo, —$NH_2$, —CN, —$NO_2$, —C(=O)OH, —C(=O)$OR_{15}$, —$OCF_3$, —$OR_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl, aryl or arylalkyl.

In still yet another embodiment, compounds of formula I are those in which:

A is a 7- to 14-membered non-aromatic bi-, tri- or polycyclic ring system optionally containing 1-3 heteroatoms selected from N, O, S, S(O) and S(O)$_2$, which may be optionally substituted with one or more R$_4$'s;

X is —C(=O)OH, or —C(=O)NR$_9$R$_9$;

W is absent, (—CR$_{8a}$R$_{8b}$—)$_m$, (—CR$_{8a}$R$_{8b}$)$_m$—O— or alkenyl, wherein the alkenyl may be optionally substituted with one or more R$_{8a}$'s;

m is 1-2;

Z is aryl, arylalkyl or heterocyclylalkyl, all of which may be optionally substituted with one or more R$_4$'s, and the heterocyclylalkyl contain 1-4 heteroatoms selected from N, O, and S;

provided that W and Z, or when W is absent, X and Z, are attached to the same carbon on Ring A;

R$_4$, at each occurrence, is independently selected from hydrogen, alkyl, aryl, cycloalkyl, heterocyclyl, halo, =O, —NH$_2$, —CN, —NO$_2$, —C(=O)OH, —C(=O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$, wherein the alkyl, aryl, cycloalkyl or heterocyclyl may be optionally substituted with one or more R$_5$'s;

R$_5$, at each occurrence, is independently selected from hydrogen, alkyl, haloalkyl, aryl, cycloalkyl, cycloalkylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

R$_8$, at each occurrence, is independently alkyl, aryl or heterocyclyl;

R$_{8a}$, at each occurrence, is independently hydrogen, alkyl or aryl;

R$_{8b}$, at each occurrence, is independently hydrogen, —C(=O)OH, alkyl, —OH, halo, —CN, —OR$_{10}$, —C(=O)R$_{10}$ or —C(=O)NR$_9$R$_9$, wherein the alkyl may be optionally substituted with one or more R$_{9a}$'s; or R$_{8a}$ and R$_{8b}$ are taken together with the carbon to which both are attached to form a 3- to 7-membered ring, which may optionally contain 1-4 heteroatoms selected from N, O, and S and be optionally substituted with 0-3 R$_{9a}$;

R$_9$, at each occurrence, is independently hydrogen, alkyl, alkoxy, cycloalkyl, aryl, arylalkyl, or heterocyclyl, wherein the alkyl, cycloalkyl, aryl, arylalkyl or heterocyclyl may be optionally substituted with 0-5 R$_{9a}$, and the heterocyclyl contains 1-4 heteroatoms selected from N, O, and S; or two R$_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more R$_{9a}$'s;

R$_{9a}$, at each occurrence, is independently selected from alkyl, haloalkyl, aryl, cycloalkyl, cycloalkylalkyl, heterocyclyl, heterocyclylalkyl, halo, =O, —NH$_2$, —CN, —NO$_2$, —C(=O)OH, —C(=O)OR$_{14}$, —OCF$_3$, —OR$_{10}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —C(=O)R$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_{10}$, at each occurrence, is independently selected from alkyl, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

R$_{14a}$, at each occurrence, is independently selected from alkyl, haloalkyl, aryl, cycloalkyl, cycloalkylalkyl, heterocyclyl, heterocyclylalkyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl, aryl or arylalkyl.

In another embodiment, compounds of formula I are those compounds in which:

A is a 7- to 14-membered non-aromatic bi-, tri- or polycyclic ring system optionally containing 1-3 heteroatoms selected from N, O, S, S(O) and S(O)$_2$, which may be optionally substituted with one or more R$_4$'s;

X is —C(=O)OH, or —C(=O)NR$_9$R$_9$;

W is absent, (—CR$_{8a}$R$_{8b}$—)$_m$ or (—CR$_{8a}$R$_{8b}$)$_m$—O—;

m is 1-2;

Z is aryl, arylalkyl or heterocyclylalkyl, all of which may be optionally substituted with one or more R$_4$'s, and the heterocyclylalkyl contain 1-4 heteroatoms selected from N, O, and S;

provided that W and Z, or when W is absent, X and Z, are attached to the same carbon on Ring A;

R$_4$, at each occurrence, is independently selected from hydrogen, alkyl, aryl, cycloalkyl, heterocyclyl, halo, =O, —NH$_2$, —CN, —NO$_2$, —C(=O)OH, —C(=O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$, wherein the alkyl, aryl, cycloalkyl, or heterocyclyl may be optionally substituted with one or more R$_5$'s;

R$_5$, at each occurrence, is independently selected from hydrogen, alkyl, haloalkyl, aryl, cycloalkyl, cycloalkylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

R$_8$, at each occurrence, is independently alkyl, aryl or heterocyclyl;

R$_{8a}$, at each occurrence, is independently hydrogen, alkyl or aryl;

R$_{8b}$, at each occurrence, is independently hydrogen, —C(=O)OH, alkyl, —OH, halo, —CN, —OR$_{10}$ or —C(=O)NR$_9$R$_9$, wherein the alkyl may be optionally substituted with one or more R$_{9a}$'s; or R$_9$, at each occurrence, is independently hydrogen, alkyl, alkoxy, cycloalkyl, aryl, arylalkyl, or heterocyclyl, wherein the alkyl, cycloalkyl, aryl, arylalkyl or heterocyclyl may be optionally substituted with 0-5 R$_{9a}$, and the heterocyclyl contains 1-4 heteroatoms selected from N, O, and S; or two R$_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more R$_{9a}$'s;

R$_{9a}$, at each occurrence, is independently selected from alkyl, haloalkyl, aryl, cycloalkyl, cycloalkylalkyl, heterocyclyl, heterocyclylalkyl, halo, =O, —NH$_2$, —CN, —NO$_2$, —C(=O)OH, —C(=O)OR$_{14}$, —OCF$_3$, —OR$_{10}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —C(=O)R$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl and heterocyclylalkyl may be optionally substituted with 0-3 R$_{10a}$;

R$_{10}$, at each occurrence, is independently selected from alkyl, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, or aryl, wherein the alkyl, cycloalkyl or aryl may be optionally substituted with 0-3 R$_{14a}$;

R$_{14a}$, at each occurrence, is independently selected from alkyl, haloalkyl, aryl, cycloalkyl, cycloalkylalkyl, heterocyclyl, heterocyclylalkyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl or aryl.

In another embodiment, compounds of formula I are those compounds in which:

A is a 7- to 14-membered non-aromatic bi-, tri- or polycyclic ring system optionally containing 1-3 heteroatoms selected from N, O, S, S(O) and S(O)$_2$, which may be optionally substituted with one or more R$_4$'s;

X is —C(=O)OH, or —C(=O)NR$_9$R$_9$;

W is absent, (—CR$_{8a}$R$_{8b}$—)$_m$ or —(CR$_{8a}$R$_{8b}$)$_m$—O—;

m is 1-2;

Z is aryl or arylalkyl, both of which may be optionally substituted with one or more R$_4$'s;

provided that W and Z, or when W is absent, X and Z, are attached to the same carbon on Ring A;

R$_4$, at each occurrence, is independently selected from hydrogen, alkyl, aryl, cycloalkyl, heterocyclyl, halo, =O, —NH$_2$, —CN, —NO$_2$, —C(=O)OH, —C(=O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$, wherein the alkyl, aryl, cycloalkyl, or heterocyclyl may be optionally substituted with one or more R$_5$'s;

R$_5$, at each occurrence, is independently selected from hydrogen, alkyl, haloalkyl, aryl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

R$_8$, at each occurrence, is independently alkyl, aryl or heterocyclyl;

R$_{8a}$, at each occurrence, is independently hydrogen, alkyl or aryl;

R$_{8b}$, at each occurrence, is independently hydrogen, —C(=O)OH, alkyl, —OH, halo, —CN, —OR$_{10}$ or —C(=O)NR$_9$R$_9$, wherein the alkyl may be optionally substituted with one or more R$_{9a}$'s; or R$_9$, at each occurrence, is independently hydrogen, alkyl, alkoxy, cycloalkyl, aryl or heterocyclyl, wherein the alkyl, cycloalkyl, aryl or heterocyclyl may be optionally substituted with 0-5 R$_{9a}$, and the heterocyclyl contains 1-4 heteroatoms selected from N, O, and S; or two R$_9$'s together with the nitrogen to which they are attached form a unsaturated, saturated or partially saturated cyclic ring system containing from 2-10 carbon atoms and from 0-4 additional heteroatoms selected from N, O, S, S(O)

and $S(O)_2$, wherein said ring system may be optionally substituted or fused with one or more $R_{9a}$'s;

$R_{9a}$, at each occurrence, is independently selected from alkyl, haloalkyl, aryl, cycloalkyl, cycloalkylalkyl, heterocyclyl, halo, =O, —$NH_2$, —CN, —$NO_2$, —C(=O)OH, —C(=O)$OR_{14}$, —$OCF_3$, —$OR_{10}$, —OH, —SH, —$SR_{14}$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_{10}$, —$S(O)_2NR_{14}C(=O)OR_{10}$, —$S(O)_2NR_{14}C(=O)NR_{14}R_{14}$, —C(=O)$NR_{14}S(O)_2R_{14}$, —C(=O)$R_{14}$, —$NR_{14}C(=O)R_{14}$, —OC(=O)$R_{14}$, —S(=O)$R_{14}$, —$S(O)_2R_{14}$, —$OS(O)_2R_{14}$, —$NR_{14}C(=O)OR_{10}$, —$NR_{14}S(O_2)R_8$, —C(=O)$R_{10}$, —OC(=O)$NR_{14}R_{14}$, —$NR_{14}C(=O)NR_{14}R_{14}$ or arylalkyl, wherein the alkyl, aryl, cycloalkyl, cycloalkylalkyl and heterocyclyl may be optionally substituted with 0-3 $R_{10a}$;

$R_{10}$, at each occurrence, is independently selected from alkyl, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, cycloalkyl, cycloalkylalkyl, heterocyclyl, halo, —$NH_2$, —CN, —$NO_2$, —C(=O)OH, —C(=O)$OR_{14}$, —$OCF_3$, —$OR_{14}$, —OH, —SH, —$SR_{14}$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_{14}$, —$S(O)_2NR_{14}C(=O)OR_{14}$, —$S(O)_2NR_{14}C(=O)NR_{14}R_{14}$, —C(=O)$NR_{14}S(O)_2CF_3$, —C(=O)$R_{14}$, —$NR_{14}C(=O)R_{14}$, —OC(=O)$R_{14}$, —S(=O)$R_{14}$, —$S(O)_2R_{14}$, —$NR_{14}C(=O)OR_8$, —$NR_{14}S(O_2)R_8$ or arylalkyl;

$R_{14}$, at each occurrence, is independently selected from hydrogen, alkyl, cycloalkyl, or aryl, wherein the alkyl, cycloalkyl or aryl may be optionally substituted with 0-3 $R_{14a}$;

$R_{14a}$, at each occurrence, is independently selected from alkyl, haloalkyl, aryl, cycloalkyl, cycloalkylalkyl, heterocyclyl, halo, —$NH_2$, —CN, —$NO_2$, —C(=O)OH, —C(=O)$OR_{15}$, —$OCF_3$, —$OR_{15}$, —OH, —SH, —$SR_{15}$, —C(=O)$NR_{15}R_{15}$, —$NR_{15}R_{15}$, —$S(O)_2NR_{15}R_{15}$, —$NR_{15}S(O)_2CF_3$, —C(=O)$NR_{15}S(O)_2R_{15}$, —$S(O)_2NR_{15}C(=O)OR_{15}$, —$S(O)_2NR_{15}C(=O)NR_{15}R_{15}$, —C(=O)$NR_{15}S(O)_2CF_3$, —C(=O)$R_{15}$, —$NR_{15}C(=O)R_{15}$, —OC(=O)$R_{15}$, —S(=O)$R_{15}$, —$S(O)_2R_{15}$, —$NR_{15}C(=O)OR_8$, —$NR_{15}S(O_2)R_8$ or arylalkyl; and $R_{15}$, at each occurrence, is independently selected from hydrogen, alkyl, cycloalkyl or aryl.

In another embodiment, compounds of formula I are those compounds in which:

A is a 7- to 14-membered non-aromatic bi-, tri- or polycyclic ring system optionally containing 1-3 heteroatoms selected from N, O, S, S(O) and $S(O)_2$, which may be optionally substituted with one or more $R_4$'s;

X is —C(=O)$NR_9R_9$;

W is absent, (—$CR_{8a}R_{8b}$—)$_m$ or —$(CR_{8a}R_{8b})_m$—O—;

m is 1-2;

Z is aryl or arylalkyl, both of which may be optionally substituted with one or more $R_4$'s;

provided that W and Z, or when W is absent, X and Z, are attached to the same carbon on Ring A;

$R_4$, at each occurrence, is independently selected from hydrogen, alkyl, aryl, cycloalkyl, heterocyclyl, halo, =O, —$NH_2$, —CN, —$NO_2$, —C(=O)OH, —C(=O)$OR_{10}$, —$OR_{10}$, —OH, —$OCF_3$, —SH, —$SR_{10}$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C(=O)OR_9$, —$S(O)_2NR_9C(=O)NR_9R_9$, —C(=O)$NR_9S(O)_2CF_3$, —C(=O)$R_{10}$, —$NR_9C(=O)R_{10}$, —OC(=O)$R_{10}$, —S(=O)$R_{10}$, —$S(O)_2R_{10}$, —O—$S(O)_2R_{10}$, —$NR_9C(=O)OR_8$ or —$NR_9S(O_2)R_8$, wherein the alkyl, aryl, cycloalkyl or heterocyclyl may be optionally substituted with one or more $R_5$'s;

$R_5$, at each occurrence, is independently selected from hydrogen, alkyl, haloalkyl, aryl, cycloalkyl, heterocyclyl, halo, —$NH_2$, —CN, —$NO_2$, —C(=O)OH, —C(=O)$OR_{10}$, —$OCF_3$, —$OR_{10}$, —OH, —SH, —$SR_{10}$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C(=O)OR_9$, —$S(O)_2NR_9C(=O)NR_9R_9$, —C(=O)$NR_9S(O)_2CF_3$, —C(=O)$R_{10}$, —$NR_9C(=O)R_{10}$, —OC(=O)$R_{10}$, —S(=O)$R_{10}$, —$S(O)_2R_{10}$, —O—$S(O)_2R_{10}$, —$NR_9C(=O)OR_8$ or —$NR_9S(O_2)R_8$;

$R_8$, at each occurrence, is independently alkyl, aryl or heterocyclyl;

$R_{8a}$, at each occurrence, is independently hydrogen, alkyl or aryl;

$R_{8b}$, at each occurrence, is independently hydrogen, —C(=O)OH, alkyl, —OH, halo, —CN, —$OR_{10}$ or —C(=O)$NR_9R_9$, wherein the alkyl may be optionally substituted with one or more $R_{9a}$'s; or $R_9$, at each occurrence, is independently hydrogen, alkyl, alkoxy, cycloalkyl, aryl or heterocyclyl, wherein the alkyl, cycloalkyl, aryl or heterocyclyl may be optionally substituted with 0-5 $R_{9a}$, and the heterocyclyl contains 1-4 heteroatoms selected from N, O, and S; or two $R_9$'s together with the nitrogen to which they are attached form a unsaturated, saturated or partially saturated cyclic ring system containing from 2-10 carbon atoms and from 0-4 additional heteroatoms selected from N, O, S, S(O) and $S(O)_2$, wherein said ring system may be optionally substituted or fused with one or more $R_{9a}$'s;

$R_{9a}$, at each occurrence, is independently selected from alkyl, haloalkyl, aryl, cycloalkyl, heterocyclyl, halo, =O, —$NH_2$, —CN, —$NO_2$, —C(=O)OH, —C(=O)$OR_{14}$, —$OCF_3$, —$OR_{10}$, —OH, —SH, —$SR_{14}$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_{10}$, —$S(O)_2NR_{14}C(=O)OR_{10}$, —$S(O)_2NR_{14}C(=O)NR_{14}R_{14}$, —C(=O)$NR_{14}S(O)_2R_{14}$, —C(=O)$R_{14}$, —$NR_{14}C(=O)R_{14}$, —OC(=O)$R_{14}$, —S(=O)$R_{14}$, —$S(O)_2R_{14}$, —$OS(O)_2R_{14}$, —$NR_{14}C(=O)OR_{10}$, —$NR_{14}S(O_2)R_8$, —C(=O)$R_{10}$, —OC(=O)$NR_{14}R_{14}$, —$NR_{14}C(=O)NR_{14}R_{14}$ or arylalkyl, wherein the alkyl, aryl, cycloalkyl and heterocyclyl may be optionally substituted with 0-3 $R_{10a}$;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, cycloalkyl, heterocyclyl, halo, —$NH_2$, —CN, —$NO_2$, —C(=O)OH, —C(=O)$OR_{14}$, —$OCF_3$, —$OR_{14}$, —OH, —SH, —$SR_{14}$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_{14}$, —$S(O)_2NR_{14}C(=O)OR_{14}$, —$S(O)_2NR_{14}C(=O)NR_{14}R_{14}$, —C(=O)$NR_{14}S(O)_2CF_3$, —C(=O)$R_{14}$, —$NR_{14}C(=O)R_{14}$, —OC(=O)$R_{14}$, —S(=O)$R_{14}$, —$S(O)_2R_{14}$, —$NR_{14}C(=O)OR_8$, —$NR_{14}S(O_2)R_8$ or arylalkyl;

$R_{14}$, at each occurrence, is independently selected from hydrogen, alkyl, cycloalkyl or aryl, wherein the alkyl, cycloalkyl or aryl may be optionally substituted with 0-3 $R_{14a}$;

$R_{14a}$, at each occurrence, is independently selected from alkyl, haloalkyl, aryl, cycloalkyl, heterocyclyl, halo, —$NH_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O) NR$_{15}$S(O)$_2$R$_{15}$, —S(O)$_2$NR$_{15}$C(=O)OR$_{15}$, —S(O)$_2$NR$_{15}$C (=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S (O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl or aryl.

In another embodiment, compounds of formula I are those compounds in which:

A is a 7- to 12-membered non-aromatic bi-, tri- or polycyclic ring system optionally containing 1-3 heteroatoms selected from N, O, S, S(O) and S(O)$_2$, which is substituted with one or more R$_4$'s;

X is —C(=O)NR$_9$R$_9$;

W is absent or (—CR$_{8a}$R$_{8b}$—)$_m$;

m is 1-2;

Z is aryl or arylalkyl, both of which may be optionally substituted with one or more R$_4$'s;

provided that W and Z, or when W is absent, X and Z, are attached to the same carbon on Ring A;

R$_4$, at each occurrence, is independently selected from hydrogen, alkyl, aryl, cycloalkyl, heterocyclyl, halo, =O, —NH$_2$, —CN, —NO$_2$, —C(=O)OH, —C(=O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O) NR$_9$S(O)$_2$R$_9$, —S(O)$_2$NR$_9$C(=O)OR$_9$, —S(O)$_2$NR$_9$C (=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S (O)$_2$R$_{10}$, —O—S(O)$_2$R$_{10}$, —NR$_9$C(=O)OR$_8$ or —NR$_9$S (O$_2$)R$_8$, wherein the alkyl, aryl, cycloalkyl, or heterocyclyl may be optionally substituted with one or more R$_5$'s;

R$_5$, at each occurrence, is independently selected from hydrogen, alkyl, haloalkyl, aryl, cycloalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O) NR$_9$S(O)$_2$R$_9$, —S(O)$_2$NR$_9$C(=O)OR$_9$, —S(O)$_2$NR$_9$C (=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S (O)$_2$R$_{10}$, —O—S(O)$_2$R$_{10}$, —NR$_9$C(=O)OR$_8$ or —NR$_9$S (O$_2$)R$_8$;

R$_8$, at each occurrence, is independently alkyl, aryl or heterocyclyl;

R$_{8a}$, at each occurrence, is independently hydrogen or alkyl;

R$_{8b}$, at each occurrence, is independently hydrogen, —C(=O)OH, alkyl, —OH, halo, —CN, —OR$_{10}$ or —C(=O)NR$_9$R$_9$, wherein the alkyl may be optionally substituted with one or more R$_{9a}$'s; or R$_9$, at each occurrence, is independently hydrogen, alkyl, alkoxy, cycloalkyl, aryl or heterocyclyl, wherein the alkyl, cycloalkyl, aryl or heterocyclyl may be optionally substituted with 0-5 R$_{9a}$, and the heterocyclyl contains 1-4 heteroatoms selected from N, O, and S; or two R$_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more R$_{9a}$'s;

R$_{9a}$, at each occurrence, is independently selected from alkyl, haloalkyl, aryl, cycloalkyl, heterocyclyl, halo, =O, —NH$_2$, —CN, —NO$_2$, —C(=O)OH, —C(=O)OR$_{14}$, —OCF$_3$, —OR$_{10}$, —OH, —SH, —SR$_{14}$, —C(=O) NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(=O) OR$_{10}$, —NR$_{14}$S(O)$_2$R$_8$, —C(=O)R$_{10}$, —OC(=O) NR$_{14}$R$_{14}$, —NR$_{14}$C(=O)NR$_{14}$R$_{14}$ or arylalkyl, wherein the alkyl, aryl, cycloalkyl and heterocyclyl may be optionally substituted with 0-3 R$_{10a}$;

R$_{10}$, at each occurrence, is independently selected from alkyl, aryl, arylalkyl or heterocyclyl, wherein the alkyl, aryl, arylalkyl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, cycloalkyl, heterocyclyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O) NR$_{14}$S(O)$_2$R$_{14}$, —S(O)$_2$NR$_{14}$C(=O)OR$_{14}$, —S(O)$_2$NR$_{14}$C (=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S (O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl or aryl, wherein the alkyl, cycloalkyl or aryl may be optionally substituted with 0-3 R$_{14a}$;

R$_{14a}$, at each occurrence, is independently selected from alkyl, haloalkyl, aryl, cycloalkyl, heterocyclyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O) NR$_{15}$S(O)$_2$R$_{15}$, —S(O)$_2$NR$_{15}$C(=O)OR$_{15}$, —S(O)$_2$NR$_{15}$C (=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S (O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl or aryl.

In another embodiment, compounds of formula I are those compounds in which:

A is a 7- to 12-membered non-aromatic bi-, tri- or polycyclic ring system optionally containing 1-3 heteroatoms selected from N, O, S, S(O) and S(O)$_2$, which is substituted with one or more R$_4$'s;

X is —C(=O)NR$_9$R$_9$;

W is absent or (—CR$_{8a}$R$_{8b}$—)$_m$;

m is 1;

Z is aryl or arylalkyl, both of which may be optionally substituted with one or more R$_4$'s;

provided that W and Z, or when W is absent, X and Z, are attached to the same carbon on Ring A;

R$_4$, at each occurrence, is independently selected from hydrogen, alkyl, aryl, cycloalkyl, heterocyclyl, halo, =O, —NH$_2$, —CN, —NO$_2$, —C(=O)OH, —C(=O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O) NR$_9$S(O)$_2$R$_9$, —S(O)$_2$NR$_9$C(=O)OR$_9$, —S(O)$_2$NR$_9$C (=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S (O)$_2$R$_{10}$, —O—S(O)$_2$R$_{10}$, —NR$_9$C(=O)OR$_8$ or —NR$_9$S (O$_2$)R$_8$, wherein the alkyl, aryl, cycloalkyl or heterocyclyl may be optionally substituted with one or more R$_5$'s;

R$_5$, at each occurrence, is independently selected from hydrogen, alkyl, haloalkyl, aryl, cycloalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O) NR$_9$S(O)$_2$R$_9$, —S(O)$_2$NR$_9$C(=O)OR$_9$, —S(O)$_2$NR$_9$C (=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S (O)$_2$R$_{10}$, —O—S(O)$_2$R$_{10}$, —NR$_9$C(=O)OR$_8$ or —NR$_9$S (O$_2$)R$_8$;

R$_8$, at each occurrence, is independently alkyl or aryl;

R$_{8a}$, at each occurrence, is independently hydrogen or alkyl;

R$_{8b}$, at each occurrence, is independently hydrogen, —C(=O)OH, alkyl, —OH, halo, —CN or —OR$_{10}$, wherein the alkyl may be optionally substituted with one or more R$_{9a}$'s; or R$_9$, at each occurrence, is independently hydrogen, alkyl, alkoxy, aryl or heterocyclyl, wherein the alkyl, aryl or heterocyclyl may be optionally substituted with 0-5 R$_{9a}$, and the heterocyclyl contains 1-4 heteroatoms selected from N, O, and S; or two R$_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more R$_{9a}$'s;

R$_{9a}$, at each occurrence, is independently selected from alkyl, haloalkyl, aryl, cycloalkyl, heterocyclyl, halo, =O, —NH$_2$, —CN, —NO$_2$, —C(=O)OH, —C(=O)OR$_{14}$, —OCF$_3$, —OR$_{10}$, —OH, —SH, —SR$_{14}$, —C(=O) NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(=O) OR$_{10}$, —NR$_{14}$S(O$_2$)R$_8$, —C(=O)R$_{10}$, —OC(=O) NR$_{14}$R$_{14}$, or —NR$_{14}$C(=O)NR$_{14}$R$_{14}$, wherein the alkyl, aryl, cycloalkyl and heterocyclyl may be optionally substituted with 0-3 R$_{10a}$;

R$_{10}$, at each occurrence, is independently selected from alkyl, aryl or heterocyclyl, wherein the alkyl, aryl or heterocyclyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, cycloalkyl, heterocyclyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O) NR$_{14}$S(O)$_2$R$_{14}$, —S(O)$_2$NR$_{14}$C(=O)OR$_{14}$, —S(O)$_2$NR$_{14}$C (=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S (O)$_2$R$_{14}$, —NR$_{14}$C(=O)OR$_8$, or —NR$_{14}$S(O)$_2$R$_8$;

R$_{14}$, at each occurrence, is independently selected from hydrogen, alkyl or aryl, wherein the alkyl or aryl may be optionally substituted with 0-3 R$_{14a}$;

R$_{14a}$, at each occurrence, is independently selected from alkyl, haloalkyl, aryl, cycloalkyl, heterocyclyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O) NR$_{15}$S(O)$_2$R$_{15}$, —S(O)$_2$NR$_{15}$C(=O)OR$_{15}$, —S(O)$_2$NR$_{15}$C (=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S (O)$_2$R$_{15}$, —NR$_{15}$C(=O)OR$_8$, or —NR$_{15}$S(O$_2$)R$_8$; and R$_{15}$, at each occurrence, is independently selected from hydrogen, alkyl or aryl.

In another embodiment, compounds of formula I are those compounds in which:

A is a 7- to 10-membered non-aromatic bi-, tri- or polycyclic ring system optionally containing 1-3 heteroatoms selected from N, O, S, S(O) and S(O)$_2$, which is substituted with one or more R$_4$'s;

X is —C(=O)NR$_9$R$_9$;

W is absent or (—CR$_{8a}$R$_{8b}$—)$_m$;

m is 1;

Z is aryl or arylalkyl, both of which may be optionally substituted with one or more R$_4$'s;

provided that W and Z, or when W is absent, X and Z, are attached to the same carbon on Ring A;

R$_4$, at each occurrence, is independently selected from hydrogen, alkyl, aryl, cycloalkyl, heterocyclyl, halo, =O, —NH$_2$, —CN, —NO$_2$, —C(=O)OH, —C(=O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O) NR$_9$S(O)$_2$R$_9$, —S(O)$_2$NR$_9$C(=O)OR$_9$, —S(O)$_2$NR$_9$C (=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S (O)$_2$R$_{10}$, —O—S(O)$_2$R$_{10}$, —NR$_9$C(=O)OR$_8$ or —NR$_9$S (O$_2$)R$_8$, wherein the alkyl, aryl, cycloalkyl or heterocyclyl may be optionally substituted with one or more R$_5$'s;

R$_5$, at each occurrence, is independently selected from hydrogen, alkyl, haloalkyl, aryl, cycloalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O) NR$_9$S(O)$_2$R$_9$, —S(O)$_2$NR$_9$C(=O)OR$_9$, —S(O)$_2$NR$_9$C (=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S (O)$_2$R$_{10}$, —O—S(O)$_2$R$_{10}$, —NR$_9$C(=O)OR$_8$ or —NR$_9$S (O$_2$)R$_8$;

R$_8$, at each occurrence, is independently alkyl or aryl;

R$_{8a}$, at each occurrence, is independently hydrogen or alkyl;

R$_{8b}$, at each occurrence, is independently hydrogen, —C(=O)OH, alkyl, —OH, halo, —CN, or —OR$_{10}$;

R$_9$, at each occurrence, is independently hydrogen, alkyl, alkoxy or aryl, wherein the alkyl or aryl may be optionally substituted with 0-5 R$_{9a}$; or two R$_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more R$_{9a}$'s;

R$_{9a}$, at each occurrence, is independently selected from alkyl, haloalkyl, aryl, cycloalkyl, heterocyclyl, halo, =O, —NH$_2$, —CN, —NO$_2$, —C(=O)OH, —C(=O)OR$_{14}$, —OCF$_3$, —OR$_{10}$, —OH, —SH, —SR$_{14}$, —C(=O) NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(=O) OR$_{10}$, —NR$_{14}$S(O$_2$)R$_8$, —C(=O)R$_{10}$, —OC(=O) NR$_{14}$R$_{14}$, or —NR$_{14}$C(=O)NR$_{14}$R$_{14}$, wherein the alkyl, aryl, cycloalkyl and heterocyclyl may be optionally substituted with 0-3 R$_{10a}$;

R$_{10}$, at each occurrence, is independently selected from alkyl or aryl, wherein the alkyl or aryl may be optionally substituted with 0-3 R$_{10a}$;

R$_{10a}$, at each occurrence, is independently selected from alkyl, haloalkyl, aryl, cycloalkyl, heterocyclyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)

$NR_{14}S(O)_2R_{14}$, —$S(O)_2NR_{14}C(=O)OR_{14}$, —$S(O)_2NR_{14}C(=O)NR_{14}R_{14}$, —$C(=O)NR_{14}S(O)_2CF_3$, —$C(=O)R_{14}$, —$NR_{14}C(=O)R_{14}$, —$OC(=O)R_{14}$, —$S(=O)R_{14}$, —$S(O)_2R_{14}$, —$NR_{14}C(=O)OR_8$, or —$NR_{14}S(O_2)R_8$;

$R_{14}$, at each occurrence, is independently selected from hydrogen, alkyl or aryl, wherein the alkyl or aryl may be optionally substituted with 0-3 $R_{14a}$;

$R_{14a}$, at each occurrence, is independently selected from alkyl, haloalkyl, aryl, cycloalkyl, heterocyclyl, halo, —$NH_2$, —$CN$, —$NO_2$, —$C(=O)OH$, —$C(=O)OR_{15}$, —$OCF_3$, —$OR_{15}$, —$OH$, —$SH$, —$SR_{15}$, —$C(=O)NR_{15}R_{15}$, —$NR_{15}R_{15}$, —$S(O)_2NR_{15}R_{15}$, —$NR_{15}S(O)_2CF_3$, —$C(=O)NR_{15}S(O)_2R_{15}$, —$S(O)_2NR_{15}C(=O)OR_{15}$, —$S(O)_2NR_{15}C(=O)NR_{15}R_{15}$, —$C(=O)NR_{15}S(O)_2CF_3$, —$C(=O)R_{15}$, —$NR_{15}C(=O)R_{15}$, —$OC(=O)R_{15}$, —$S(=O)R_{15}$, —$S(O)_2R_{15}$, —$NR_{15}C(=O)OR_8$, or —$NR_{15}S(O_2)R_8$; and $R_{15}$, at each occurrence, is independently selected from hydrogen or alkyl.

In another embodiment, compounds of the present invention are selected from the compounds exemplified in the examples.

In another embodiment, the present invention relates to pharmaceutical compositions comprised of a therapeutically effective amount of a compound of the present invention, alone or, optionally, in combination with a pharmaceutically acceptable carrier and/or one or more other agent(s).

In another embodiment, the present invention relates to methods of inhibiting the activity of the enzyme 11-beta-hydroxysteroid dehydrogenase type I comprising administering to a mammalian patient, for example, a human patient, in need thereof a therapeutically effective amount of a compound of the present invention, alone, or optionally, in combination with another compound of the present invention and/or at least one other type of therapeutic agent.

In another embodiment, the present invention relates to a method for preventing, inhibiting, or treating the progression or onset of diseases or disorders associated with the activity of the enzyme 11-beta-hydroxysteroid dehydrogenase type I comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis, acute coronary syndrome, myocardial infarction, angina pectoris, peripheral vascular disease, intermitant claudication, abnormal heart function, myocardial ischemia, stroke, Metabolic Syndrome, hypertension, obesity, dislipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma, rheumatoid arthritis, Cushing's Disease, Alzheimer's Disease and osteoarthritis.

In another embodiment, the present invention relates to a method for preventing, inhibiting, or treating the progression or onset of diabetes, hyperglycemia, obesity, dislipidemia, hypertension, cognitive impairment, rheumatoid arthritis, osteoarthritis, glaucoma, Cushing's Disease and Metabolic Syndrome comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In still another embodiment, the present invention relates to a method for preventing, inhibiting, or treating the progression or onset of diabetes, comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In yet still another embodiment, the present invention relates to a method for preventing, inhibiting, or treating the progression or onset of hyperglycemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of obesity comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In one embodiment, the present invention relates to a method for preventing, inhibiting, or treating the progression or onset of dislipidemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of hypertension comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of cognitive impairment comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of rheumatoid arthritis comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of osteoarthritis comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of Metabolic Syndrome comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of glaucoma comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of Cushing's Disease comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In one embodiment, the present invention provides a process for the preparation of a compound of Formula Ih or Ii

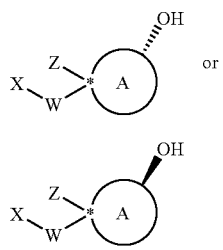

wherein A, X, W and Z are as defined above;

comprising reducing a racemic compound of Formula If

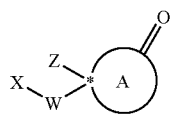

with an enzymatic reductase, such as a ketoreductase, produced by a microorganism from the group consisting of *Pichia, Hansenula, Candida* or *Rhodotorula*.

In one embodiment, the strain of *Pichia* is *Pichia membranafaciens, Pichia anomala, Pichia ciferrii* or *Pichia silvicola*. In another embodiment, the strain of *Hansenula* is *Hansenula fabiani* or *Hansenula polymorpha*. In a further embodiment, the strain of *Candida* is *Candida utilis* or *Candida boidini*. In yet a further embodiment, the strain of *Rhodotorula* is *Rhodotorula glutinis*.

In another embodiment, processes for preparing compounds of formula Ih or Ii are provided wherein the reduction with an enzyme is carried out either by:

introducing a ketone compound of formula If into a medium in which the microorganism is being fermented to form a reaction mixture in which the enzyme is concurrently being formed and reduces the racemic compound; or fermenting the microorganism until sufficient growth is realized, and introducing the racemic compound to the microorganism in which the ketone compound of formula If is reduced with the enzyme.

In still another embodiment, processes for preparing compounds of formula Ih or Ii are provided wherein the amount of the ketone compound of formula If added to the reaction mixture is up to about 50 g/L of the reaction mixture.

In still yet another embodiment, processes for preparing compounds of formula Ih or Ii are provided wherein an enzyme is isolated and optionally purified.

In one embodiment, processes for preparing compounds of formula Ih or Ii are provided wherein the reduction by an enzyme is carried out by reacting the ketone compound of formula If with the enzyme that was previously isolated and optionally purified before contacting with the ketone compound.

In another embodiment, processes for preparing compounds of formula Ih or Ii are provided wherein the enzyme is derived from cell extracts.

In still yet another embodiment, processes for preparing compounds of formula Ih or Ii are provided wherein the enzyme is obtained from *Hansenula fabiani*. In one embodiment, the enzyme is obtained from *Hansenula fabiani* strain SC13894 (ATCC 58045).

In another embodiment, processes for preparing compounds of formula Ih or Ii are provided wherein the enzyme provides a reaction yield of greater than 60% by weight of the compound of formula Ih or Ii, based on the weight of the ketone input.

In still another embodiment, processes for preparing compounds of formula Ih or Ii are provided wherein the process provides the compounds of formula Ih or Ii in an enantiomeric excess greater than 95%.

In yet another embodiment, processes for preparing compounds of formula Ih or Ii are provided wherein the reduction by an enzyme is carried out at a pH of between about 5.0 and about 9.0.

In one embodiment, the present invention provides processes for the preparation of an enzyme for the preparation of compounds of formula Ih or Ii from a compound of formula If comprising:

(a) either
(i) providing a microorganism selected from the group consisting of *Pichia, Hansenula, Candida* or *Rhodotorula* in a growth medium under conditions which allow for expression of an enzyme, or
(ii) introducing a gene which encodes for the enzyme into a host microorganism for recombinant expression, introducing the host microorganism in a growth medium under conditions which allow for expression of the enzyme and allowing it to grow and express the enzyme;

(b) optionally, extracting the enzyme from the growth medium; and (c) optionally, purifying the enzyme.

In another embodiment, processes for the preparation of an enzyme for the preparation of compounds of formula Ih or Ii are provided wherein the process of extracting the enzyme comprises lysing the cells of the microorganism and isolating the enzyme.

In still another embodiment, processes for the preparation of an enzyme for the preparation of compounds of formula Ih or Ii are provided wherein the processes of purifying the enzyme comprises ion-exchange, hydrophobic, and hydroxyapatite chromatography.

In one embodiment, processes for preparing compounds of formula Ih or Ii are provided wherein (a) either (i) providing a microorganism in a growth medium under conditions which allow for expression of an enzyme, or (ii) introducing a gene which encodes for the enzyme into a host microorganism for recombinant expression, introducing the host microorganism in a growth medium under conditions which allow for expression of the enzyme and allowing it to grow and express the enzyme; and (b) reacting the enzyme with a compound of formula If to produce the desired compounds.

In another embodiment, the present invention provides processes for preparing a compound of formula Ih which comprises reacting a compound of the formula If with NADP or NADPH, glucose dehydrogenase, glucose, and a ketoreductase to afford Compound Ih or Ii.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Steven D. Young et al., *Antimicrobial Agents and Chemotherapy*, 2602-2605 (1995).

To the extent that compounds of the formula I, and salts thereof, may exist in their tautomeric form, all such tautomeric forms are contemplated herein as part of the present invention.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

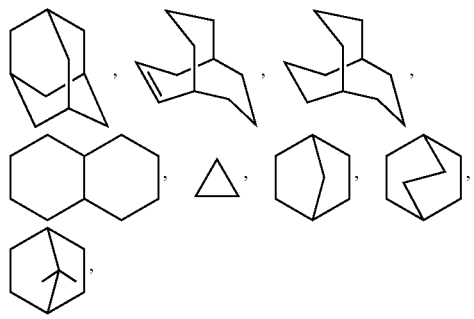

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example $—C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings for example

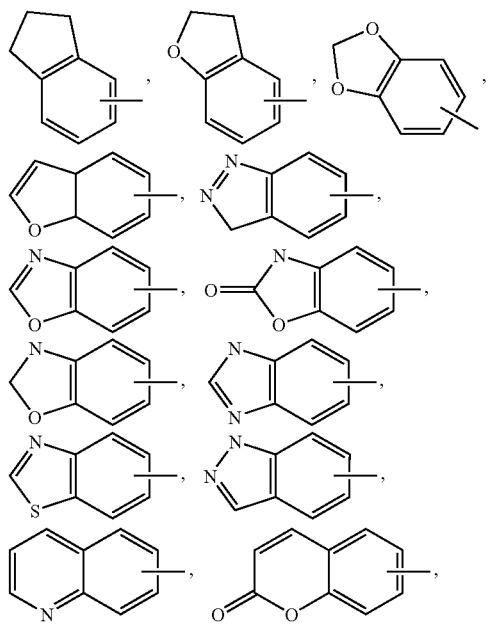

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl", "heterocyclic system" or "heterocyclic ring" is intended to mean a stable 3- to 14-membered monocyclic, bicyclic or tricyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, piperidonyl, 4-piperidonyl, pteridinyl, purinyl, pyranyl, pyrazinyl, pyrazolidinyl, pyrazolinyl, pyrazolyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoindolyl, piperidinyl, piperidonyl, 4-piperidonyl, piperonyl, pyrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO₂ group.

The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418, (1985), the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch. 5, pp. 113-191 (Harwood Academic Publishers, 1991); and
d) *Hydrolysis in Drug and Prodrug Metabolism*, Bernard Testa and Joachim M. Mayer, (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization. In addition, the compounds of formula I may exist in tautomeric form. Such tautomeric forms of the formula I are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MIP-1α or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

Compounds of formula I may be prepared as shown in the following reaction schemes and description thereof, as well as relevant literature procedures that may be used by one skilled in the art. Exemplary reagents and procedures for these reactions appear hereinafter and in the working Examples.

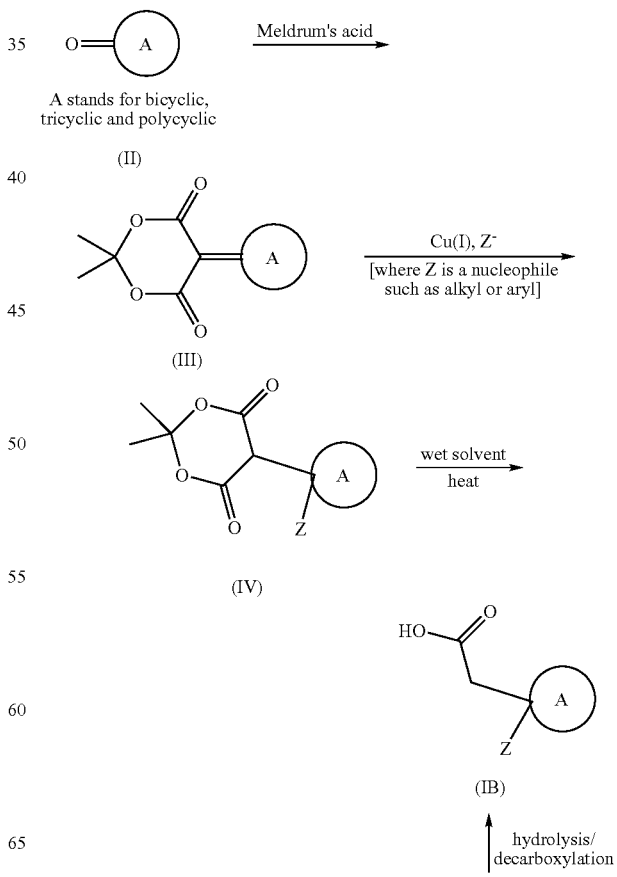

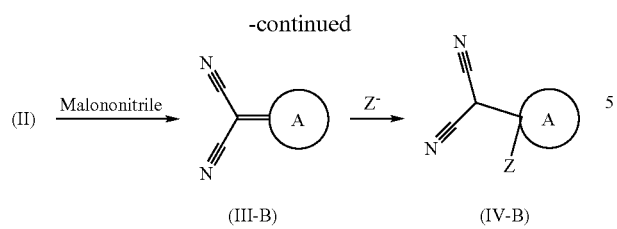

Scheme I describes a method for preparing compounds of formula IB (a subset of compounds of formula I). A ketone intermediate II can be obtained commercially, prepared by methods known in the literature or by other methods known to one skilled in the art. The reaction of ketone II with Meldrum's acid, commonly known as a Knoevenagel condensation, can be carried out in anhydrous pyridine in the presence of a catalytic amount of piperidine (Baty, J. D., Jones, G., Moore, C., *J. Org. Chem.*, 34:3295-3302 (1969)) or molecular sieves (Vogt, P. F., Molino, B. F., Robichaud, A. J., *Synth. Commun.*, 31:679-684 (2001)), or via dehydrative condensation with $TiCl_4$ in $CH_2Cl_2$ (Brown, R. F. C., Coulston, K. J., Eastwood, F. W., Gatehouse, B. M., Guddatt, L. W., Luke, W., Pfenninger, M., Rainbow, I., *Aust. J. Chem.*, 37:2509-2524 (1984)). The disubstituted Meldrum's acid alkylidene III can be purified by recrystallization from alcohols such as ethanol or methanol, or via flash column chromatography. The 1,4-conjugate addition of nucleophiles such alkyl or aryl Grignard's reagents (Haslego, M. L., Smith, F. X., *Synth. Commun.*, 10:421-427 (1980)) or other organometallic reagents can be carried out in the presence or in the absence of $Cu^+$ salts (such as CuBr, CuCN etc.) at room temperature or at 40° C. The isopropylidene malonate (IV) can be converted to compounds IB via deprotection and subsequent decarboxylation in wet organic solvent at 100 to 110° C. (*J. Am. Chem. Soc.*, 125:6054-6055 (2003)). Alternatively, Knoevenagel condensation of ketone II with malononitrile in the presence of a wide range of catalysts such as $NH_4OAc$ or amino acids provides alkylidene III-B, which can be easily purified by recrystallization and/or via flash column chromatography. The 1,4-conjugate addition of nucleophiles such alkyl or aryl Grignard's reagents can be carried out in the absence of $Cu^+$ salts at 0° C. to room temperature to facilitate the adducts IV-B, which can be easily converted to compounds IB via standard nitrile hydrolysis and subsequent decarboxylation.

SCHEME II

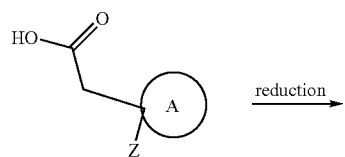

A stands for bicyclic, tricyclic and polycyclic (IB)

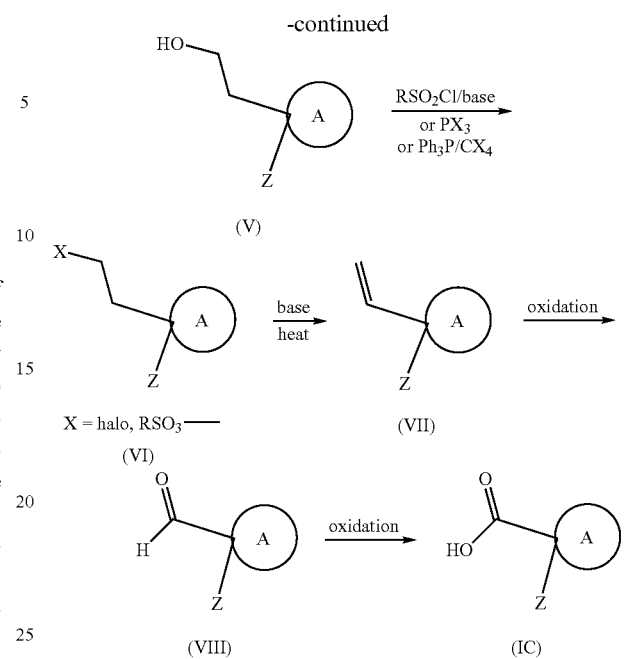

Scheme II describes a method for preparing compounds of formula IC (a subset of compounds of formula I) from compounds of formula IB. The alcohol V, obtained from the reduction of IB, for example, with LAH or diborane, can be converted to the corresponding mesylate or halide VI, followed by the subsequent elimination under basic condition to afford the olefin VII. Upon oxidative cleavage of the C=C bond and further oxidation of the resulting aldehyde VIII, the compounds IC can be obtained.

SCHEME III

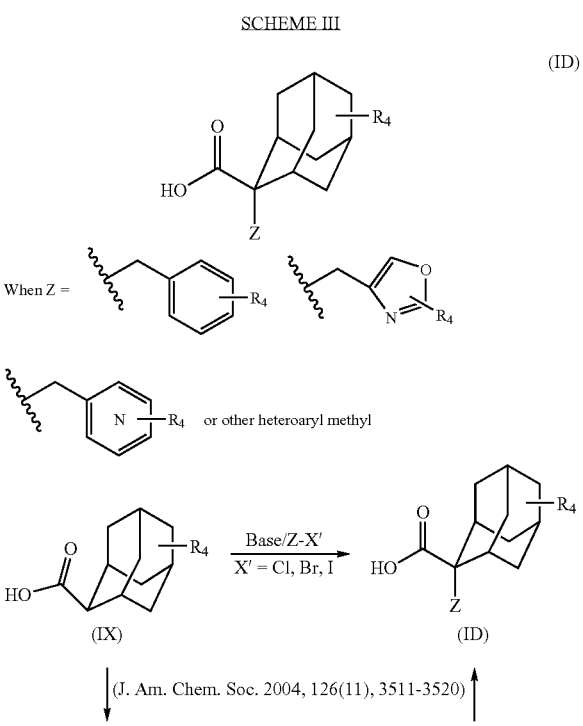

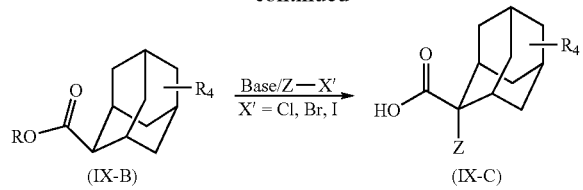

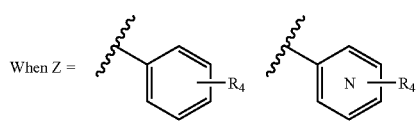

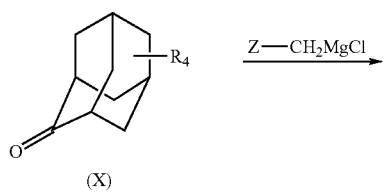

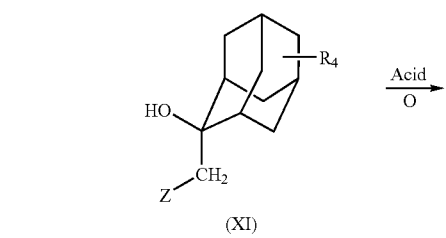

Scheme III describes methods for preparing compounds of formula ID (a subset of compounds of formula IC, exemplified here where Z is adamantane or substituted adamantane). When Z is benzyl, substituted benzyl, or other heteroaryl methyl, the direct alkylation of the dianion of compound IX (generated for example with LiN(TMS)$_2$ or LDA) with the alkyl halide Z-X gives ID. Alternatively, compound ID can be synthesized by converting compound Ix to the corresponding ester IX-B, α-alkylation of IX-B to IX-C, followed by ester hydrolysis to provide compound ID. When Z is aryl, substituted aryl, heteroaryl or other aromatic groups, ketone X can be reacted with nucleophiles such as organolithium reagents (ZCH$_2$Li) or Grignard reagents (ZCH$_2$Mghalide) to afford the tertiary alcohol XI, which can be converted to aldehyde XII via acid-catalyzed rearrangement. Further oxidation of aldehyde XII gives compounds ID.

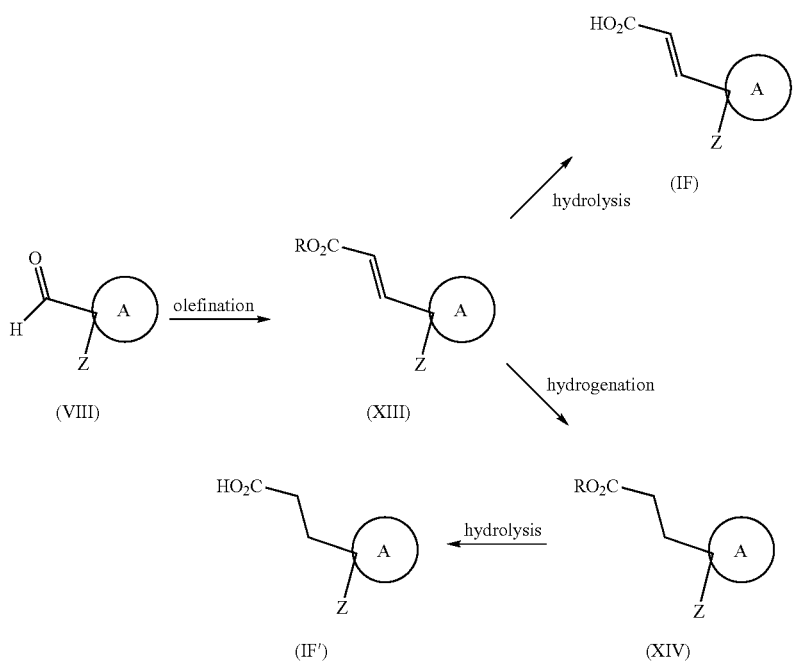

Scheme IV describes a method for preparing compounds of formula IF and IF' (subsets of compounds of formula I). Aldehyde VIII (see Scheme II for the synthesis) can be reacted with triethyl phosphoryl acetate to give α,β-unsaturated ester XIII, which may be subsequently converted to ester XIV by metal-catalyzed hydrogenation (for example Pd/C or Pt in the presence of H$_2$). Hydrolysis of the ester in basic condition gives the carboxylic acid IF'. Alternatively, XIII may be hydrolyzed to provide the corresponding acid IF directly.

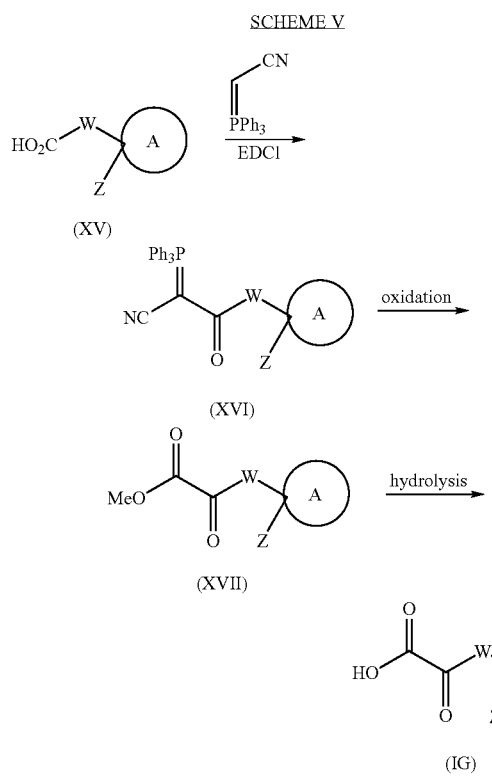

There are numerous methods for the conversion of carboxylic acids to α-keto acids (see reviews: (a) Kovacs, L., *Recl. Trav. Chim. Pays-Bas*, 112:471 (1993); (b) Cooper, A., *Chem. Rev.*, 83:321 (1983)). Scheme V exemplifies a method of using (cyanomethylene)phosphorane as a carbonyl synthon for preparing compounds of formula IG (a subset of compounds of formula I). Other methods known in the literature or known to one skilled in the art can also be applied. The carboxylic acid XV (see Scheme I to IV) can be reacted with (cyanomethylene)triphenylphosphorane in the presence of coupling reagents such as EDCI to form cyano keto phosphoranes XVI, which can be oxidatively cleaved to form α-keto esters XVII. Further hydrolysis of ester XVII gives compounds IG (Wasserman, H., *J. Org. Chem.*, 59:4364 (1994)).

SCHEME VI

A stands for bicyclic, tricyclic and polycyclic (II)

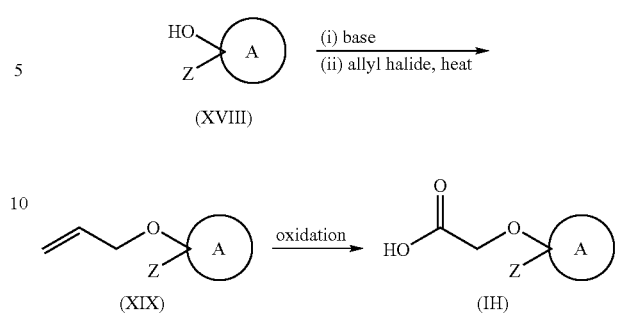

Scheme VI describes a method for preparing compounds of formula IH (a subset of compounds of formula I). Ketone II reacts with Grignard reagent ZMgX or organolithium to give the tertiary alcohol XVIII. The O-allylation with an allyl halide can be carried out in the presence of bases such as NaH in reflux condition to give XIX, which can be further converted to IH via oxidative cleavage of the C=C bond.

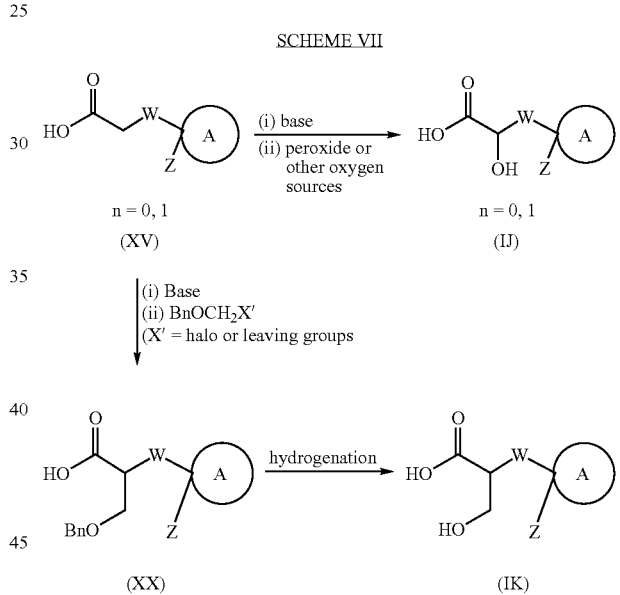

Scheme VII describes a method for preparing compounds of formula IJ, formula XX, and formula IK (subsets of compounds of formula I). The enolate anions, obtained by treating carboxylic acid XV with bases such as LDA/DMPU, can react with a variety of electrophilic hydroxylating agents, such as oxygen (Wassermann, H. H. et al., *Tetrahedron Lett.*, 1731 (1975)), molybdenum peroxide-pyridine-hexamethylphosphoramide (Vedejs, E., *J. Am. Chem. Soc.*, 96:5944 (1974)), 2-sulfonyloxaziridine (Davis, F. A. et al., *J. Org. Chem.*, 49:3243 (1984)), dibenzyl peroxydicarbonate (Gore, M. P., Vederas, J. C., *J. Org. Chem.*, 51:3700 (1986)), and bis(trimethylsilyl)peroxide (TMSOOTMS) (Pohmakotr, M., Winotai, C., *Synthetic Communications*, 18:2141-2146 (1988)) to form compound IJ. On the other hand, the enolate anions can react with chloromethyl benzyl ether to give XX. Upon the cleavage of benzyl group, the acid IK can be obtained.

SCHEME VIII

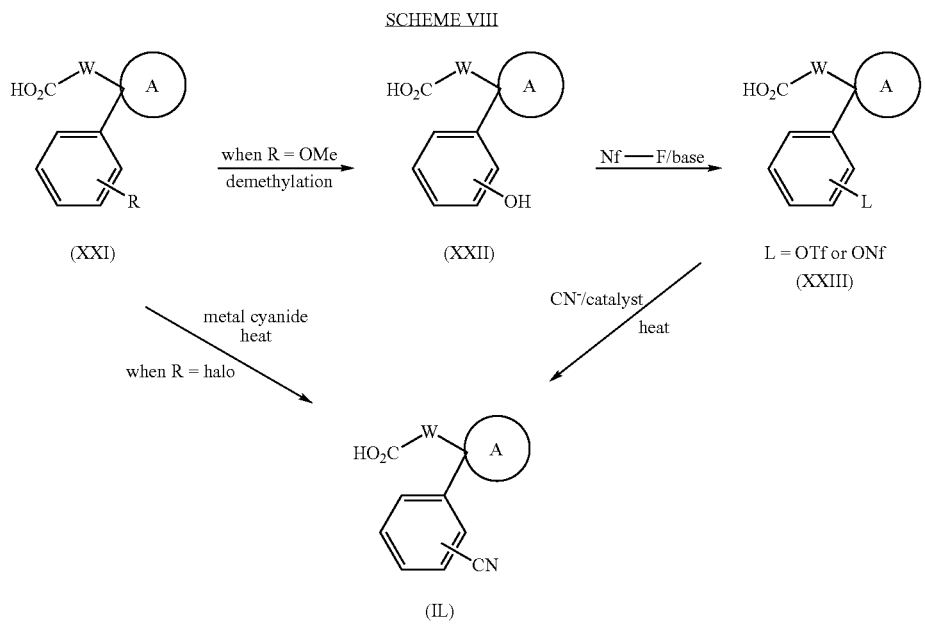

Scheme VIII describes a method for preparing compounds of formula IL (subset of compounds of formula I) from readily accessible material XXI (see Scheme I to III for the synthesis of XXI). Phenol XXII, obtained from demethylation of XXI (when R=OMe) using $BBr_3$ or HBr in acetic acid, can be converted to the corresponding trifluoromethanesulphonate (triflate) or nonaflate XXIII by treatment with corresponding sulfonyl halide or sulphonic anhydride. Subsequent displacement of TfO or NfO with —CN can be catalyzed by transition metals such as palladium(0) or nickel(0), yielding compound IL. Compound XXIII may also be useful for the incorporating of a variety of $R_4$ groups via Pd or Ni catalyzed coupling conditions well known in the literature. Alternatively, aryl halide XXI (when R=halo) can be converted to the corresponding nitrile IL through direct nucleophilic displacement catalyzed by transition metal such as Cu(I), Pd, Co, Ni (Ellis, G. P., Romney-Alexander, T. M., *Chem. Rev.*, 87:779-794 (1987), Arvela, R., Leadbeater, N. E., *J. Org. Chem.*, 68:9122-9125 (2003)).

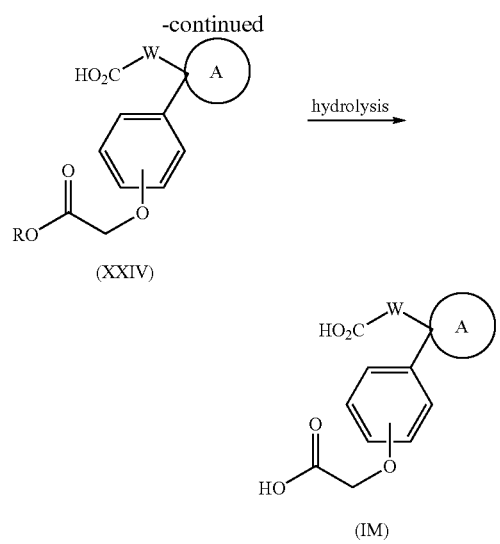

Scheme IX describes a method of preparing compounds of formula IM (subset of compounds of formula I). The alkylation of phenol XXII (see Scheme VIII) can be carried out in the presence of base such as NaH, to form XXIV. Upon the hydrolysis of the ester, IM can be obtained.

SCHEME IX

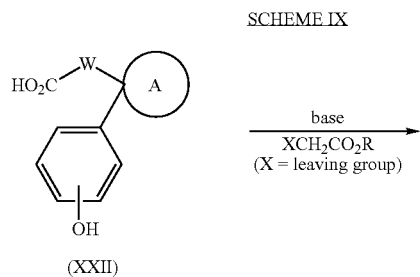

SCHEME X

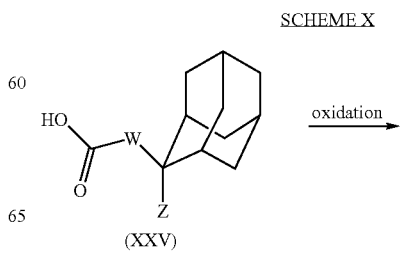

-continued

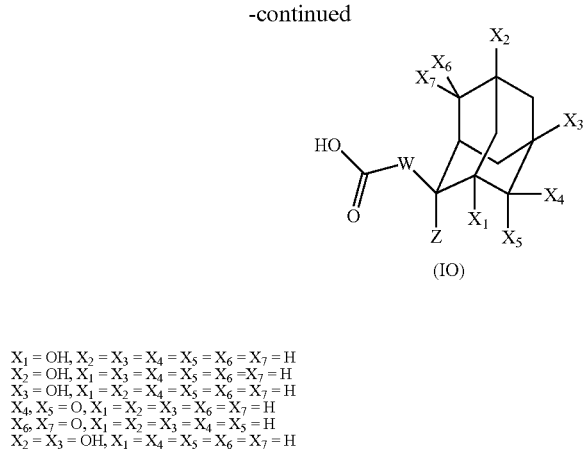

X₁ = OH, X₂ = X₃ = X₄ = X₅ = X₆ = X₇ = H
X₂ = OH, X₁ = X₃ = X₄ = X₅ = X₆ = X₇ = H
X₃ = OH, X₁ = X₂ = X₄ = X₅ = X₆ = X₇ = H
X₄, X₅ = O, X₁ = X₂ = X₃ = X₆ = X₇ = H
X₆, X₇ = O, X₁ = X₂ = X₃ = X₄ = X₅ = H
X₂ = X₃ = OH, X₁ = X₄ = X₅ = X₆ = X₇ = H

Scheme X describes a method for preparing compounds of formula IO (subset of compounds of formula I, when A represents adamantane). The oxidation of compounds XXV (see Scheme I to III for synthesis) can be carried out under a wide variety of oxidative conditions such as dimethyldioxirane, potassium permanganate, ferrous iron-molecular oxygen, etc. The products and their yields are depended on the reaction conditions. These products can be separated by preparative HPLC, and their structures can be fully elucidated by 2D NMR technique.

Scheme XI describes a method of preparing compounds of formula IP (subset of compounds of formula I, when A represents adamantane). Compounds IP can be readily synthesized using Scheme I, II, and III.

SCHEME XII

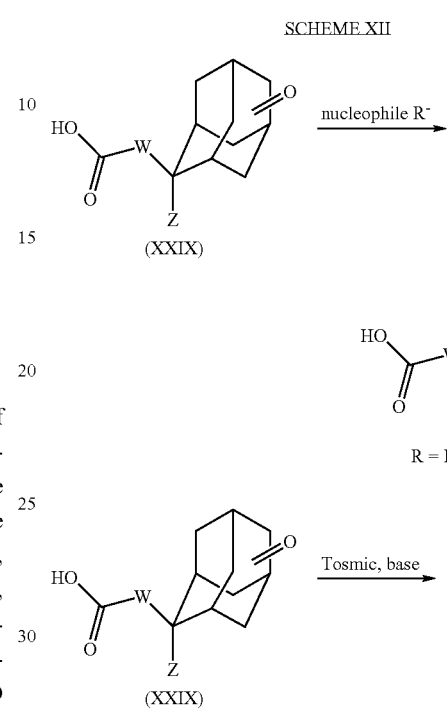

SCHEME XI

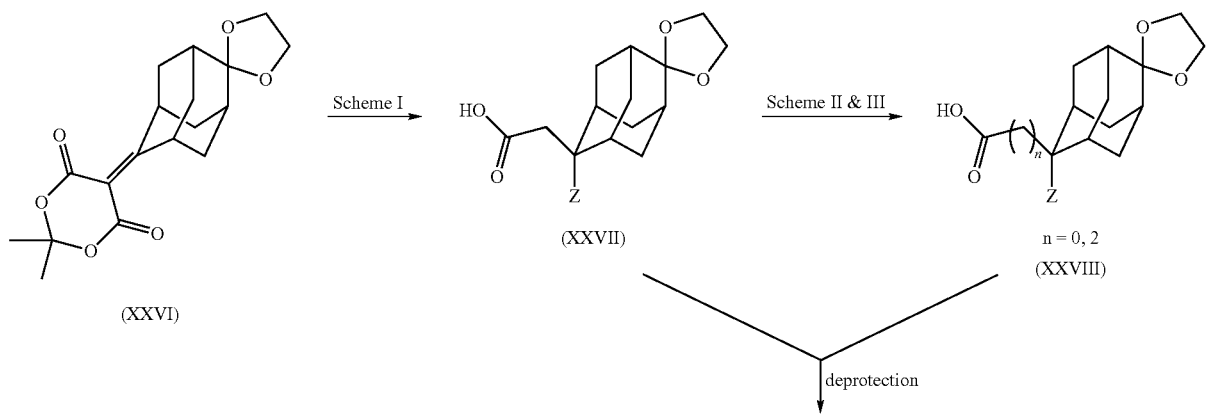

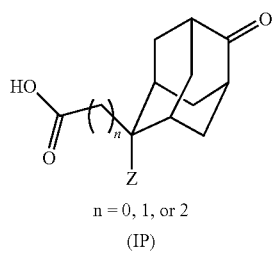

n = 0, 1, or 2
(IP)

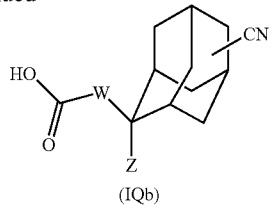

(IQb)

Scheme XII describes a method of preparing compounds of formula IQa and IQb (subsets of compounds of formula I, when A represents adamantane). Ketone XXIX (see Scheme X and XI) reacts with reducing agents such as $NaBH_4$, $LiBH_4$, or reductases or other nucleophiles such as organo magnesium halides or organolithiums to form compounds IQa. On the other hand, Ketone XXIX can react with TOSMIC under basic condition to afford IQb.

SCHEME XIII

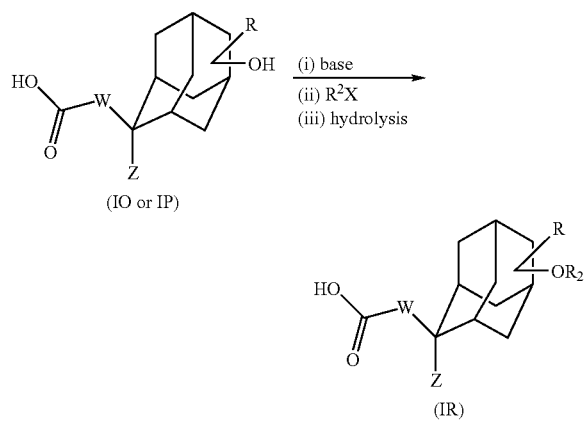

[$R^2$ = Me, allyl, etc]

Scheme XIII describes a method for preparing compounds of formula IR (subset of compounds of formula I when Z represents adamantane). Compounds IP and IO (see Scheme IX for synthesis) can react with alkyl halides in the presence of a base such as NaH to form the O-alkylation product, which can be hydrolyzed to form compounds IR.

SCHEME XIV

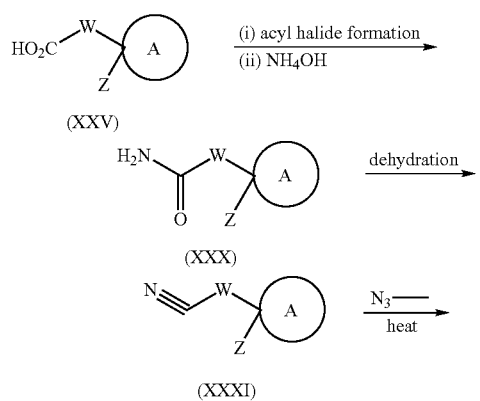

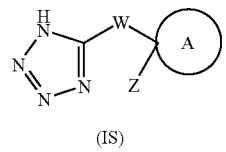

(IS)

Scheme XIV describes a method of preparing compounds of formula IS (a subset of compound of formula I). The acids XXV (see Scheme I to III) can be converted to the corresponding acyl halides using a wide variety of reagents such as thionyl chloride, sulfuryl chloride, oxalyl chloride, and phosphorus trichloride, or alkyl or aryl chloroformate, etc. The acyl halide can react with ammonium hydroxide to form the amide XXX, which can be further converted to nitrile XXXI by treating with dehydration reagents such as acetic anhydride, acyl halide, $POCl_3$, chloroformate, etc. The nitrites XXXI can react with azide such as sodium azide, $Me_3SnN_3$, etc to form the tetrazole IS.

SCHEME XV

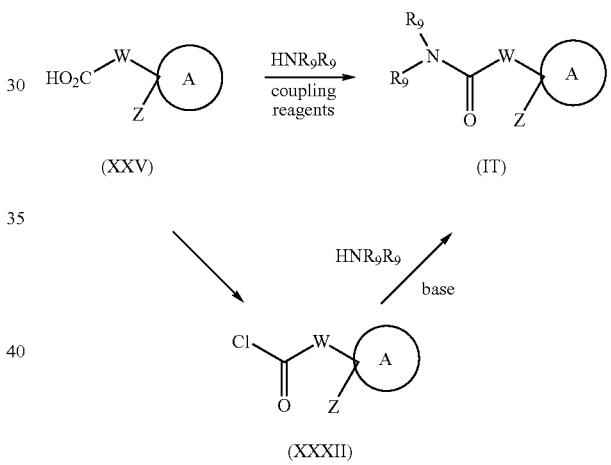

Scheme XV describes a method of preparing compounds of formula IT (a subset of compounds of formula I). The acid XXV can readily react with amine $HNR_9R_9$ or its salt to form amide IT in the presence of a wide variety of peptide coupling reagents, such as carbodiimide type reagents (DCC, EDAC, DIC etc.), imidazolium type reagents (CDI, CBMIT, BOI, CMBI etc.), phosphonium type reagents (such as BOP, PyBOP etc.), uronium type reagents (HBTU, TBTU etc). Alternatively, the acid XXV can be converted to acyl chloride XXXII, which reacts with amine $HNR_9R_9$ in the presence of base such as i-$Pr_2NEt$, $Et_3N$ to form compound IT.

SCHEME XVI

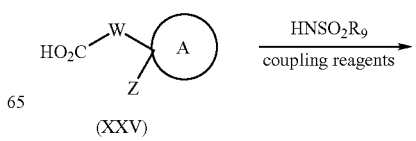

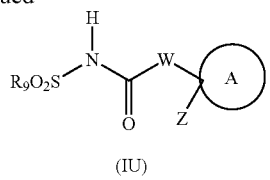

(IU)

Scheme XVI describes a method of preparing compounds of formula IU (a subset of compounds of formula I). The acid XXV can readily react with sulfonamide $H_2NSO_2R_9$ to form acyl sulfonamide IU in the presence of a wide variety peptide coupling reagents, such as EDAC.

Scheme XVII describes a method of preparing compounds of formula IW (a subset of compounds of formula I). Exemplified in this scheme is the synthesis of a variety of cyclic amines such as compounds XXXV, XXXVII, and XXXIX, but not limited to these structures. For example, when X″=O, XXXIII can react with isocyanate to form the corresponding carbamate. Alternatively, XXXIII can be converted to corresponding chloroformate by reacting with phosgene, then to carbamate by further reacting to appropriate amines. On the other hand, when X″=CO₂ (carboxylic acid), XXXV can be converted to heterocycles, such as oxazole, oxadiazole, etc. Alternatively, XXXV can be converted to nitrile, then to other heterocycles such as tetrazole etc. Compound IW can be synthesized by reacting acid XXV with appropriate amines XXXV or XXXVII or XXXIX using the protocol described in Scheme XV.

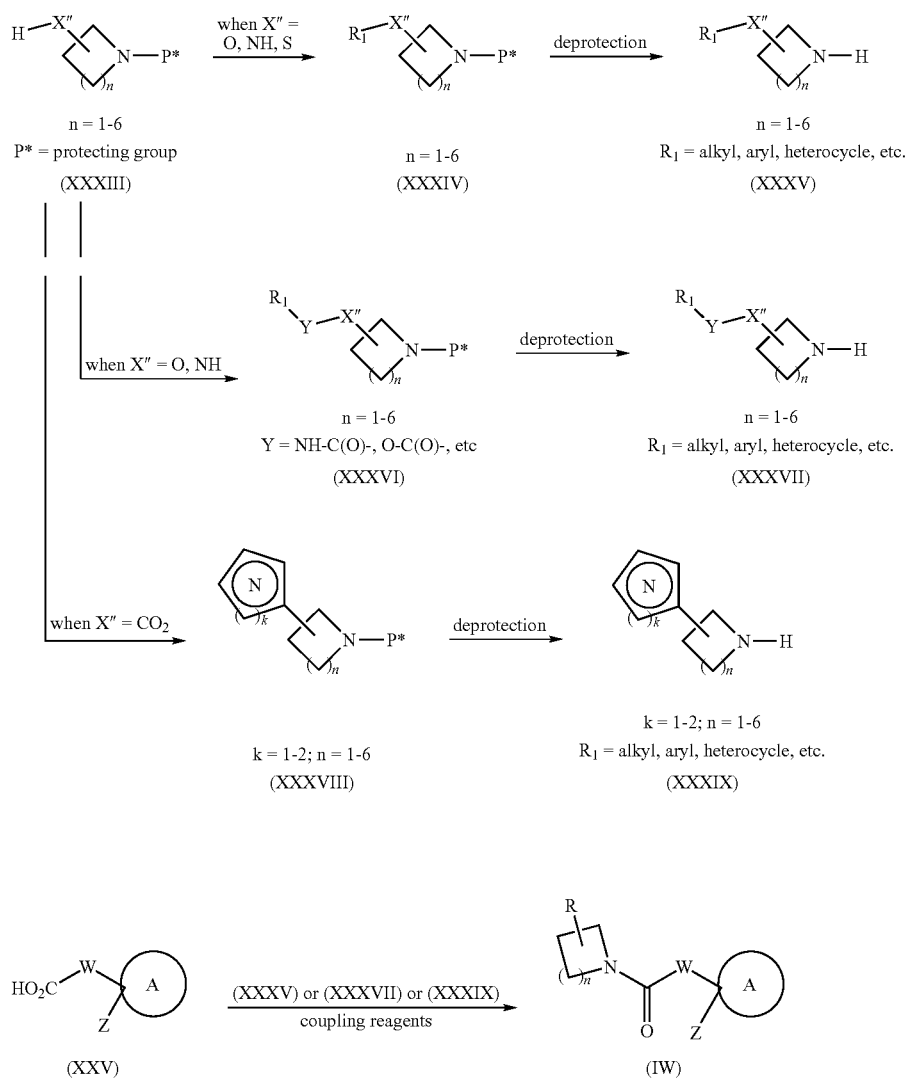

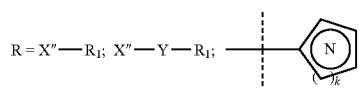

EXAMPLES

The following working Examples serve to better illustrate, but not limit, some of the preferred embodiments of the present invention.

General

The term HPLC refers to a Shimadzu high performance liquid chromatography with one of following methods:

Method A: Zorbax SB C18 4.6×75 mm column, Gradient solvent system: from 50% A: 50% B to 0% A: 100% B (A=90% $H_2O$/10% MeOH+0.2% $H_3PO_4$); (B=90% MeOH/10% $H_2O$+0.2% $H_3PO_4$) for 8 min; with 2.5 mL/min flow rate and a 2 min. hold, an ultra violet (UV) detector set at 220 nm.

Method B: Zorbax SB C18 4.6×75 mm column, Gradient solvent system: from 100% A: 0% B to 0% A: 100% B (A=90% $H_2O$/10% MeOH+0.2% $H_3PO_4$); (B=90% MeOH/10% $H_2O$+0.2% $H_3PO_4$) for 8 min; with 2.5 mL/min flow rate and a 2 min. hold, an ultra violet (UV) detector set at 220 nm.

Method C: Sunfire 3.5×150 mm column, Gradient solvent system: from 90% A: 10% B to 0% A: 100% B (A=95% $H_2O$/5% MeCN+0.05% TFA); (B=95% MeCN/5% $H_2O$+0.05% TFA) for 10 min, with 2.5 mL/min flow rate and a 5 min. hold, an ultra violet (UV) detector set at 220 nm.

The term Prep HPLC refers to an automated Shimadzu HPLC system using a mixture of solvent A (10% MeOH/90% $H_2O$/0.2% TFA) and solvent B (90% MeOH/10% $H_2O$/0.2% TFA). The preparative columns were packed with YMC or Phenomenex Luna C18 5 micron resin or equivalent.

Abbreviations

The following abbreviations are employed in the Examples and elsewhere herein:

Ph=phenyl
Bn=benzyl
i-Bu=iso-butyl
Me=methyl
Et=ethyl
Pr=propyl
Bn=benzyl
Bu=butyl
Cbz=carbobenzyloxy or carbobenzoxy or benzyloxycarbonyl
BOI=2-(1H-benzotriazol-1-yloxy)-4,5-dihydro-1,3-dimethyl-1H-Imidazolium
BOP=2-(1H-Benzotriazol-1-yl)tris(dimethylamino)phosphonium hexafluorophosphate
CBMIT=1,1'-Carbonylbis(3-methylimidazolium)triflate
CDI=1,1'-Carbonyldiimidazole
CMBI=2-chloro-1,3-dimethyl-1H-benzimidazolium hexafluorophosphate
DCC=1,3-Dicyclohexylcarbodiimide
DCM=dichloromethane
DEAD=Diethyl azodicarboxylate
DIAD=Diisopropyl azodicarboxylate
DIC=1,3-Diisopropylcarbodiimide
DIEA=N,N-diisopropylethylamine
DMA=N,N-dimethylacetylamide
DMAP=4-(Dimethylamino)pyridine
DMPU=N,N'-Dimethyl-3,4,5,6-tetrahydro-2(1H)-pyrimidinone
DMF=N,N-dimethylformamide
DMSO=dimethylsulfoxide
EtOAc=ethyl acetate
EDC/EDCI/EDAC=3-ethyl-3'-(dimethylamino)propyl-carbodiimide hydrochloride (or 1-[(3-(dimethyl)amino)propyl])-3-ethylcarbodiimide hydrochloride)
HBTU=1-[Bis(dimethylamino)methylene]-1H-benzotriazoliumhexa-fluorophosphate(1-)3-oxide
HOAc or AcOH=acetic acid
HOAT=1-hydroxy-7-azabenzotriazole
HOBT=1-hydroxybenzotriazole
HRMS=high resolution mass spectrum
LAH=lithium aluminum hydride
LDA=lithium diisopropylamide
$LiN(TMS)_2$=lithium bis(trimethylsilyl)amide
mCPBA=3-Chloroperoxybenzoic acid
MsCl=Methanesulphonyl chloride
Nf=Nonafluoro-1-butanesulfonyl
Nf-F=Nonafluoro-1-butanesulfonyl fluoride
NMP=N-Methylpyrrolidone
NBS=N-Bromosuccinimide
n-BuLi=n-butyllithium
Pd/C=palladium on carbon
$PtO_2$=platinum oxide
PyBOP=benzotriazol-1-yloxytrispyrrolidino phosphonium hexafluorophosphate
$SOCl_2$=Thionyl chloride
TBAF=tetrabutylammonium fluoride
TBS=tert-Butyldimethylsilyl
TBTU=O-Benzotriazolyl tetramethylisouronium tetrafluoroborate
Tf=Trifluoromethanesulfonyl
TMS=trimethylsilyl
TEA=triethylamine
TFA=trifluoroacetic acid
THF=tetrahydrofuran
TOSMIC=Tosylmethyl isocyanide
equiv=equivalent(s)
min=minute(s)
h or hr=hour(s)
L=liter
mL=milliliter
μL=microliter
g=gram(s)
mg=milligram(s)
mol=mole(s)
mmol=millimole(s)
meq=milliequivalent
RT=room temperature
sat or sat'd=saturated
aq.=aqueous
TLC=thin layer chromatography
HPLC=high performance liquid chromatography
HPLC Rt=HPLC retention time
LC/MS=high performance liquid chromatography/mass spectrometry
MS or Mass Spec=mass spectrometry
NMR=nuclear magnetic resonance

Examples 1 and 2

2-(4'-Fluorophenyl)-tricyclo[3.3.1.1 3,7]decane-2-acetic acid and 2-(4'-Fluorophenyl)-tricyclo[3.3.1.1 3,7]dec-2-yl-propanedioic acid, Respectively

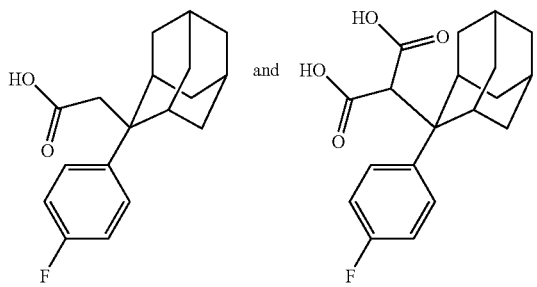

Compound 1A. 5-(2-Adamantylidene)-2,2-dimethyl-1,3-dioxane-4,6-dione

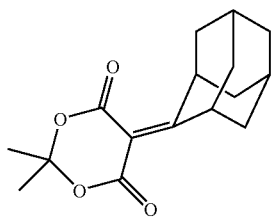

This material is commercially available from the Aldrich Company. It can also be synthesized using the following procedure: A solution of 2-adamantanone (1.5 g, 10 mmol), Meldrum's acid (1.73 g, 12 mmol), and a catalytic amount of piperidine (5 drops) in anhydrous pyridine (10 mL) was stirred under argon for 5 days. After this time, the solution was poured into ice water (30 mL), and the resulting mixture was stirred at room temperature for 20 min. At the conclusion of this period, the resulting precipitate was collected by filtration and washed with cold water (15 mL). The resulting solid was dried in vacuo to provide compound 1A (2.43 g, 88% yield) as a white solid.

Compound 1B. 2,2-Dimethyl-5-(2-(4'-fluorophenyl)tricyclo[3.3.1.1 3,7]dec-2-yl)-1,3-dioxane-4,6-dione

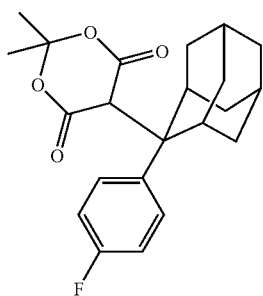

To a suspension of copper(I)bromide (1.14 g, 7.947 mmol) in dry THF (10 mL) at −2° C. under argon was added 4-fluorophenylmagnesium bromide (7.9 mL, 15.9 mmol, 2.0 M in THF) dropwise. Upon completion of addition, the resulting mixture was stirred at −2° C. for 10 min, and then a solution of compound 1A (0.732 g, 2.649 mmol) in THF (10 mL) was added through a cannula. The reaction mixture was then allowed to warm to RT where it was stirred under argon for about 16 hours. At the conclusion of this period, the reaction mixture was quenched with NH$_4$Cl (saturated aqueous solution, 20 mL) and then extracted with CH$_2$Cl$_2$ (3×30 mL). The combined organic layers were dried over Na$_2$SO$_4$ and filtered. The filtrate was concentrated under reduced pressure to provide a crude product. The crude product was purified via column chromatography (SiO$_2$, 10% EtOAc/n-Hexane) to provide compound 1B (0.75 g, 76% yield) as a white solid. $^1$H NMR (400 MHz, CDCl$_3$) δ ppm 7.18-7.25 (m, 2H), 7.04 (t, J=8.79 Hz, 2H), 4.29 (s, 1H), 2.97 (s, 2H), 2.38 (d, J=14.06 Hz, 2H), 2.04 (s, 1H), 1.95 (d, J=13.18 Hz, 2H), 1.61-1.78 (m, 7H), 1.55 (s, 1H), 1.49 (s, 3H), 0.77 (s, 3H); $^{19}$F NMR (376 MHz, CDCl$_3$) δ ppm −115.28; $^{13}$C NMR (101 MHz, CDCl$_3$) δ ppm 164.6, 129.1, 129.0, 115.5, 115.3, 105.2, 52.3, 51.3, 38.3, 33.5, 33.2, 31.8, 30.6, 27.0, 26.7, 26.4; HPLC Rt (Method A): 7.38 min.

Examples 1 and 2

A suspension of compound 1B (54.5 mg, 0.126 mmol) in a DMF-H$_2$O mixture (v/v 10:1) (1.3 mL) was heated at 100° C. under argon in an oil bath for 6 h. After this time, the solvent was evaporated under reduced pressure to provide a residue. The residue was purified via Prep HPLC to yield Examples 1 (25.3 mg, 60% yield) and 2 (9.7 mg, 20% yield). Example 1: $^1$H NMR (400 MHz, CDCl$_3$) δ ppm 7.27-7.31 (m, 2H), 6.95-7.02 (m, 2H), 2.69-2.73 (m, 2H), 2.54-2.61 (m, 2H), 2.20 (d, 2H), 1.91-1.99 (m, 1H), 1.78-1.87 (m, 4H), 1.68-1.76 (m, 3H), 1.58 (d, 2H); $^{19}$F NMR (376 MHz, CDCl$_3$) δ ppm −117.16; HPLC Rt (Method A): 7.02 min; LC/MS (m/z)= 287.3 (M−H)$^-$. Example 2: $^1$H NMR (400 MHz, CDCl$_3$) δ ppm 7.18-7.25 (m, 2H), 6.96-7.04 (m, 2H), 4.51-4.56 (m, 1H), 2.67-2.73 (m, 2H), 2.41 (d, 2H), 2.04 (s, 1H), 1.91 (d, 2H), 1.81 (d, 2H), 1.69-1.76 (m, 3H), 1.59-1.67 (m, 2H), 1.59 (none, 1H); $^{19}$F NMR (376 MHz, CDCl$_3$) δ ppm −115.14; HPLC Rt (Method A): 6.18 min; LC/MS (m/z)=331.3 (M−H)$^-$ In an alternate experiment, a suspension of compound 1B in a DMF-H$_2$O mixture was heated at 110° C. in an oil bath under argon for 12 h. After this time, Example 1 was isolate in the manner described above in 80% yield.

Example 3

2-(4-Fluorophenyl)-2-adamantane carboxylic acid

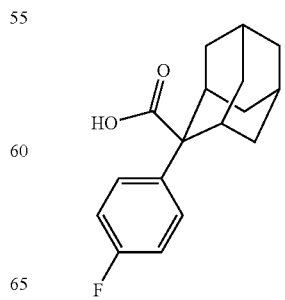

Compound 3A

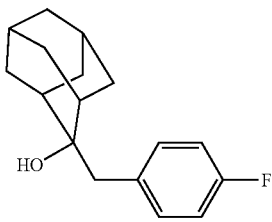

A solution of 2-admantanone (5.0 g, 33 mmol) in THF (25 mL) was stirred at 0° C. and 4-F-benzylmagnesium bromide (132 mL, 33 mmol) was added slowly. Upon completion of addition, the reaction mixture was warmed to room temperature where it was stirred for 16 hours. At the conclusion of this period, the reaction mixture was cooled at 0° C., quenched with saturated $NH_4Cl$ solution (30 mL), and extracted with $Et_2O$ (3×30 mL). The combined organic layers were dried over $MgSO_4$, filtered, and concentrated to provide compound 3A (8.0 g, 93%) as a yellow solid. LC/MS (m/z)=263 $(M+H)^+$.

Compound 3B

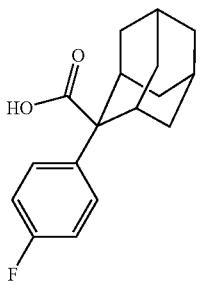

To a stirred suspension of compound 3A (8.0 g, 30.7 mmol) in formic acid (32 mL) at 40° C. was added $H_2O_2$ (30% solution, 5.6 mL). Upon completion of addition, the reaction was heated at 40° C. in oil bath for about 16 hours. After this time, the reaction mixture was allowed to cool to RT. Once at the prescribed temperature, the reaction mixture was poured into ice, stirred for 10 min, and then extracted with $Et_2O$ (3×30 mL). The combined organic layers were washed with sat. $NaHCO_3$, dried over $MgSO_4$, and concentrated to yield a residue. The residue was purified via column chromatography ($SiO_2$, 0-15% EtOAc in hexanes) to provide compound 3B (1.15 g, 14%) as a light yellow oil. LC/MS (m/z)=259 $(M+H)^+$. $^1H$ NMR (400 MHz, $CDCl_3$) δ ppm 9.28 (s, 1H), 7.32 (dd, J=8.79, 5.27 Hz, 2H), 7.05 (t, J=8.57 Hz, 2H), 2.83 (s, 2H), 1.50-2.00 (m, 12H).

Example 3

To a solution of compound 3B (50 mg, 0.194 mmol) and 2-methyl-2-butene (2.0 mL) in a t-BuOH—$H_2O$ mixture (2.3 mL, v/v 3:1) was added $NaH_2PO_4$ (267.7 mg, 1.94 mmol), followed by sodium chlorite (131.6 mg, 1.16 mmol). Upon completion of addition, the reaction mixture was stirred at RT for 3 h. After this time, $Na_2SO_3$ (aq.) was added to quench the reaction, and the resulting mixture was extracted with EtOAc (3×5 mL). The combined organic layers were dried over $MgSO_4$, filtered, and then concentrate to yield a crude product. The crude product was purified via Prep HPLC to provide Example 3 (21.2 mg, 40%). HPLC Rt (Method A): 6.686 min;

HRMS (high resolution mass spectrum): Calculated for $C_{17}H_{18}O_2F$: 273.1291, found: 273.1298. $^1H$ NMR (400 MHz, $CDCl_3$) δ ppm 7.42-7.49 (m, 2H), 6.98-7.07 (m, 2H), 2.91 (br. s., 2H), 2.03 (d, J=12.3 Hz, 2H), 1.82-1.94 (m, 3H), 1.65-1.79 (m, 6H), 1.59 (d, 2H). $^{19}F$ NMR (376 MHz, $CDCl_3$) δ ppm −115.67 (s).

Example 4

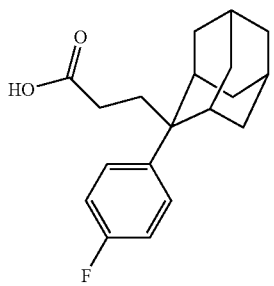

Compound 4A

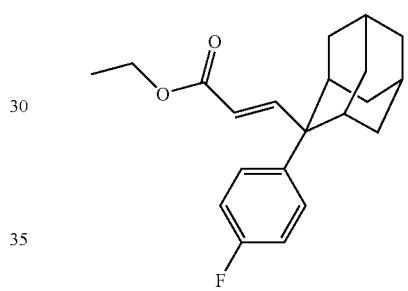

To a suspension of NaH (86 mg, 2.15 mmol) in THF (2 mL) was added triethyl phosphonoacetate (481 mg, 2.15 mmol) dropwise. Upon completion of addition, the mixture was stirred at RT for 1 h and then a solution of compound 3B (170 mg, 0.65 mmol, see Example 3) in THF (1.5 mL) was added dropwise. The reaction mixture was stirred at RT for about 16 hours and then the solvent was evaporated to dryness to yield a residue. The residue was purified via column chromatography ($SiO_2$, 0-10% EtOAc in hexanes) to provide compound 4A (100 mg, 46%) as a colorless oil. LC/MS (m/z)=329 $(M+H)^+$.

Compound 4B

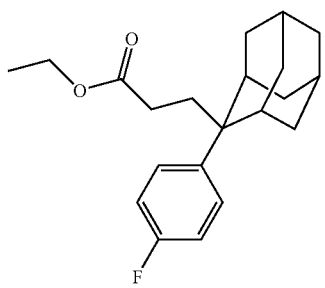

To a solution of compound 4A (60 mg, 0.18 mmol) in MeOH (2.0 mL) was added Pd/C catalyst (12 mg, 20%).

Upon completion of addition, the reaction mixture was charged with a H₂ balloon for about 16 hours. After this time, the Pd/C catalyst was filtered off, and the filter cake was rinsed with MeOH. The solvent was evaporated to provide compound 4B (60 mg, 100%) as a colorless oil. LC/MS (m/z)=331 (M+H)⁺.

Example 4

To a solution of compound 4B (60 mg, 0.18 mmol) in THF (1.0 mL) was added saturated LiOH (1.0 mL, aqueous). Upon completion of addition, the reaction mixture was stirred at room temperature for three days during which time a few drops of MeOH were added. At the conclusion of the three day period, the reaction mixture was acidified with 1N HCl to pH=2. Once at the prescribed pH, the resulting mixture was extracted with EtOAc (3×5 mL). The combined organic layers were evaporated to dryness to yield a residue. The residue was purified via Prep HPLC to provide Example 4 (5.8 mg, 10% yield) as white solid. LC/MS (m/z)=301 (M–H)⁻. HPLC Rt (Method A): 7.62 min; ¹H NMR (400 MHz, CDCl₃) δ ppm 7.15 (dd, J=8.35, 5.71 Hz, 2H), 6.93 (t, J=8.35 Hz, 2H), 2.23 (s, 2H), 2.14 (d, J=12.30 Hz, 2H), 1.89-1.97 (m, 2H), 1.79-1.89 (m, 3H), 1.58-1.77 (m, 7H), 1.49 (d, J=12.74 Hz, 2H).

Example 5

2-Benzyl-2-adamantane carboxylic acid

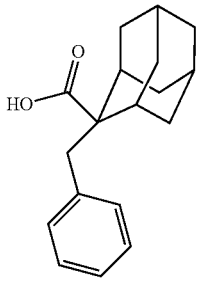

To a stirred solution of 2-adamantane carboxylic acid (114.5 mg, 0.635 mmol) in dry THF (6 mL) at –40° C. under argon was slowly added LDA (0.79 mL, 1.588 mmol), followed by DMPU (93 μL, 0.688 mmol). Upon completion of addition, the mixture was gradually warmed to RT, where it stirred for 1 hour. After this time, the reaction mixture was cooled to 0° C., and benzyl bromide (83 μL, 0.699 mmol) was added. The resulting mixture was warmed to RT over a 2 hour period. Once at the prescribed temperature, aqueous HCl (1 mL, 1 N) was added to quench the reaction. The reaction mixture was extracted with EtOAc (3×5 mL), and the combined organic layers were dried (Na₂SO₄) and then concentrated to afford a crude product. The crude product was purified via column chromatography (SiO₂, 2% MeOH in CH₂Cl₂, with 0.1% HOAc) to afford a less crude product. This less crude product was further purified via Prep HPLC to provide Example 5 (29 mg, 17% yield) as a white solid. HPLC Rt (Method A): 7.301 min; ¹H NMR (400 MHz, CDCl₃) δ ppm 7.17-7.26 (m, 3H), 7.09-7.15 (m, 2H), 3.08 (s, 2H), 2.27 (d, J=11.9 Hz, 2H), 2.14 (s, 2H), 1.83-1.98 (m, 4H), 1.69-1.79 (m, 6H).

Example 6

2-(4-Fluorophenyl)-tricyclo[3.3.1.1,3,7]decane-2-hydroxymethyl-2-acetic acid

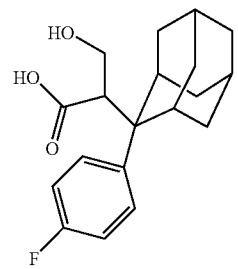

Compound 6A. 2-(4-Fluorophenyl)-tricyclo[3.3.1.13, 7]decane-2-benzyloxy-2-acetic acid

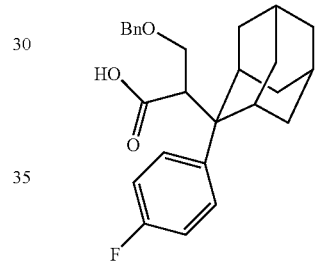

To a solution of Example 2 (33 mg, 0.114 mmol) in dry THF (1 mL) at –40° C. under argon was slowly added LDA (0.13 mL, 0.267 mmol), followed by DMPU (15.3 μL, 0.124 mmol). Upon completion of addition, the reaction mixture was gradually warmed to RT, where it stirred for 1 hour. At the conclusion of this period, the reaction mixture was cooled to 0° C., and benzyl chloromethyl ether (17.2 mL, 0.124 mmol) was added. The resulting mixture was warmed to RT in 2 hours and then aqueous HCl (1 mL, 1 N) was added to quench the reaction. The resulting mixture was extracted with EtOAc (3×5 mL). The combined organic layers were washed with 1 N HCl, brine, dried over Na₂SO₄ and concentrated to yield a crude product. The crude product was purified via Prep HPLC to afford compound 6A (15 mg, 32% yield) as a white solid. HRMS (high resolution mass spectrum): Calculated for C₂₆H₃₀O₃F: 409.2179, found: 409.2176. ¹H NMR (400 MHz, CDCl₃) δ ppm 7.22-7.40 (m, 5H), 7.02-7.17 (m, 2H), 6.80-7.01 (m, 2H), 4.33-4.50 (m, 2H), 3.73 (dd, J=10.1, 3.5 Hz, 1H), 3.67 (dd, J=9.0, 3.7 Hz, 1H), 3.18-3.30 (m, 1H), 2.42-2.66 (m, 3H), 2.19 (d, J=12.3 Hz, 1H), 1.98 (br. s., 1H), 1.63-1.88 (m, 7H), 1.45-1.62 (m, 2H).

Example 6

Under argon, to a solution of compound 6A (12 mg, 0.029 mmol) in EtOH (0.5 mL) was added 10% Pd/C catalyst (5 mg). Upon completion of addition, the reaction mixture was charged with H₂ balloon for 2 h. After this time, the Pd/C catalyst was filtered off, and the filter cake was rinsed with EtOH. The filtrate was concentrated under reduced pressure to afford a crude product. The crude product was purified via Prep HPLC to afford Example 6 (3.2 mg, 34% yield) as white solid. HPLC Rt (Method A): 5.935 min; LC/MS (m/z)=319 (M+H)⁺. ¹H NMR (400 MHz, CDCl₃) δ ppm 7.07-7.17 (m, 1H), 6.99-7.07 (m, 1H), 6.81-6.95 (m, 2H), 3.52-3.70 (m, 4H), 3.48 (dd, J=10.8, 3.3 Hz, 1H), 3.24-3.39 (m, 2H), 2.64 (br. s., 1H), 2.50 (br. s., 1H), 2.38 (br. s., 1H), 2.11 (br. s., 1H), 1.91 (br. s., 1H), 1.54-1.80 (m, 5H), 1.46 (d, 2H).

Example 7

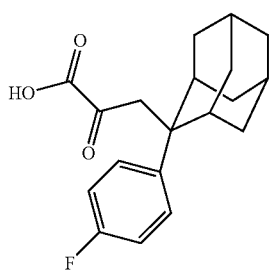

Compound 7A

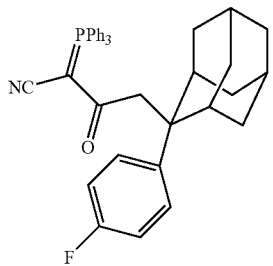

To a solution of Example 1 (100 mg, 0.35 mmol), (Triphenylphosphoranylidene)acetonitrile (137 mg, 0.45 mmol), and DMAP (55 mg, 0.45 mmol) in CH₂Cl₂ (4.0 mL) was added EDC (86 mg, 0.45 mmol). Upon completion of addition, the reaction mixture was stirred at RT for about 16 hours. After this time, the solvent was removed under reduced pressure to yield a residue. The residue was purified via column chromatography (SiO₂, 0-30% EtOAc in hexanes) to provide compound 7A (200 mg, 100%) as a colorless oil. LC/MS (m/z)=572 (M+H)⁺.

Compound 7B

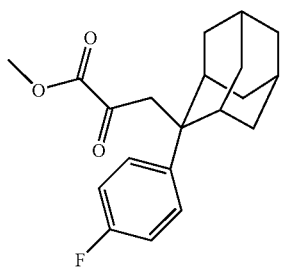

To a solution of Compound 7A (200 mg, 0.35 mmol) in a CH₂Cl₂/MeOH (3.5 mL/1.5 mL) mixture at −78° C. was bubbled O₃ gas until a light blue color appeared (about 10 min). Once at the prescribed color, the reaction mixture was aspirated with argon gas for about 10 min to remove any excess O₃ and then a few drops of Me₂S were added. Upon completion of addition, the reaction mixture was warmed to RT. Once at the prescribed temperature, the solvent was evaporated to yield a residue. The residue was purified via column chromatography (SiO₂, 0-15% EtOAc in hexanes) to provide compound 7B (90 mg, 77%) as a white solid. LC/MS (m/z)=331 (M+H)⁺.

Example 7

To a solution of compound 7B (30 mg, 0.09 mmol) in THF (1.0 mL) was added a saturated LiOH solution (1.0 mL, aqueous). Upon completion of addition, the reaction mixture was stirred at room temperature for about 16 hours. At the conclusion of this period, the reaction mixture was acidified with 1 N HCl to a pH of less than 5. Once at the prescribed pH, the reaction mixture was extracted with CH₂Cl₂ (3×5 mL). The combined organic layers were dried over MgSO₄ and concentrated to yield a crude product. The crude product was purified via Prep HPLC to provide Example 7 (14.4 mg, 50% yield) as a white solid. LC/MS (m/z)=315 (M−H)⁻. HPLC Rt (Method A): 6.85 min; ¹H NMR (400 MHz, CDCl₃) δ ppm 7.23 (dd, J=9.23, 5.27 Hz, 2H), 6.96 (t, J=8.57 Hz, 2H), 3.35 (s, 2H), 2.57 (s, 2H), 2.21 (d, J=11.86 Hz, 2H), 1.98 (s, 1H), 1.77-1.92 (m, 4H), 1.71 (s, 3H), 1.58 (m, 2H).

Example 8

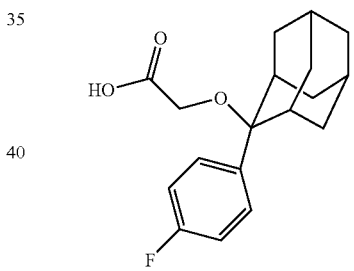

Compound 8A. 2-(4-Fluorophenyl)-2-adamantanol

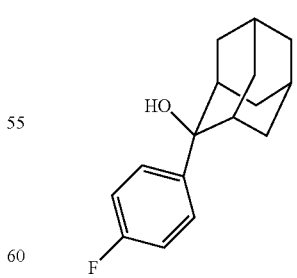

To a solution of 2-adamantanone (1.214 g, 8.081 mmol) in THF (10 mL) at RT was slowly added 4-fluorophenyl magnesium bromide (4.45 mL, 8.89 mmol, 2.0 M in Et₂O). The reaction mixture was heated to 65° C., where it stirred for 1 h. After this time, the reaction mixture was cooled to RT, quenched with NH₄Cl (saturated aqueous solution, 10 mL), and then extracted with Et₂O (2×20 mL). The combined organic layers were washed with H₂O and brine, dried over Na₂SO₄ and filtered. The filtrate was concentrated under reduced pressure to yield compound 8A (1.59 g, 80%) as a lightly yellow solid.

Compound 8B. 2-Allyloxy-2-(4-fluorophenyl)-tricyclo[3.3.1.1³,⁷]decane

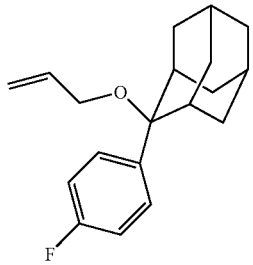

A suspension of NaH (44 mg, 1.741 mmol, 95%) and compound 8A (306 mg, 1.244 mmol) in THF (6 mL) was heated to 65° C. for 30 min. After this time, the reaction mixture was cooled to RT, and allyl bromide (0.155 mL, 1.74 mmol) was added. Upon completion of addition, the resulting mixture was heated at reflux for 2 h. At the conclusion of this period, the reaction mixture was analyzed by HPLC, which showed that the reaction was complete. The reaction mixture was cooled to RT, quenched with dilute HCl (aq.), and then extracted with CH₂Cl₂ (3×10 mL). The combined organic layers were washed with H₂O and brine and then dried over Na₂SO₄. The solvent was evaporated to afford a crude product. The crude product was purified via column chromatography (SiO₂, 5% EtOAc in Hexanes) to afford compound 8B (0.217 g, 61% yield). $^1$H NMR (400 MHz, CDCl₃) δ ppm 7.39-7.50 (m, 2H), 6.96-7.08 (m, 2H), 5.61-5.79 (m, 1H), 4.90-5.20 (m, 2H), 3.40 (dd, J=3.5, 1.5 Hz, 2H), 2.60 (s, 2H), 2.37 (d, J=10.9 Hz, 2H), 1.88 (s, J=2.8 Hz, 1H), 1.59-1.80 (m, 9H); $^{19}$F NMR (376 MHz, CDCl₃) δ ppm −116.01.

Compound 8C

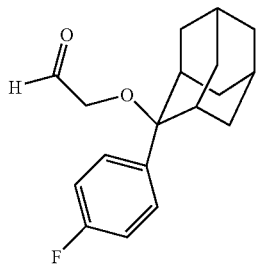

Ozone (ca. 5% in O₂) was bubbled into a well-stirred solution of compound 8B (0.217 g, 0.757 mmol) in CH₂Cl₂ (7.5 mL) at −78° C. After a pale blue color appeared, the gas flow was stopped and Me₂S (6 drops) was added. The reaction mixture was allowed to warm to RT, where it stirred for 3 h. After this time, the solvent was removed under reduced vacuum to yield a residue. The residue was purified via column chromatography (SiO₂, 5% EtOAc in n-hexane) to provide compound 8C (46 mg, 21% yield). $^1$H NMR (400 MHz, CDCl₃) δ ppm 9.42 (s, 1H), 7.37-7.57 (m, 2H), 6.94-7.14 (m, 2H), 3.53 (d, J=1.0 Hz, 2H), 2.61 (s, 2H), 2.33 (d, J=11.9 Hz, 2H), 1.91 (d, J=2.5 Hz, 1H), 1.57-1.82 (m, 9H); $^{19}$F NMR (376 MHz, CDCl₃) δ ppm −114.84.

Example 8

Example 8 was prepared in a similar manner as described in Example 4, utilizing compound 8C and the other appropriate reagents. $^1$H NMR (400 MHz, CDCl₃) δ ppm 7.38-7.49 (m, 2H), 6.97-7.16 (m, 2H), 3.59 (s, 2H), 2.63 (s, 2H), 2.23 (s, 2H), 1.94 (s, 1H), 1.56-1.84 (m, 10H); HRMS (ESI): Calculated for C₁₈H₂₀O₃F: 303.1396, found: 303.1401.

Example 9

2-(3'-Cyanophenyl)-tricyclo[3.3.1.1³,⁷]decane-2-acetic acid

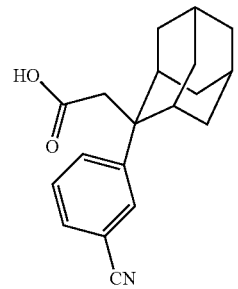

Compound 9A. 2-(3'-Hydroxyphenyl)-tricyclo[3.3.1.1³,⁷]decane-2-acetic acid

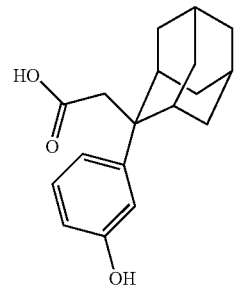

To a solution of 2-(3'-methoxyphenyl)-tricyclo[3.3.1.1³,⁷]decane-2-acetic acid (199 mg, 0.667 mmol, as prepared following the procedure described in Example 1) in CH₂Cl₂ (5 mL) at −78° C. under argon was added BBr₃ (1.33 mL, 1.33 mmol, 1 M solution in CH₂Cl₂). The mixture was carefully warmed to RT, and then stirred at RT for 2 h. Upon completion of this period, the reaction mixture was quenched with saturated NaHCO₃ (aq. 1 mL) and then the solvent was evaporated to dryness to provide a residue. The residue was purified via Prep HPLC to provide compound 9A (152.7 mg, 80% yield) as a white solid. HPLC Rt (Method A): 5.480 min; $^1$H NMR (400 MHz, CDCl₃) δ ppm 7.11 (t, J=7.9 Hz, 1H), 6.84 (d, J=8.8 Hz, 1H), 6.74-6.80 (m, 1H), 6.60 (dd, J=7.9, 1.8 Hz, 1H), 3.04 (br. 1H), 2.37-2.65 (m, J=31.2 Hz, 3H), 2.14 (s, 2H), 1.83-1.96 (m, 3H), 1.77 (d, J=13.6 Hz, 3H), 1.62-1.72 (m, 4H), 1.53 (d, J=12.3 Hz, 2H).

Compound 9B

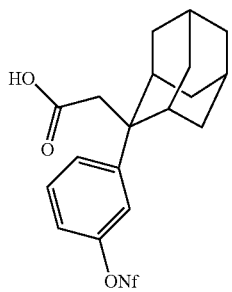

To a solution of compound 9A (30 mg, 0.105 mmol) in DMF (1.2 mL) at −10° C. was added Et$_3$N (45 μL, 0.325 mmol) followed by Nf-F (40 μL, 0.2199 mmol). Upon completion of addition, the reaction mixture was warmed to RT, where it stirred for 3 h. After this time, the solvent was evaporated to provide a residue. The residue was purified via Prep HPLC to afford compound 9B (51 mg, 86% yield) as a white solid. LC/MS (m/z)=567.0 (M−H)$^-$.

Example 9

To a solution of compound 9B (51 mg, 0.09 mmol) and Zn(CN)$_2$ (21.1 mg, 0.18 mmol) in anhydrous DMF (2 mL) under argon was added Pd(PPh$_3$)$_4$ (20.8 mg, 0.018 mmol). Upon completion of addition, the reaction mixture was stirred in an 85° C. oil bath for 8 h. At the conclusion of this period, the solvent was removed under reduced pressure to provide a residue. The residue was purified via Prep HPLC to afford Example 9 (7.3 mg, 27% yield) as a white solid. HPLC Rt (Method A): 6.023 min; $^1$H NMR (400 MHz, CDCl$_3$) δ ppm 7.62 (s, 1H), 7.58 (d, J=7.9 Hz, 1H), 7.46-7.52 (m, 1H), 7.41 (t, J=7.7 Hz, 1H), 2.73 (s, 2H), 2.58 (s, 2H), 2.21 (d, J=13.6 Hz, 2H), 1.99 (s, 1H), 1.85 (d, J=13.6 Hz, 2H), 1.67-1.79 (m, 5H), 1.54-1.67 (m, 2H).

Example 10

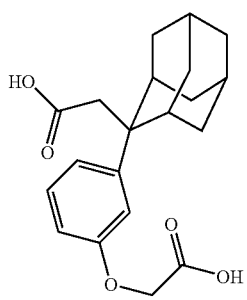

A mixture of compound 9A (24 mg, 0.084 mmol), K$_2$CO$_3$ (24.8 mg, 0.251 mmol), and ethyl iodoacetate (20 μL, 0.168 mmol) in THF (1 mL) was refluxed under argon for 3 h. At the conclusion of this period, the reaction mixture was cooled to RT, neutralized with 1 N HCl (aq.) to a pH=3, and then extracted with EtOAc (3×5 mL). The combined organic layers were evaporated to dryness and then THF (1 mL) and saturated LiOH (aq., 0.5 mL) were added. The resulting mixture was heat to 70° C., where it stirred for about 16 h. After this time, the mixture was neutralized with 1 N HCl (aq.) to a pH=1, and then extracted with EtOAc (3×5 mL). The combined organic layers were evaporated to dryness to yield a residue. The residue was purified via Prep HPLC to provide Example 10 (7.8 mg, 27% yield). HPLC Rt (Method A): 5.703 min; HRMS (ESI): Calculated for C$_{20}$H$_{23}$O$_5$: 343.1545, found: 343.1540; $^1$H NMR (400 MHz, CD$_3$OD) δ ppm 7.22 (t, J=8.1 Hz, 1H), 7.00 (d, J=7.8 Hz, 1H), 6.96 (s, 1H), 6.74 (dd, J=8.2, 1.9 Hz, 1H), 4.61 (s, 2H), 2.56-2.76 (m, 4H), 2.30 (d, J=13.4 Hz, 2H), 1.93 (s, 3H), 1.84 (d, J=13.4 Hz, 2H), 1.75 (s, 2H), 1.69 (s, 1H), 1.61 (d, J=12.4 Hz, 2H).

Examples 11 to 16

Example 11

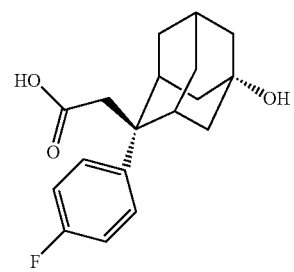

Example 12

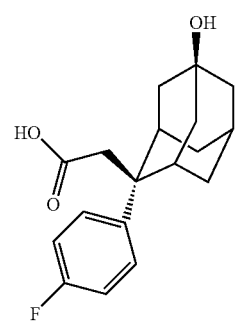

Example 13

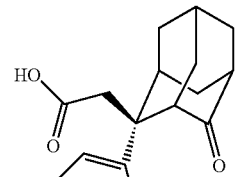

Example 14

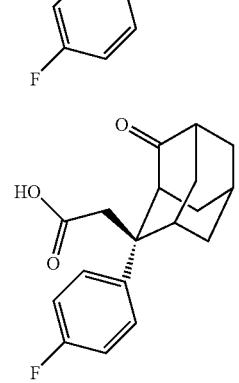

Example 15

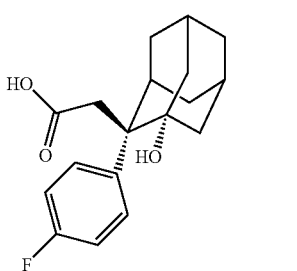

Example 16

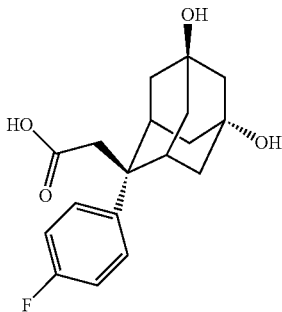

To a solution of potassium hydroxide (106.6 mg, 1.618 mmol) in water (3.2 mL) was added $KMnO_4$ (290 mg, 1.78 mmol). The resulting solution was warmed in an oil bath (about. 50° C.) and then Example 1 (460 mg, 1.618 mmol) was added portionwise. After the addition was complete, the reaction mixture was allowed to warm to a gentle reflux, where it stirred until all of the $KMnO_4$ was consumed (about 1.5 h). Once the $KMnO_4$ was completely consumed, the reaction mixture was cooled to RT, and then acidified with 6 N HCl (aq.). Sodium metabisulfite was added to remove $MnO_2$ (until all the brown color became white). The resulting solid was collected by filtration and then subjected to Prep HPLC to provide Examples 11 to 16. Some Example 1 starting material was also recovered (260 mg, white solid).

Example 11 (45.6 mg, white solid, 21.6% yield based on the recovery of starting material). HPLC Rt (Method B): 5.933 min; HRMS (ESI): Calculated for $C_{18}H_{20}O_3F$: 303.1396, found: 303.1401; $^1$H NMR (400 MHz, $CDCl_3$) δ ppm 7.28-7.38 (m, 2H), 7.00 (t, J=8.8 Hz, 2H), 2.84 (br. s., 2H), 2.66 (s, 2H), 2.08-2.29 (m, 4H), 1.80 (d, J=11.9 Hz, 2H), 1.63-1.74 (m, 4H), 1.53 (d, 2H). $^{19}$F NMR (376 MHz, $CDCl_3$) δ ppm −117.60.

Example 12 (70.5 mg, white solid, 33.4% yield based on the recovery of starting material). HPLC Rt (Method B): 6.986 min; $^1$H NMR (400 MHz, DMSO-$d_6$) δ ppm 11.56 (br. s., 1H), 7.34 (dd, J=8.6, 5.6 Hz, 2H), 7.09 (t, J=8.8 Hz, 2H), 3.31 (br. s, 3H), 2.75 (br. s, 2H), 2.43-2.63 (m, 2H), 2.09 (d, J=12.4 Hz, 2H), 1.87 (br. s., 1H), 1.46-1.68 (m, 2H), 1.36 (d, J=12.6 Hz, 2H); $^{19}$F NMR (376 MHz, DMSO-$d_6$) δ ppm −118.4; HRMS (ESI): Calculated for $C_{18}H_{20}O_3F$: 303.1396, found: 303.1396.

Example 13 (10 mg, white solid, 4.7% yield based on the recovery of starting material). HPLC Rt (Method B): 6.638 min; HRMS (ESI): Calculated for $C_{18}H_{18}O_3F$: 301.1240, found: 301.1241; $^1$H NMR (500 MHz, $CD_3OD$) δ ppm 7.39 (dd, J=9.1, 5.2 Hz, 2H), 6.98 (t, J=8.8 Hz, 2H), 3.55 (br. s., 1H), 3.23 (d, J=13.7 Hz, 1H), 2.61-2.70 (m, 2H), 2.55 (br. s., 1H), 2.39-2.48 (m, 1H), 2.27 (br. s., 1H), 2.08-2.17 (m, J=12.6, 3.2, 3.2, 3.0 Hz, 1H), 1.96-2.06 (m, 2H), 1.89-1.96 (m, 2H), 1.78-1.86 (m, 1H), 1.67-1.75 (m, 1H).

Example 14 (15 mg, white solid, 7.1% yield based on the recovery of starting material). HRMS (ESI): Calculated for $C_{18}H_{18}O_3F$: 301.1240, found: 301.1231.

Example 15 (15 mg, white solid, 7.1% yield based on the recovery of starting material). HPLC Rt (Method B): 7.665 min; LC/MS (m/z)=303.2 (M−H)$^-$; HRMS (ESI): Calculated for $C_{18}H_{20}O_3F$: 303.1396, found: 303.1391; $^1$H NMR (500 MHz, $CD_3OD$) δ ppm 7.81-8.01 (m, 2H), 6.95 (t, J=9.1 Hz, 2H), 3.25 (d, J=14.3 Hz, 1H), 2.77 (d, J=14.3 Hz, 2H), 2.29-2.39 (m, 2H), 2.09-2.20 (m, 2H), 1.91-1.98 (m, 1H), 1.63-1.74 (m, 5H), 1.61 (d, J=12.1 Hz, 1H), 1.45 (dd, J=12.9, 2.5 Hz, 1H).

Example 16 (3 mg, white solid) LC/MS (m/z)=319.3 (M−H)$^-$.

Example 17

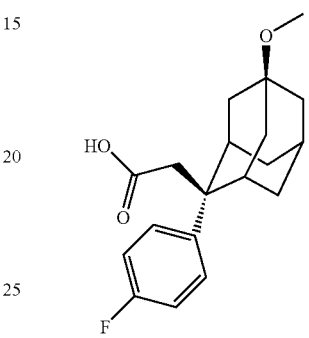

To a suspension of NaH (21 mg, 0.831 mmol, 95%) in anhydrous THF (2 mL) was added Example 12 (25.8 mg, 0.085 mmol). Upon completion of addition, the reaction mixture was heated to reflux under argon where it stirred for 1 h and then iodomethane was added (0.1 mL). Upon completion of addition, the resulting mixture was heated at reflux for about 16 h. After this time, the solvent was removed under reduced pressure to yield a residue. The residue was dissolved in THF (1 mL) and saturated LiOH (0.5 mL, aqueous). The resulting mixture was heated to 67° C., where it stirred for about 16 h. At the conclusion of this period, the mixture was cooled to RT, acidified with 1 N HCl to pH=1, and then extracted with a EtOAc-MeOH solution (8:2, v/v) (5×5 mL). The combined organic layers were evaporated to dryness to yield a residue. The residue was purified via Prep HPLC to provide Example 17 (15.2 mg, 56% yield) as a white solid. HPLC Rt (Method B): 7.753 min; HRMS (ESI): Calculated for $C_{19}H_{22}O_3F$: 317.1553, found: 317.1541; 1H NMR (400 MHz, CDCl3) δ ppm 7.26-7.39 (m, 2H), 6.99 (t, J=8.7 Hz, 2H), 3.29 (s, 3H), 2.86 (s, 2H), 2.67 (s, 2H), 2.21 (d, J=12.4 Hz, 2H), 2.03 (s, 1H), 1.69-1.87 (m, 6H), 1.45 (d, J=12.9 Hz, 2H); $^{19}$F NMR (376 MHz, $CDCl_3$) δ ppm −118.23.

Example 18

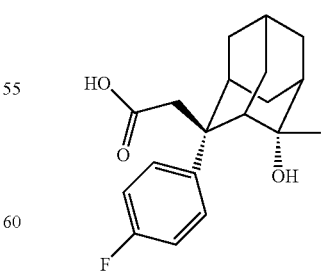

To a stirred solution of Example 13 (14.4 mg, 0.047 mmol) in dry THF (1.0 mL) at RT under argon was added methyl magnesium bromide (0.4 mL, 0.56 mmol, 1.4 M in THF). Upon completion of addition, the reaction mixture was heated to 65° C., where it stirred for 1 h. After this time, the solvent was removed under reduced pressure to yield a residue. The residue was purified via Prep HPLC to provide Example 18 (7.2 mg, 48% yield) as a white solid. HPLC Rt (Method B): 7.00 min; HRMS (ESI): Calculated for $C_{19}H_{22}O_3F$: 317.1553, found: 317.1544; $^1$H NMR (400 MHz, CD$_3$OD) δ ppm 7.41-7.56 (m, 1H), 7.19-7.32 (m, 1H), 6.83-7.04 (m, 2H), 3.11 (d, J=13.6 Hz, 1H), 2.76-2.91 (m, 1H), 2.39-2.52 (m, 3H), 2.32 (d, J=13.6 Hz, 1H), 2.19 (dd, J=14.3, 2.7 Hz, 1H), 1.81-2.03 (m, 3H), 1.70-1.81 (m, 2H), 1.57-1.67 (m, 1H), 1.51 (s, 1H), 1.35 (s, 3H).

Example 19

2-(4-Fluorophenyl)-2-(1H-tetrazol-5-ylmethyl)adamantine

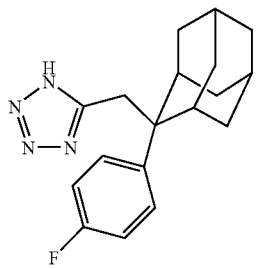

Compound 19A. 2-(4-Fluorophenyl)-tricyclo[3.3.1.1$^{3,7}$]decane-2-acetamide

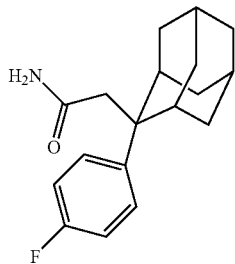

To a stirred solution of Example 1 (120 mg, 0.42 mmol) in CH$_2$Cl$_2$ (2 mL) at 0° C. was added triethylamine (71 μL, 0.5 mmol), followed by i-butyl chlorformate (57 μL, 0.44 mmol). Upon completion of addition, the reaction mixture was stirred at 0° C. for 45 min. At the conclusion of this period, NH$_4$OH (2.0 mL) was added, and the resulting mixture was warmed to RT where it stirred for about 16 hours. After this time, water was added, and the resulting mixture was extracted with CH$_2$Cl$_2$ (3×5 mL). The combined organic layers were dried over MgSO$_4$ and concentrated to provide compound 19A (150 mg, 100%) as a light yellow solid. LC/MS (m/z)=288 (M+H)$^+$. $^1$H NMR (400 MHz, CD$_3$CN) δ ppm 7.26-7.38 (m, 2H), 6.94-7.07 (m, 2H), 5.14-5.40 (m, 2H), 2.58 (br. s., 2H), 2.51 (s, 2H), 2.26 (d, J=11.4 Hz, 2H), 1.85-1.95 (m, 1H), 1.76 (d, J=13.6 Hz, 4H), 1.63-1.71 (m, 3H), 1.56 (d, 2H). $^{19}$F NMR (376 MHz, Solvent) δ ppm −121.40.

Compound 19B

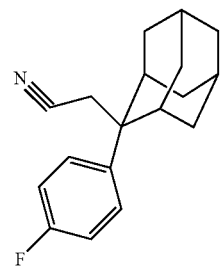

To a stirred solution of compound 19A (150 mg, 0.4 mmol) in pyridine (2.5 mL) was slowly added MsCl (316 μL, 4.0 mmol). Upon completion of addition, the reaction mixture was stirred at room temperature for about 16 h. After this time, the reaction mixture was quenched with water (1 mL), and then extracted with EtOAc (3×5 mL). The combined organic layers were washed with water, dried over MgSO$_4$, and concentrated to yield a residue. The residue was purified via column chromatography (SiO$_2$, 0-10% EtOAc in hexanes) to afford compound 19B (90 mg, 83%) as a white solid. LC/MS (m/z)=270 (M+H)$^+$.

Example 19

To a stirred solution of compound 19B (80 mg, 0.29 mmol) in toluene (3.0 mL) was added azidotrimethyltin (103 mg, 0.49 mmol). Upon completion of addition, the resulting mixture was heated to 100° C. where it stirred for 18 hr. After this time, the solvent was removed under reduced pressure to yield a residue. The residue was purified via Prep HPLC to afford Example 19 (7.6 mg, 8.3% yield) as a white solid. LC/MS (m/z)=313 (M+H)$^+$. $^1$H NMR (400 MHz, CD$_3$OD) δ ppm 6.98-7.05 (m, 2H), 6.95 (t, J=9.0 Hz, 2H), 2.45-2.56 (m, 4H), 2.09-2.24 (m, 5H), 2.02 (br. s., 1H), 1.74 (d, J=19.8 Hz, 5H), 1.59-1.67 (m, 2H). $^{19}$F NMR (376 MHz, CD$_3$OD) δ ppm −118.87 (s).

Example 20

2-(4-Fluorophenyl)-2-(1H-tetrazol-5-yl)adamantane

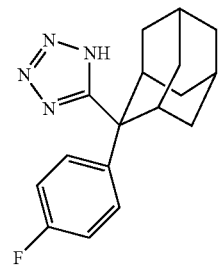

Compound 20A

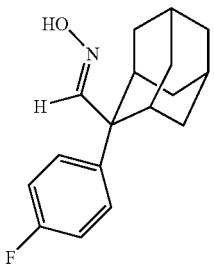

A mixture of compound 3B (400 mg, 1.55 mmol), sodium acetate (500 mg), and hydroxylamine hydrochloride (400 mg) in acetic acid (45 mL) was heated at 50° C. for 2 h. After this time, the reaction mixture was allowed to cool to RT, where it stirred for about 16 hours. At the conclusion of this period, the solvent was evaporated under reduced pressure to yield a residue. The residue was dissolved in water (3 mL) and then extracted with $CH_2Cl_2$ (3×5 mL). The combined organic layers were washed (saturated $NaHCO_3$ aqueous solution), dried over $MgSO_4$, and concentrated to yield compound 20A (360 mg, 85% yield) as a lightly yellow oil. LC/MS (m/z)= 274 (M+H)+.

Compound 20B.
2-(4-Fluorophenyl)-2-cyanoadamantane

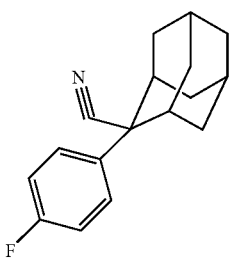

A stirred solution of compound 20A (360 mg, 1.3 mmol) in acetic anhydride (8.0 mL) was heated at reflux for 1 h. At the conclusion of this period, the reaction mixture was allowed to cool to RT, where it stirred for about 16 hours. After this time, MeOH (8 mL) and a few drops of concentrated $H_2SO_4$ were added to the reaction mixture. The resulting mixture was diluted with $H_2O$ (20 mL) and extracted with $Et_2O$ (3×10 mL). The combined organic layers were dried over $MgSO_4$ and concentrated to yield a residue. The residue was purified via column chromatography ($SiO_2$, 0-10% EtOAc in hexanes) to yield compound 20B (110 mg, 33%) as a lightly yellow oil. LC/MS (m/z)=256 (M+H)+.

Example 20

A mixture of compound 20B (110 mg, 0.43 mmol) and azidotrimethyltin (205 mg, 0.86 mmol) in toluene (3.0 mL) was heated at 100° C. for 2 days. At the conclusion of this period, the solvent was removed under reduced pressure to yield a residue. The residue was purified via Prep HPLC to provide Example 20 (10 mg, 7.8% yield) as a white solid. LC/MS (m/z)=299 (M+H)+. $^1$H NMR (400 MHz, $CDCl_3$) δ ppm 7.53 (dd, J=9.0, 5.1 Hz, 2H), 6.98 (t, J=8.6 Hz, 2H), 3.32 (br. s., 2H), 2.01 (d, J=12.7 Hz, 2H), 1.81-1.97 (m, 6H), 1.76 (br. s., 4H). $^{13}$C NMR (101 MHz, $CDCl_3$) δ ppm 163.21, 160.75, 134.45, 128.34, 128.26, 123.66, 116.15, 115.93, 45.43, 37.18, 34.94, 33.33, 31.13, 26.79, 26.27.

Example 21

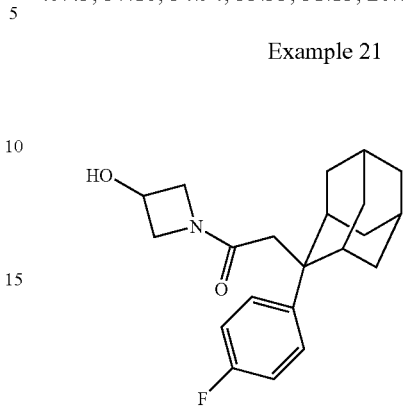

To a stirred suspension of Example 1 (30 mg, 0.1 mmol), EDAC (28 mg, 0.15 mmol), HOBT (20 mg, 0.15 mmol), and 3-hydroxyazetidine hydrochloride (16 mg, 0.15 mmol) in $CH_2Cl_2$ (1.5 mL) was added N,N-diisopropylethylamine (20 mg, 0.15 mmol). Upon completion of addition, the reaction mixture was stirred at RT for about 16 hours, and then the solvent was removed under reduced pressure to yield a residue. The residue was purified via Prep HPLC to provide Example 21 (15 mg, 43% yield) as a white solid. LC/MS (m/z)=344 (M+H)+; $^1$H NMR (400 MHz, $CDCl_3$) δ ppm 7.36 (dd, J=9.1, 5.2 Hz, 2H), 6.97-7.12 (m, 2H), 4.10-4.23 (m, 1H), 3.92 (dd, J=11.5, 6.0 Hz, 1H), 3.49 (dd, J=10.7, 4.1 Hz, 1H), 3.22-3.33 (m, 1H), 2.91 (dd, J=9.1, 4.1 Hz, 1H), 2.64 (br. s., 2H), 2.36-2.50 (m, 2H), 2.32 (d, J=12.6 Hz, 2H), 1.97 (br. s., 1H), 1.82 (t, J=12.1 Hz, 2H), 1.64-1.75 (m, 2H), 1.50-1.63 (m, 1H).

Example 22

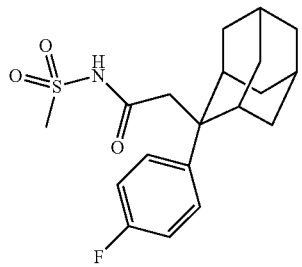

Example 1 (50 mg, 0.17 mmol), EDCI (42 mg, 0.22 mmol), DMAP (27 mg, 0.22 mmol), and methanesulfonamide (21 mg, 0.22 mmol) were dissolved in $CH_2Cl_2$ (1.5 mL). The resulting mixture was stirred at RT for about 16 h. After this time, the solvent was evaporated under reduced pressure to provide a residue. The residue was purified via PrepHPLC to provide Example 22 as a white solid (54 mg, 67% yield). LC/MS (m/z)=366 (M+H)+. $^1$H NMR (400 MHz, $CDCl_3$) δ ppm 7.30 (dd, J=9.01, 5.49 Hz, 2H), 7.17 (s, 1H), 7.04 (t, J=8.57 Hz, 2H), 2.93 (s, 3H), 2.62 (s, 2H), 2.43-2.57 (m, 2H), 2.09-2.29 (m, 2H), 1.90-2.02 (m, 1H), 1.49-1.89 (m, 9H).

Example 23

2-(9-(4-Fluorophenyl)-3-hydroxybicyclo[3.3.1]nonan-9-yl)-1-(3-hydroxyazetidine-1-yl)ethanone

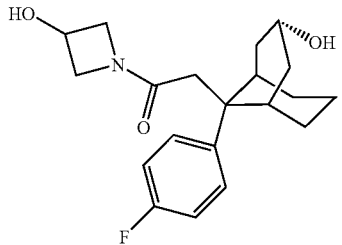

Compound 23A. 2,2-Dimethyl-5-(3-methylenebicyclo[3.3.1]nonan-9-ylidene)-1,3-dioxane-4,6-dione

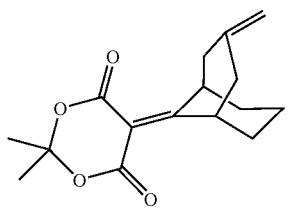

Compound 23A can be prepared from 3-methylenebicyclo[3.3.1]nonan-9-one (reference: Buono, F., Tenaglia, A., *J. Org. Chem.*, 65:3869-3874 (2000)) and Meldrum's acid by following the procedure in Example 1 and 2. $^1$H NMR (400 MHz, CDCl$_3$) δ ppm 4.82 (t, J=2.1 Hz, 2H), 4.06 (s, 2H), 2.56-2.77 (m, 4H), 2.33-2.55 (m, 1H), 1.98-2.14 (m, 2H), 1.80-1.95 (m, 2H), 1.77 (s, 3H), 1.80 (s, 3H), 1.29-1.40 (m, 1H).

Compound 23B. 5-(9-(4-Fluorophenyl)-3-methylenebicyclo[3.3.1]nonan-9-yl)-2,2-dimethyl-1,3-dioxane-4,6-dione and its Regioisomer

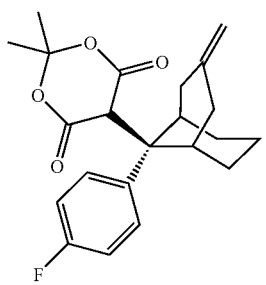

23B

-continued

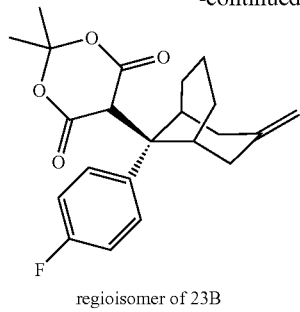

regioisomer of 23B

To a suspension of copper(I)bromide (0.416 g, 2.90 mmol) in dry THF (15 mL) at −2° C. under argon was added 4-fluorophenylmagnesium bromide (6.4 mL, 6.37 mmol, 1.0 M in THF) dropwise. Upon completion of addition, the resulting mixture was stirred at −2° C. for 10 min, and then a solution of compound 23A (0.8 g, 2.90 mmol) in THF (15 mL) was added through a cannula. The reaction mixture was then allowed to warm to RT where it was stirred under argon for about 16 hours. At the conclusion of this period, the reaction mixture was quenched with NH$_4$Cl (saturated aqueous solution, 20 mL) and then extracted with EtOAc (3×30 mL). The combined organic layers were dried over Na$_2$SO$_4$ and filtered. The filtrate was concentrated under reduced pressure to provide compound 23B and its regioisomer as yellow oil.

Compound 23C. 2-(9-(4-Fluorophenyl)-3-methylenebicyclo[3.3.1]nonan-9-yl)acetic acid and its Regioisomer 23D

23C

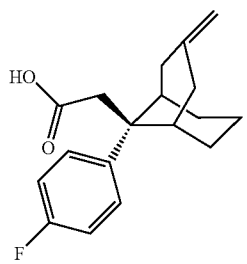

23D

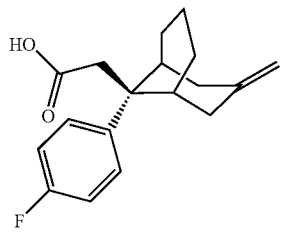

(regioisomer of 23C)

Compound 23B and its regioisomer in DMF-H$_2$O (5 mL, 10:1 v/v) were heated in 110° C. oil bath for 12 hours. Solvent was removed and the residue was purified via PrepHPLC to provide 23C as a lightly yellow solid (59 mg, 7.1% yield), along with its regioisomer 23D as white solid (186 mg, 22.3% yield). $^1$H NMR of 23C suggests that it contains about 32% of its regioisomer (as the structure shown above). 23D (Regioisomer of 23C): $^1$H NMR (400 MHz, CD$_3$OD) δ ppm 7.32-7.38 (m, 2H), 7.00 (t, J=8.6 Hz, 2H), 4.55 (t, J=2.6 Hz, 2H), 2.76 (s, 2H), 2.69 (s, 2H), 2.62 (d, J=12.7 Hz, 2H), 2.19-2.26 (m, 3H), 2.05-2.19 (m, 2H), 1.71-1.81 (m, 2H), 1.37-1.47 (m, 1H). LC/MS (m/z)=287 (M–H)+

Compound 23E. 2-(9-(4-Fluorophenyl)-3-oxobicyclo[3.3.1]nonan-9-yl)acetic acid

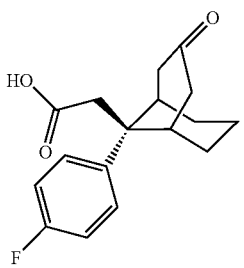

To a solution of compound 23C (59 mg, 0.205 mmol) in MeOH (3 mL) and CH₂Cl₂ (3 mL) at −78° C. was bubbled O₃/O₂ until a light blue color persisted for 10 minutes. Nitrogen gas was bubbled into the above solution to get rid of excess O₃. Then 2 mL of Me₂S was added in one portion. The mixture was gradually warmed to room temperature overnight. Solvent was removed under reduced pressure. The residue was purified via Prep HPLC to afford compound 23E as white solid (21 mg, 35% yield). LC/MS (m/z)=289 (M–H)+; ¹H NMR (400 MHz, CDCl₃) δ ppm 7.33-7.41 (m, 2H), 6.99-7.09 (m, 2H), 3.03 (s, 2H), 2.88-2.99 (m, 2H), 2.67 (s, 2H), 2.51 (d, J=18.9 Hz, 2H), 1.73-1.89 (m, 2H), 1.48 (dd, J=13.8, 2.4 Hz, 2H), 1.30-1.42 (m, 2H).

Compound 23F. 2-((3s,9s)-9-(4-Fluorophenyl)-3-hydroxybicyclo[3.3.1]nonan-9-yl)acetic acid

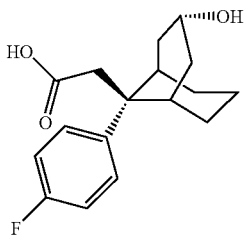

To a solution of compound 23E (20 mg, 0.069 mmol) in dry THF (0.7 mL) at −78° C. under nitrogen was added L-selectride (0.17 mL, 1 M in THF, 0.17 mmol) dropwise. The mixture was stirred at this temperature for 5 hours, then at −20° C. overnight. It was quenched with 20 μL of H₂O₂ (30% aqueous), acidified with HOAc (30 μL). Solvent was evaporated and the residue was purified via Prep HPLC to afford compound 23F as white solid (16 mg, 80% yield). HPLC Rt (Method B): 6.705 min; HRMS (ESI): Calculated for C₁₇H₂₁FO₃: 292.1474, found: 291.1406 (M–H)−. ¹H NMR (400 MHz, CDCl₃) δ ppm 7.30-7.35 (m, 2H), 6.93-7.10 (m, 2H), 4.26 (t, J=7.5 Hz, 1H), 3.75 (br., 1H, —OH), 3.34-3.40 (m, 1H), 2.86-3.10 (m, 1H), 2.57-2.71 (m, 3H), 2.45-2.56 (m, 1H), 2.43 (s, 2H), 1.63-1.80 (m, 3H), 1.30-1.53 (m, 2H), 1.07-1.21 (m, 1H).

Example 23

To a suspension of compound 23F (17 mg, 0.058 mmol), 3-hydroxyazetidine hydrochloride salt (9.6 mg, 0.087 mmol), EDAC (16.7 mg, 0.087 mmol), HOBt (11.8 mg, 0.087 mmol) in CH₂Cl₂ (1 mL) was added i-Pr₂NEt (15.2 μL, 0.087 mmol). The mixture was stirred at room temperature overnight. Solvent was removed under reduced pressure and the residue was purified via Prep HPLC to afford example 23 as white solid (11 mg, 54% yield). HPLC Rt (Method B): 6.320 min; LC/MS (m/z)=348 (M–H)+; ¹H NMR (400 MHz, CDCl₃) δ ppm 7.19-7.34 (m, 2H), 6.97 (t, J=8.6 Hz, 2H), 4.18 (t, J=8.0 Hz, 1H), 3.98 (tt, J=6.8, 4.5 Hz, 1H), 3.66-3.83 (m, 1H), 3.39 (dd, J=10.9, 5.3 Hz, 1H), 3.21-3.34 (m, 1H), 2.80-3.12 (m, 6H), 2.30-2.78 (m, 4H), 2.07-2.30 (m, 1H), 1.86-2.07 (m, 1H), 1.54-1.73 (m, 2H), 1.22-1.40 (m, 2H), 0.97-1.20 (m, 1H).

Example 24

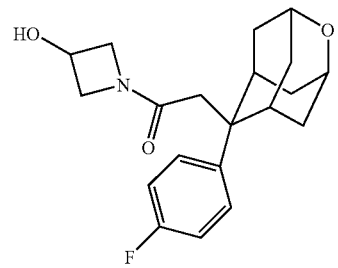

Compound 24A

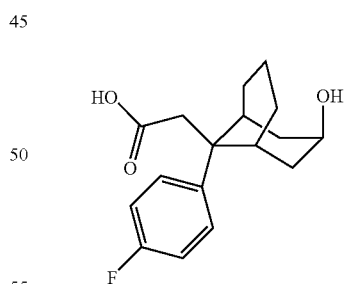

Compound 24A was synthesized via ozonolysis of compound 23D, followed by L-selectride reduction (see the procedure described in Example 23). Yield 34% (two steps). HPLC Rt (Method B): 5.906 min; LC/MS (m/z)=291 (M–H)−, ¹H NMR (400 MHz, CDCl₃) δ ppm 7.30-7.39 (m, 2H), 6.93-7.05 (m, 2H), 3.24 (quin, J=7.8 Hz, 1H), 2.77 (d, J=9.3 Hz, 2H), 2.63 (s, 2H), 2.21-2.34 (m, 2H), 2.01-2.14 (m, 2H), 1.86-2.00 (m, 2H), 1.47-1.60 (m, 3H), 1.25-1.38 (m, 2H).

Compound 24B. Methyl 2-(9-(4-fluorophenyl)-3-hydroxybicyclo[3.3.1]nonan-9-yl)acetate

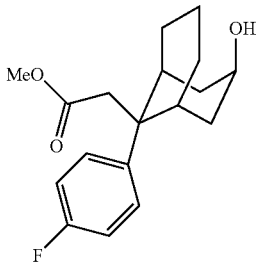

To a solution of KOH (aqueous, prepared from 5.0 g of KOH and 7.6 mL of H$_2$O) and Et$_2$O (8 mL) at 0° C. was added 1-methyl-3-nitro-1-nitrosoguanidine (MNNG, 460 mg) in portion. The ether layer turned to yellow. After 5 minutes, the flask was cooled to –78° C. The ether layer was added dropwise to a solution of compound 24A (89.6 mg, 0.307 mmol) in CH$_2$Cl$_2$ (4 mL) at 0° C., until the yellow color remained for 10 minutes. Solvent was removed and the residue was purified in column chromatography (SiO$_2$, 45% EtOAc in n-hexane) to provide compound 24B as white solid (93 mg, 99% yield). HPLC Rt (Method B): 7.011 min; LC/MS (m/z)=307 (M+H)$^+$, $^1$H NMR (400 MHz, CDCl$_3$) δ ppm 7.29-7.36 (m, 2H), 6.91-7.06 (m, 2H), 3.30 (s, 3H), 3.16-3.28 (m, 1H), 2.76 (d, J=9.1 Hz, 2H), 2.61 (s, 2H), 2.21-2.34 (m, 2H), 1.89-2.14 (m, 3H), 1.47-1.60 (m, 2H), 1.23-1.40 (m, 3H).

Compound 24C

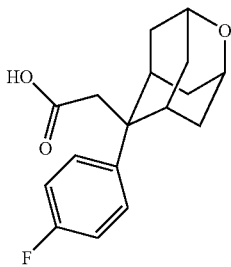

Compound 24B (46.5 mg, 0.152 mmol), iodobenzene diacetate (IBD, 58.7 mg, 0.182 mmol), and iodine (38.6 mg, 0.152 mmol) in cyclohexane (2.5 mL) was heated to 50-65° C. for 4 hours, under the irradiation of a 100 W normal light bulb. A solution of sodium sulfite (saturated aqueous, 4 mL) was added to remove excess I$_2$. It was extracted with Et$_2$O (3×5 mL). Combined organic layers were concentrated to dryness. The residue and Bu$_3$SnH (0.1 mL) in Benzene (3 mL) was heated to reflux for 4 hours. Solvent was removed. The resulting residue was heated in THF (0.5 mL) and LiOH (saturated aqueous, 0.5 mL) at 70° C. overnight. It was acidified with HOAc (0.4 mL) and the solvent was then removed. The residue was purified via Prep HPLC to afford compound 24C as white solid (20 mg, 45% yield). HPLC Rt (Method B): 6.460 min; LC/MS (m/z)=289 (M–H)$^-$, $^1$H NMR (400 MHz, CD$_3$OD) δ ppm 7.30-7.37 (m, 2H), 6.98-7.06 (m, 2H), 4.05 (br. s., 1H), 3.83 (br. s., 1H), 2.79 (br. s., 2H), 2.70 (s, 2H), 2.15-2.25 (m, 2H), 2.10 (m, 2H), 1.96 (d, J=12.6 Hz, 2H), 1.70 (m, 2H).

Example 24

Example 24 was synthesized from compound 24B and 3-hydroxyazetidine hydrochloride via standard peptide coupling reaction (see procedure in Example 23). Yield: 59%. HPLC Rt (Method B): 5.918 min; LC/MS (m/z)=346 (M+H)$^+$, $^1$H NMR (400 MHz, CDCl$_3$) δ ppm 7.37 (dd, J=8.7, 5.4 Hz, 2H), 7.07 (t, J=7.8 Hz, 2H), 4.18 (tt, J=6.7, 4.3 Hz, 1H), 4.05 (br. s., 1H), 3.88-3.98 (m, 1H), 3.82 (br. s., 1H), 3.52 (dd, J=10.9, 3.5 Hz, 1H), 3.22-3.30 (m, 1H), 2.95 (dd, J=8.7, 3.7 Hz, 1H), 2.81 (d, J=14.9 Hz, 2H), 2.32-2.49 (m, 2H), 2.09-2.25 (m, 4H), 1.95 (d, J=12.4 Hz, 2H), 1.53-1.68 (m, 2H).

Example 25

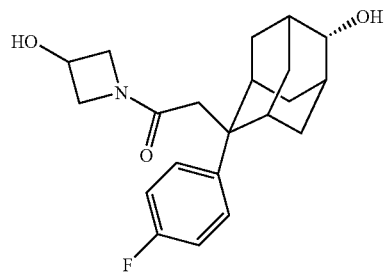

Compounds 25A and 25B

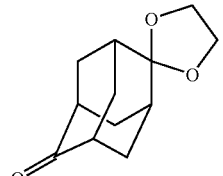

25A

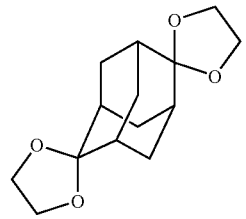

25B

A solution of 2,6-adamantanedione (9.5 g, 57.85 mmol), ethylene glycol (3.22 mL), and TsOH monohydrate (1.099 g, 5.785 mmol) in dry CH$_2$Cl$_2$ (870 mL) was stirred at room temperature overnight. Solvent was removed under reduced pressure and the residue was purified via column chromatography (SiO$_2$, 300 g ISCO cartridge, 25% EtOAc in n-Hexane) to provide compound 25A as white solid (8.688 g, 72% yield), along with compound 25B as white solid (1.868 g, 12.8% yield). 25A: $^1$H NMR (400 MHz, CDCl$_3$) δ ppm 3.72 (s, 4H), 2.12 (br. s., 2H), 1.95-2.08 (m, 4H), 1.54-1.68 (m, 6H).

Compound 25C

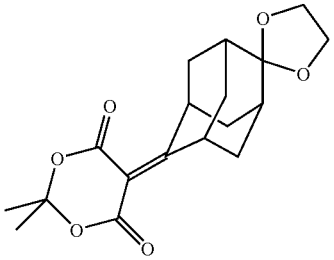

Compound 25C was synthesized from compound 25A and Meldrum's acid according to the procedure described in Example 1. $^1$H NMR (400 MHz, CDCl$_3$) δ ppm 4.00 (s, 4H), 3.97 (br. s., 2H), 2.32 (d, J=12.1 Hz, 4H), 1.91 (br. s., 2H), 1.84 (d, J=12.6 Hz, 4H), 1.76 (s, 6H).

Compound 25D

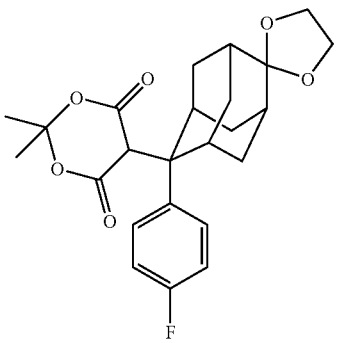

Compound 25D was synthesized from compound 25C and 4-fluorophenyl magnesium bromide according to the procedure described in Example 1. Yield 87%. HPLC Rt (Method B): 5.66 min; LC/MS (m/z)=429 (M−H)$^−$, $^1$H NMR (400 MHz, CDCl$_3$) δ ppm 7.20-7.25 (m, 2H), 7.01-7.09 (m, 2H), 4.28 (s, 1H), 3.88-4.00 (m, 4H), 2.91 (br. s., 2H), 2.13-2.34 (m, 4H), 1.90 (d, J=12.4 Hz, 3H), 1.67 (br. s., 2H), 1.53-1.60 (m, 1H), 1.49 (s, 3H), 0.79 (s, 3H).

Compound 25E

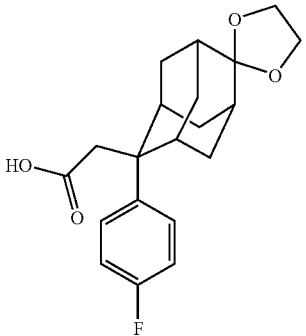

Compound 25E was synthesized from compound 25D via decarboxylation in DMF-H$_2$O at 110° C. according to the procedure described in Example 1. HPLC Rt (Method B): 4.60 min; LC/MS (m/z)=345 (M−H)$^−$; $^1$H NMR (400 MHz, CDCl$_3$) δ ppm 7.30 (dd, J=8.8, 5.3 Hz, 2H), 7.00 (t, J=8.8 Hz, 2H), 3.89-3.99 (m, 4H), 2.72 (s, 2H), 2.51 (br. s, 2H), 2.02-2.18 (m, 4H), 1.71-1.89 (m, 5H), 1.62 (br. s., 1H).

Compound 25F

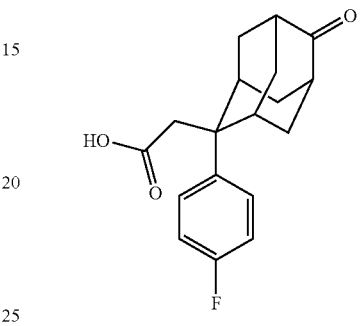

A solution of compound 25E (73.7 mg, 0.213 mmol) and TsOH monohydrate (4.81 mg, 0.025 mmol) in 70% acetone-water (1.2 mL) was heated in a 50° C. oil bath for 12 hours. Solvent was removed and the residue was purified via Prep HPLC to provide compound 25F as white solid (49.4 mg, 77% yield). HPLC Rt (Method A): 2.333 min; LC/MS (m/z)= 301 (M−H)$^−$; $^1$H NMR (400 MHz, CDCl$_3$) δ ppm 7.29-7.37 (m, 2H), 7.04 (t, J=8.7 Hz, 2H), 2.84 (s, 2H), 2.75 (br. s., 2H), 2.61 (br. s., 1H), 2.45-2.57 (m, 2H), 2.38 (br. s., 1H), 2.19 (d, J=13.1 Hz, 2H), 2.06 (d, J=14.1 Hz, 2H), 1.84 (d, J=13.6 Hz, 2H).

Compound 25G

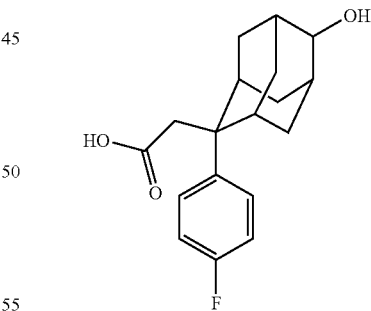

To a solution of compound 25F (20 mg, 0.066 mmol) in THF (0.5 mL) was added sodium borohydride (25 mg, 0.66 mmol) slowly. The mixture was stirred at room temperature for 30 minutes. It was quenched with HOAc (0.1 mL). Solvent was removed and the residue was purified via Prep HPLC to provide compound 25G as white solid (17 mg, 84% yield). HPLC Rt (Method A): 2.260 min; LC/MS (m/z)=303 (M−H)$^−$; $^1$H NMR (400 MHz, CDCl$_3$) δ ppm 7.22-7.33 (m, 2H), 6.99 (t, J=8.8 Hz, 2H), 3.81 (br. s., 1H), 2.62-2.70 (dd, 2H), 2.40-2.58 (m, 2H), 2.29 (dd, J=13.6, 3.1 Hz, 1H), 2.11-

2.23 (m, 1H), 1.82-1.99 (m, 4H), 1.66-1.80 (m, 2H), 1.60 (dd, J=13.0, 2.4 Hz, 1H), 1.52 (dd, J=13.2, 2.2 Hz, 1H).

Compounds 25H and 25I

25H

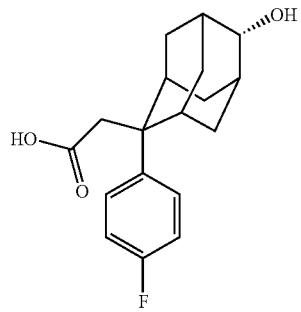

25I

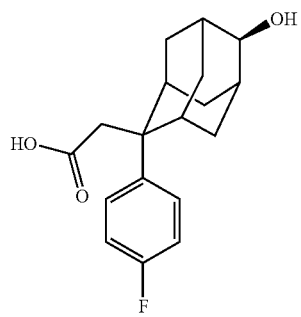

(enantiomer of 25H)

Racemic 25G (2.0 g) was subjected to chiral SFC purification (Chiralpak AD-H, 250×30 mm ID; 5 µm, Mobile Phase: CO$_2$/MeOH (70/30), Flow rate: 65 ml/min; UV Detection: 220 nm; Injection volume: 2 ml of 76 mg/ml in methanol) to provide compound 25H (retention time=15.2 minutes) and compound 25I (retention time=6.1 minutes). HPLC Rt (Method A): 2.260 min; LC/MS (m/z)=303 (M−H)$^-$; NMR spectra of 25H and 25I are identical to that of 25G.

25H: [α]$^D$=+30.6° (c=3.6 mg/mL, pyridine, t=25.5° C.). Chiral analytic HPLC: Chiralpak AD, 250×4.6 mm ID; 10 µm, room temperature, mobile phase: CO$_2$/MeOH/(80/20), Flow rate: 2 mL/min, UV Detection: 220 nm, Retention Time (min): 6.4. e.e.>99.9%.

25I: [α]$^D$=−26.5° (c=3.34 mg/mL, pyridine, t=25.5° C.). Chiral analytic HPLC: Chiralpak AD, 250×4.6 mm ID; 10 µm, room temperature, mobile phase: CO$_2$/MeOH/(80/20), Flow rate: 2 mL/min, UV Detection: 220 nm, Retention Time (min): 3.3. e.e.>99.9%.

Alternatively, compounds 25H and 25I can be prepared according to the following enzymatic conversions:

Screening of Ketoreductases

One mL of a solution containing 50 mM potassium phosphate buffer pH 7, 0.1 M KCl, 0.5 mM dithiothreitol, 5 mg/mL NADPH tetrasodium salt (6 mM), and compound 25F (1 mg/mL, 3.307 mM) was added to a microfuge tube or well of a 24-well plate containing about 1 to 5 mg of ketoreductase (available from Biocatalytics Inc.). The solutions were incubated for 15 to 17 h at 28° C. and then analyzed by HPLC. Enzymes that gave the most enantioselective reduction are set forth in Table 25-1 below.

TABLE 25-1

| Ketoreductase | Time hrs | Compound 25F mg/mL | Alcohol mg/mL | Compound 25H % e.e. |
|---|---|---|---|---|
| KRED 106 | 15 | 0.716 | 0.389 | 95.49 |
| KRED c1q | 15 | 0.844 | 0.186 | 95.03 |
| KRED A1Y | 16 | 0.806 | 0.200 | 94.84 |
| KRED 125 | 17 | 0.869 | 0.214 | 94.14 |
| KRED 102 | 15 | 0.034 | 1.039 | 93.27 |
| KRED A1K | 17 | 0.316 | 0.716 | 93.22 |
| KRED C1K | 15 | 0.930 | 0.092 | 91.42 |
| KRED A1O | 17 | 0.780 | 0.273 | 90.41 |
| KRED EXP-A1X | 16 | 0.195 | 0.760 | 80.81 |
| KRED A1L (c1) | 17 | 0.807 | 0.256 | 80.45 |
| KRED EXP-B1N | 16 | 0.088 | 0.875 | 76.34 |
| KRED b1y | 15 | 0.048 | 0.886 | 75.73 |
| KRED A1P (c5) | 17 | 1.032 | 0.026 | 75.58 |
| KRED A1H (b3) | 17 | 1.017 | 0.027 | 68.62 |
| KRED EXP-A1U | 16 | 0.104 | 0.830 | 65.18 |
| KRED b1t | 15 | 0.991 | 0.028 | 62.76 |
| KREDEXP-B1G | 16 | 0.373 | 0.649 | 61.19 |

Screening of Yeast Strains for Reduction of Compound 25F

Two mL F7 medium (1% malt extract, 1% yeast extract, 0.1% peptone and 2% dextrose adjusted to pH 7) was added to each well of 24-well plates containing 69 frozen yeast cultures (0.1 mL broth with 20% glycerol) for screening for reduction of compound 25F. The plates were incubated for 21 h at 28° C. and 600 rpm, then 10 µL of 100 mg/mL compound 25F slurried in methanol was added to each well. Incubation was continued for 48 h before analysis by HPLC as described above. Strains that gave the most enantioselective reduction are set forth in Table 25-2 below.

TABLE 25-2

| Strain | SC # | ATCC # | Compound 25F mg/mL | Alcohol mg/mL | Compound 25H % e.e. |
|---|---|---|---|---|---|
| *Pichia membranafaciens* | 13859 | 20101 | 0.399 | 0.010 | 100.00 |
| *Pichia anomala* | 16139 | 8168 | 0.323 | 0.009 | 100.00 |
| *Pichia anomala* | 16140 | 20029 | 0.350 | 0.010 | 100.00 |
| *Pichia anomala* | 16141 | 36995 | 0.395 | 0.020 | 100.00 |
| *Pichia anomala* | 16143 | 66346 | 0.489 | 0.022 | 100.00 |
| *Pichia anomala* | 16145 | 20144 | 0.448 | 0.013 | 100.00 |
| *Pichia ciferrii* | 16170 | 14091 | 0.234 | 0.031 | 100.00 |
| *Hansenula fabianii* | 13894 | 58045 | 0.074 | 0.516 | 100.00 |
| *Candida utilis* | 16524 | 42181 | 0.213 | 0.108 | 100.00 |
| *Candida boidini* | 13821 | | 0.300 | 0.082 | 100.00 |
| *Pichia silvicola* | 16160 | 16768 | 0.180 | 0.110 | 69.79 |
| *Rhodotorula glutinis* | 16293 | 201718 | 0.206 | 0.225 | 69.35 |
| *Hansenula polymorpha* | 13896 | 62809 | 0.268 | 0.315 | 51.54 |

Enzymatic Conversion of Compound 25F to Compound 25H

A 350 mL reaction mixture containing 0.1 M potassium phosphate buffer pH 8, 0.1 M KCl, 1 mM dithiothreitol, 1 mM NADP, glucose dehydrogenase (35 mg, 1540 U from Amano), glucose (3.5 g, 1.389 mmoles), ketoreductase KRED-102 (70 mg, 511 U from Biocatalytics) and compound 25F (700 mg, 0.165 mmoles) was incubated at 28° C. HPLC analysis after 17 h showed there was no remaining compound 25F.

The reaction mixture (350 mL, pH 7.56) was then acidified to pH 3.0 with 5M $H_2SO_4$ (4.75 g) and extracted with ethylacetate (2×250 mL). The combined ethylacetate phases were washed with 100 mL of 15% NaCl, dried over $MgSO_4$ for 2 h, and filtered. Solvent removal of the filtrate gave a white solid, which was further dried in a vacuum oven at room temperature overnight to give 745 mg of crude compound 25H (Yield 108%, AP 94, e.e. 96.1%).

Enzymatic Conversion of Ketone Compound 25F to Compound 25I Screening of Ketoreductases One mL of a solution containing 50 mM potassium phosphate buffer pH 7, 0.1 M KCl, 0.5 mM dithiothreitol, 5 mg/mL NADPH tetrasodium salt (6 mM), and compound 25F (1 mg/mL, 3.307 mM) was added to a microfuge tube or well of a 24-well plate containing about 1 to 5 mg keto reductase (available from Biocatalytics Inc.). The solutions were incubated for 15 to 17 h at 28° C. then analyzed by HPLC. Enzymes giving the most enantioselective reduction are shown in the Table 25-3 set forth below.

TABLE 25-3

| Ketoreductase | Time hrs | Compound 25F mg/mL | Alcohol mg/mL | Compound 25I % e.e. |
|---|---|---|---|---|
| KRED 101 | 15 | 0.570 | 0.537 | 93.08 |
| KRED 103 | 15 | 0.668 | 0.447 | 92.82 |
| KRED 112 | 15 | 0.725 | 0.391 | 92.39 |
| KRED A1V | 16 | 0.028 | 0.897 | 92.09 |
| KRED 114 | 15 | 0.669 | 0.448 | 85.03 |

Screening of Yeast Strains for Reduction of Compound 25F to Compound 25I

Yeast strains were screened for reduction of Compound 25F in a similar manner as described above. Strains giving the most enantioselective reduction are set forth in the Table 25-4 below.

TABLE 25-4

| Strain | SC # | ATCC # | Compound 25F mg/mL | Alcohol mg/mL | Compound 25I % e.e. |
|---|---|---|---|---|---|
| Pichia methanolica | 13825 | 58403 | 0.070 | 0.245 | 100.00 |
| Pichia methanolica | 16413 | 58372 | 0.260 | 0.245 | 100.00 |
| Pichia methanolica | 16414 | 56508 | 0.237 | 0.408 | 100.00 |
| Pichia methanolica | 16415 | 56509 | 0.120 | 0.472 | 100.00 |
| Pichia methanolica | 16416 | 46071 | 0.097 | 0.320 | 100.00 |
| Rhodotorula glutinis | 16267 | 26207 | 0.277 | 0.086 | 100.00 |
| Pichia methanolica | 13860 |  | 0.107 | 0.302 | 100.00 |
| Pichia methanolica | 16413 |  | 0.166 | 0.175 | 100.00 |
| Pichia methanolica | 16116 | 56508 | 0.035 | 0.286 | 94.98 |
| Pichia methanolica | 13860 | 56510 | 0.023 | 0.303 | 94.95 |

Example 25

Example 25 was synthesized from compound 25H and 3-hydroxyazetidine hydrochloride according to the procedure in Example 21. HPLC Rt (Method C): 5.376 min; LC/MS (m/z)=360 (M−H)$^-$; $^1$H NMR (400 MHz, CD$_3$OD) δ ppm 7.38 (br. s, 2H), 7.09 (t, J=8.3 Hz, 2H), 3.99-4.13 (m, 1H), 3.77-3.87 (m, 1H), 3.74 (br. s, 1H), 3.40 (ddd, J=10.4, 5.1, 4.9 Hz, 1H), 3.20-3.36 (m, 1H), 2.98-3.14 (m, 1H), 2.33-2.68 (m, 5H), 2.21 (d, J=13.6 Hz, 1H), 1.82-2.12 (m, 4H), 1.75 (d, J=13.6 Hz, 1H), 1.66 (br. s., 1H), 1.46-1.60 (m, 2H). Chiral analytic HPLC: Chiralpak AD, 250×4.6 mm ID; 10 μm, room temperature, mobile phase: CO$_2$/MeOH/(80/20), Flow rate: 2 mL/min, UV Detection: 220 nm, Retention Time (min): 10.64. e.e>99.9%.

Example 26

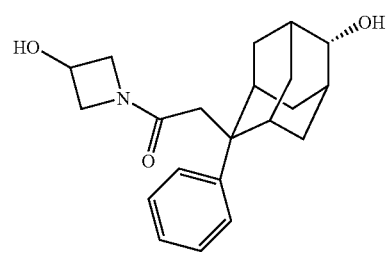

Compound 26A

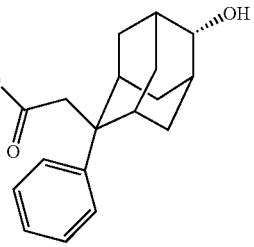

Compound 26A was synthesized from compound 25C by following the procedures described in Example 25. HPLC Rt (Method B): 6.263 min; LC/MS (m/z)=285 (M−H)$^-$; $^1$H NMR (400 MHz, CDCl$_3$) δ ppm 7.27-7.39 (m, 4H), 7.15-7.24

(m, 1H), 3.81 (br. s., 1H), 2.64-2.80 (m, 2H), 2.47-2.62 (m, 2H), 2.30 (dq, J=13.7, 3.3 Hz, 1H), 2.14-2.24 (m, 1H), 1.87-2.02 (m, 4H), 1.68-1.79 (m, 2H), 1.65 (dd, J=13.0, 2.7 Hz, 1H), 1.47-1.57 (m, 1H). $^{13}$C NMR (101 MHz, CDCl$_3$) δ ppm 176.06, 144.22, 128.27, 126.41, 126.00, 74.25, 45.95, 44.86, 34.03, 33.38, 32.34, 32.26, 31.56, 31.44, 26.86, 26.26. Chiral analytic HPLC: Chiralpak AD, 250×4.6 mm ID; 10 μm, room temperature, mobile phase: CO$_2$/MeOH/(70/30), Flow rate: 3 ml/min, UV Detection: 220 nm, Retention Time (min): 6.9. e.e>99.9%.

Example 26

Example 26 was synthesized from compound 26A by following the procedures described in Example 25. HPLC Rt (Method C): 7.89 min; LC/MS (m/z)=342 (M+H)$^+$; $^1$H NMR (400 MHz, CD$_3$OD) δ ppm 7.27 (br. s., 4H), 7.11-7.21 (m, 1H), 3.78-3.93 (m, 1H), 3.60-3.75 (m, 2H), 3.24-3.34 (m, 1H), 3.02 (t, J=7.3 Hz, 0.5H), 2.92 (d, J=5.7 Hz, 1H), 2.83 (dd, J=9.0, 4.2 Hz, 0.5H), 2.49-2.63 (m, 2H), 2.17-2.49 (m, 3H), 2.06-2.17 (m, 1H), 1.75-2.06 (m, 4H), 1.66 (d, J=13.6 Hz, 1H), 1.38-1.59 (m, 3H).

Example 27

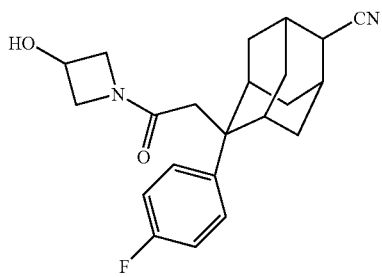

Compound 27A

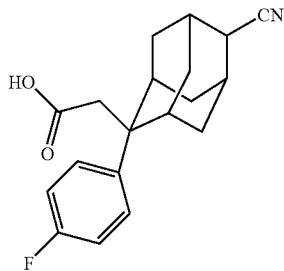

Potassium tert-butoxide (39.5 mg, 0.352 mmol) was added in a small portion to a well stirred, moisture-protected suspension of compound 25F (21.3 mg, 0.070 mmol), TOSMIC (19.26 mg, 0.099 mmol), and ethanol (6.89 μL) in 1,2-dimethoxyethane (403 μL) at 0° C. (ice water bath). After completion, the mixture was warmed to room temperature, then placed in a 37° C. oil bath and stirred for 1 hour. LCMS showed the reaction was completed. The reaction was quenched with HOAc (0.1 mL). Solvent was removed under reduced pressure. The residue was dissolved in MeOH, and purified via Prep HPLC (Phenomenex AXIA 5 u C18 30×100 mm, Flow rate: 40 mL, Solvent A: 90% H$_2$O and 10% MeOH with 0.1% TFA, Solvent B: 90% MeOH and 10% H$_2$O with 0.1% TFA. 0% to 100% B in 12 min gradient, stop at 15 min, the product RT=11.146 min) to provide compound 27A as white solid (14.6 mg, 66% yield). HPLC Rt (Method B): 7.125 min; LC/MS (m/z)=312 (M−H)$^−$; $^1$H NMR (400 MHz, CD$_3$OD) δ ppm 7.37 (dd, J=8.7, 5.4 Hz, 2H), 7.03 (t, J=8.8 Hz, 2H), 3.03 (br. s., 1H), 2.63-2.79 (m, 4H), 2.42 (dd, J=13.9, 2.8 Hz, 1H), 2.32 (d, J=13.6 Hz, 1H), 2.09-2.26 (m, 2H), 1.90-2.01 (m, 3H), 1.80-1.90 (m, 2H), 1.60-1.69 (m, 1H).

Example 27

Example 27 was synthesized from compound 27A and 3-hydroxyazetidine hydrochloride via standard peptide coupling reaction (see procedure in Example 23). Yield: 62.3%. HPLC Rt (Method C): 6.741 min; LC/MS (m/z)=369 (M+H)$^+$; $^1$H NMR (400 MHz, CD$_3$OD) δ ppm 7.38 (br. s., 2H), 7.11 (t, J=8.8 Hz, 2H), 4.00-4.12 (m, 1H), 3.76-3.87 (m, 1H), 3.40 (dd, J=10.4, 4.5 Hz, 1H), 3.32-3.37 (m, 1H), 2.96-3.12 (m, 2H), 2.72 (br. s., 2H), 2.58 (dd, J=18.8, 13.3 Hz, 1H), 2.30-2.52 (m, 3H), 2.09-2.23 (m, 2H), 1.77-1.99 (m, 5H), 1.66 (d, J=2.8 Hz, 1H).

Example 28

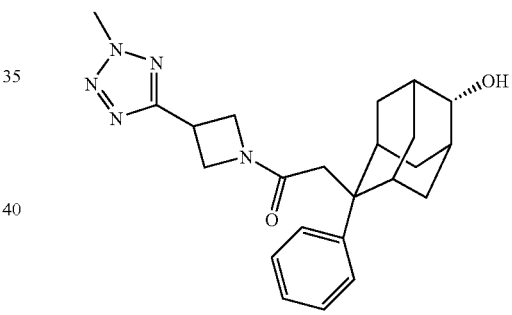

Compound 28A. tert-Butyl 3-(2H-tetrazol-5-yl)azetidine-1-carboxylate

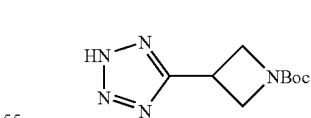

Tert-butyl 3-cyanoazetidine-1-carboxylate (493.8 mg, 2.713 mmol) and azidotrimethyltin (920 mg, 4.34 mmol) in dry toluene (13 mL) were placed in sealed tube and heated in 100° C. oil bath for 18 hours. Solvent was removed under reduced pressure and the residue was purified via Prep HPLC to provide compound 28A as a light yellow oil (474 mg, 77.6% yield). $^1$H NMR (400 MHz, CDCl$_3$) δ ppm 4.42-4.52 (m, 2H), 4.28-4.35 (m, 2H), 4.18-4.28 (m, 1H), 1.43-1.49 (s, 9H).

Compound 28B and Regioisomer 28C

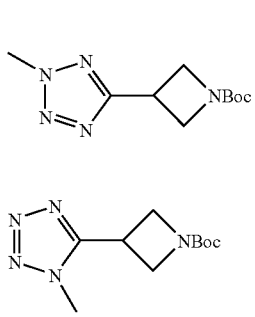

Compound 28A (0.474 mg, 2.107 mmol) and K$_2$CO$_3$ (291 mg, 2.107 mmol) in acetone (4 mL) was heated to reflux for 2 hours under argon. Methyl iodide (138 μL, 2.21 mmol) was introduced. The resulting mixture was heated to reflux for another 6 hours. EtOAc (10 mL) was added to the cooled mixture, which was stirred for 5 minutes. Solid was filtered off and rinsed with EtOAc (3×5 mL). Organic solvent was evaporated. The residue was purified via column chromatography (SiO$_2$, 40-60% EtOAc/n-Hexane) to provide compound 28B as colorless oil (228 mg, 45.3% yield), along with compound 28C as colorless oil (131 mg, 26% yield). 28B: $^1$H NMR (400 MHz, CDCl$_3$) δ ppm 4.30-4.40 (m, 2H), 4.35 (s, 3H), 4.17-4.25 (m, 2H), 3.99-4.11 (m, 1H), 1.46 (s, 9H). 28C: $^1$H NMR (400 MHz, CDCl$_3$) δ ppm 4.39 (t, J=8.6 Hz, 2H), 4.30 (br. s., 2H), 3.95-4.06 (m, 1H), 4.01 (s, 3H), 1.41-1.50 (m, 9H).

Compound 28D

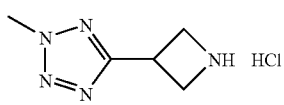

To a solution of compound 28B (228 mg, 0.954 mmol) in MeOH (8.5 mL) was added 4 M HCl in dioxane (3.3 mL). The mixture was stirred at room temperature for 5 hours. Solvent was removed under reduced pressure to afford compound 28D as lightly yellow solid (198 mg, 100% yield).

Example 28

Example 28 was synthesized from compound 28D and the corresponding carboxylic acid 26A by following the procedures described in Example 26. HPLC Rt (Method B): 6.450 min; LC/MS (m/z)=408 (M+H)$^+$; $^1$H NMR (400 MHz, CDCl$_3$) δ ppm 7.28-7.45 (m, 4H), 7.09-7.22 (m, 1H), 4.31 (d, rotomers, 3H), 4.16-4.28 (m, 2H), 4.06-4.16 (m, 1H), 3.96-4.06 (m, 1H), 3.83 (br. s., 1H), 3.44-3.59 (m, rotomer, 1.5H), 3.21-3.36 (m, 1H), 3.05-3.15 (m, rotomer, 0.5H), 2.69-2.80 (m, 1H), 2.32-2.69 (m, 3H), 1.46-2.26 (m, 9H).

Example 29

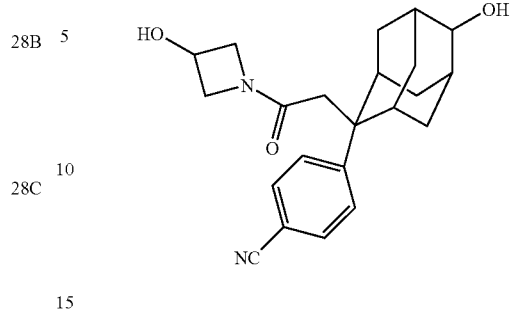

Compound 29A

Compound 29A was synthesized from compound 25C by following the procedures described in Example 25. HPLC Rt (Method C): 7.27 min; LC/MS (m/z)=319 (M−H)$^-$; $^1$H NMR (400 MHz, CD$_3$OD) δ ppm 7.31-7.40 (m, 2H), 7.24-7.31 (m, 2H), 3.75 (br. s., 1H), 2.63-2.79 (m, 2H), 2.47-2.61 (m, 2H), 2.31-2.42 (m, 1H), 2.22 (dd, J=13.5, 2.1 Hz, 1H), 1.95-2.06 (m, 2H), 1.85-1.95 (m, 2H), 1.75 (dd, J=13.6, 2.3 Hz, 1H), 1.67 (br. s., 1H), 1.56 (d, 2H).

Compound 29B

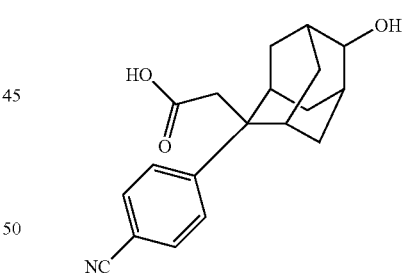

Compound 29A (56 mg, 0.175 mmol), nickel(II)bromide (275 mg, 1.257 mmol), sodium cyanide (25.7 mg, 0.524 mmol), and zinc cyanide (36.5 mg, 0.311 mmol) were placed in microwave vial under argon atmosphere. NMP (14 mL) was added. The reaction mixture was heated to 200° C. in microwave for 40 min. The resulting solid was filtered off and rinsed with MeOH. The filtrate was concentrated under reduced pressure to afford the crude product. The crude product was purified via Prep HPLC to provide compound 29B as a light brown oil (35 mg, 60.7% yield). LC/MS (m/z)=310 (M−H)$^-$; $^1$H NMR (400 MHz, CD$_3$OD) δ ppm 7.68 (t, J=8.6 Hz, 2H), 7.59 (t, J=8.1 Hz, 2H), 3.98 (s, 2H), 2.71-2.86 (m, 2H), 2.54-2.70 (m, 2H), 2.32-2.53 (m, 1H), 2.06-2.29 (m, 2H), 2.02 (dd, J=13.4, 2.5 Hz, 1H), 1.43-1.98 (m, 6H).

Example 29

Example 29 was synthesized from compound 29B and 3-hydroxyazetidine hydrochloride via standard peptide coupling reaction (see procedure in Example 23). Yield: 64.8%. HPLC Rt (Method C): 4.925 min; LC/MS (m/z)=367 (M+H)$^+$; $^1$H NMR (400 MHz, CDCl$_3$) δ ppm 7.67 (d, J=7.5 Hz, 2H), 7.52 (d, J=8.3 Hz, 2H), 4.15-4.27 (m, 1H), 3.84-3.97 (m, 1H), 3.82 (br. s., 1H), 3.75 (t, J=6.4 Hz, 1H), 3.50 (td, J=10.9, 4.2 Hz, 1H), 3.21-3.44 (m, 1H), 2.86-3.12 (m, 1H), 2.67 (d, J=15.4 Hz, 1H), 2.46-2.60 (m, 2H), 2.29-2.46 (m, 2H), 2.15-2.29 (m, 1H), 1.93-2.12 (m, 1H), 1.39-1.92 (m, 6H).

Example 30

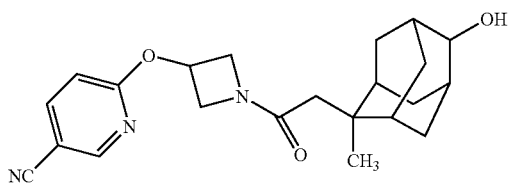

Compound 30A

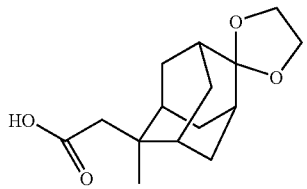

To a solution of compound 25C (0.278 g, 0.831 mmol) in dry THF (5 mL) at −78° C. under argon was added methyl magnesium bromide (0.97 mL, 2.91 mmol, 3.0 M solution in THF) slowly. The mixture was stirred and gradually warmed to room temperature overnight. NH$_4$Cl (saturated aqueous, 10 mL) was added to quench the reaction. It was extracted with EtOAc (3×15 mL). Combined organic layers were dried (Na$_2$SO$_4$), concentrated to afford white solid. A suspension of this solid in DMF-H$_2$O (5 mL, 10:1 v/v) was heated in 110° C. oil bath for 12 hours. Solvent was removed under reduced pressure. The residue was purified via Prep HPLC to provide compound 30A as white solid (120 mg, 54.3% two steps).

Compound 30B

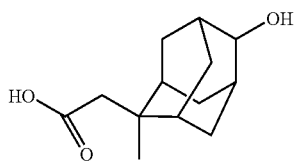

Compound 30B was synthesized from compound 30A via the procedure described in Example 25. Yield: 69% for two steps. LC/MS (m/z)=223 (M−H)$^-$; $^1$H NMR (400 MHz, CD$_3$OD) δ ppm 3.67-3.75 (m, 1H), 2.41-2.58 (m, 2H), 2.22 (ddd, J=13.6, 6.8, 3.4 Hz, 2H), 2.00 (dd, J=13.0, 1.6 Hz, 2H), 1.86 (br. s., 1H), 1.75-1.85 (m, 3H), 1.59 (br. s., 1H), 1.54 (br. s., 1H), 1.51 (br. s., 2H), 1.20 (s, 3H). $^{13}$C NMR (101 MHz, CD$_3$OD) δ ppm 176.87, 75.69, 44.54, 39.36, 37.05, 36.10, 35.40, 35.16, 32.94, 32.90, 27.52, 23.89.

Compound 30C

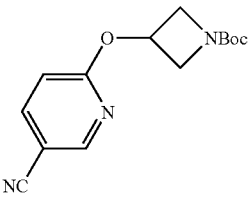

To a suspension of NaH (114 mg, 95%, 4.51 mmol) in dry DMF (10 mL) at 0° C. was added tert-butyl 3-hydroxyazetidine-1-carboxylate (724.7 mg, 4.1 mmol) under argon. The mixture was heated in 40° C. oil bath for 1 hour. To the above mixture at room temperature was added 6-chloronicotinonitrile (638 mg, 4.51 mmol). After heating at 40° C. in an oil bath for 3 hours, the mixture was allowed to cool to room temperature overnight. It was quenched with water (50 mL) and then extracted with EtOAc (3×20 mL). The combined organic layers were dried (Na$_2$SO$_4$) and concentrated. The crude product was purified via column chromatography (SiO$_2$, 25-30% EtOAc/n-Hexane) to provide compound 30C as a white solid (1.0 g, 88.6%). LC/MS (m/z)=276 (M+H)$^+$; $^1$H NMR (400 MHz, CDCl$_3$) δ ppm 8.45 (d, J=2.2 Hz, 1H), 7.84 (dd, J=8.8, 2.2 Hz, 1H), 6.89 (d, J=9.2 Hz, 1H), 5.30-5.42 (m, 1H), 4.34 (dd, J=11.0, 6.6 Hz, 2H), 3.98 (dd, J=11.2, 4.2 Hz, 2H), 1.46 (s, 9H). $^{13}$C NMR (101 MHz, CDCl$_3$) δ ppm 164.26, 156.11, 151.86, 141.43, 116.88, 112.00, 103.38, 79.84, 65.78, 56.32, 28.35.

Compound 30D

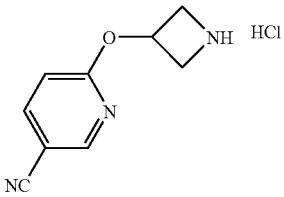

Compound 30D was synthesized from compound 30C via the procedure described in Example 28. LC/MS (m/z)=176 (M+H)$^+$.

Example 30

Example 30 was synthesized from compound 30B and 30D via standard peptide coupling reaction (see procedure in Example 23). LC/MS (m/z)=382 (M+H)$^+$; $^1$H NMR (400 MHz, CDCl$_3$) δ ppm 8.46 (d, J=2.2 Hz, 1H), 7.85 (dd, J=8.6, 2.4 Hz, 1H), 6.91 (d, J=8.3 Hz, 1H), 5.33-5.45 (m, 1H), 4.56 (dd, J=8.3, 6.6 Hz, 1H), 4.40 (dd, J=11.2, 6.8 Hz, 1H), 4.14 (dd, J=9.7, 4.0 Hz, 1H), 4.05 (dd, J=11.2, 4.2 Hz, 1H), 3.77 (br. s., 1H), 3.50 (s, 1H), 2.32-2.43 (m, 1H), 2.11-2.29 (m, 3H), 1.89-2.03 (m, 2H), 1.85 (br. s., 3H), 1.72 (br. s., 1H), 1.44-1.64 (m, 3H), 1.17 (s, 3H).

Example 31

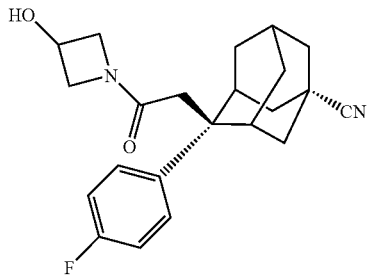

Compound 31A

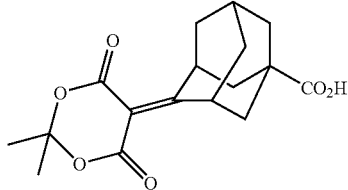

Compound 31A was synthesized from 4-oxo-1-adamantanecarboxylic acid and Meldrum's acid via the procedure described in Example 25. $^1$H NMR (400 MHz, CD$_3$OD) δ ppm 4.06 (br. s., 2H), 2.00-2.26 (m, 9H), 1.86-1.99 (m, 2H), 1.75 (s, 3H), 1.74 (s, 3H); $^{13}$C NMR (101 MHz, CD$_3$OD) δ ppm 187.06, 162.36, 113.90, 105.28, 41.94, 40.86, 40.40, 38.89, 36.78, 28.72, 27.11, 26.93.

Compound 31B and its Regioisomer 31C

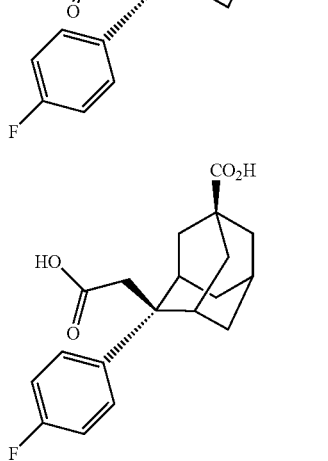

Compound 31B and its regioisomer 31C were synthesized from compound 31A and 4-fluorophenyl magnesium bromide via cuprate addition reaction and decarboxylation reaction using the procedures described in Example 25. The ratio of 31B:31C is about 2.3:1.

31B: LC/MS (m/z)=331 (M–H)$^-$; $^1$H NMR (400 MHz, CD$_3$OD) δ ppm 7.33-7.44 (m, 2H), 7.02 (t, J=8.8 Hz, 2H), 2.77 (br. s., 2H), 2.72 (s, 2H), 2.30 (d, J=12.9 Hz, 2H), 2.08 (br. s., 1H), 1.98 (d, J=12.9 Hz, 2H), 1.87 (br. s., 2H), 1.66-1.82 (m, 4H)

31C: LC/MS (m/z)=331 (M–H)$^-$; $^1$H NMR (400 MHz, CD$_3$OD) δ ppm 7.35-7.42 (m, 2H), 6.98-7.06 (m, 2H), 2.73-2.81 (m, 2H), 2.68 (s, 2H), 2.43 (d, J=13.1 Hz, 2H), 1.94 (d, J=13.1 Hz, 2H), 1.79-1.90 (m, 6H), 1.57 (d, 2H).

Compound 31D

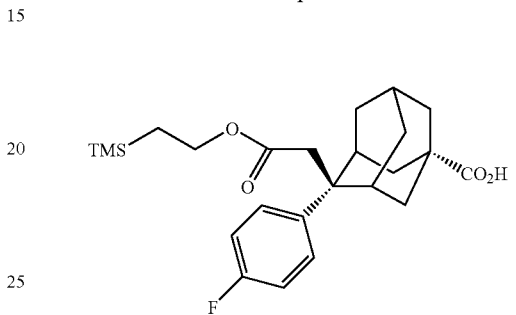

To a solution of Compound 31B (27.6 mg, 0.083 mmol), 2-(trimethylsilyl)ethanol (10.3 mg, 0.087 mmol), and DMAP (15.2 mg, 0.125 mmol) in dry CH$_2$Cl$_2$ at 0° C. was added EDAC (19.1 mg, 0.10 mmol), followed by i-Pr$_2$NEt (17.4 μL, 0.10 mmol). The mixture was stirred and gradually warmed to room temperature overnight. Solvent was removed under reduced pressure; the residue was purified via Prep HPLC to provide compound 31D as white solid (25.3 mg, 70.4% yield). HPLC Rt (Method A): 6.335 min; $^1$H NMR (400 MHz, CDCl$_3$) δ ppm 7.19-7.27 (m, 2H), 6.97 (t, J=8.5 Hz, 2H), 3.71-3.81 (m, 2H), 2.70 (br. s., 2H), 2.65 (s, 2H), 2.21 (d, J=12.6 Hz, 2H), 2.10 (br. s., 1H), 1.95 (d, J=12.6 Hz, 2H), 1.84 (br. s., 2H), 1.74 (t, J=14.6 Hz, 4H), 0.57-0.67 (m, 2H), –0.06 (s, 9H).

Compound 31E

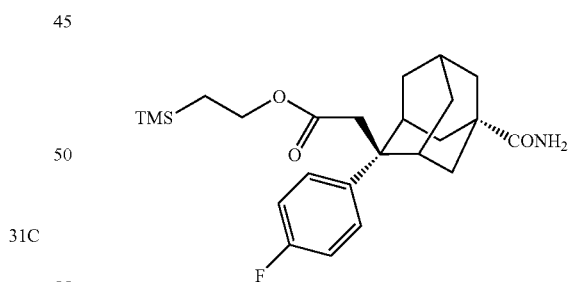

A mixture of compound 31D (24 mg, 0.0556 mmol), HOBt (11.3 mg, 0.0834 mmol), NH$_4$Cl (6 mg, 0.111 mmol), EDAC (16 mg, 0.0834 mmol), and i-Pr$_2$NEt (34 μL, 0.195 mmol) in dry DMF (0.7 mL) was heated in 65° C. oil bath for 2 hours. Solvent was removed and the residue was purified via Prep HPLC to provide compound 31E as white solid (22.8 mg, 95% yield). HPLC Rt (Method A): 7.266 min; LC/MS (m/z)= 432 (M+H)$^+$; $^1$H NMR (400 MHz, CDCl$_3$) δ ppm 7.26-7.36 (m, 2H), 7.00-7.11 (m, 2H), 6.82 (br. s., 1H), 5.76 (br. s., 1H), 3.78-3.88 (m, 2H), 2.82 (br. s, 2H), 2.72 (s, 2H), 2.30 (d, J=13.1 Hz, 2H), 2.21 (d, J=2.8 Hz, 1H), 2.00 (d, J=12.4 Hz, 2H), 1.90 (br. s., 2H), 1.72-1.88 (m, 4H), 0.62-0.74 (m, 2H), −0.03-0.04 (m, 9H). $^{13}$C NMR (101 MHz, CDCl$_3$) δ ppm 182.45, 171.51, 162.27, 161.20, 159.83, 139.65, 139.62, 127.90, 127.81, 115.32, 115.11, 62.20, 45.38, 44.78, 40.36, 40.10, 34.80, 32.67, 31.65, 26.71, 17.06, −1.67.

Compound 31F

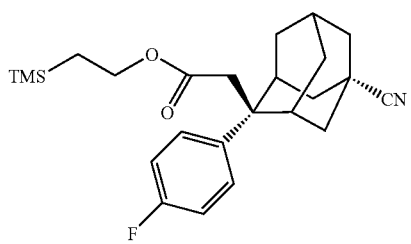

To a solution of compound 31E (22.8 mg, 0.0529 mmol) in pyridine (0.5 mL) at room temperature was added MsCl (16.4 mL, 0.211 mmol). The mixture was stirred at room temperature overnight. Solvent was removed and the residue was purified via Prep HPLC to provide compound 31F as white solid (16.7 mg, 76.4% yield). $^1$H NMR (400 MHz, CDCl$_3$) δ ppm 7.25-7.34 (m, 2H), 7.08 (t, J=8.6 Hz, 2H), 3.79-3.88 (m, 2H), 2.79 (br. s., 2H), 2.70 (s, 2H), 2.14-2.34 (m, 4H), 2.07 (br. s., 2H), 1.80-1.99 (m, 4H), 1.75 (br. s., 1H), 0.63-0.73 (m, 2H), −0.04-0.04 (m, 9H).

Compound 31G

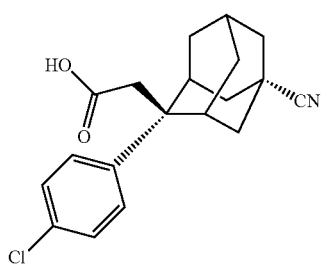

A solution of compound 31F (16.7 mg, 0.040 mmol) in TBAF-HOAc (0.25 mL, prepared from 1.0 M TBAF in THF and HOAc in equal molar ratio) was placed in sealed tube and heated in 70° C. oil bath for 48 hours. Solvent was removed and the residue was purified via Prep HPLC to provide compound 31G as white solid (10 mg, 79% yield). LC/MS (m/z)= 312 (M−H)$^-$; $^1$H NMR (400 MHz, CDCl$_3$) δ ppm 7.24 (dd, J=8.8, 5.3 Hz, 2H), 7.03 (t, J=8.6 Hz, 2H), 2.73 (br. s., 2H), 2.69 (s, 2H), 2.08-2.24 (m, 5H), 2.03 (br. s., 2H), 1.88 (d, J=12.7 Hz, 2H), 1.81 (d, 2H).

Example 31

Example 31 was synthesized from compound 31G and 3-hydroxyazetidine hydrochloride via standard peptide coupling reaction (see procedure in Example 23). HRMS (ESI): Calculated for C$_{22}$H$_{25}$FN$_2$O$_2$: 368.1900, found: 369.1977 (M+1). LC/MS (m/z)=369 (M+H)$^+$; $^1$H NMR (400 MHz, CDCl$_3$) δ ppm 7.31 (dd, J=8.8, 5.3 Hz, 2H), 7.10 (d, J=6.2 Hz, 2H), 4.19 (d, J=4.0 Hz, 1H), 3.92 (dd, J=9.7, 7.0 Hz, 1H), 3.51 (dd, J=10.3, 3.7 Hz, 1H), 3.22-3.30 (m, 1H), 2.95 (dd, J=8.8, 3.5 Hz, 1H), 2.79 (d, J=18.9 Hz, 2H), 2.33-2.47 (m, 2H), 2.32 (dd, J=6.6, 3.5 Hz, 2H), 2.12 (d, J=9.7 Hz, 3H), 2.02 (br. s., 2H), 1.76-1.92 (m, 4H).

Example 32

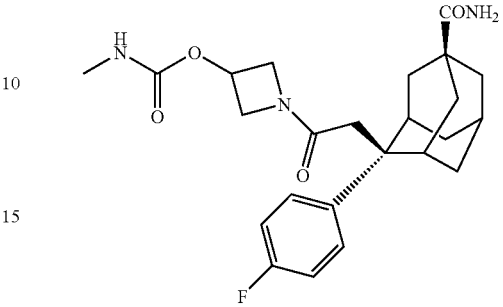

Compound 32A

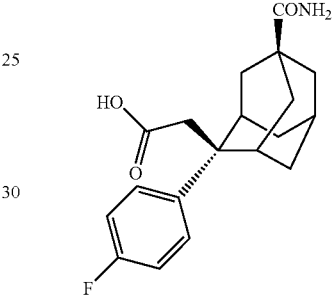

Compound 32A was synthesized from compound 31C via the procedures described in Example 31. LC/MS (m/z)=330 (M+H)$^+$; $^1$H NMR (400 MHz, CD$_3$OD) δ ppm 7.31-7.34 (m, 2H), 6.96-7.07 (m, 2H), 3.39 (dt, J=3.3, 1.6 Hz, 2H), 2.76 (br. s., 2H), 2.68 (s, 2H), 2.39 (d, J=14.4 Hz, 2H), 1.80-1.96 (m, 6H), 1.55 (d, 2H).

Compound 32B

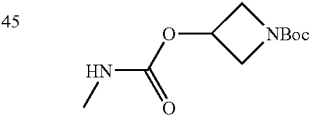

To a solution of tert-butyl 3-hydroxyazetidine-1-carboxylate (0.7 g, 4.041 mmol) and phosgene (2.2 mL, 1 M in PhMe, 4.243 mmol) in dry CH$_2$Cl$_2$ (10 mL) at −15° C. was added Et$_3$N (0.62 mL, 4.445 mmol) slowly. The mixture was carefully warmed to room temperature overnight. Solvent was removed under reduced pressure. Et$_2$O (15 mL) was added. The precipitate was filtered off and rinsed with Et$_2$O (3×5 mL). The combined organic layers were evaporated to dryness to afford the crude chloroformate. To a mixture of methyl amine (1.04 mL, 12.123 mmol, 40% w/w aqueous) in THF (5 mL) and Na$_2$CO$_3$ (4 mL, saturated aqueous) was added slowly the above crude chloroformate. The mixture was stirred at room temperature for 40 minutes. The organic layer was separated and the aqueous layer was extracted with Et$_2$O (3×5 mL). The combined organic layers were dried and evaporated. The residue was purified via column chromatography (SiO$_2$, 35-40% EtOAc in n-hexane) to provide compound 32B as white solid (0.656 g, 70.5% yield). $^1$H NMR (400 MHz, CDCl$_3$) δ ppm 5.20 (br. s., 1H), 5.11 (dd, J=6.2, 3.7 Hz, 1H), 4.15-4.29 (m, 2H), 3.81-3.97 (m, 2H), 2.79 (d, J=4.8 Hz, 3H), 1.39-1.51 (m, rotomer, 9H); $^{13}$C NMR (101 MHz, CDCl$_3$) δ ppm 156.18, 156.01, 79.75, 63.34, 28.31, 27.39, 22.92.

Compound 32C

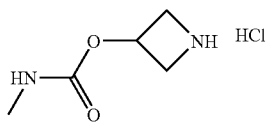

Compound 32C was synthesized from compound 32B via Boc-deprotection in 4 M HCl in dioxane followed the procedure described in Example 28.

Example 32

Example 32 was synthesized from compound 32A and 32C via standard peptide coupling reaction (see procedure in Example 23). LC/MS (m/z)=444 (M+H)$^+$; $^1$H NMR (400 MHz, CDCl$_3$) δ ppm 7.26 (dd, J=8.6, 5.6 Hz, 2H), 7.00 (br. s., 2H), 6.53 (br. s., 1H), 5.86 (br. s., 1H), 4.53-4.71 (m, 2H), 3.90 (dd, J=10.7, 7.5 Hz, 1H), 3.51 (d, J=7.6 Hz, 1H), 3.39-3.47 (m, 1H), 2.77-2.85 (m, 1H), 2.72-2.77 (m, 1H), 2.70 (d, J=4.8 Hz, 3H), 2.58-2.66 (m, 1H), 2.46 (d, J=13.1 Hz, 1H), 2.37-2.44 (m, 1H), 2.26-2.37 (m, 1H), 2.15 (d, 1H), 1.66-1.94 (m, 7H), 1.47 (dd, 2H).

Example 33

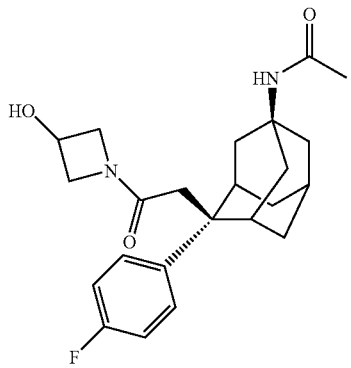

Compound 33A

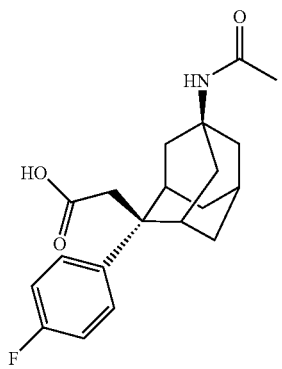

A mixture of Example 12 (30 mg, 0.10 mmol), acetonitrile (0.073 mL) and concentrated sulfuric acid (0.154 mL) was heated at 45° C. overnight. The mixture was poured onto ice (5 g) and warmed to room temperature. It was extracted with Et$_2$O (2×10 mL). The combined organic phases were dried (MgSO$_4$) and concentrated. The residue was purified via Prep-HPLC to provide compound 33A as a white solid (11.0 mg, 33% yield). HPLC Rt (Method A): 3.70 min; LC/MS (m/z)=344 (M−H)$^−$. $^1$H NMR (400 MHz, CD$_3$OD) δ ppm 7.53 (s, 1H), 7.37 (dd, J=8.79, 5.27 Hz, 2H), 7.00 (t, J=8.79 Hz, 2H), 2.76-2.84 (m, 3H), 2.73 (s, 3H), 1.83-1.95 (m, 8H), 1.79 (d, J=13.62 Hz, 2H), 1.54 (d, J=11.86 Hz, 2H).

Example 33

Example 33 was synthesized from compound 33A and 3-hydroxyazetidine hydrochloride via standard peptide coupling reaction (see the procedure described in Example 23). HRMS (ESI): Calculated for C$_{23}$H$_{29}$FN$_2$O$_3$: 400.2162, found: 401.2223 (M+1). HPLC Rt (Method B): 6.82 min; $^1$H NMR (400 MHz, CD$_3$OD) δ ppm 7.38 (br. s., 2H), 7.09 (t, J=8.6 Hz, 2H), 4.01-4.12 (m, 1H), 3.81 (dd, J=9.9, 7.7 Hz, 1H), 3.39 (dd, J=10.5, 4.4 Hz, 1H), 3.31-3.37 (m, 2H), 3.09 (dd, J=8.6, 4.6 Hz, 1H), 2.70-2.90 (m, 4H), 2.61 (d, J=13.2 Hz, 1H), 2.45 (d, J=13.2 Hz, 1H), 1.83-1.98 (m, 7H), 1.76 (t, J=12.5 Hz, 2H), 1.53 (d, 2H).

Example 34

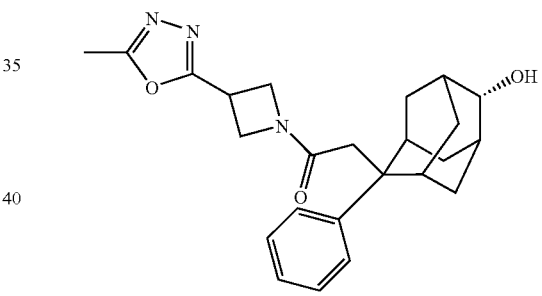

Compound 34A. N'-acetyl-1-benzhydrylazetidine-3-carbohydrazide

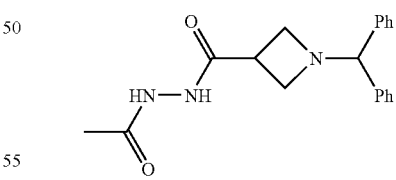

To a solution of 1-benzhydrylazetidine-3-carboxylic acid (2.097 g, 7.845 mmol) and acetohydrazine (0.967 g, 11.767 mmol) in DMF (40 mL) was added HOBt (1.59 g, 11.767 mmol) and EDAC (2.255 g, 11.767 mmol), followed by i-Pr$_2$NEt (2.1 mL, 11.767 mmol). The mixture was stirred at room temperature overnight. Solvent was removed and the residue was purified via Prep HPLC to provide compound 34A as white solid (2.4 g, 95% yield). LC/MS (m/z)=324 (M+H)$^+$. $^1$H NMR (400 MHz, CDCl$_3$) δ ppm 7.48 (d, J=7.1 Hz, 4H), 7.28-7.42 (m, 6H), 5.40 (s, 1H), 4.30 (br. s., 2H), 3.84-4.10 (m, 3H), 1.84-2.07 (m, rotomer, 3H).

Compound 34B

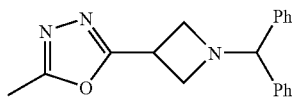

To a solution of compound 34A (760 mg, 2.350 mmol) in acetonitrile (15 ml) was added i-Pr₂NEt (2.372 ml, 13.58 mmol) and triphenylphosphine (1.091 g, 4.16 mmol). After stirring at RT for 5 mins, hexachloroethane (0.351 mL, 3.10 mmol) was added. The mixture was stirred at RT overnight. Solvent was evaporated off. The residue was partitioned between EtOAc (50 mL) and H₂O (25 mL). Organic layer was separated; the aqueous layer was extracted with EtOAc (50 mL). The combined organic layers were dried (MgSO₄), concentrated. The residue was purified first via column chromatography (0-15% EtOAc in n-hexane), then via Prep HPLC to provide compound 34B as a colorless oil (10 mg, 1.5% yield). LC/MS (m/z)=306 (M+H)⁺. ¹H NMR (400 MHz, CD₃OD) δ ppm 6.98-7.63 (m, 10H), 5.76 (s, 1H), 4.24-4.56 (m, 5H), 2.49-2.62 (m, 3H).

Compound 34C

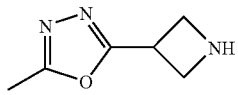

To a solution of compound 34B (10 mg, 0.033 mmol) in MeOH (2.0 mL) was added Pd/C (3.0 mg, 10% activated). The reaction mixture was stirred at room temperature for 2.5 hours under an H₂ atmosphere (balloon). The catalyst was filtered off and solvent was evaporated to provide compound 34C as a colorless oil (12 mg). LC/MS (m/z)=140 (M+H)⁺.

Example 34

Example 34 was synthesized from compound 26A and 34C via standard peptide coupling reaction (see the procedure described in Example 23). LC/MS (m/z)=408 (M+H)⁺. HPLC Rt (Method B): 6.08 min; ¹H NMR (400 MHz, CDCl₃) δ ppm 7.21-7.35 (m, 4H), 7.04-7.16 (m, 1H), 3.93-4.03 (m, 1H), 3.83-3.91 (m, 1H), 3.74 (br. s., 1H), 3.31-3.45 (m, 1H), 3.23-3.30 (m, 0.5H), 3.15 (t, J=8.6 Hz, 0.5H), 3.05-3.12 (m, 0.5H), 2.99 (t, J=8.8 Hz, 0.5H), 2.47-2.64 (m, 2H), 2.45 (two singlets, rotomers, 3H), 2.29-2.43 (m, 2H), 1.36-2.22 (m, 11H).

Example 35

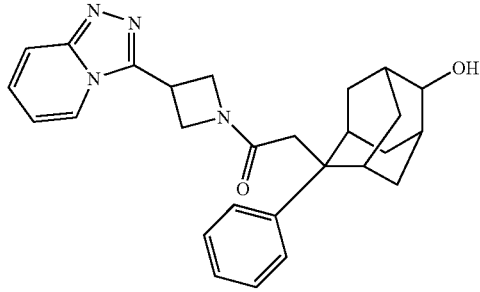

Compound 35A

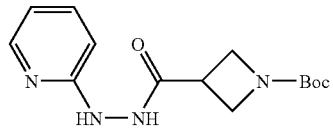

To a solution of 1-(tert-butoxycarbonyl)azetidine-3-carboxylic acid (200 mg, 1.0 mmol) in THF (10 mL) at 0° C. was added Et₃N (102 mg, 2.0 mmol), followed by ethyl chloroformate (130 mg, 1.3 mmol). After stirring at 0° C. for 30 minutes, a solution of 2-hydrazinylpyridine in THF (2.0 ml) was added. The mixture was warmed up and stirred at room temperature overnight. The precipitate was filtered off, the solvent was evaporated, and the resulting residue was purified via column chromatography (SiO₂, 0-100% EtOAc in n-hexanes) to provide compound 35A as a yellow oil (189 mg, 64% yield). LC/MS (m/z)=294 (M+H)⁺. ¹H NMR (400 MHz, CDCl₃) δ ppm 7.87-8.23 (m, 1H), 7.30-7.70 (m, 1H), 6.70-6.93 (m, 1H), 6.65 (d, J=8.25 Hz, 1H), 4.05-4.16 (m, 2H), 4.02 (t, J=8.52 Hz, 2H), 3.94 (t, J=8.79 Hz, 1H), 1.32-1.45 (m, 9H).

Compound 35B

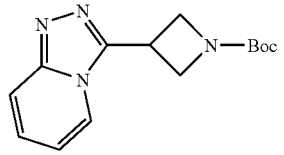

To a solution of compound 35A in CH₂Cl₂/CCl₄ (12.0 mL/6.0 mL) at 0° C. was added i-Pr₂NEt (838 mg, 6.5 mmol), followed by PEt₃ (381 mg, 3.23 mmol). The mixture was warmed to room temperature and stirred overnight. The solvent was evaporated and the residue was purified via column chromatography (SiO₂, 0-100% EtOAc in n-hexanes) to provide compound 35B as a yellow oil (158 mg). LC/MS (m/z)= 275 (M+H)⁺. ¹H NMR (400 MHz, CDCl₃) δ ppm 7.88 (d, J=7.03 Hz, 1H), 7.77 (d, J=9.23 Hz, 1H), 7.25-7.30 (m, 1H), 6.87 (t, J=6.81 Hz, 1H), 4.44 (t, J=8.57 Hz, 4H), 4.12-4.27 (m, 1H), 1.44 (s, 9H).

Compound 35C

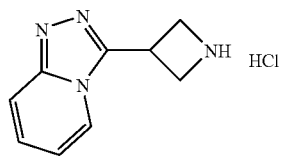

Compound 35C was synthesized from compound 35B via Boc-deprotection in 4 M HCl in dioxane following the procedure described in Example 28. LC/MS (m/z)=175 (M+H)⁺.

Example 35

Example 35 was synthesized from compound 26A and compound 35C via standard peptide coupling reaction (see procedure in Example 23). HPLC Rt (Method B): 5.550 min; LC/MS (m/z)=275 (M+H)⁺. ¹H NMR (400 MHz, CD₃OD) δ ppm 8.09-8.19 (m, 1H), 7.81-7.90 (m, 1H), 7.68-7.81 (m, 1H), 7.17-7.37 (m, 3H), 6.99-7.17 (m, 2H), 6.65-6.83 (m, 1H), 4.04-4.20 (m, 2H), 3.80-3.94 (m, 1H), 3.50-3.72 (m, 2H), 3.30-2.95 (m, 2H), 2.27-2.64 (m, 5H), 2.08-2.19 (m, 1H), 1.93-2.08 (m, 1H), 1.73-1.92 (m, 3H), 1.67 (d, J=13.6 Hz, 1H), 1.55 (br. s., 1H), 1.39-1.51 (m, 2H).

Example 36

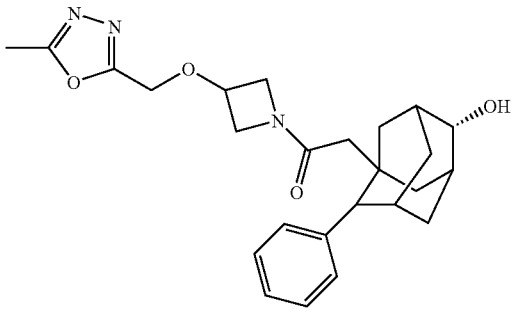

Compound 36A. tert-Butyl 3-((5-methyl-1,3,4-oxa-diazol-2-yl)methoxy)azetidine-1-carboxylate

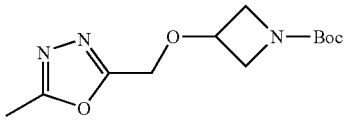

To a solution of 1-Boc-3-(hydroxyl)azetidine (250 mg, 1.443 mmol) in THF (3 mL) at 0° C., was added NaH (75 mg, 1.876 mmol) in portions. The mixture was stirred at 0° C. for 0.5 hour, then at RT for 0.5 hour. To the above mixture was added a solution of 2-(Chloromethyl)-5-methyl-1,3,4-oxa-diazole (191 mg, 1.443 mmol) in THF (3 mL) slowly. After stirring at RT overnight, the mixture was quenched with NH$_4$Cl (10 mL, saturated aqueous), then extracted with EtOAc (3×30 mL). Combined organic layers were dried (MgSO$_4$), concentrated, and purified via column chromatography (SiO$_2$, 0-70% EtOAc in n-hexane) to provide compound 36A as colorless oil (100 mg, 25.7% yield). LC/MS (m/z)=270 (M+H)$^+$. $^1$H NMR (400 MHz, CDCl$_3$) δ ppm 4.60 (s, 2H), 4.29-4.39 (m, 1H), 4.04-4.10 (m, 2H), 3.81 (dd, J=9.67, 4.39 Hz, 2H), 2.55 (s, 3H), 1.38-1.42 (s, 9H).

Compound 36B. 2-((Azetidin-3-yloxy)methyl)-5-methyl-1,3,4-oxadiazole hydrochloride

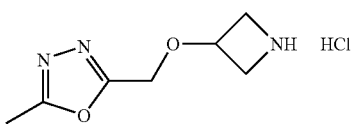

Compound 36B was synthesized from compound 36A via Boc-deprotection in 4 M HCl in dioxane followed the procedure described in Example 28. LC/MS (m/z)=170 (M+H)$^+$.

Example 36

Example 36 was synthesized from compound 26A and compound 36B via standard peptide coupling reaction (see procedure in Example 23). HPLC Rt (Method B): 6.25 min; LC/MS (m/z)=438 (M+H)$^+$. $^1$H NMR (400 MHz, CDCl$_3$) δ ppm 7.22-7.33 (m, 4H), 7.12-7.20 (m, 1H), 4.29-4.39 (m, 2H), 3.70-3.86 (m, 3H), 3.42-3.53 (m, 1H), 2.97-3.05 (m, 0.5H), 2.80-2.93 (m, 1H), 2.70 (dd, J=9.9, 3.3 Hz, 0.5H), 2.19-2.62 (m, 9H), 2.11 (d, J=13.7 Hz, 1H), 1.77-2.04 (m, 4H), 1.60-1.72 (m, 2H), 1.49-1.60 (m, 1H), 1.44 (dd, 1H).

Example 37

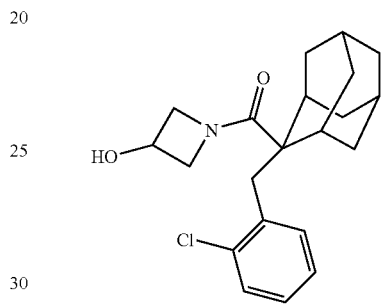

Compound 37A

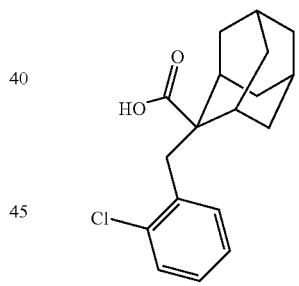

Compound 37A was synthesized from 2-adamantane carboxylic acid via direct α-alkylation by following the procedure described in Example 5. Alternatively, compound 37A was synthesized via stepwise procedures described by Scheffer, John R. (*Journal of the American Chemical Society*, 126 (11):3511-3520 (2004)). LC-MS (m/z)=303 (M–H)$^−$.

Example 37

Compound 37A (15 mg, 0.05 mmol) in SOCl$_2$ (0.5 ml) was heated at 60° C. under Ar overnight. Excess SOCl$_2$ was evaporated off under reduced pressure to provide the corresponding acid chloride as a yellow oil. To a solution of above acid chloride in CH$_2$Cl$_2$ (2.0 mL) was added Et$_3$N (15 mg, 0.15 mmol), followed by 3-hydroxyazetidine (8.0 mg, 0.075 mmol). The mixture was stirred at RT overnight. Solvent was evaporated. The residue was purified via Prep HPLC to provide Example 37 as a white solid (13 mg, 72% yield). HPLC Rt (Method A): 6.80 min; LC/MS (m/z)=360 (M+H)+. 1H NMR (400 MHz, CDCl3) δ ppm 7.11-7.45 (m, 4H), 4.15-4.42 (m, 1H), 4.01-4.15 (m, 1H), 3.97 (s, 2H), 3.63-3.79 (m, 2H), 3.44-3.64 (m, 3H), 3.15-3.30 (m, 1H), 2.81 (t, J=14.29 Hz, 2H), 2.63-2.73 (m, 1H), 2.38-2.59 (m, 2H), 2.33 (s, 2H), 2.10 (dd, J=29.41, 13.47 Hz, 3H), 1.59-1.97 (m, 2H).

Example 38

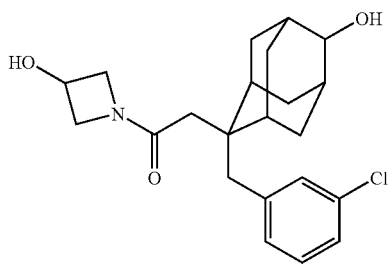

Compound 38A

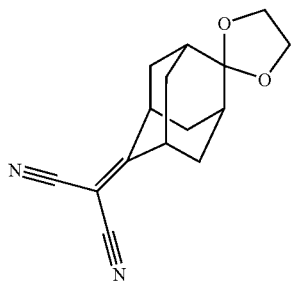

A mixture of compound 25A (1.84 g, 8.84 mmol), malononitrile (0.561 mL, 8.84 mmol), and ammonium acetate (0.068 g, 0.884 mmol) in EtOH (110 mL) was stirred at room temperature under argon for 6 hours. After evaporating the solvent, the residue was purified via column chromatography (SiO2, 0-60% EtOAc in n-hexane) to provide compound 38A (2.01 g, 89% yield) as a white solid. LC/MS (m/z)=257 (M+H)+. 1H NMR (400 MHz, CDCl3): δ ppm 4.00 (s, 4H), 3.17 (br. s., 2H), 2.37 (br. s., 2H), 2.34 (br. s., 2H), 1.93 (br. s., 2H), 1.82 (br. s., 2H), 1.79 (br. s., 2H).

Compound 38B

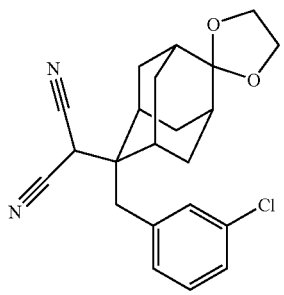

To a solution of 3-chlorobenzylmagnesium chloride (7.02 mL, 1.756 mmol) in THF (10 mL) at −5° C. under argon was added a solution of compound 38A (150 mg, 0.585 mmol) in THF (20 mL) dropwise while maintaining the temperature below 0° C. After stirring at this temperature for additional 1 hour, the mixture was warmed to room temperature over a period of 1 hour. The mixture was then diluted with saturated NH4Cl (50 mL) and extracted with ethyl acetate (50 mL). The organic layer was washed (brine), dried (Na2SO4), filtered and concentrated. The residue was purified via Prep HPLC provide compound 38B (200 mg, 0.522 mmol, 89% yield) as a white solid. LC/MS (m/z)=383 (M+H)+. 1H NMR (400 MHz, CDCl3): δ ppm 7.37-7.27 (m, 4H), 4.55 (s, 1H), 3.97 (s, 4H), 3.21 (s, 2H), 2.23-2.34 (m, 2H), 2.06-2.18 (m, 4H), 2.01 (br. s., 2H), 1.93 (br. s., 1H), 1.83 (br. s., 1H), 1.70 (br. s., 1H), 1.67 (br. s., 1H).

Compound 38C

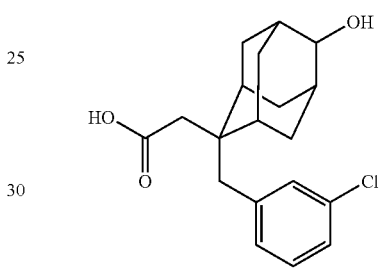

A mixture of compound 38B (160 mg, 0.418 mmol), KOH (258 mg, 4.60 mmol), and ethylene glycol (2 mL) was placed in a 10 mL sealed tube reactor and heated at 205° C. oil bath for 18 hours. The mixture was cooled to room temperature, diluted with a solution of citric acid (50 mL, 10% w/v) and extracted with EtOAc (3×25 mL). The organic layer was washed (brine), dried (Na2SO4), filtered and concentrated. The residue was then diluted with HCl (aqueous, 10 mL, 2.0 M) and THF (10 mL) and heated at 60° C. for 6 hours. The THF was concentrated and the remaining aqueous phase was diluted with brine and extracted with ethyl acetate. The organic layer was washed (brine), dried (Na2SO4), filtered and concentrated. The residue was then dissolved in MeOH (20 mL) and sodium borohydride (47.4 mg, 1.25 mmol) was added in portions. The mixture was stirred for 1 hour and quenched with aqueous HCl (5 mL). The solvent was concentrated and the residue was purified via Prep HPLC (Gradient Solvent System: From 50% A: 50% B to 0% A: 100% B; [A=10% MeOH/90% H2O+0.1% TFA]; [B=90% MeOH/10% H2O+0.1% TFA]; detection at 220 nm: 10 min gradient; Phenomenex Luna AXIA 30×100 mm) to provide compound 38C (73 mg, 50% yield) as an off-white solid. LC/MS (m/z)= 333 (M-H)−. 1H NMR (400 MHz, CDCl3) δ ppm 7.24-7.33 (m, 2H), 7.14-7.23 (m, 2H), 3.79-3.89 (m, 1H), 3.07-3.24 (m, 2H), 2.50 (d, J=7.03 Hz, 2H), 2.41-2.48 (m, 1H), 2.17 (dd, J=14.06, 3.52 Hz, 1H), 2.10 (d, J=2.64 Hz, 1H), 2.04 (dd, J=14.06, 2.20 Hz, 1H), 1.99 (br. s., 1H), 1.90 (br. s., 1H), 1.82 (d, J=14.50 Hz, 1H), 1.76 (br. s., 1H), 1.71 (br. s., 1H), 1.53-1.67 (m, 3H).

Alternatively, compound 38C was synthesized via the stepwise procedures described in Example 25.

Example 38

Example 38 was synthesized from compound 38C and 3-hydroxyazetidine hydrochloride via standard peptide coupling reaction (see procedure in Example 23). 38: white solid; Yield 23%. HPLC Rt (Method C): 6.380 min; LC/MS (m/z)= 390 (M+H)$^+$. $^1$H NMR (400 MHz, CDCl$_3$): δ ppm 7.20 (br. s., 2H), 7.14 (br. s., 1H), 7.06 (br. s., 1H), 4.59 (d, J=3.52 Hz, 1H), 4.27 (br. s., 1H), 3.76-3.93 (m, 3H), 3.49-3.66 (m, 1H), 3.05-3.33 (m, 2H), 2.40 (d, J=9.67 Hz, 1H), 2.27 (br. s., 3H), 1.93-2.16 (m, 5H), 1.82-1.91 (m, 2H), 1.69 (t, J=11.42 Hz, 1H), 1.58 (t, J=12.08 Hz, 2H).

Examples 39 to 386

Examples 39 to 386 in Table 1 were synthesized according to the procedures described in Examples 1 to 38, the schemes, or by other similar methods known to one skilled in the art, with other appropriate reagents. In the structures set forth in Table 1, the "—O" attached to an adjacent carbon atom substituted with =O is used to denote an "—OH" group. Similarly, in the structures set forth in Table 1, the "N" attached to an adjacent carbon atom substituted with =O is used to denote an "NH" moiety. The compounds set forth in Table 1 below are racemic, achiral or diastereomeric unless indicated to the contrary.

TABLE 1

| Example | Structure | LC/MS Mass [(M − H)$^-$/(M + H)$^+$] | HPLC purity (%) |
|---|---|---|---|
| 39 | 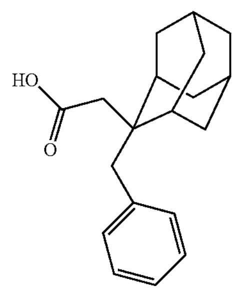 | 283 | 94.8 |
| 40 | 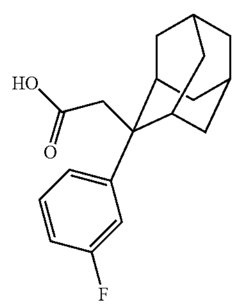 | 287 | >95 |
| 41 | 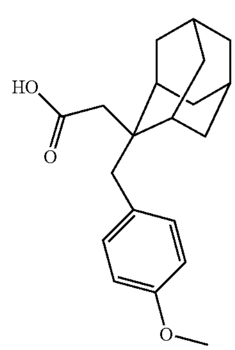 | 313 | >98 |

TABLE 1-continued
| Example | Structure | LC/MS Mass [(M − H)⁻/(M + H)⁺] | HPLC purity (%) |
|---|---|---|---|
| 42 | 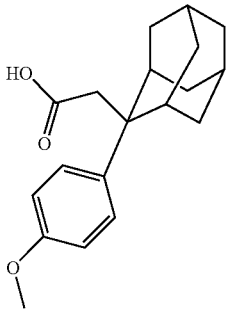 | 299 | 99 |
| 43 | 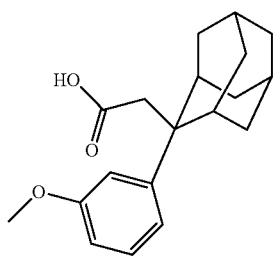 | 299 | >97 |
| 44 | 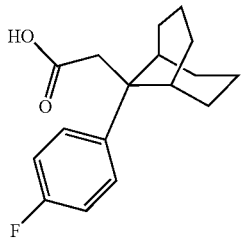 | 275 | >95 |
| 45 | 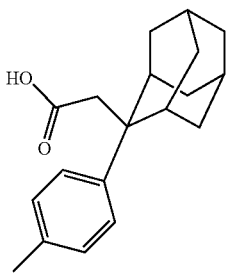 | 283 | 96 |
| 46 | 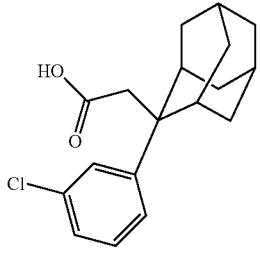 | 303 | 98.5 |

TABLE 1-continued

| Example | Structure | LC/MS Mass [(M − H)⁻/(M + H)⁺] | HPLC purity (%) |
|---|---|---|---|
| 47 | 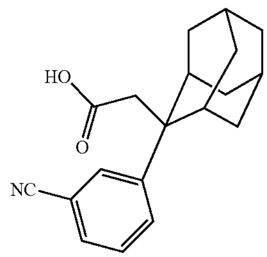 | 294 | 95.6 |
| 48 | 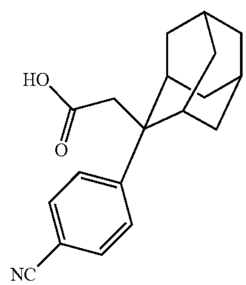 | 294 | 98 |
| 49 | 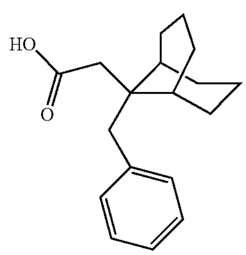 | 271 | 90 |
| 50 | 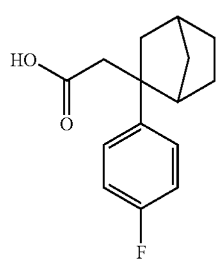 | 247 | 95 |
| 51 | 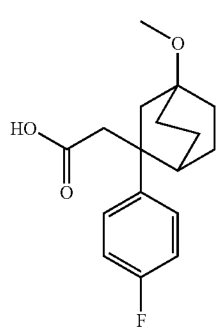 | 291 | 96 |

TABLE 1-continued

| Example | Structure | LC/MS Mass [(M − H)⁻/(M + H)⁺] | HPLC purity (%) |
|---------|-----------|-------------------------------|-----------------|
| 52 | 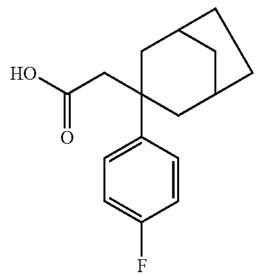 | 261 | 97 |
| 53 | 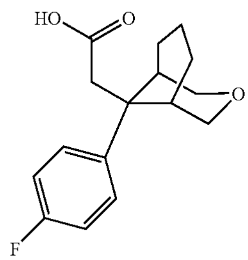 | 277 | >90 |
| 54 | 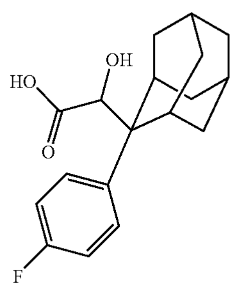 | 303 | >92 |
| 55 | 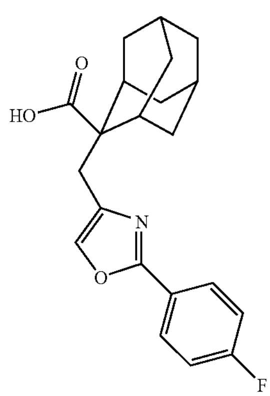 | 354 | >99 |
| 56 | 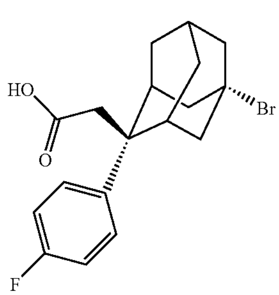 | 366 | 96.7 |

TABLE 1-continued
| Example | Structure | LC/MS Mass [(M − H)⁻/(M + H)⁺] | HPLC purity (%) |
|---|---|---|---|
| 57 | 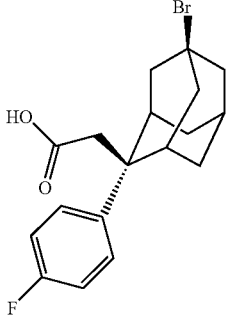 | 366 | 95.7 |
| 58 | 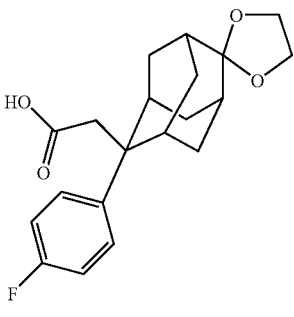 | 345 | 94.9 |
| 59 | 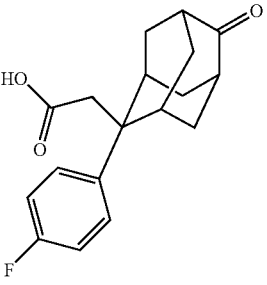 | 301 | 96.8 |
| 60 | 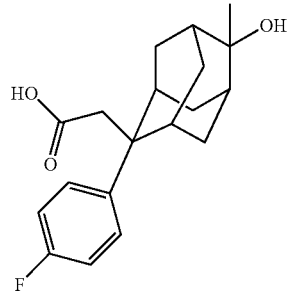 | 317 | >95 |
| 61 (chiral) | 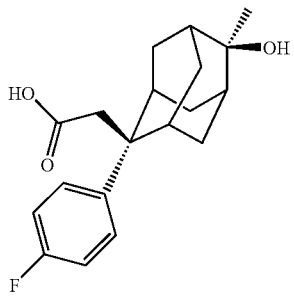 | 366 | >95 |

TABLE 1-continued

| Example | Structure | LC/MS Mass [(M − H)⁻/(M + H)⁺] | HPLC purity (%) |
|---------|-----------|-------------------------------|-----------------|
| 62 (chiral) | 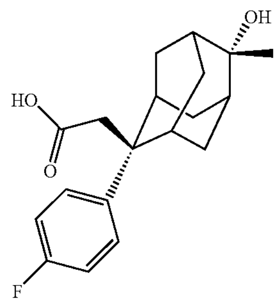 | 366 | 95 |
| 63 | 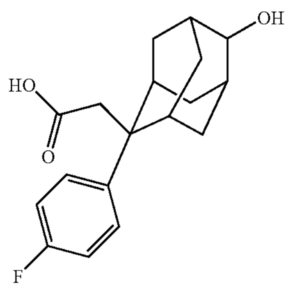 | 303 | >95 |
| 64 | 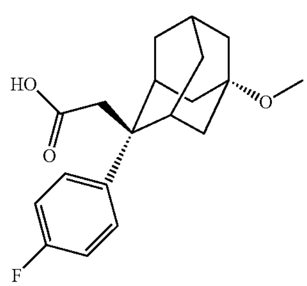 | 317 | >95 |
| 65 | 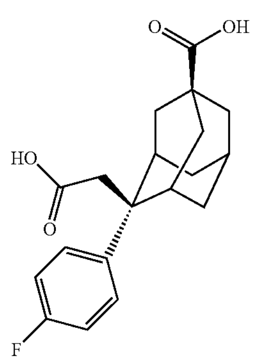 | 331 | >95 |
| 66 | 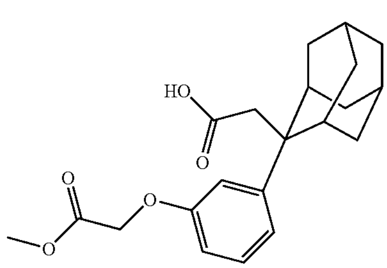 | 357 | >95.6 |

TABLE 1-continued

| Example | Structure | LC/MS Mass [(M − H)⁻/(M + H)⁺] | HPLC purity (%) |
|---------|-----------|---------------------------------|-----------------|
| 67 | 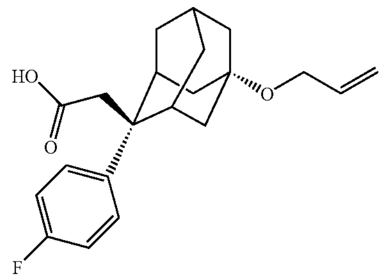 | 343 | >98 |
| 68 | 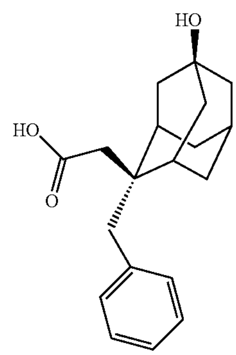 | 299 | 97 |
| 69 | 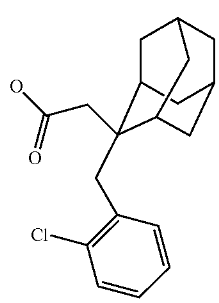 | 317 | 99.6 |
| 70 | 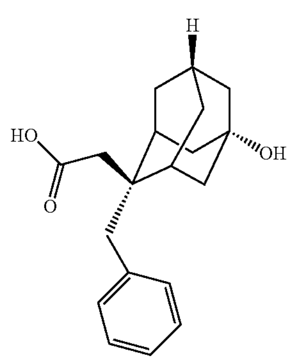 | 299 | 95 |

TABLE 1-continued

| Example | Structure | LC/MS Mass [(M − H)⁻/(M + H)⁺] | HPLC purity (%) |
|---------|-----------|-------------------------------|-----------------|
| 71 | 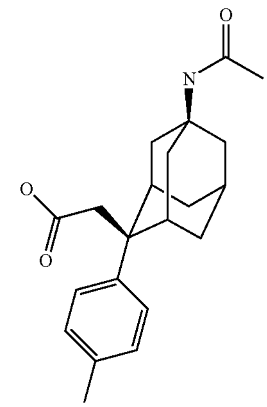 | 346 | 98 |
| 72 | 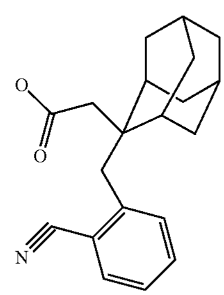 | 308 | 98.8 |
| 73 | 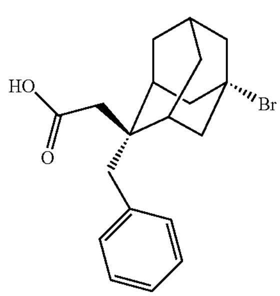 | 362 | 92.5 |
| 74 | 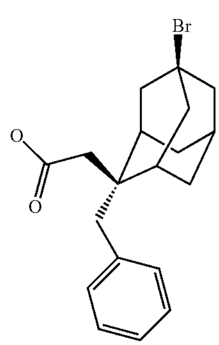 | 362 | 96.3 |

TABLE 1-continued

| Example | Structure | LC/MS Mass [(M − H)⁻/(M + H)⁺] | HPLC purity (%) |
|---|---|---|---|
| 75 | 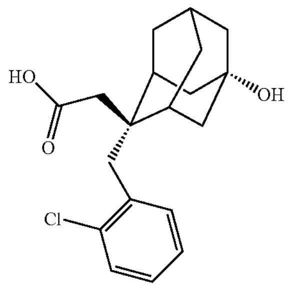 | 333 | 96.2 |
| 76 | 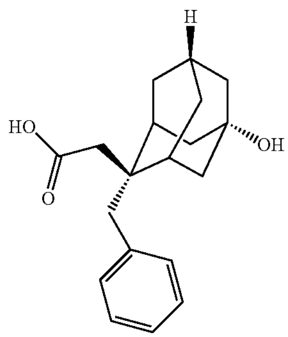 | 299 | 95 |
| 77 | 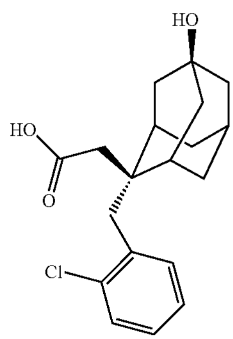 | 333 | 98.4 |
| 78 | 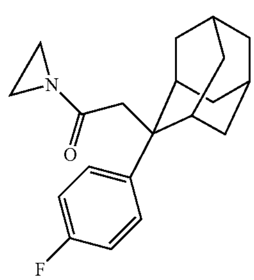 | 314 | 96 |
| 79 | 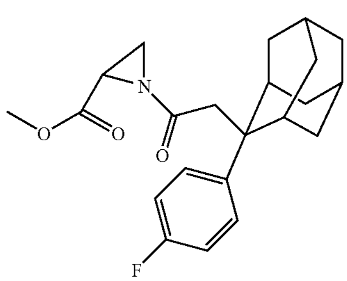 | 372 | 96.2 |

TABLE 1-continued

| Example | Structure | LC/MS Mass [(M − H)⁻/(M + H)⁺] | HPLC purity (%) |
|---|---|---|---|
| 80 | 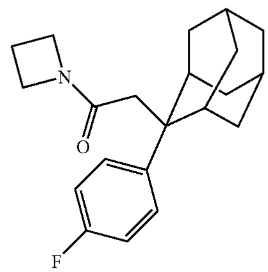 | 328 | 98 |
| 81 | 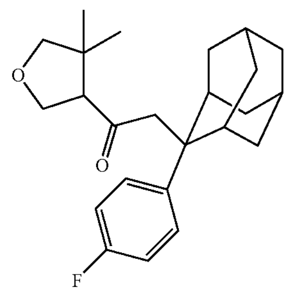 | 372 | 98 |
| 82 | 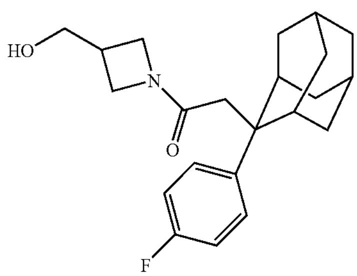 | 358 | 98 |
| 83 | 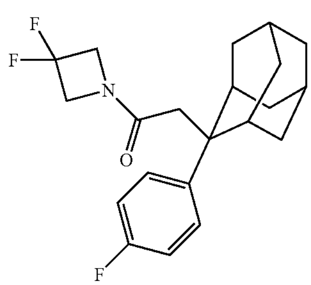 | 364 | 98 |
| 84 | 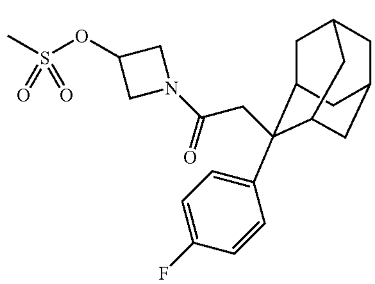 | 422 | 98 |

TABLE 1-continued

| Example | Structure | LC/MS Mass [(M − H)⁻/(M + H)⁺] | HPLC purity (%) |
|---------|-----------|-------------------------------|-----------------|
| 85 | 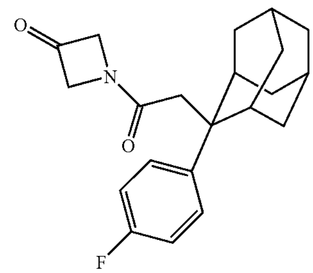 | 342 | 96 |
| 86 | 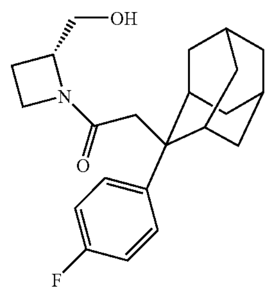 | 358 | 98 |
| 87 | 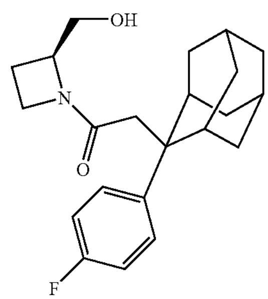 | 358 | 98 |
| 88 | 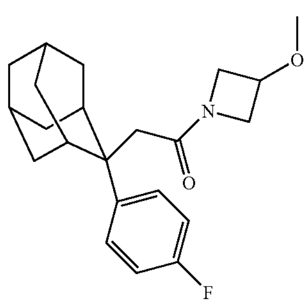 | 358 | 97.2 |
| 89 | 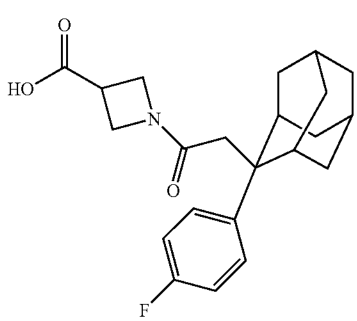 | 372 | 95 |

TABLE 1-continued

| Example | Structure | LC/MS Mass [(M − H)⁻/(M + H)⁺] | HPLC purity (%) |
|---------|-----------|-------------------------------|-----------------|
| 90 | 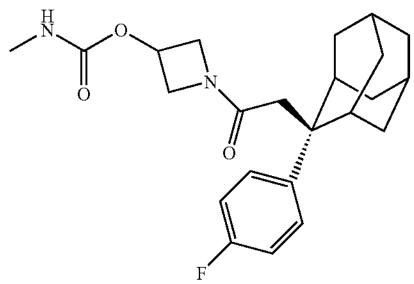 | 401 | 96 |
| 91 | 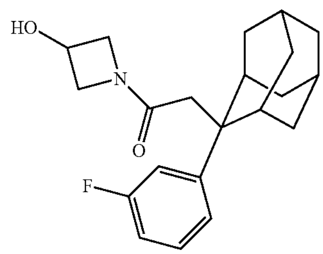 | 344 | 96.3 |
| 92 | 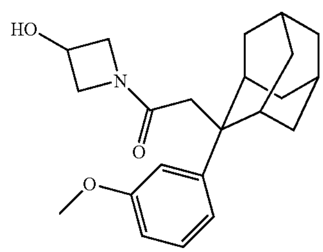 | 356 | 98 |
| 93 | 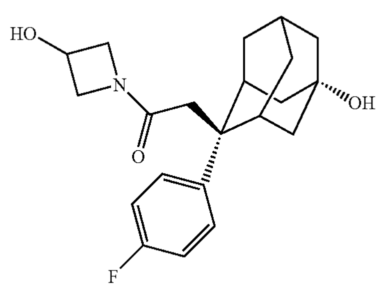 | 360 | 97 |
| 94 | 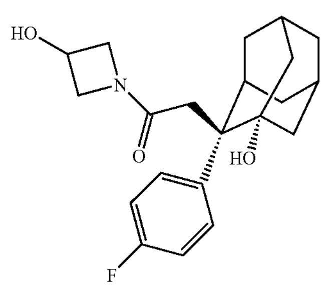 | 360 | 88 |

TABLE 1-continued

| Example | Structure | LC/MS Mass [(M − H)⁻/(M + H)⁺] | HPLC purity (%) |
|---------|-----------|--------------------------------|-----------------|
| 95 | 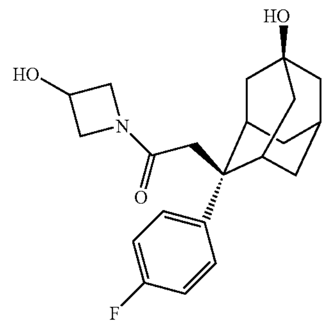 | 360 | 96 |
| 96 | 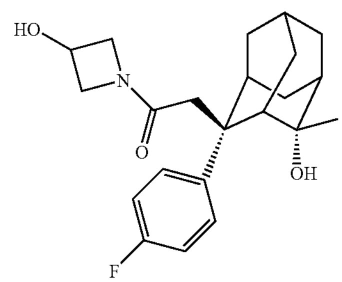 | 374 | 95 |
| 97 | 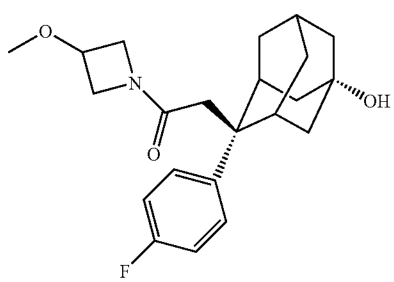 | 374 | 97 |
| 98 | 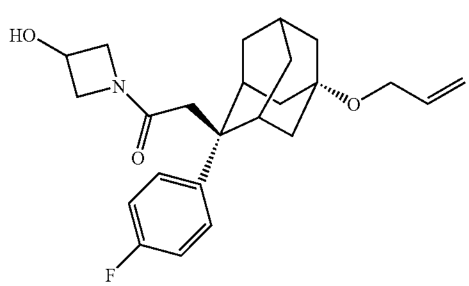 | 400 | 98 |
| 99 | 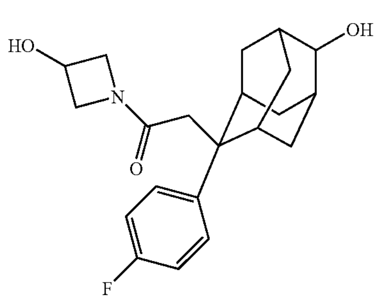 | 360 | 96.3 |

TABLE 1-continued

| Example | Structure | LC/MS Mass [(M − H)⁻/(M + H)⁺] | HPLC purity (%) |
|---|---|---|---|
| 100 | 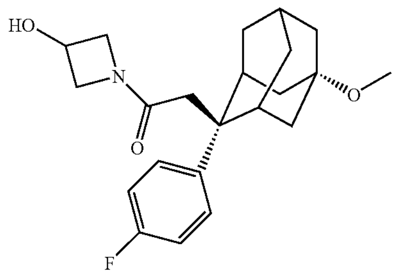 | 374 | 97.3 |
| 101 | 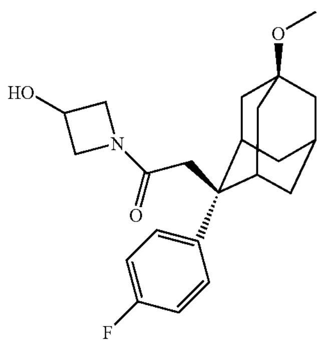 | 374 | 97.5 |
| 102 (chiral) | 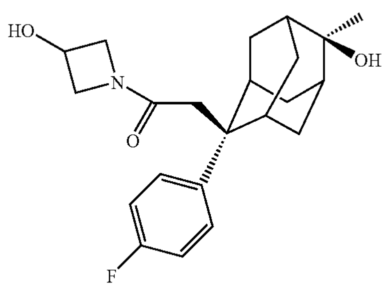 | 374 | 96.4 |
| 103 (chiral) | 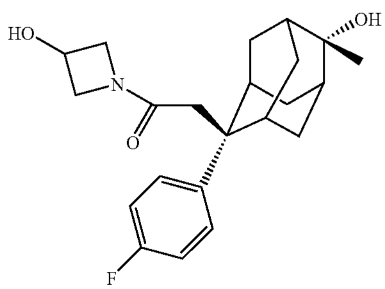 | 374 | 96.2 |
| 104 | 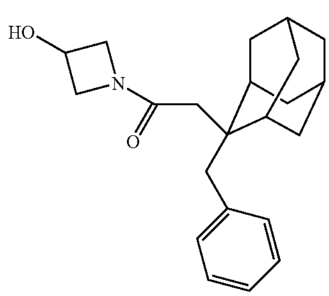 | 340 | >96 |

TABLE 1-continued

| Example | Structure | LC/MS Mass [(M − H)⁻/(M + H)⁺] | HPLC purity (%) |
|---------|-----------|-------------------------------|-----------------|
| 105 | 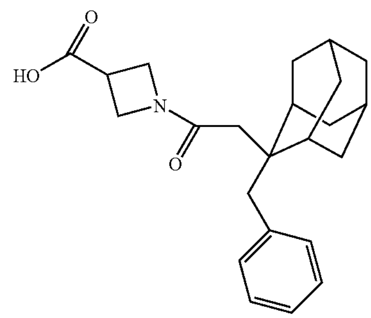 | 368 | 96.8 |
| 106 | 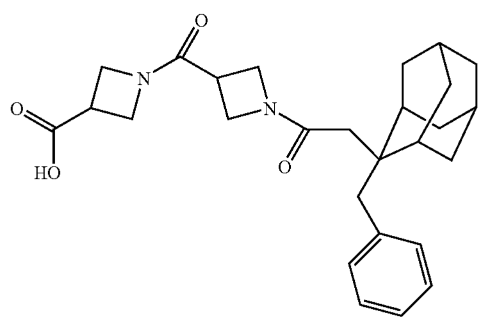 | 451 | 97.4 |
| 107 | 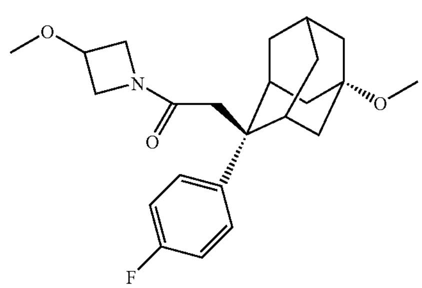 | 388 | 99.4 |
| 108 | 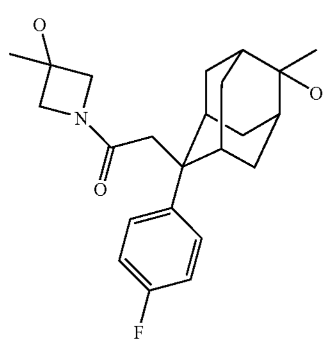 | 388 | 98 |

TABLE 1-continued

| Example | Structure | LC/MS Mass [(M − H)⁻/(M + H)⁺] | HPLC purity (%) |
|---|---|---|---|
| 109 | 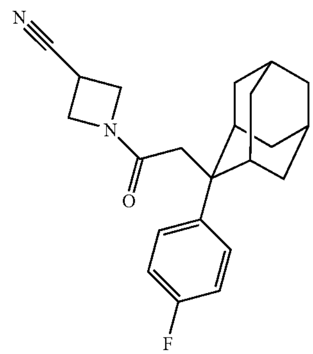 | 353 | 98 |
| 110 | 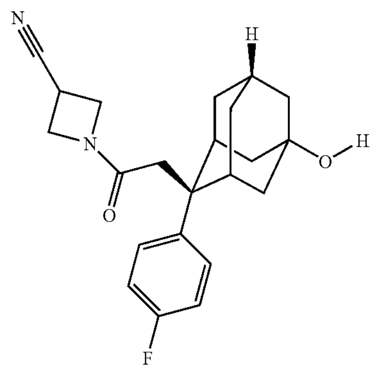 | 369 | 98 |
| 111 | 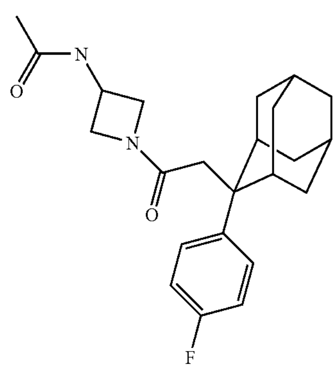 | 385 | 98 |
| 112 | 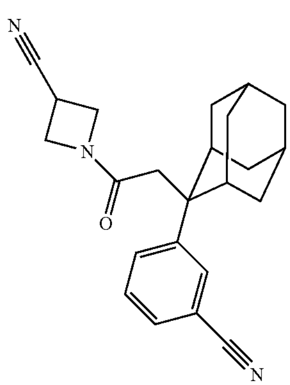 | 360 | 98 |

TABLE 1-continued

| Example | Structure | LC/MS Mass [(M − H)⁻/(M + H)⁺] | HPLC purity (%) |
|---------|-----------|-------------------------------|-----------------|
| 113 | 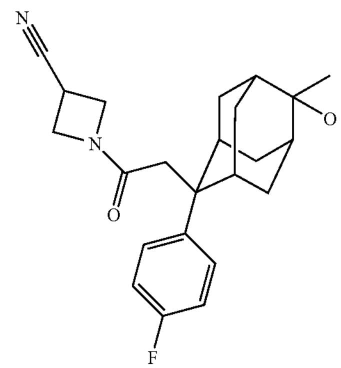 | 383 | 97 |
| 114 | 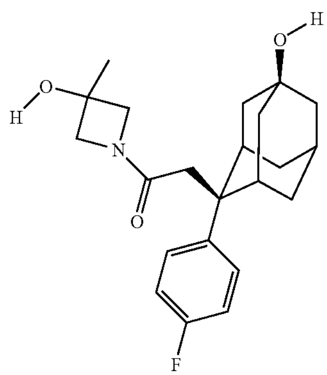 | 374 | 96 |
| 115 | 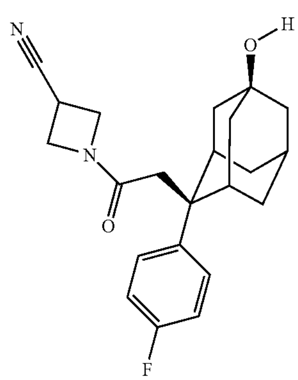 | 369 | 97 |
| 116 | 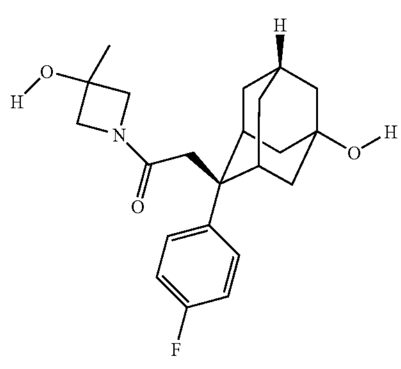 | 374 | 98 |

TABLE 1-continued
| Example | Structure | LC/MS Mass [(M − H)⁻/(M + H)⁺] | HPLC purity (%) |
|---|---|---|---|
| 117 | 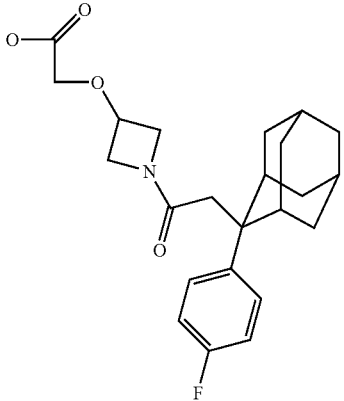 | 400 | 95 |
| 118 | 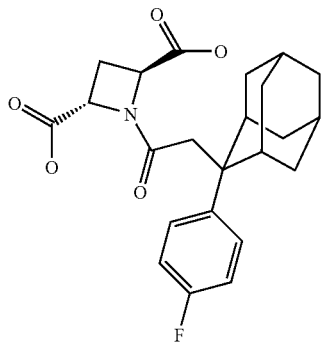 | 414 | 96 |
| 119 | 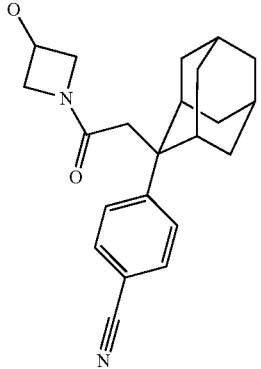 | 351 | 98 |
| 120 | 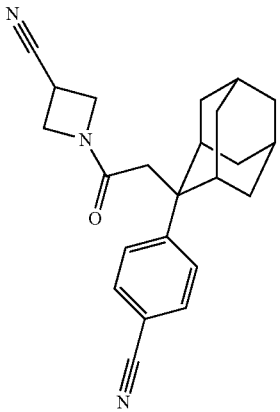 | 360 | 95 |

TABLE 1-continued

| Example | Structure | LC/MS Mass [(M − H)⁻/(M + H)⁺] | HPLC purity (%) |
|---|---|---|---|
| 121 | 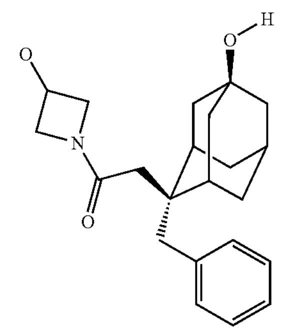 | 356 | 98 |
| 122 | 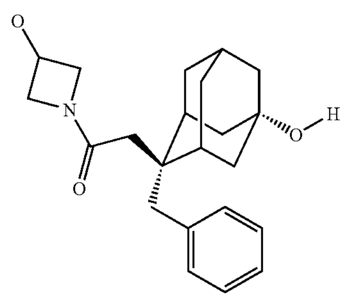 | 356 | 98 |
| 123 | 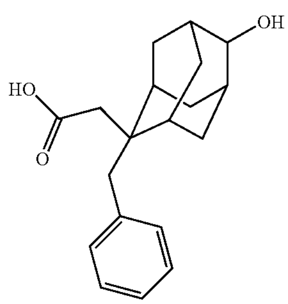 | 299 | 95 |
| 124 | 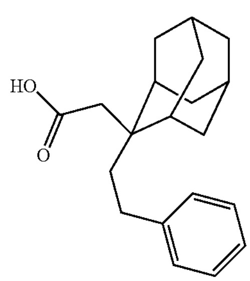 | 297 | >96 |
| 125 | 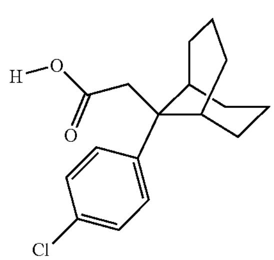 | 291 | 98.3 |

TABLE 1-continued

| Example | Structure | LC/MS Mass [(M − H)⁻/(M + H)⁺] | HPLC purity (%) |
| --- | --- | --- | --- |
| 126 | 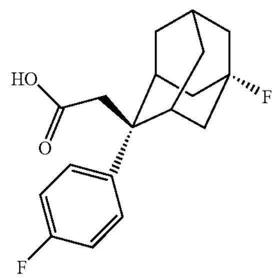 | 305 | 91 |
| 127 | 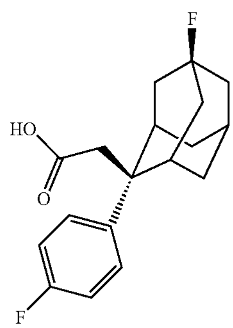 | 305 | 91 |
| 128 | 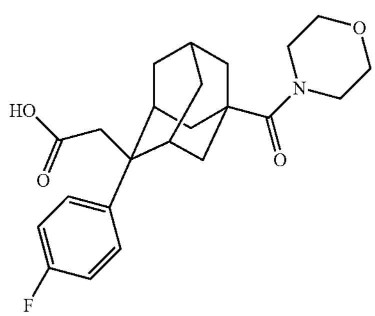 | 402 | 98.8 |
| 129 | 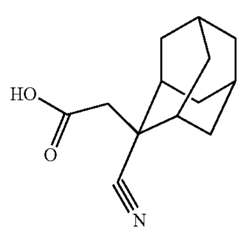 | 218 | >90 |
| 130 (chiral) | 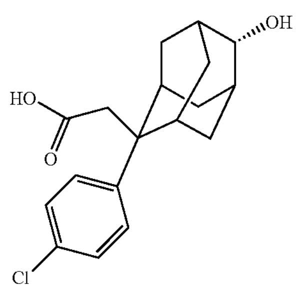 | 319 | 99 |

TABLE 1-continued

| Example | Structure | LC/MS Mass [(M − H)⁻/(M + H)⁺] | HPLC purity (%) |
|---------|-----------|--------------------------------|-----------------|
| 131 (chiral) | 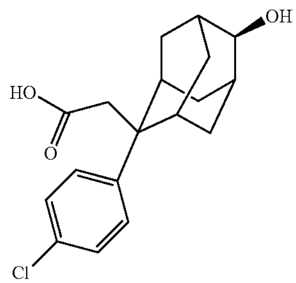 | 319 | 99 |
| 132 | 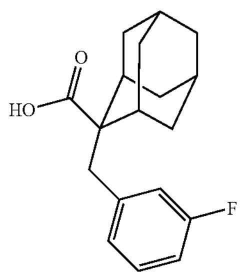 | 287 | 98 |
| 133 | 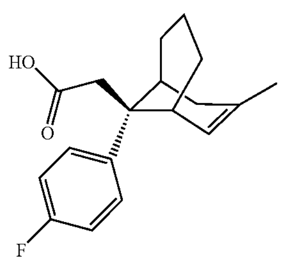 | 287 | 97.2 |
| 134 | 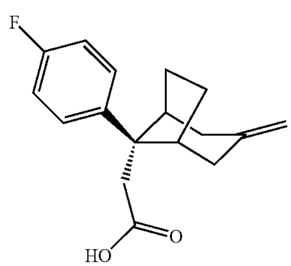 | 273 | 98.2 |
| 135 | 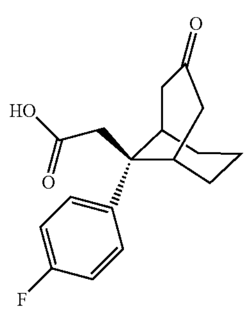 | 289 | >95 |

TABLE 1-continued

| Example | Structure | LC/MS Mass [(M − H)⁻/(M + H)⁺] | HPLC purity (%) |
|---|---|---|---|
| 136 | 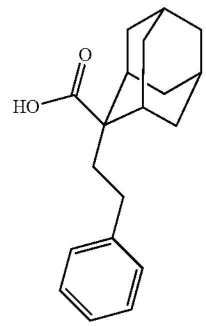 | 283 | 97 |
| 137 | 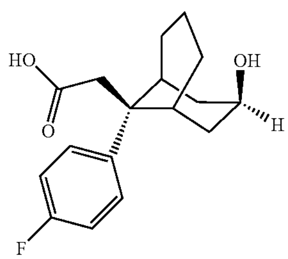 | 291 | >95 |
| 138 | 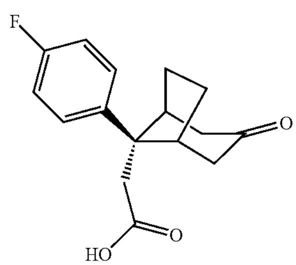 | 275 | >95 |
| 139 | 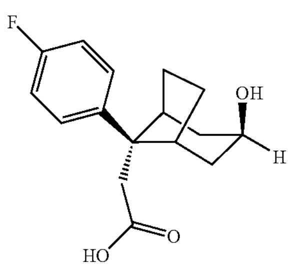 | 277 | >98 |
| 140 | 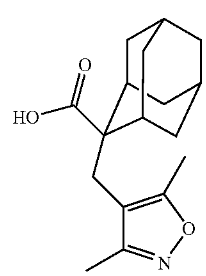 | 288 | 98 |

TABLE 1-continued

| Example | Structure | LC/MS Mass [(M − H)⁻/(M + H)⁺] | HPLC purity (%) |
| --- | --- | --- | --- |
| 141 | 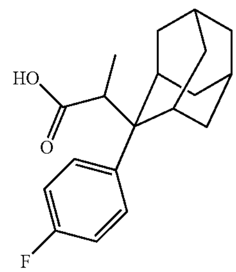 | 301 | 98 |
| 142 | 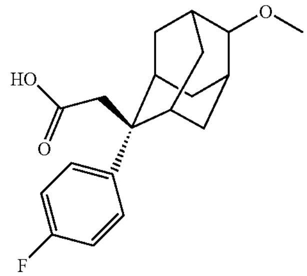 | 317 | >97 |
| 143 | 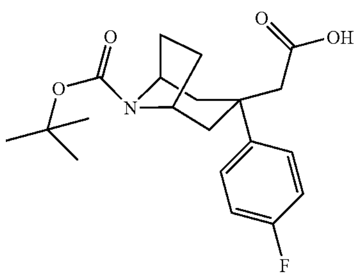 | 362 | >92 |
| 144 | 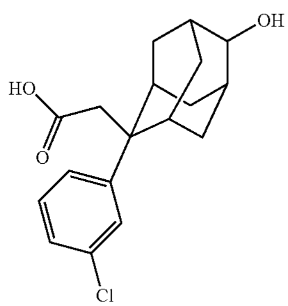 | 319 | 98.1 |
| 145 | 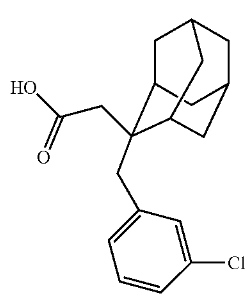 | 317 | 97.8 |

TABLE 1-continued

| Example | Structure | LC/MS Mass [(M − H)⁻/(M + H)⁺] | HPLC purity (%) |
|---|---|---|---|
| 146 | 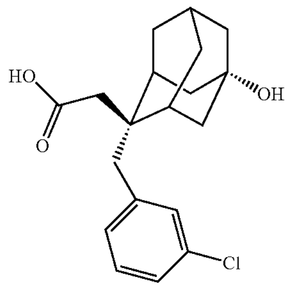 | 333 | 99.3 |
| 147 | 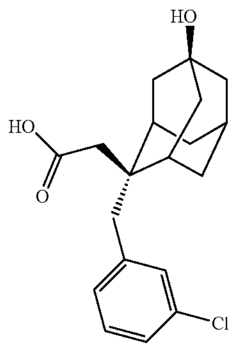 | 333 | >98 |
| 148 | 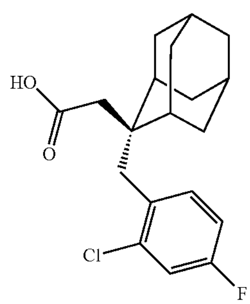 | 335 | 96 |
| 149 (chiral) | 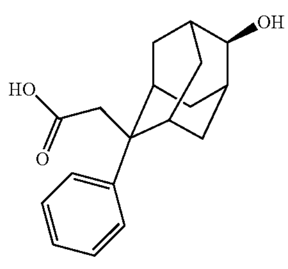 | 285 | 99 |
| 150 | 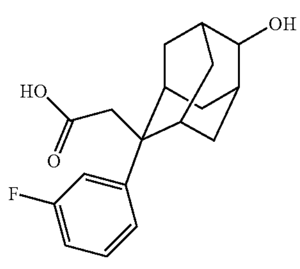 | 303 | >97 |

TABLE 1-continued

| Example | Structure | LC/MS Mass [(M − H)⁻/(M + H)⁺] | HPLC purity (%) |
|---|---|---|---|
| 151 (chiral) | 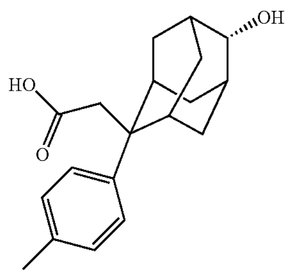 | 299 | 98 |
| 152 (chiral) | 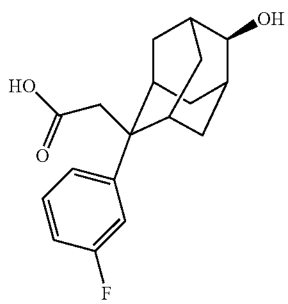 | 303 | 98 |
| 153 (chiral) | 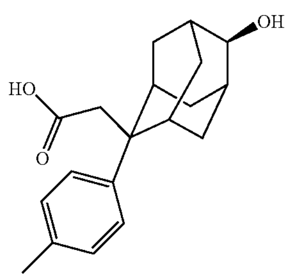 | 299 | 98 |
| 154 (chiral) | 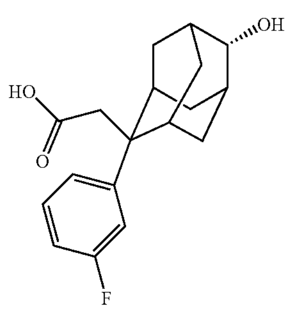 | 303 | 98 |
| 155 | 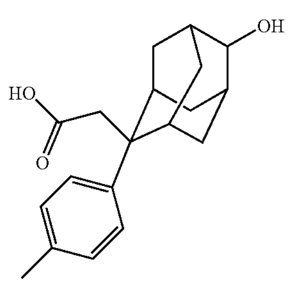 | 299 | >92 |

TABLE 1-continued

| Example | Structure | LC/MS Mass [(M − H)⁻/(M + H)⁺] | HPLC purity (%) |
|---|---|---|---|
| 156 | 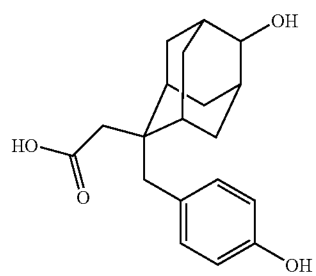 | 315 | 95.6 |
| 157 | 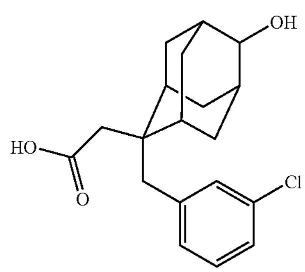 | 333 | 95.2 |
| 158 | 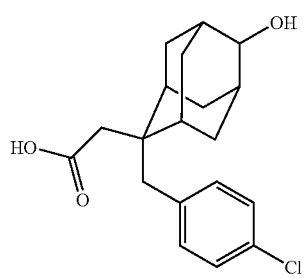 | 333 | 98.7 |
| 159 (chiral) | 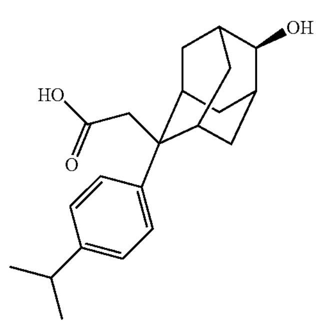 | 327 | 99 |
| 160 (chiral) | 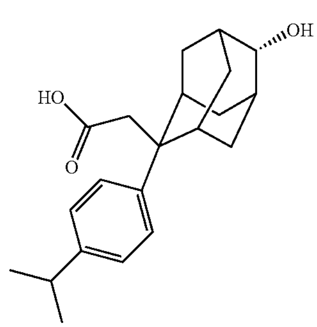 | 327 | 99 |

TABLE 1-continued

| Example | Structure | LC/MS Mass [(M − H)⁻/(M + H)⁺] | HPLC purity (%) |
|---|---|---|---|
| 161 | 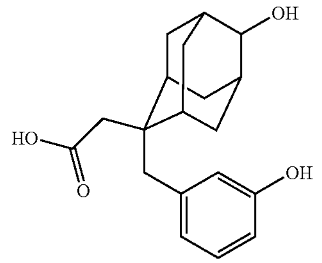 | 315 | 98 |
| 162 | 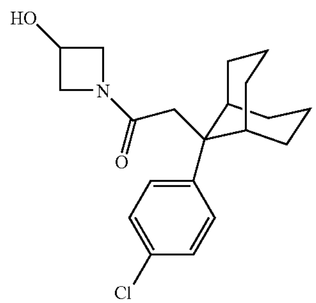 | 348 | 98 |
| 163 | 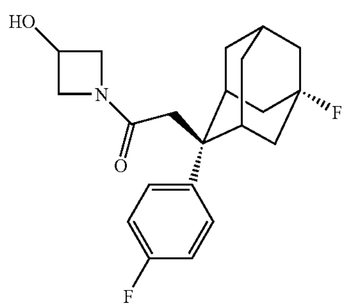 | 362 | 98 |
| 164 | 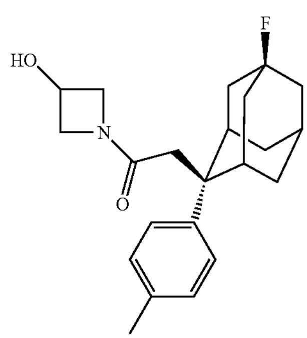 | 362 | 97 |
| 165 | 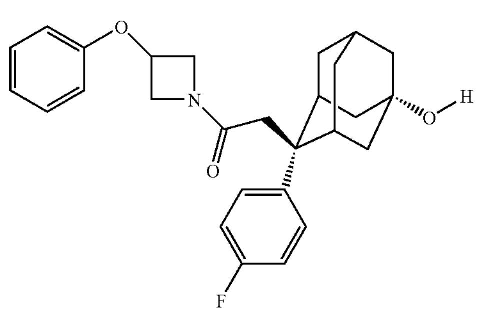 | 436 | 96 |

TABLE 1-continued

| Example | Structure | LC/MS Mass [(M − H)⁻/(M + H)⁺] | HPLC purity (%) |
|---|---|---|---|
| 166 | 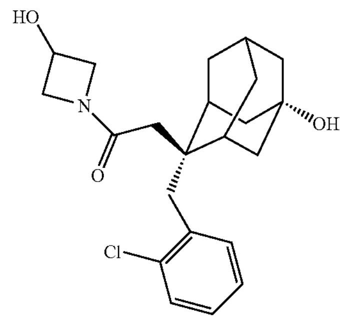 | 390 | 95 |
| 167 | 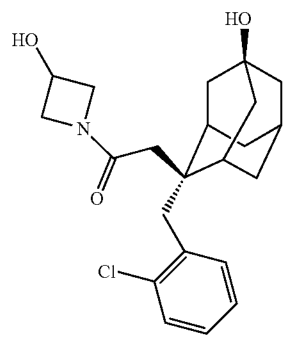 | 390 | 98.1 |
| 168 | 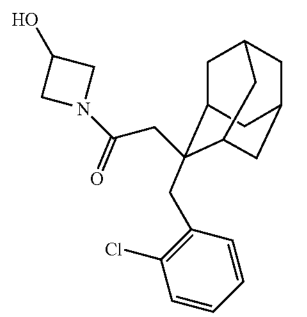 | 374 | 97.9 |
| 169 | 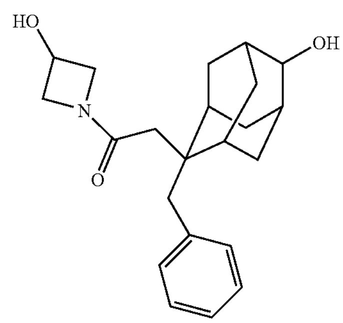 | 356 | >96 |
| 170 | 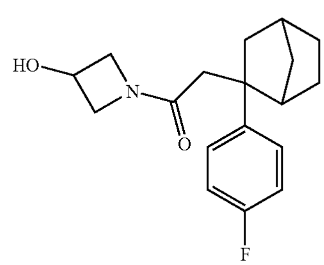 | 304 | 98 |

TABLE 1-continued

| Example | Structure | LC/MS Mass [(M − H)⁻/(M + H)⁺] | HPLC purity (%) |
|---|---|---|---|
| 171 | 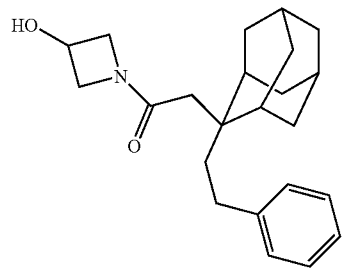 | 354 | >97 |
| 172 | 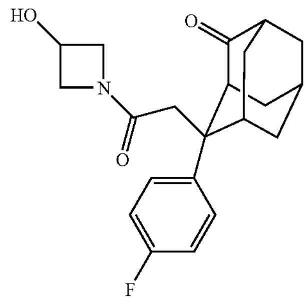 | 358 | 98 |
| 173 | 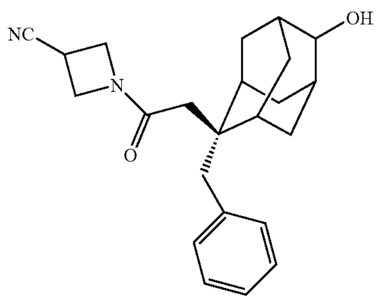 | 364 | 95 |
| 174 | 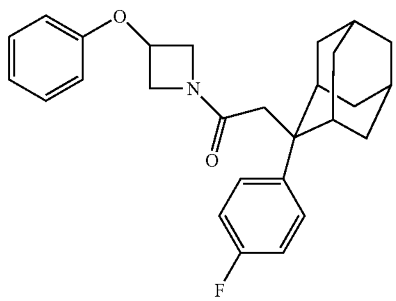 | 420 | 98 |
| 175 | 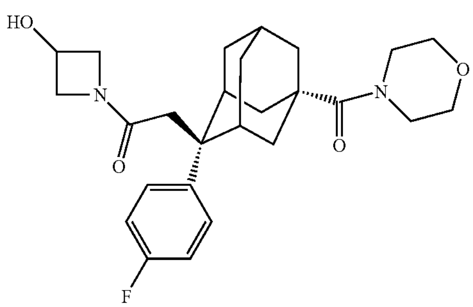 | 457 | 95 |

TABLE 1-continued

| Example | Structure | LC/MS Mass [(M − H)−/(M + H)+] | HPLC purity (%) |
|---|---|---|---|
| 176 | 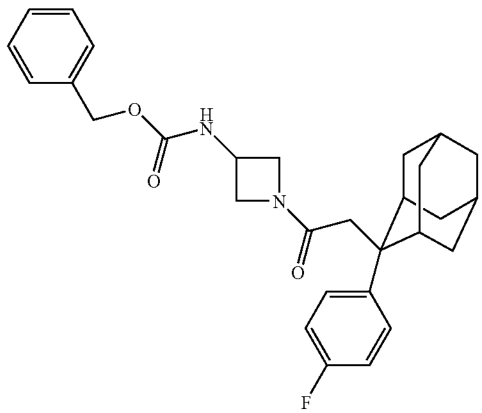 | 477 | 98 |
| 177 | 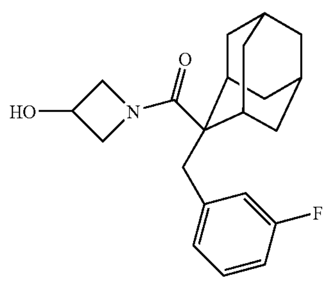 | 344 | 97 |
| 178 | 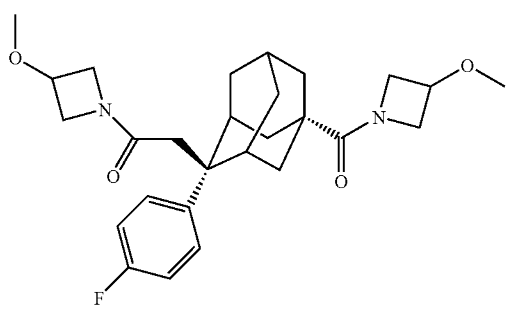 | 471 | 97.7 |
| 179 | 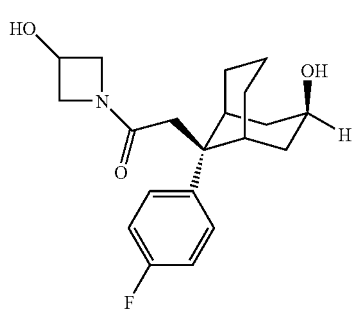 | 348 | 98 |

TABLE 1-continued

| Example | Structure | LC/MS Mass [(M − H)⁻/(M + H)⁺] | HPLC purity (%) |
|---------|-----------|-------------------------------|-----------------|
| 180 | 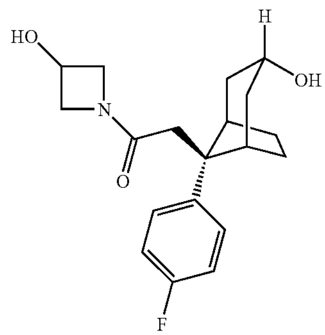 | 334 | 95 |
| 181 | 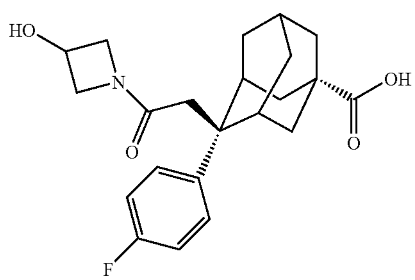 | 388 | 95 |
| 182 | 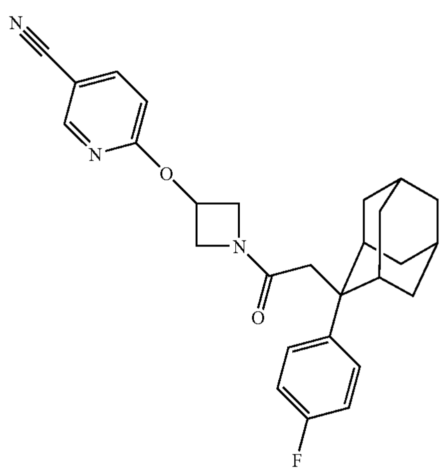 | 446 | 95 |
| 183 | 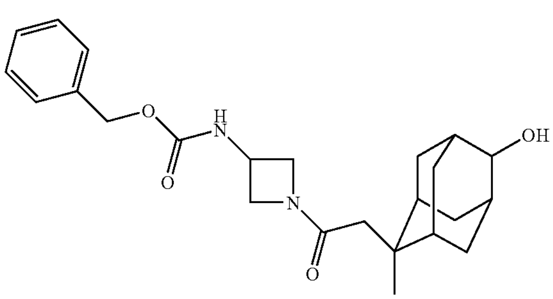 | 413 | 95 |

TABLE 1-continued

| Example | Structure | LC/MS Mass [(M − H)⁻/(M + H)⁺] | HPLC purity (%) |
|---------|-----------|-------------------------------|-----------------|
| 184 | 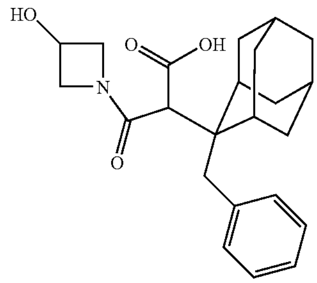 | 384 | 95 |
| 185 | 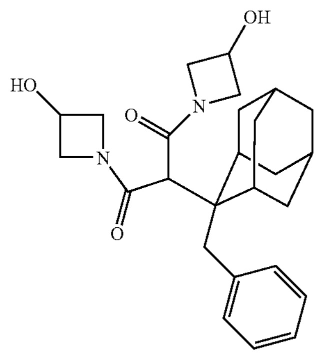 | 439 | 95 |
| 186 | 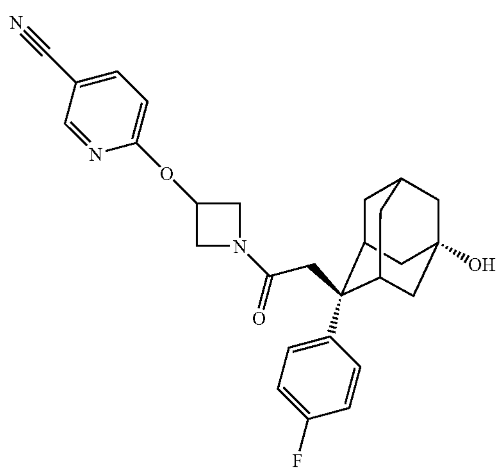 | 462 | 95 |
| 187 | 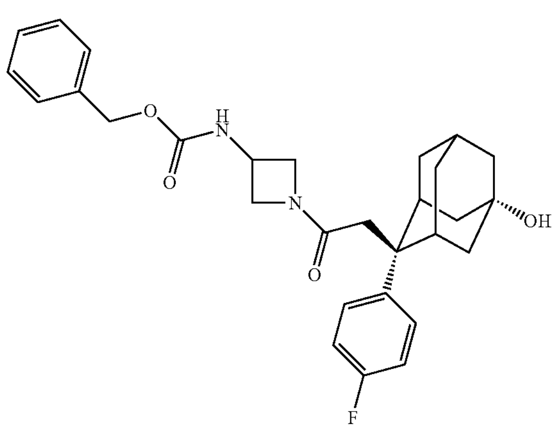 | 493 | 97 |

TABLE 1-continued
| Example | Structure | LC/MS Mass [(M − H)⁻/(M + H)⁺] | HPLC purity (%) |
|---|---|---|---|
| 188 | 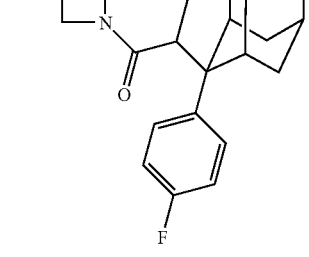 | 358 | 98 |
| 189 | 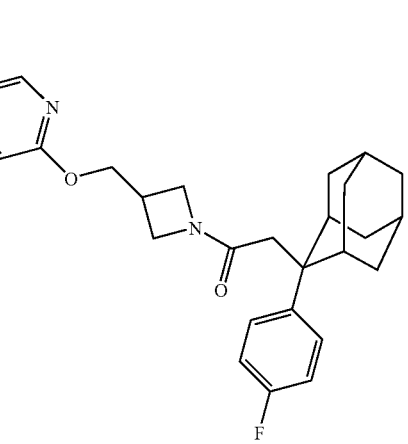 | 460 | 98 |
| 190 | 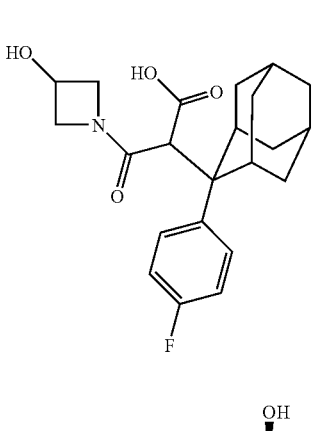 | 388 | 97 |
| 191 | 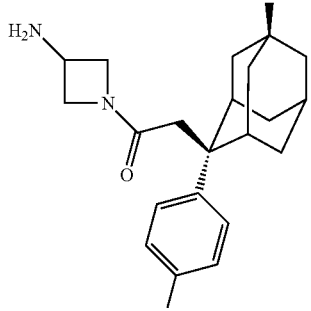 | 359 | 98 |

TABLE 1-continued

| Example | Structure | LC/MS Mass [(M − H)⁻/(M + H)⁺] | HPLC purity (%) |
| --- | --- | --- | --- |
| 192 | 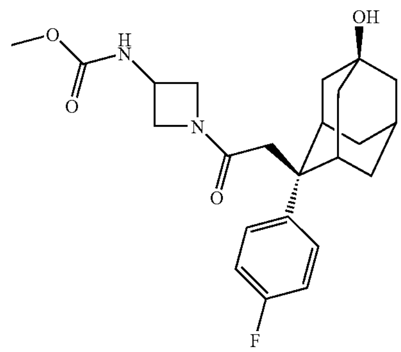 | 417 | 97 |
| 193 | 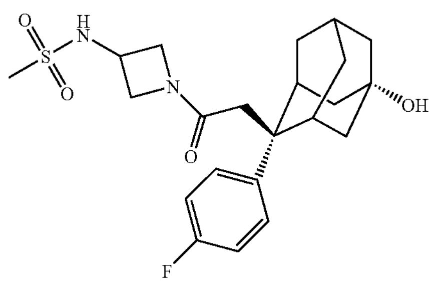 | 437 | 97.9 |
| 194 | 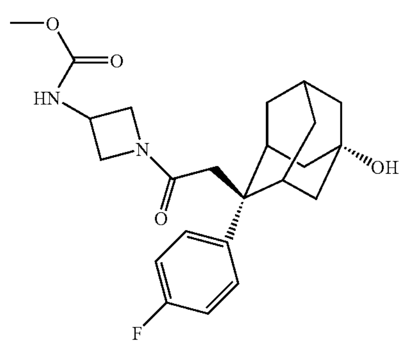 | 417 | 95 |
| 195 | 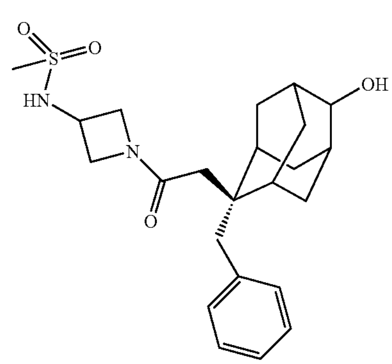 | 433 | >95 |

TABLE 1-continued

| Example | Structure | LC/MS Mass [(M − H)⁻/(M + H)⁺] | HPLC purity (%) |
|---------|-----------|-------------------------------|-----------------|
| 196 | 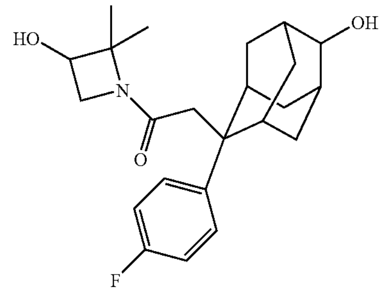 | 388 | >95 |
| 197 | 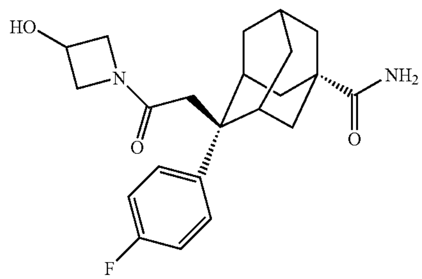 | 387 | >95 |
| 198 | 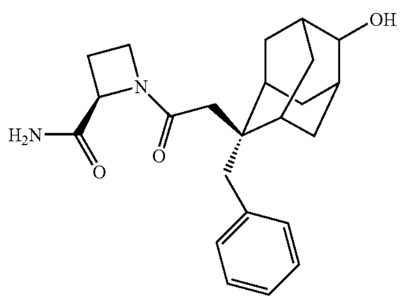 | 383 | >95 |
| 199 | 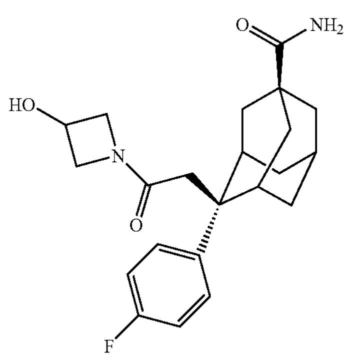 | 387 | 98 |
| 200 | 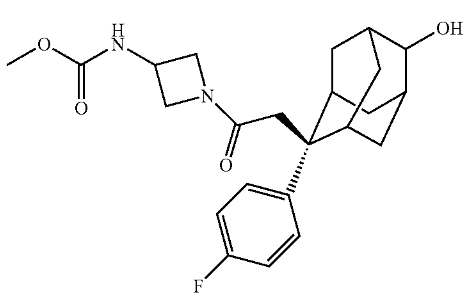 | 417 | >95 |

TABLE 1-continued

| Example | Structure | LC/MS Mass [(M − H)⁻/(M + H)⁺] | HPLC purity (%) |
|---|---|---|---|
| 201 | 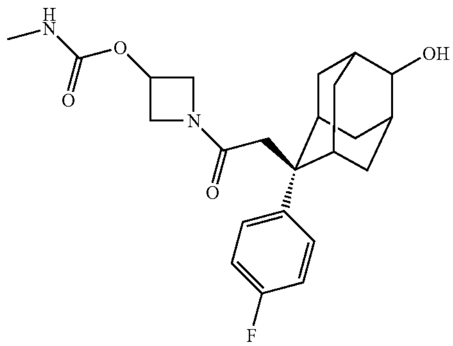 | 417 | 98 |
| 202 | 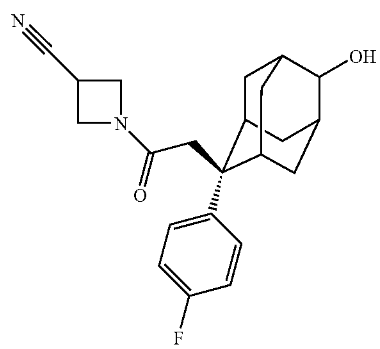 | 369 | 95 |
| 203 | 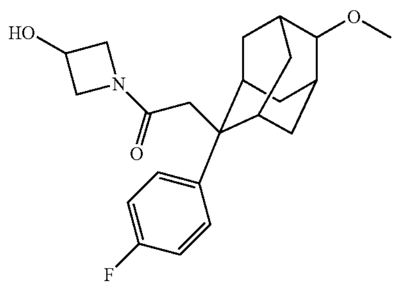 | 374 | 95.3 |
| 204 | 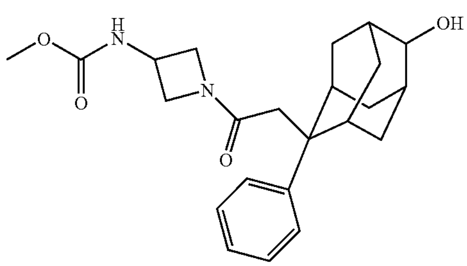 | 399 | 98 |
| 205 | 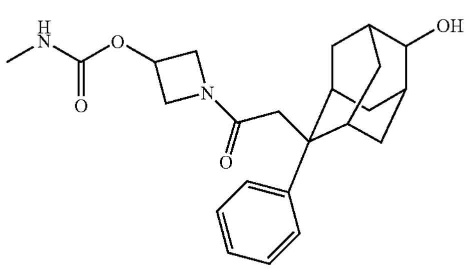 | 399 | >95 |

TABLE 1-continued

| Example | Structure | LC/MS Mass [(M − H)⁻/(M + H)⁺] | HPLC purity (%) |
|---|---|---|---|
| 206 | 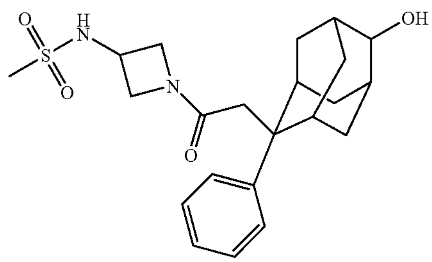 | 419 | 99 |
| 207 | 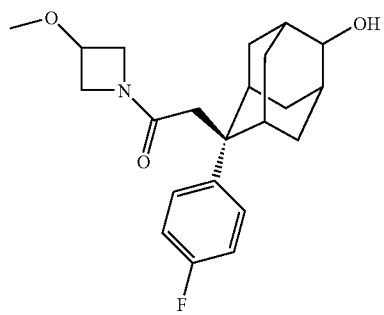 | 374 | 95 |
| 208 | 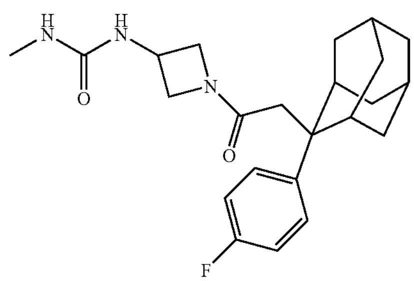 | 400 | >96 |
| 209 | 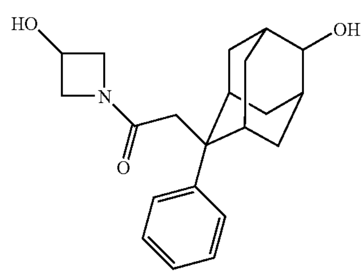 | 342 | 97 |
| 210 | 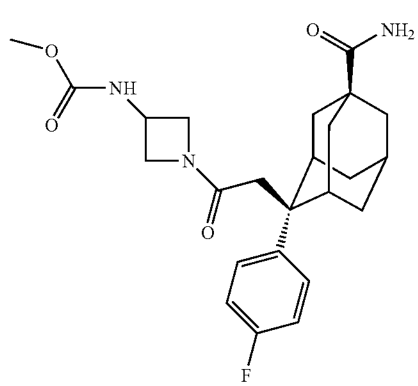 | 444 | 96 |

TABLE 1-continued

| Example | Structure | LC/MS Mass [(M − H)⁻/(M + H)⁺] | HPLC purity (%) |
|---|---|---|---|
| 211 | 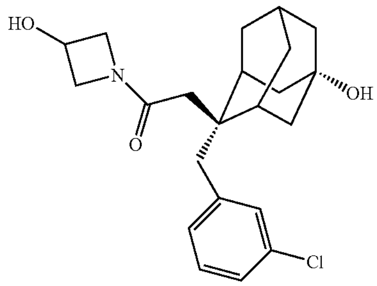 | 390 | >97 |
| 212 | 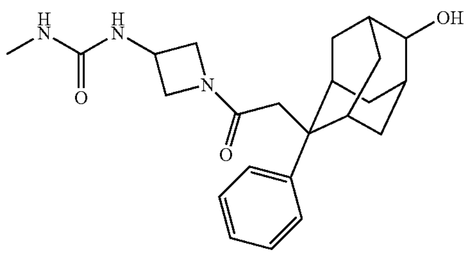 | 398 | >97.3 |
| 213 | 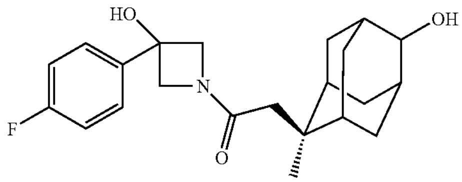 | 374 | 98 |
| 214 | 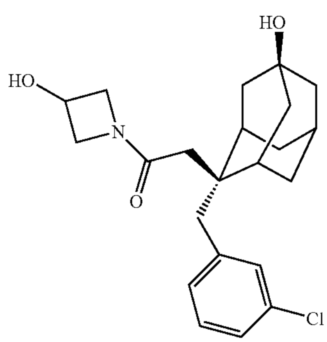 | 390 | 98 |
| 215 | 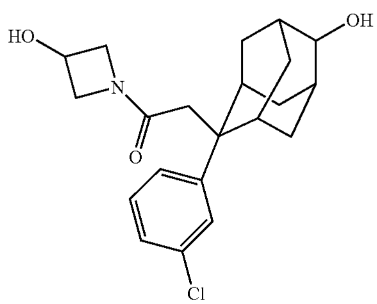 | 376 | >95 |

TABLE 1-continued

| Example | Structure | LC/MS Mass [(M − H)−/(M + H)+] | HPLC purity (%) |
|---|---|---|---|
| 216 | 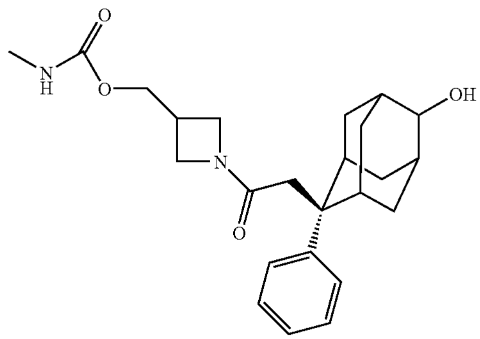 | 413 | 98 |
| 217 (chiral) | 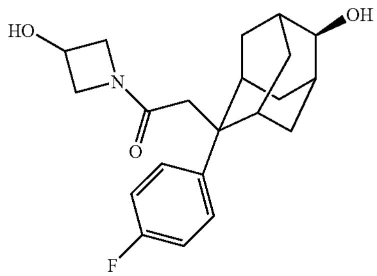 | 360 | 92 |
| 218 | 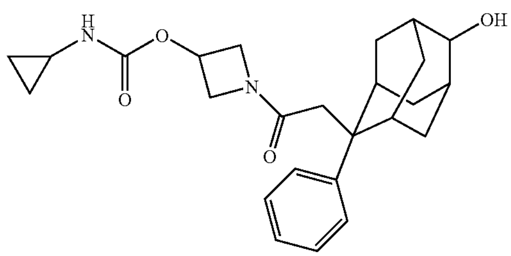 | 425 | 97 |
| 219 | 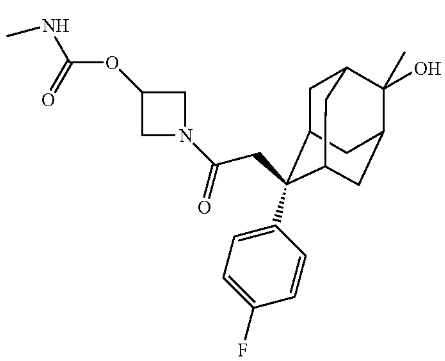 | 431 | 97 |
| 220 | 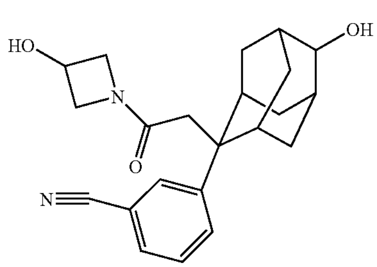 | 367 | 99 |

TABLE 1-continued

| Example | Structure | LC/MS Mass [(M − H)⁻/(M + H)⁺] | HPLC purity (%) |
|---------|-----------|-------------------------------|-----------------|
| 221 | 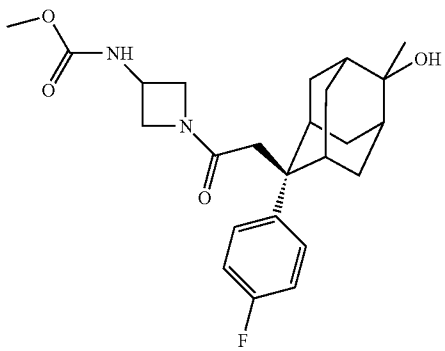 | 431 | 98 |
| 222 | 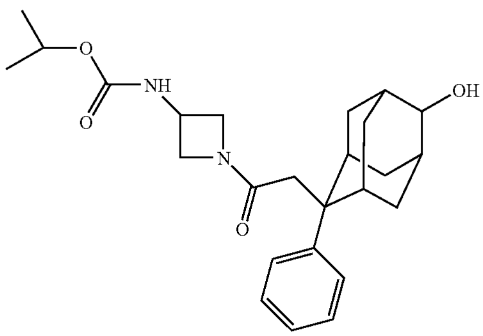 | 427 | 98 |
| 223 | 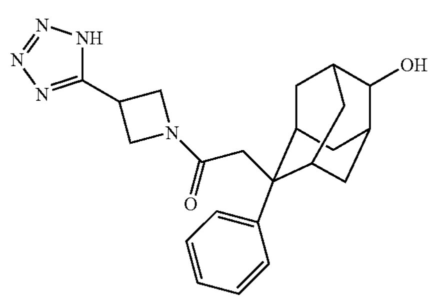 | 394 | 97.9 |
| 224 | 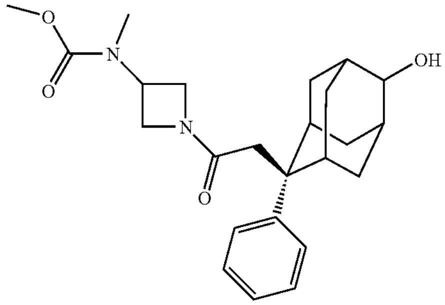 | 413 | 97 |

TABLE 1-continued

| Example | Structure | LC/MS Mass [(M − H)⁻/(M + H)⁺] | HPLC purity (%) |
|---|---|---|---|
| 225 | 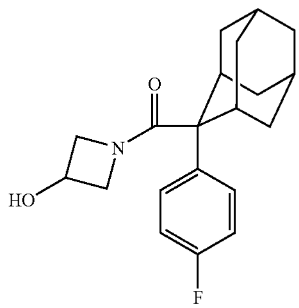 | 330 | 94 |
| 226 | 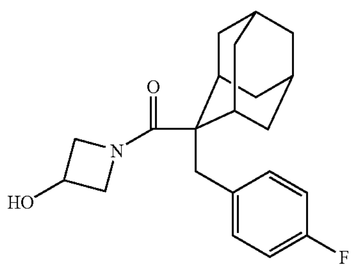 | 344 | 98 |
| 227 (chiral) | 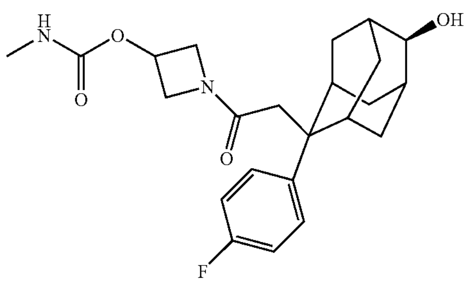 | 417 | 92 |
| 228 (chiral) | 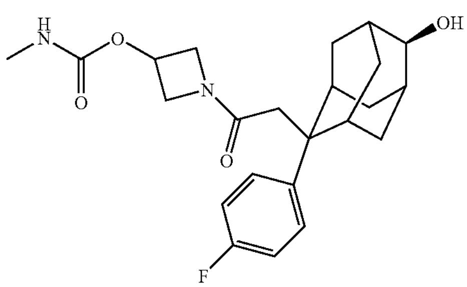 | 417 | 92 |
| 229 | 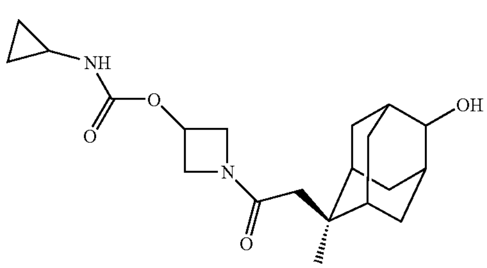 | 363 | 96 |

TABLE 1-continued
| Example | Structure | LC/MS Mass [(M − H)⁻/(M + H)⁺] | HPLC purity (%) |
|---|---|---|---|
| 230 (chiral) | 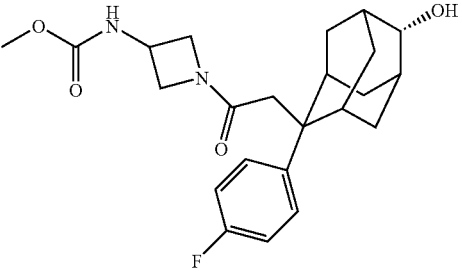 | 417 | 98 |
| 231 | 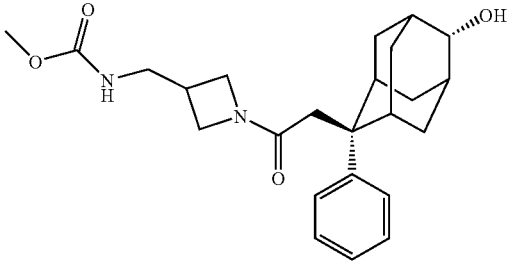 | 413 | 95 |
| 232 (chiral) | 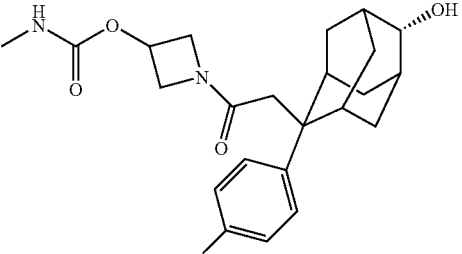 | 417 | 98 |
| 233 | 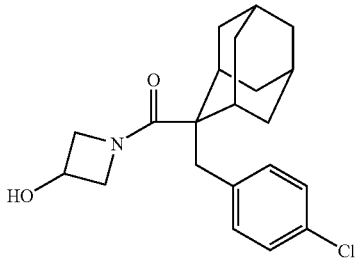 | 360 | 97 |
| 234 | 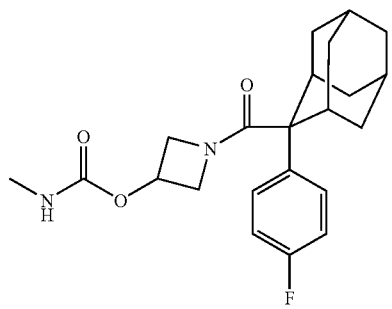 | 387 | 99 |

TABLE 1-continued

| Example | Structure | LC/MS Mass [(M − H)⁻/(M + H)⁺] | HPLC purity (%) |
|---|---|---|---|
| 235 | 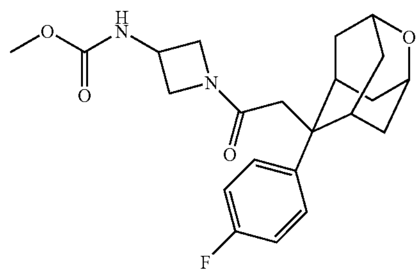 | 403 | >97 |
| 236 | 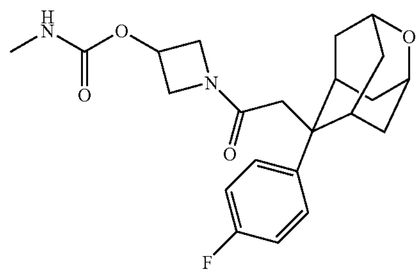 | 403 | 95 |
| 237 | 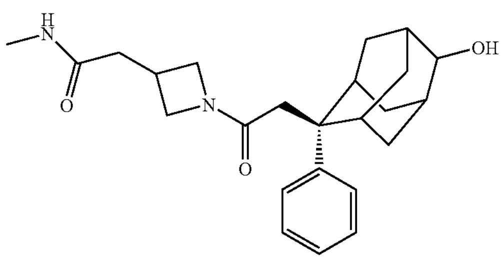 | 397 | 96 |
| 238 (chiral) | 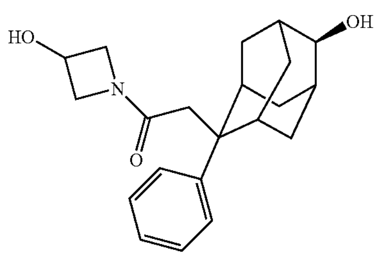 | 342 | >95 |
| 239 | 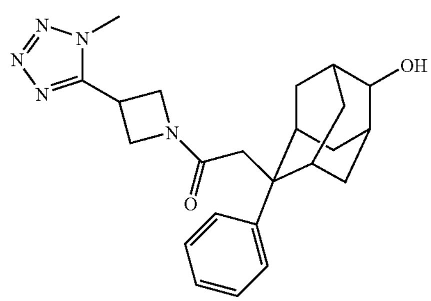 | 408 | >95 |

TABLE 1-continued

| Example | Structure | LC/MS Mass [(M − H)⁻/(M + H)⁺] | HPLC purity (%) |
|---|---|---|---|
| 240 | 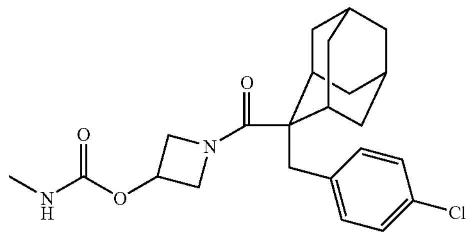 | 417 | 95 |
| 241 (chiral) | 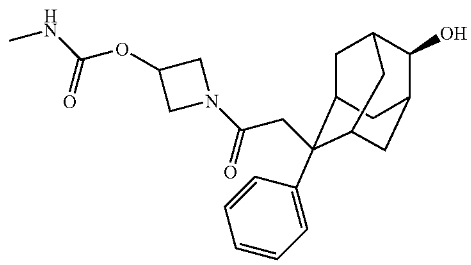 | 399 | 98 |
| 242 (chiral) | 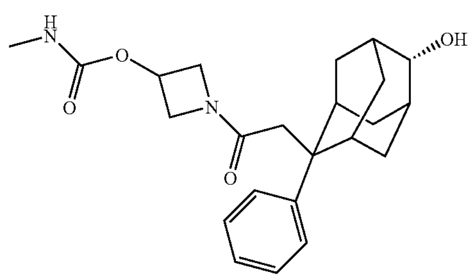 | 399 | 97 |
| 243 | 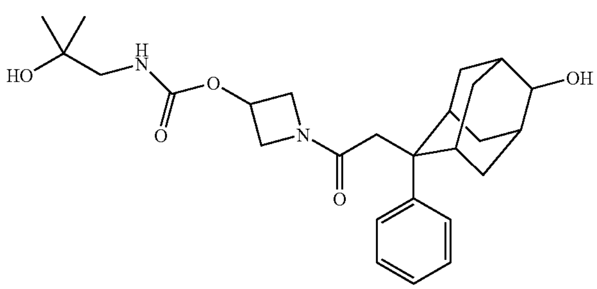 | 457 | 95 |
| 244 | 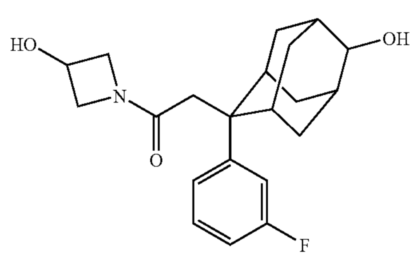 | 360 | 97 |

TABLE 1-continued

| Example | Structure | LC/MS Mass [(M − H)⁻/(M + H)⁺] | HPLC purity (%) |
|---|---|---|---|
| 245 | 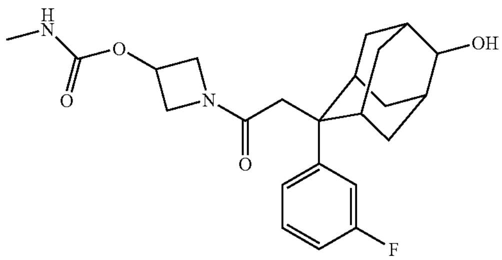 | 417 | 98 |
| 246 (chiral) | 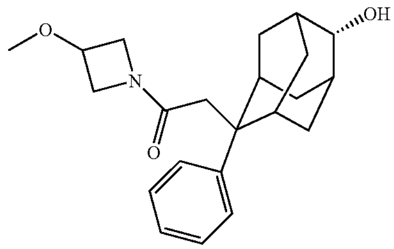 | 356 | 96 |
| 247 | 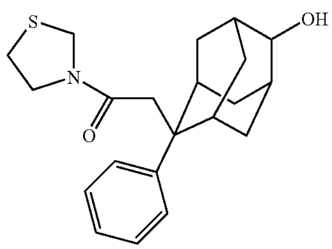 | 358 | 97 |
| 248 (chiral) | 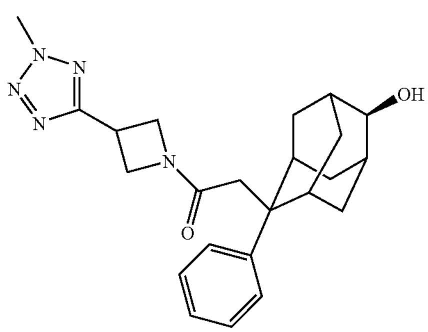 | 408 | >95 |
| 249 | 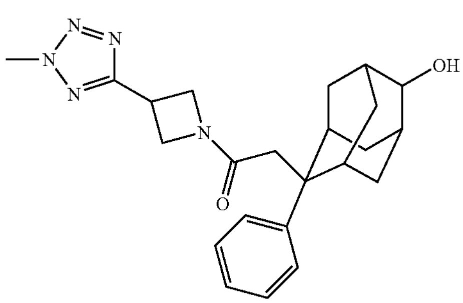 | 408 | 97 |

TABLE 1-continued

| Example | Structure | LC/MS Mass [(M − H)⁻/(M + H)⁺] | HPLC purity (%) |
|---|---|---|---|
| 250 | 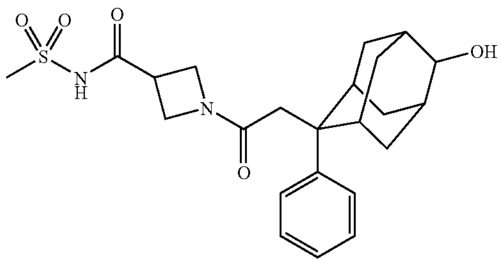 | 447 | 98 |
| 251 | 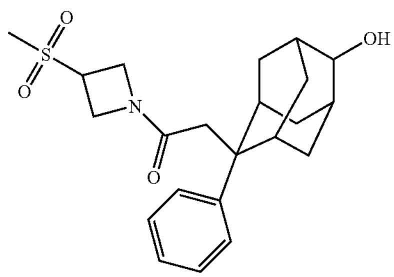 | 404 | 95 |
| 252 | 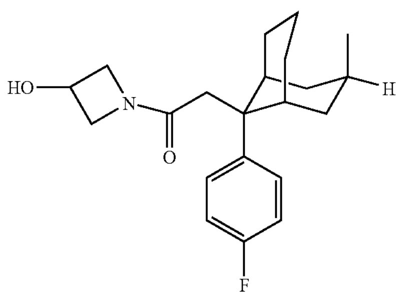 | 346 | 98 |
| 253 | 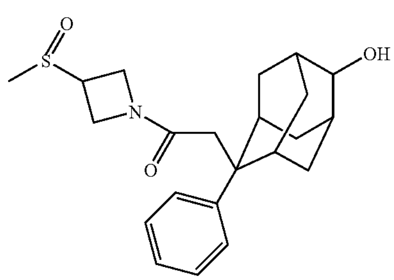 | 388 | >95 |
| 254 | 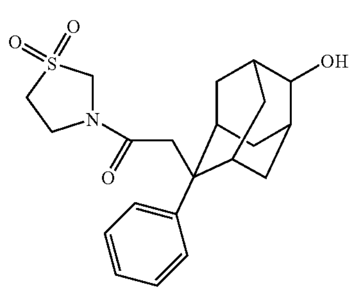 | 390 | >95 |

TABLE 1-continued

| Example | Structure | LC/MS Mass [(M − H)⁻/(M + H)⁺] | HPLC purity (%) |
|---|---|---|---|
| 255 | 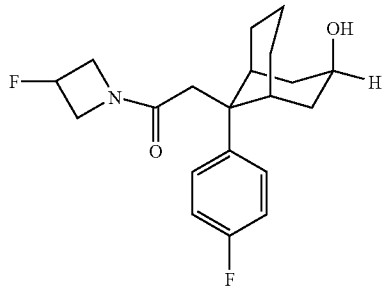 | 350 | 92 |
| 256 (chiral) | 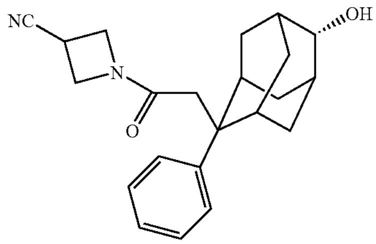 | 351 | 97 |
| 257 | 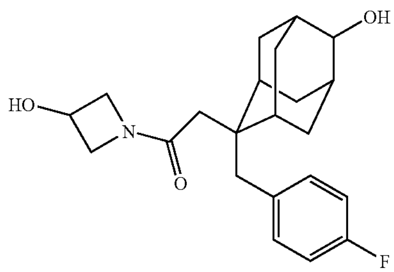 | 374 | 95.4 |
| 258 (chiral) | 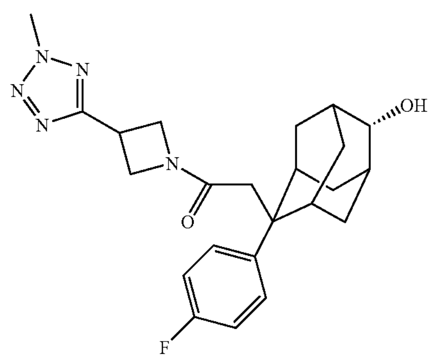 | 426 | >98.6 |
| 259 (chiral) | 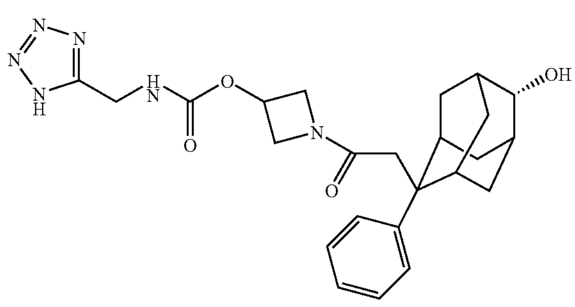 | 467 | 98 |

TABLE 1-continued

| Example | Structure | LC/MS Mass [(M − H)−/(M + H)+] | HPLC purity (%) |
|---|---|---|---|
| 260 (chiral) | 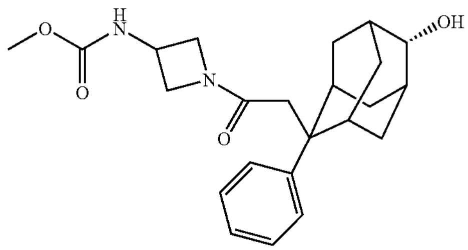 | 399 | 97 |
| 261 | 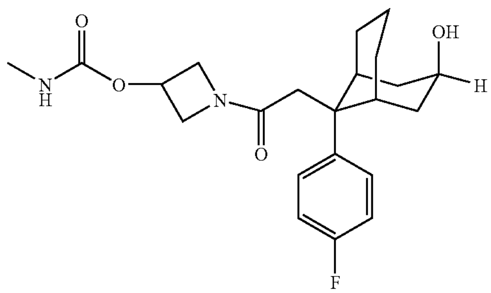 | 405 | 97 |
| 262 | 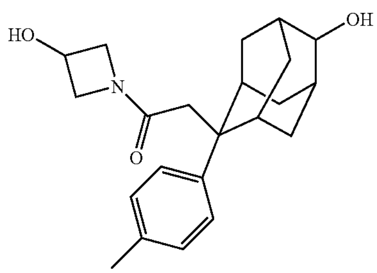 | 356 | 99 |
| 263 | 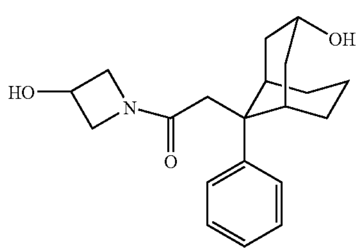 | 330 | 96 |
| 264 | 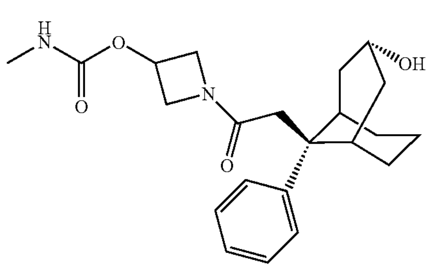 | 387 | 98 |

TABLE 1-continued

| Example | Structure | LC/MS Mass [(M − H)⁻/(M + H)⁺] | HPLC purity (%) |
|---|---|---|---|
| 265 (chiral) | 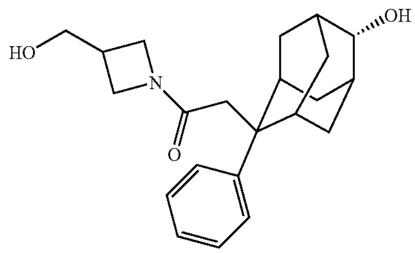 | 356 | 96 |
| 266 | 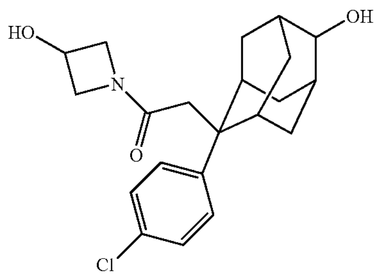 | 376 | 99 |
| 267 | 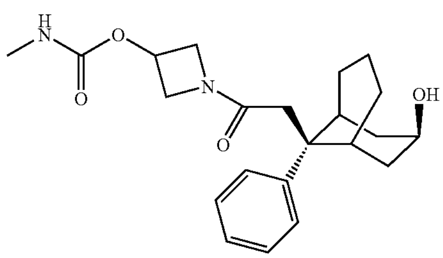 | 387 | 95 |
| 268 (chiral) | 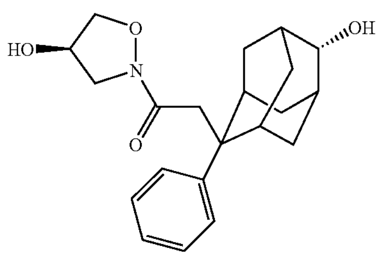 | 358 | 90 |
| 269 | 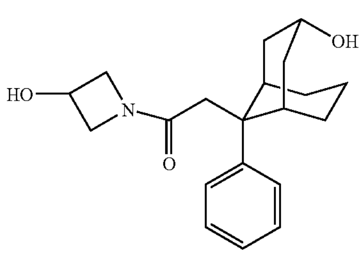 | 330 | 95 |
| 270 (chiral) | 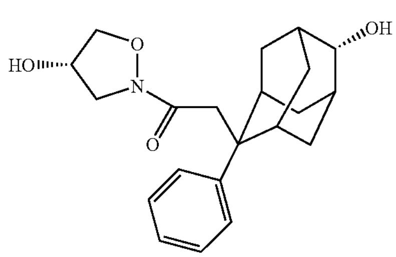 | 358 | 95 |

TABLE 1-continued

| Example | Structure | LC/MS Mass [(M − H)⁻/(M + H)⁺] | HPLC purity (%) |
|---|---|---|---|
| 271 | 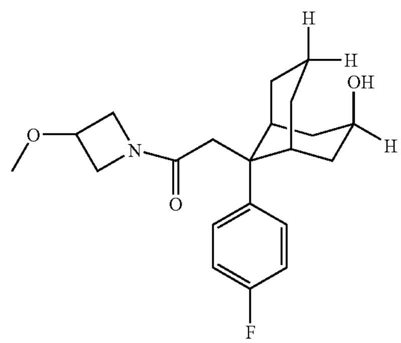 | 362 | 95 |
| 272 | 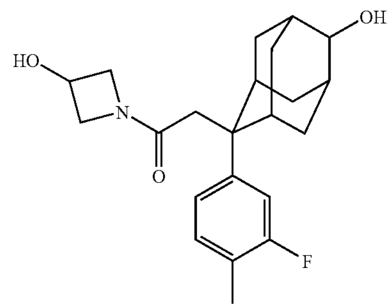 | 374 | 98 |
| 273 (chiral) | 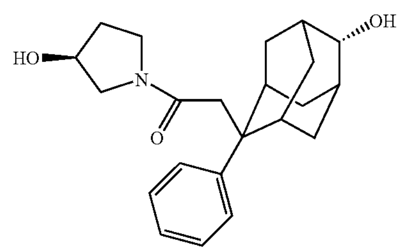 | 356 | 98 |
| 274 (chiral) | 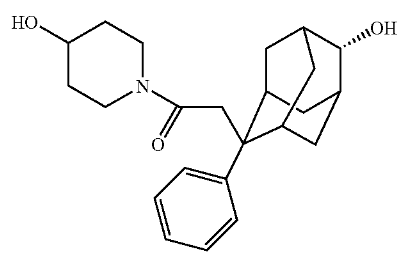 | 370 | 97 |
| 275 (chiral) | 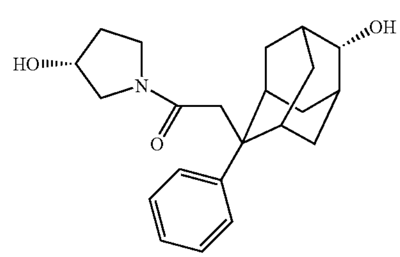 | 356 | >95 |

TABLE 1-continued

| Example | Structure | LC/MS Mass [(M − H)⁻/(M + H)⁺] | HPLC purity (%) |
|---|---|---|---|
| 276 | 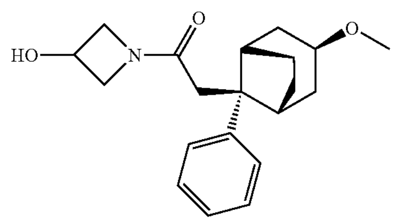 | 344 | 96 |
| 277 (chiral) | 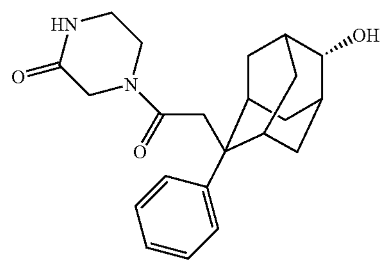 | 369 | 98 |
| 278 (chiral) | 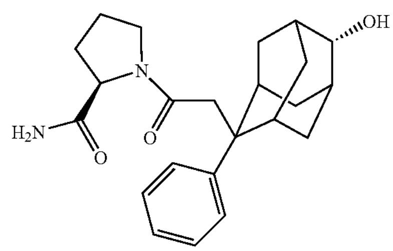 | 383 | 95 |
| 279 (chiral) | 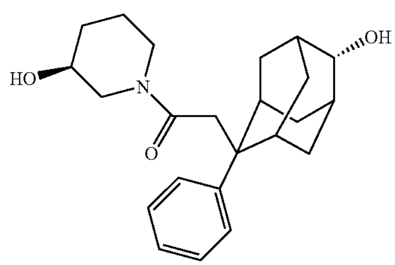 | 370 | >96 |
| 280 | 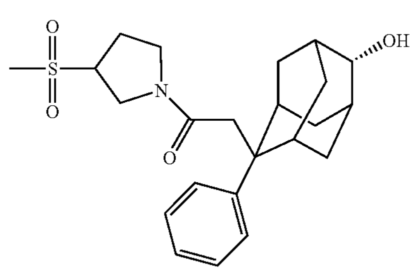 | 418 | >95 |
| 281 (chiral) | 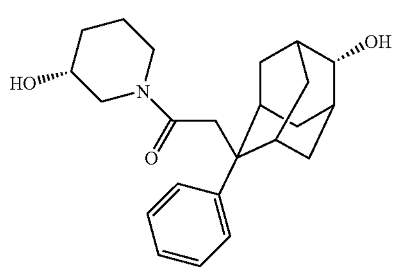 | 370 | 98 |

TABLE 1-continued

| Example | Structure | LC/MS Mass [(M − H)⁻/(M + H)⁺] | HPLC purity (%) |
|---------|-----------|-------------------------------|-----------------|
| 282 (chiral) | 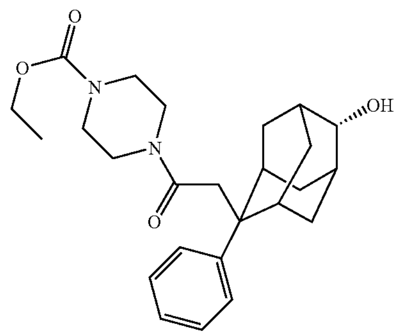 | 427 | 97 |
| 283 | 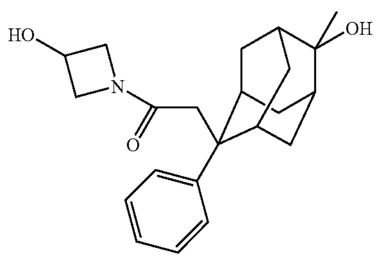 | 356 | 98 |
| 284 (chiral) | 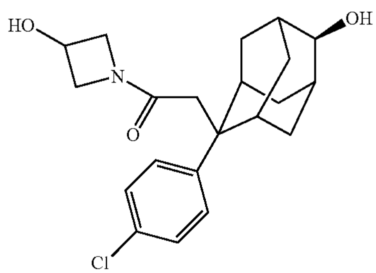 | 376 | >99 |
| 285 (chiral) | 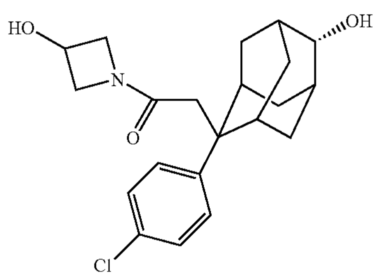 | 376 | >99 |
| 286 | 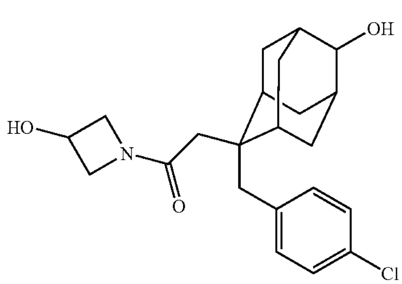 | 390 | 98.7 |

TABLE 1-continued

| Example | Structure | LC/MS Mass [(M − H)⁻/(M + H)⁺] | HPLC purity (%) |
|---------|-----------|-------------------------------|-----------------|
| 287 | 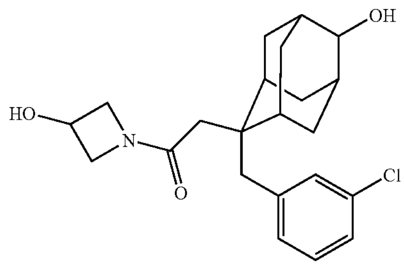 | 390 | 99.3 |
| 288 (chiral) | 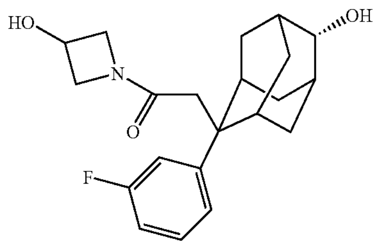 | 360 | 95 |
| 289 (chiral) | 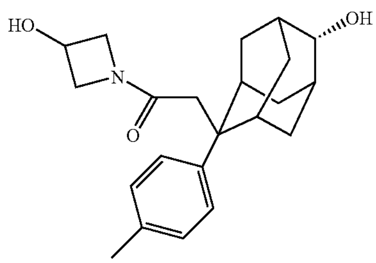 | 356 | 98 |
| 290 (chiral) | 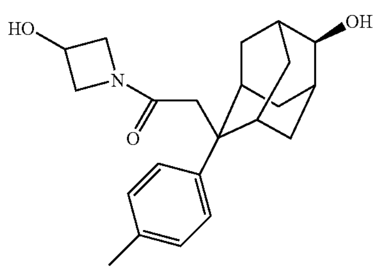 | 356 | 98 |
| 291 (chiral) | 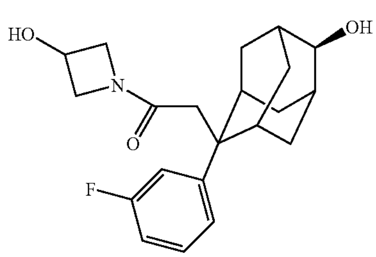 | 360 | 95 |

TABLE 1-continued

| Example | Structure | LC/MS Mass [(M − H)⁻/(M + H)⁺] | HPLC purity (%) |
|---|---|---|---|
| 292 | 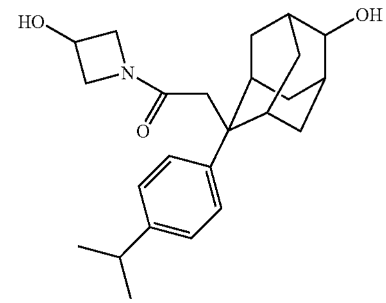 | 384 | 98 |
| 293 | 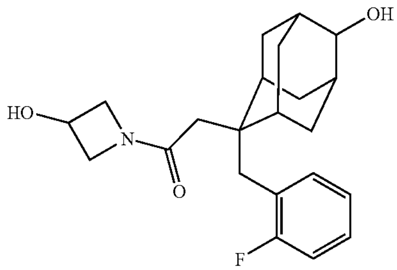 | 374 | 97.3 |
| 294 | 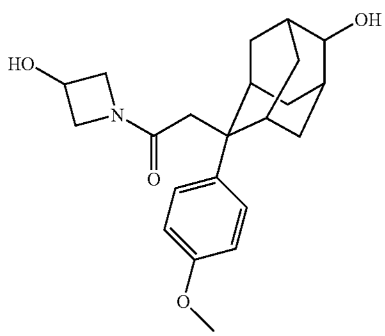 | 372 | 95 |
| 295 (chiral) | 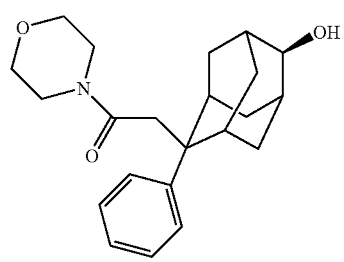 | 356 | 100 |
| 296 (chiral) | 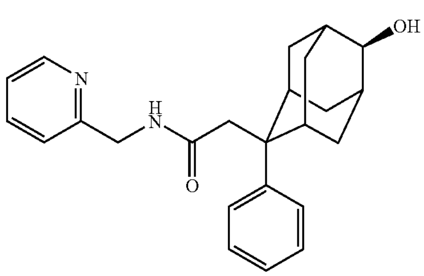 | 377 | 97.9 |

TABLE 1-continued

| Example | Structure | LC/MS Mass [(M − H)⁻/(M + H)⁺] | HPLC purity (%) |
|---|---|---|---|
| 297 (chiral) | 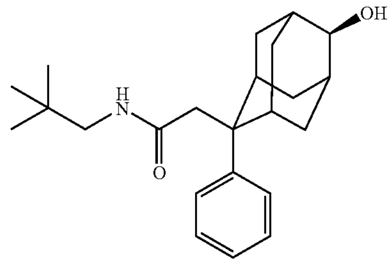 | 356 | 100 |
| 298 | 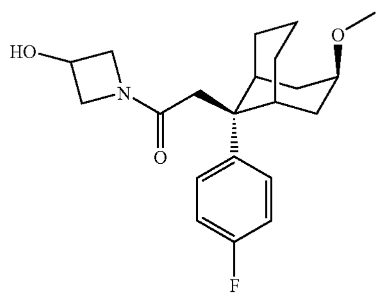 | 362 | 95 |
| 299 | 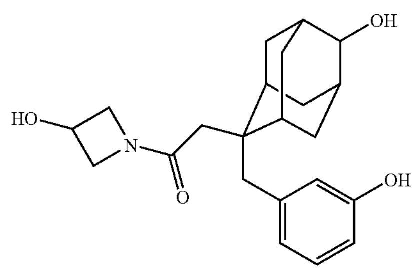 | 372 | 95.5 |
| 300 | 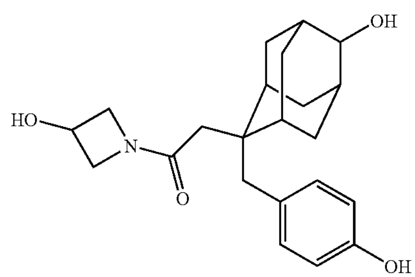 | 372 | 95.6 |
| 301 | 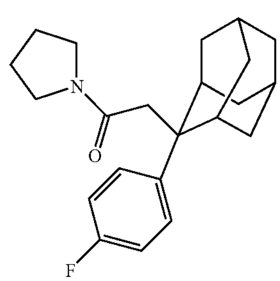 | 341 | 98 |

TABLE 1-continued
| Example | Structure | LC/MS Mass [(M − H)⁻/(M + H)⁺] | HPLC purity (%) |
|---|---|---|---|
| 302 (chiral) | 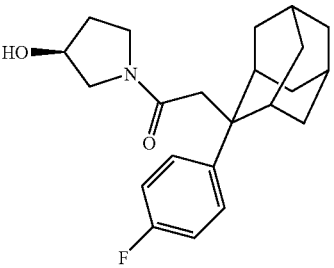 | 358 | 97 |
| 303 | 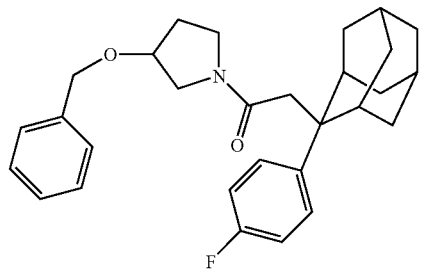 | 448 | 98 |
| 304 | 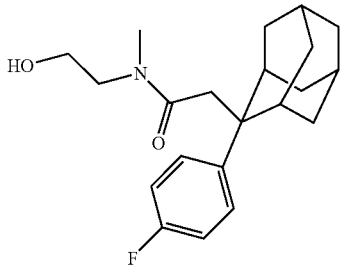 | 346 | 96 |
| 305 | 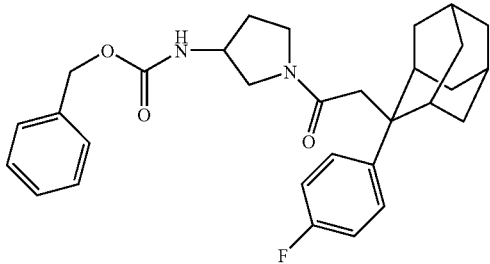 | 490 | 98 |
| 306 | 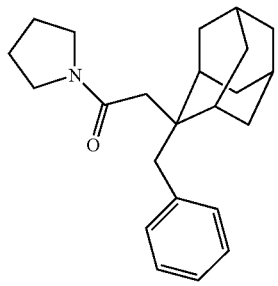 | 324 | >98 |

TABLE 1-continued
| Example | Structure | LC/MS Mass [(M − H)⁻/(M + H)⁺] | HPLC purity (%) |
|---|---|---|---|
| 307 | 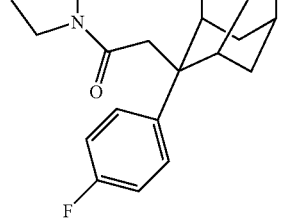 | 362 | 93 |
| 308 | 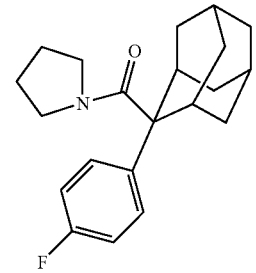 | 328 | 97 |
| 309 | 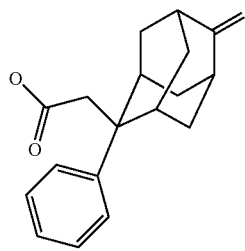 | 283 | 99 |
| 310 | 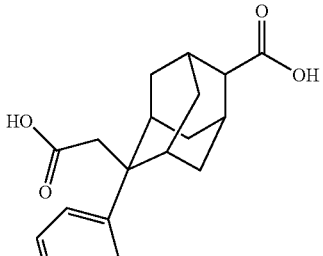 | 331 | 98 |
| 311 | 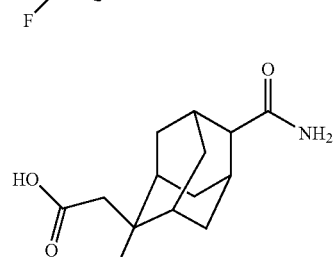 | 330 | 98 |

TABLE 1-continued

| Example | Structure | LC/MS Mass [(M − H)⁻/(M + H)⁺] | HPLC purity (%) |
|---------|-----------|-------------------------------|-----------------|
| 312 | 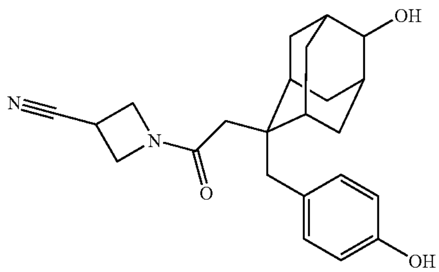 | 381 | 94.2 |
| 313 | 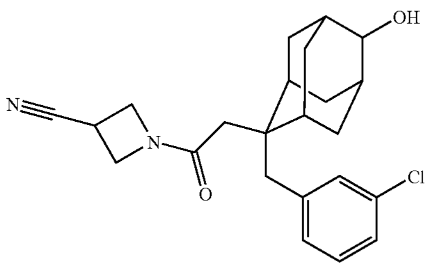 | 399 | 98.3 |
| 314 | 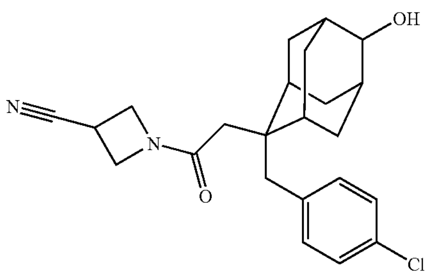 | 399 | 97.8 |
| 315 | 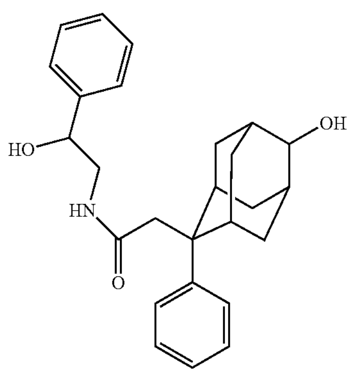 | 406 | 99.3 |
| 316 | 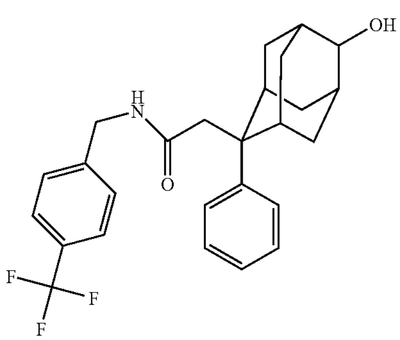 | 444 | 99.0 |

TABLE 1-continued

| Example | Structure | LC/MS Mass [(M − H)⁻/(M + H)⁺] | HPLC purity (%) |
|---|---|---|---|
| 317 | 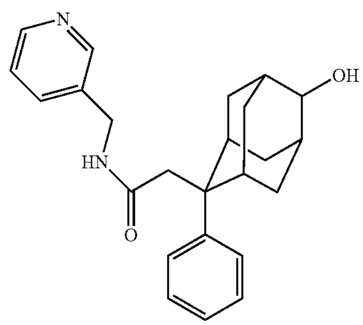 | 377 | 100.0 |
| 318 | 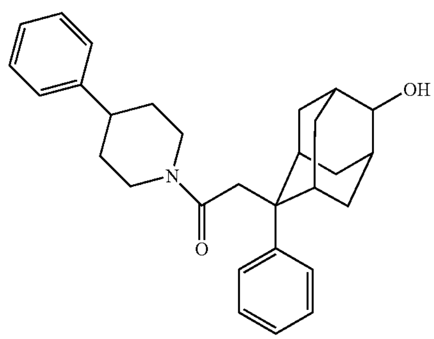 | 430 | 100.0 |
| 319 | 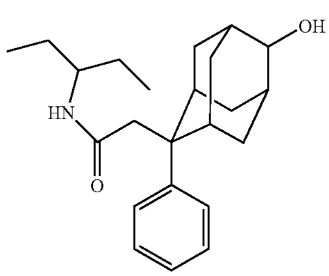 | 356 | 91.7 |
| 320 | 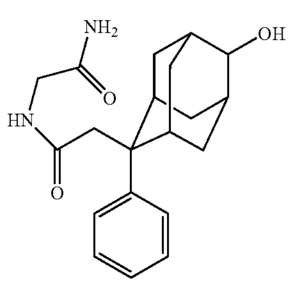 | 343 | 99.2 |

TABLE 1-continued

| Example | Structure | LC/MS Mass [(M − H)⁻/(M + H)⁺] | HPLC purity (%) |
| --- | --- | --- | --- |
| 321 | 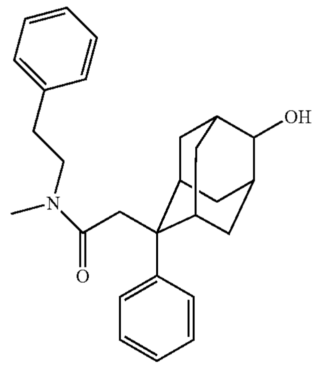 | 404 | 99.2 |
| 322 | 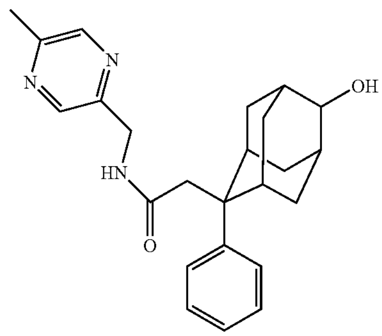 | 392 | 100.0 |
| 323 | 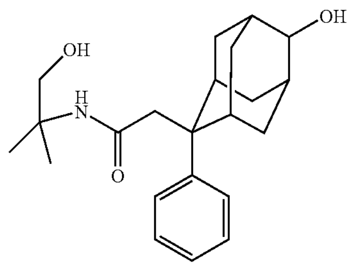 | 358 | 100.0 |
| 324 | 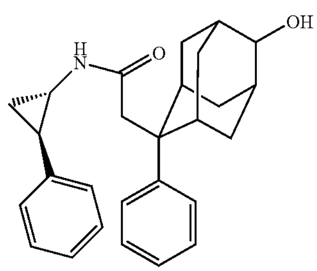 | 402 | 95.3 |
| 325 | 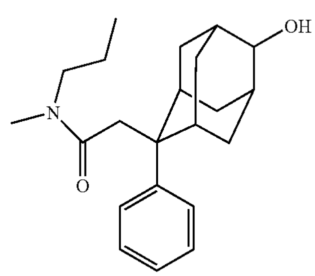 | 342 | 91.2 |

TABLE 1-continued

| Example | Structure | LC/MS Mass [(M − H)⁻/(M + H)⁺] | HPLC purity (%) |
| --- | --- | --- | --- |
| 326 | 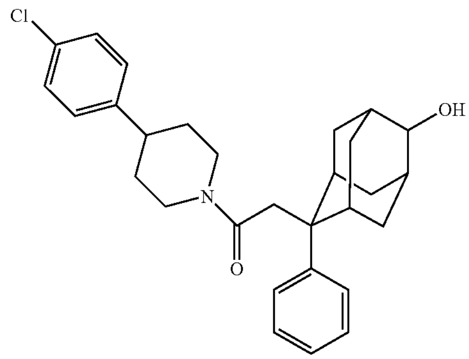 | 465 | 97.9 |
| 327 | 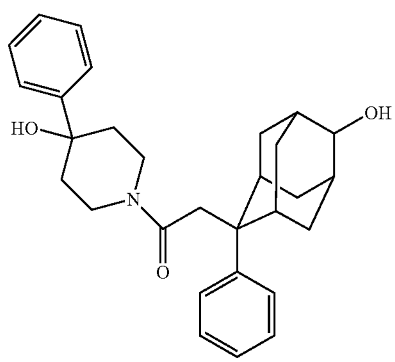 | 446 | 90.9 |
| 328 | 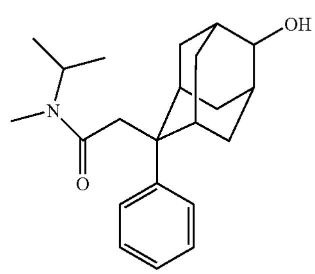 | 342 | 97.1 |
| 329 | 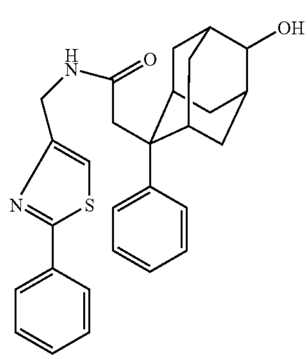 | 459 | 100.0 |

TABLE 1-continued

| Example | Structure | LC/MS Mass [(M − H)⁻/(M + H)⁺] | HPLC purity (%) |
| --- | --- | --- | --- |
| 330 | 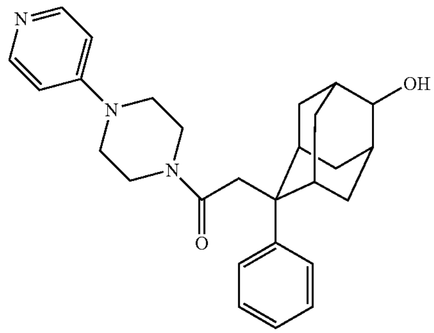 | 432 | 98.4 |
| 331 | 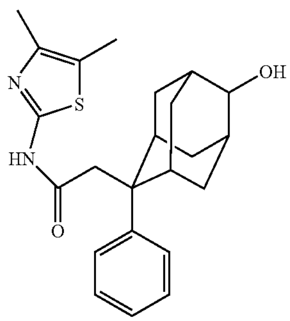 | 397 | 96.4 |
| 332 | 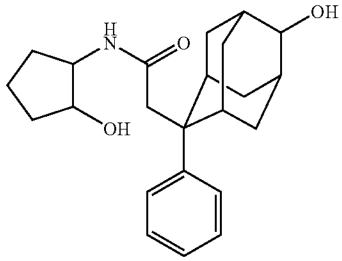 | 370 | 97.0 |
| 333 | 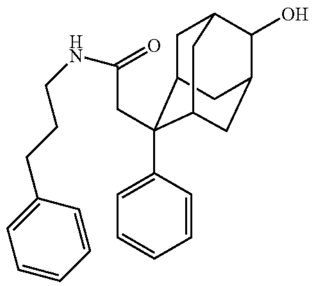 | 404 | 100.0 |
| 334 | 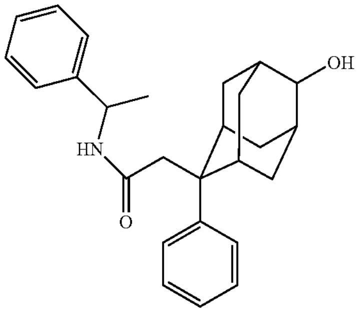 | 390 | 100.0 |

TABLE 1-continued
| Example | Structure | LC/MS Mass [(M − H)⁻/(M + H)⁺] | HPLC purity (%) |
|---|---|---|---|
| 335 | 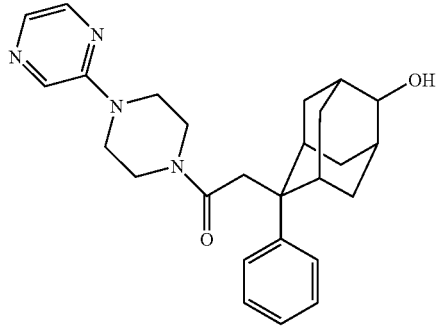 | 433 | 98.4 |
| 336 | 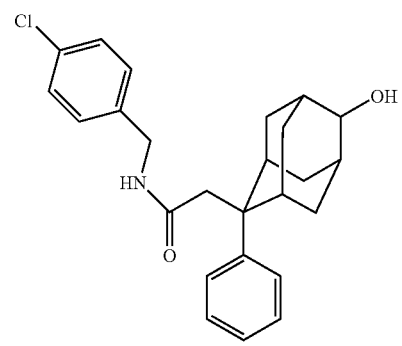 | 411 | 100.0 |
| 337 | 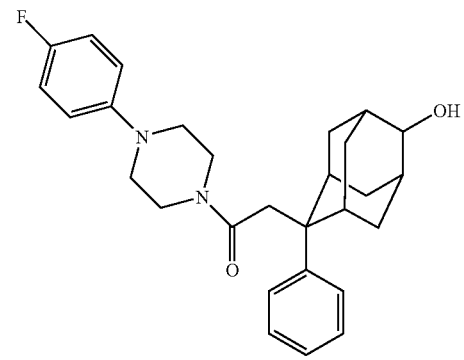 | 449 | 99.1 |
| 338 | 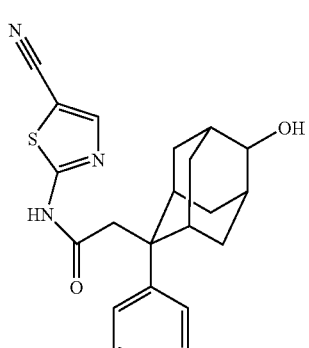 | 394 | 97.9 |

TABLE 1-continued

| Example | Structure | LC/MS Mass [(M − H)⁻/(M + H)⁺] | HPLC purity (%) |
|---|---|---|---|
| 339 | 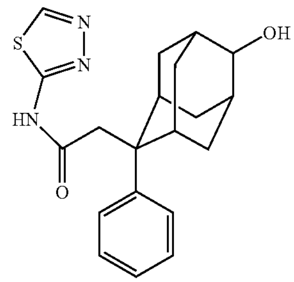 | 370 | 97.5 |
| 340 | 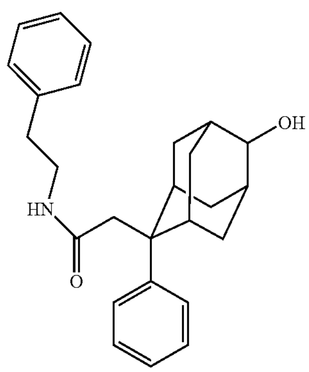 | 390 | 95.5 |
| 341 | 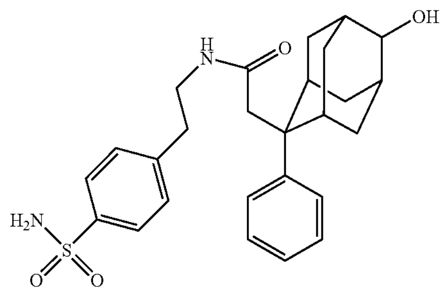 | 469 | 98.3 |
| 342 | 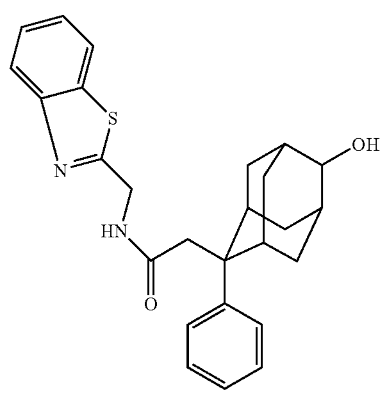 | 433 | 99.3 |

TABLE 1-continued

| Example | Structure | LC/MS Mass [(M − H)⁻/(M + H)⁺] | HPLC purity (%) |
|---|---|---|---|
| 343 | 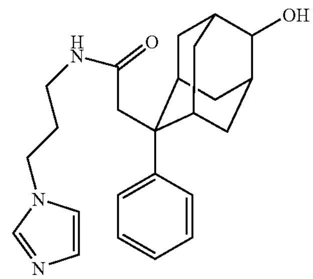 | 394 | 100.0 |
| 344 | 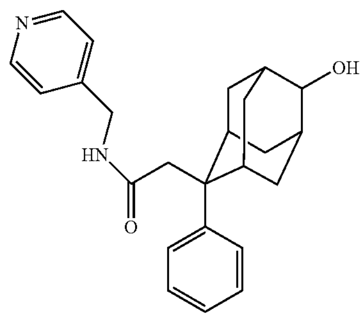 | 377 | 100.0 |
| 345 | 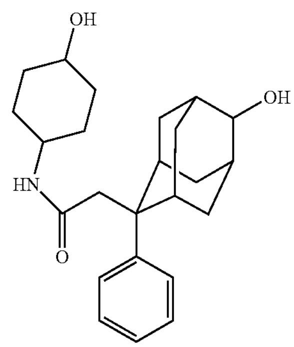 | 384 | 99.3 |
| 346 | 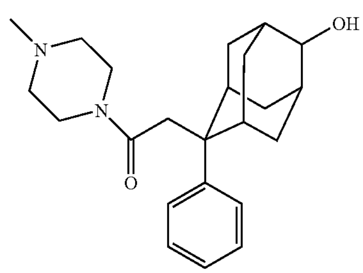 | 369 | 100.0 |
| 347 | 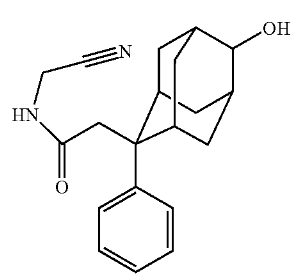 | 325 | 100.0 |

TABLE 1-continued

| Example | Structure | LC/MS Mass [(M − H)⁻/(M + H)⁺] | HPLC purity (%) |
|---------|-----------|-------------------------------|-----------------|
| 348 | 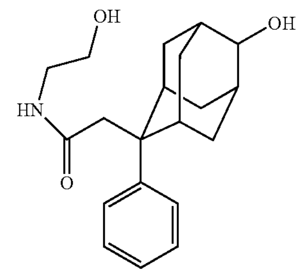 | 330 | 100.0 |
| 349 | 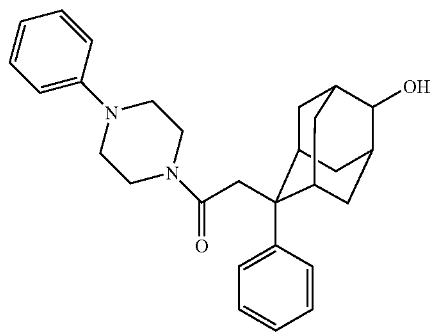 | 431 | 96.4 |
| 350 | 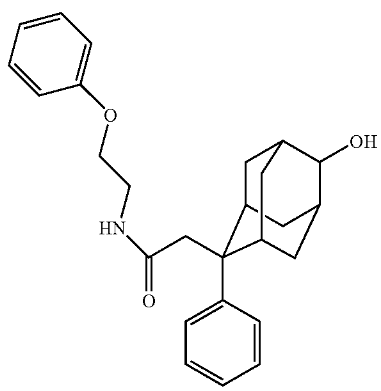 | 406 | 98.9 |
| 351 | 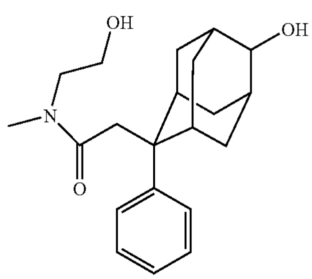 | 344 | 96.5 |
| 352 | 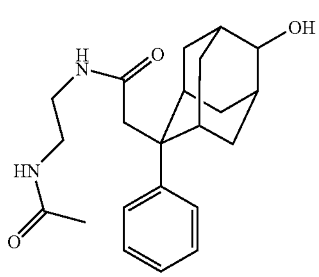 | 371 | 100.0 |

TABLE 1-continued

| Example | Structure | LC/MS Mass [(M − H)⁻/(M + H)⁺] | HPLC purity (%) |
|---|---|---|---|
| 353 | 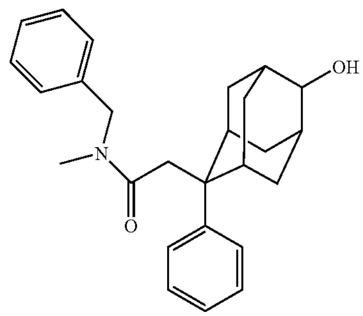 | 390 | 100.0 |
| 354 | 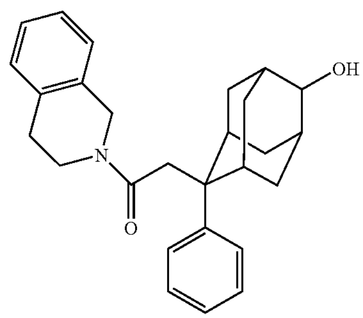 | 402 | 100.0 |
| 355 | 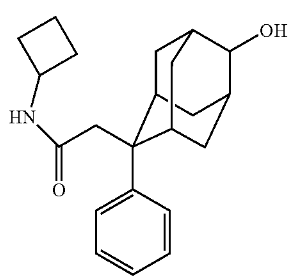 | 340 | 97.2 |
| 356 (chiral) | 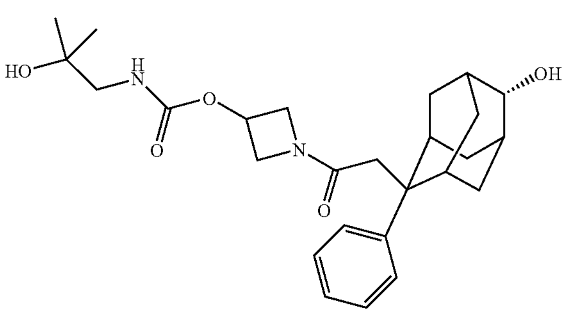 | 457 | 99 |
| 357 (chiral) | 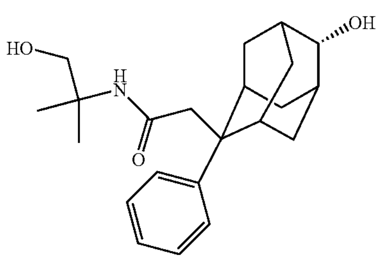 | 358 | 96 |

TABLE 1-continued

| Example | Structure | LC/MS Mass [(M − H)⁻/(M + H)⁺] | HPLC purity (%) |
|---|---|---|---|
| 358 | 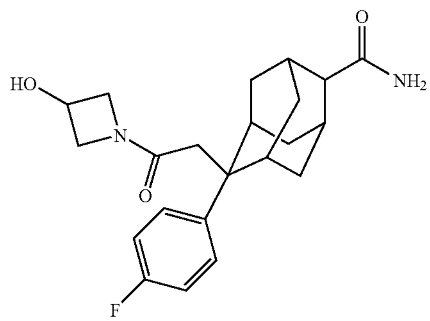 | 387 | 96 |
| 359 | 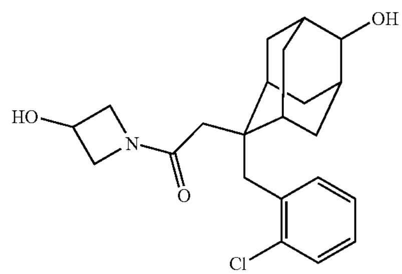 | 390 | 99 |
| 360 | 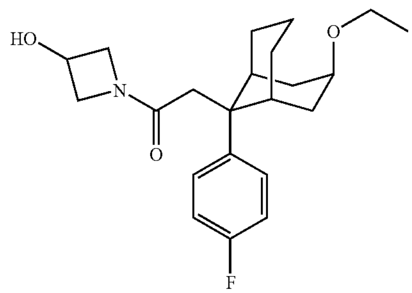 | 376 | 97 |
| 361 | 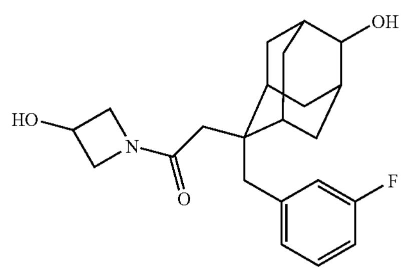 | 374 | 99 |
| 362 | 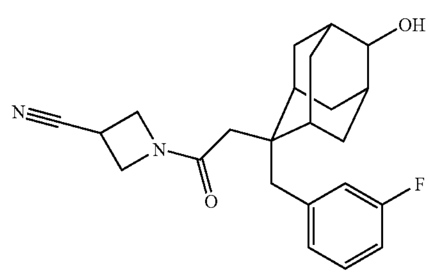 | 383 | 99 |

TABLE 1-continued

| Example | Structure | LC/MS Mass [(M − H)⁻/(M + H)⁺] | HPLC purity (%) |
|---------|-----------|-------------------------------|-----------------|
| 363 | 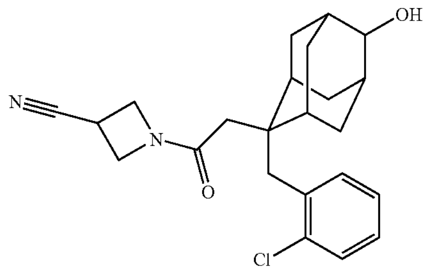 | 399 | 96 |
| 364 | 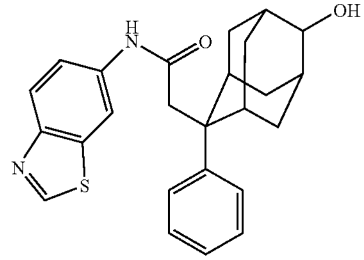 | 419 | 100 |
| 365 | 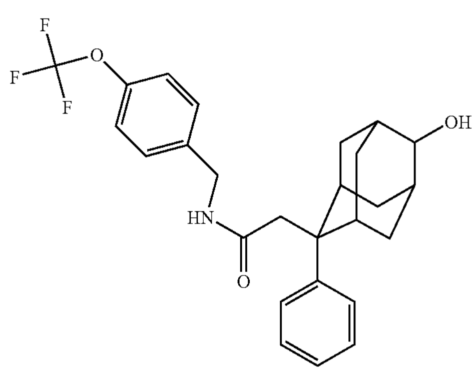 | 460 | 100 |
| 366 | 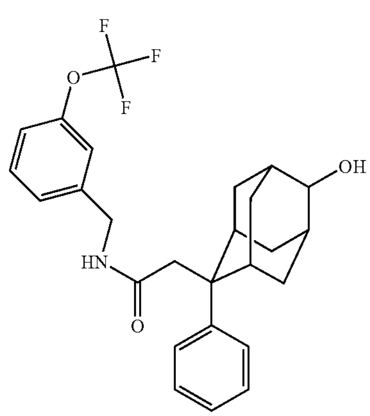 | 460 | 100 |

TABLE 1-continued

| Example | Structure | LC/MS Mass [(M − H)⁻/(M + H)⁺] | HPLC purity (%) |
|---------|-----------|-------------------------------|-----------------|
| 367 | 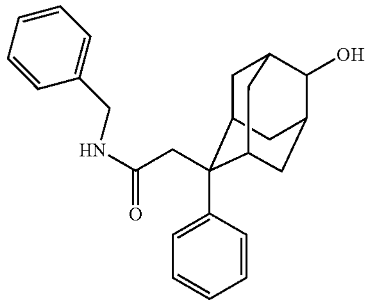 | 376 | 100 |
| 368 | 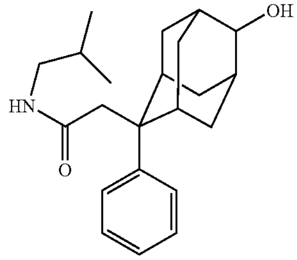 | 342 | 100 |
| 369 | 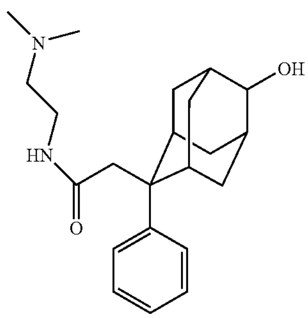 | 357 | 99.3 |
| 370 | 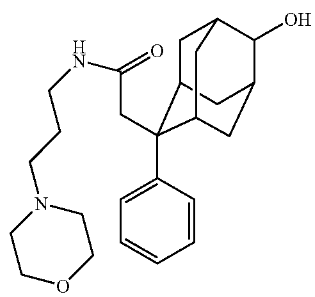 | 413 | 98.6 |
| 371 | 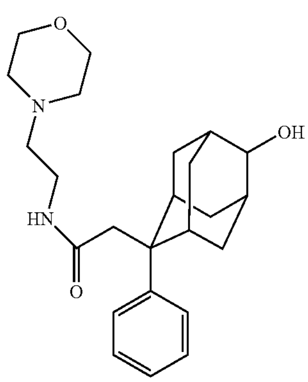 | 399 | 100 |

TABLE 1-continued

| Example | Structure | LC/MS Mass [(M − H)−/(M + H)+] | HPLC purity (%) |
|---|---|---|---|
| 372 | 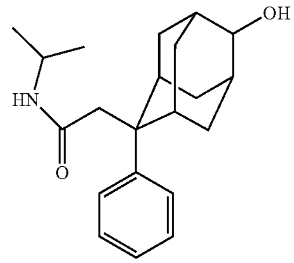 | 328 | 99.1 |
| 373 | 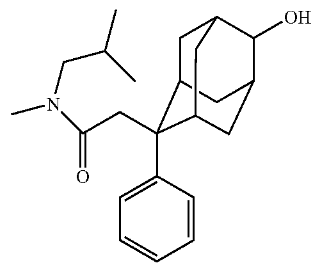 | 356 | 100 |
| 374 | 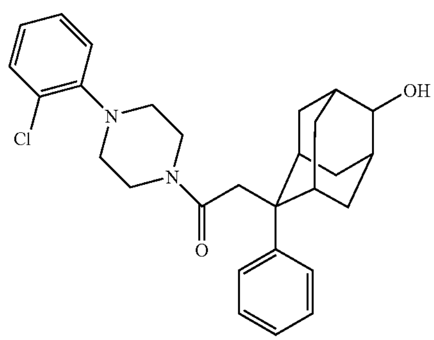 | 465 | 100 |
| 375 | 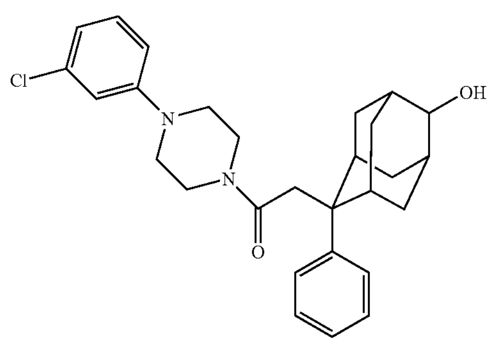 | 465 | 100 |
| 376 | 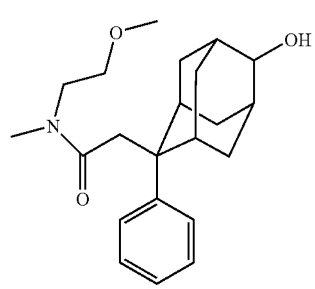 | 358 | 100 |

TABLE 1-continued

| Example | Structure | LC/MS Mass [(M − H)⁻/(M + H)⁺] | HPLC purity (%) |
|---------|-----------|-------------------------------|-----------------|
| 377 | 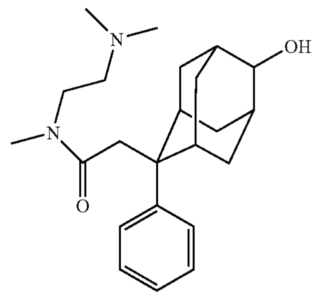 | 371 | 100 |
| 378 | 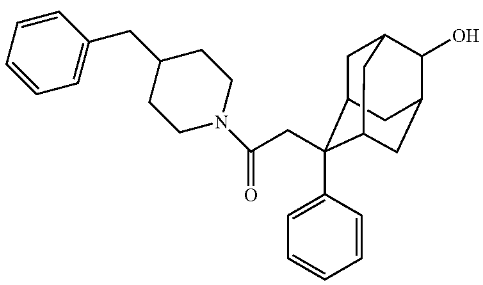 | 444 | 100 |
| 379 | 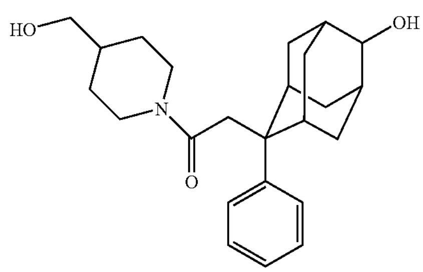 | 384 | 100 |
| 380 | 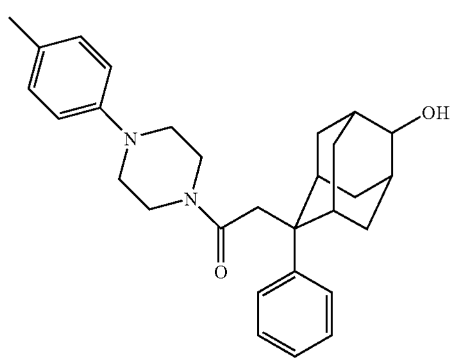 | 445 | 99.3 |

TABLE 1-continued

| Example | Structure | LC/MS Mass [(M − H)⁻/(M + H)⁺] | HPLC purity (%) |
|---------|-----------|-------------------------------|-----------------|
| 381 | 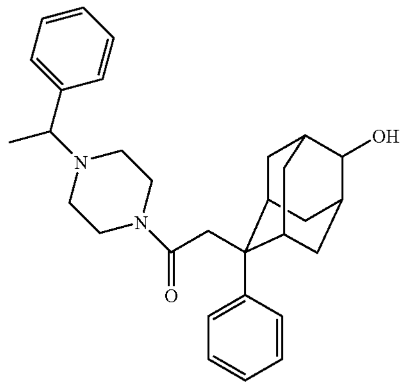 | 459 | 100 |
| 382 | 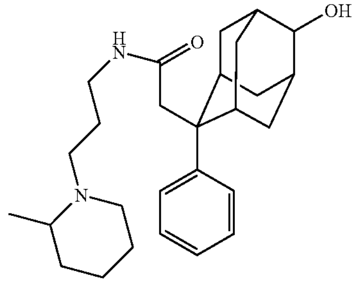 | 425 | 100 |
| 383 | 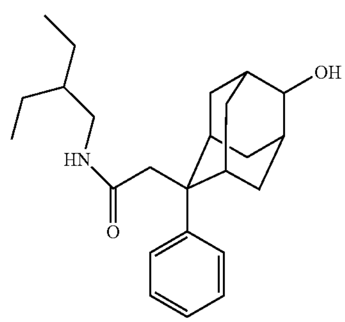 | 370 | 98.3 |
| 384 | 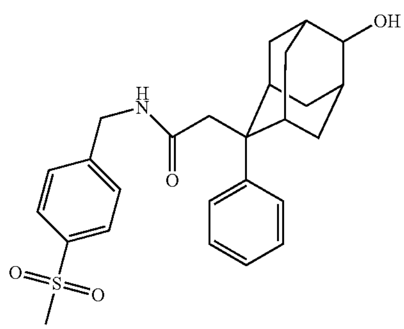 | 454 | 99.5 |

TABLE 1-continued

| Example | Structure | LC/MS Mass [(M − H)⁻/(M + H)⁺] | HPLC purity (%) |
|---|---|---|---|
| 385 | *(structure)* | 420 | 98 |
| 386 | *(structure)* | 388 | 97 |

Assay(s) for 11-Beta-Hydroxysteroid Dehydrogenase Activity

The in vitro inhibition of recombinant human 11beta-HSD1 was determined as follows.

[$^3$H]-Cortisone with a specific radioactivity of 50 Ci/mmol (ART 743, Lot: 050906) was from American Radiolabeled Chemicals, Inc. (St Louis, Mo.); monoclonal ab to Cortisol (P01-9294M-P, Lot: L-28) was from East Coast Bio., (North Berwick, Me.); Protein A-yttrium silicate, type-1, SPA bead NJ® (RPN-143) was from Amersham LifeSciences, (Piscataway, N.J.); 384 well-Optiplate384 (#6007299) was from PerkinElmer (Boston, Mass.); DPBS, pH 7.4 (14040) is from GIBCO, (Grand Island, N.Y.); carbenoxolone (C4790) is from Sigma, (St Louis, Mo.).

Full length recombinant human 11β-HSD-1 cDNAs and the cDNA encoding human 11β-HSD-2 were expressed stably in HEK 293 EBNA cells. Cells were grown in DMEM (high glucose) containing MEM non-essential amino acids, L-glutamine, hygromycin B (200 μg/ml), and G-418(200 μg/ml) in the presence of 10% FBS.

Human 11β-HSD-1 transfected HEK 293 EBNA cells were grown to 80% confluency and the cell pellet was quick frozen and stored at −80° C. before purification. Cell paste, 40 g from −80° C. storage, was thawed in water and then 100 ml of homogenization buffer H (0.01 M sodium phosphate pH 6.5 containing 0.25 M sucrose and protease inhibitor cocktail (Roche #1836145 1 tablet per 50 ml) were added to completely thaw the paste. The cell paste suspension was homogenized using a Polytron for 20 seconds to create a homogeneous mixture. Additional buffer H was added to a volume of 300 ml and cells were broken open using a N2-bomb (at 4° C.) in two batches by treating at 500 psi. The extract was centrifuged at 750×g for 30 min. The supernatant was centrifuged at 20,000×g for 30 min. The supernatant was further centrifuged at 105,000×g for 60 min. The 105,000×g pellet was resuspended in buffer H and centrifuged at 105,000×g for 60 min. The microsome pellet was scraped from the bottom of tube and resuspended in 0.01M phosphate buffer, pH 6.5 containing protease inhibitors (Roche #1836145, 1 tablet per 50 ml). Aliquots were stored at −80° C. until needed. The protein concentration was measured by the BioRad method using BSA standard.

Compounds were dissolved in DMSO to obtain 10 mM stock concentrations. From the 10 mM stock, the compounds were diluted in DMSO to achieve the concentrations.

11β-HSD-1 SPA Enzyme Assay

11β-HSD-1 was assayed by Scintillation Proximity assay in a 384-well Perkin Elmer white plate. The dose response of the compounds was determined using 11 half-log dilutions of compound in DMSO in duplicate. To each well, 0.5 μl of compound dilution in DMSO were added. 15 μl of assay buffer (for blanks) or 15 μl of human microsomes in assay buffer were added next and the plates were incubated for 10 min at room temperature. The final microsomal protein concentration was 1.1 μg/assay. Duplicates were in the same plate one row below the other. 10 μl of $^3$H-cortisone (final concentration 40 nM) was added to each well and the plate was spun down to mix and bring down the contents to the bottom of the wells. The plates were incubated at room temperature with gentle shaking for 4 hrs. The reaction was stopped with addition of 10 μl of 10 mM carbenoxolone. Then, 0.5 mg of yttrium silicate SPA beads coupled to anti-cortisol antibody in 20 μl were added to all the wells of plate, which were spun down once more and incubated at room temperature overnight. The plate was read in a TopCount® (1 min/well). Data were uploaded automatically to Tool Set, a Lead Evaluation informatics program for data capture and calculation. Graphs were generated with the Curve Master program.

Compounds of the present invention were tested in the assay described immediately above and the results shown in the Table 2 below were obtained.

TABLE 2

| Example | Structure | h HSD1 IC50 (nM) |
| --- | --- | --- |
| 4 | 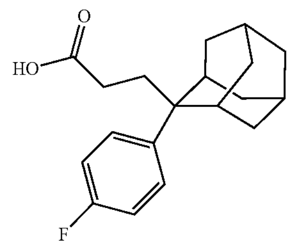 | 234 |
| 8 | 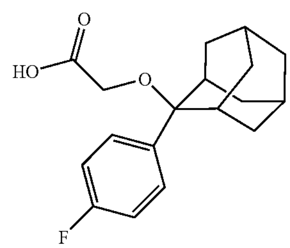 | 633 |
| 20 | 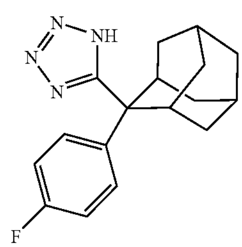 | 10000 |
| 22 | 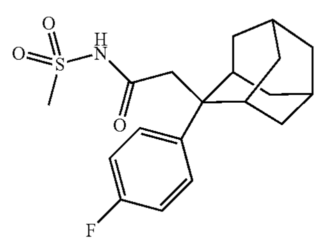 | 159 |
| 23 | 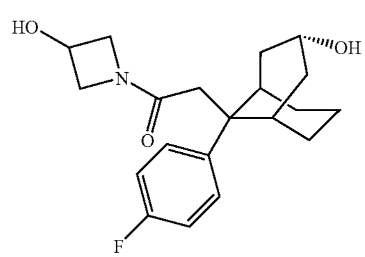 | 8.3 |

TABLE 2-continued
| Example | Structure | h HSD1 IC50 (nM) |
|---|---|---|
| 25 | 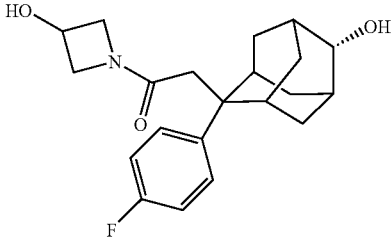 | 8.5 |
| 26 | 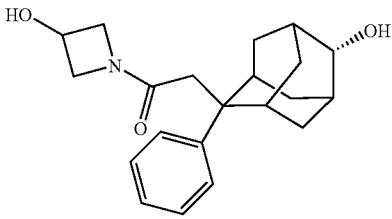 | 2.9 |
| 27 | 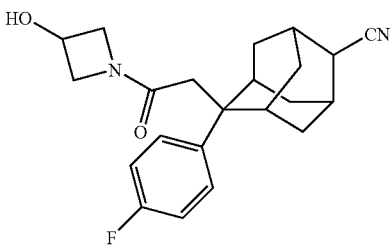 | 12 |
| 28 | 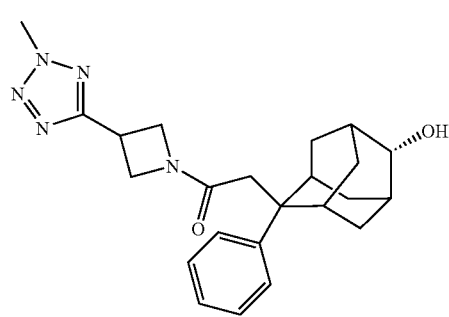 | 10 |
| 31 | 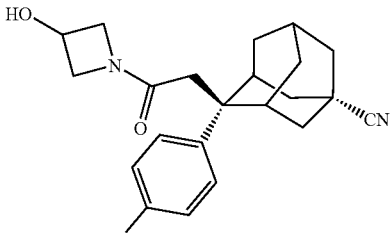 | 2.0 |

TABLE 2-continued

| Example | Structure | h HSD1 IC50 (nM) |
|---|---|---|
| 32 | 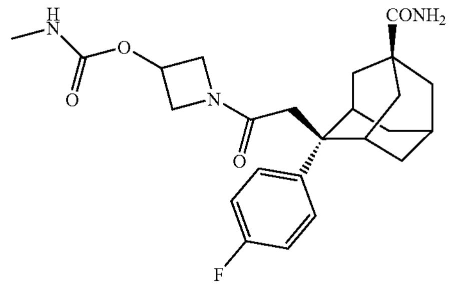 | 21 |
| 34 | 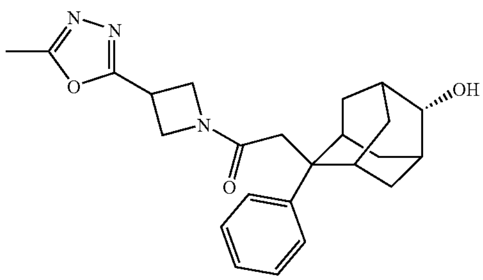 | 196 |
| 35 | 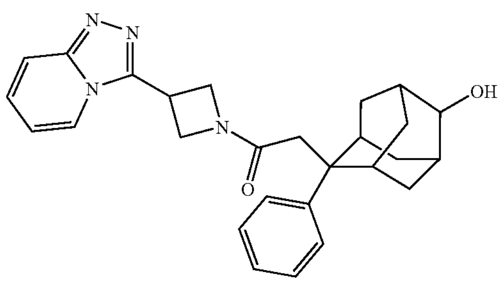 | 636 |
| 36 | 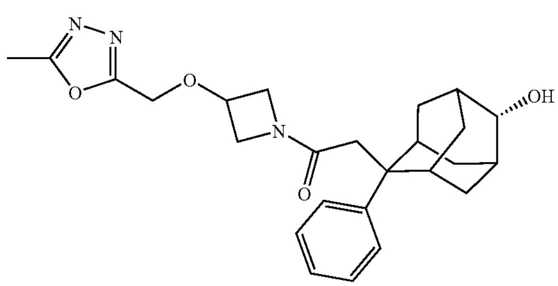 | 14 |
| 37 | 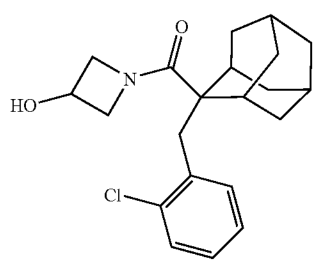 | 15 |

TABLE 2-continued
| Example | Structure | h HSD1 IC50 (nM) |
|---|---|---|
| 39 | 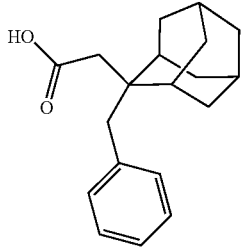 | 24 |
| 44 | 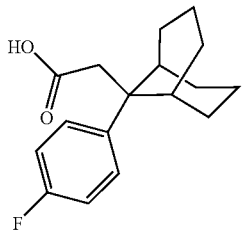 | 3.0 |
| 49 | 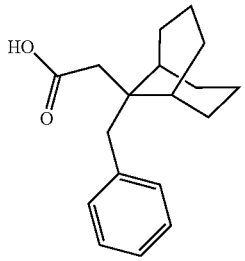 | 97 |
| 55 | 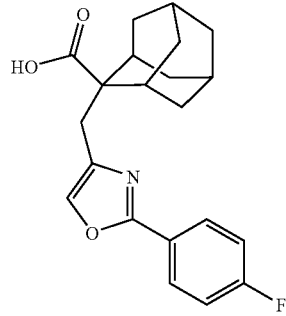 | 2982 |
| 64 | 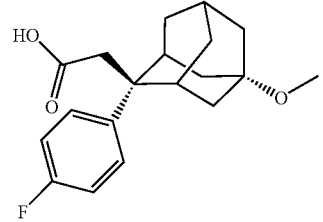 | 21 |

TABLE 2-continued

| Example | Structure | h HSD1 IC50 (nM) |
|---|---|---|
| 79 | 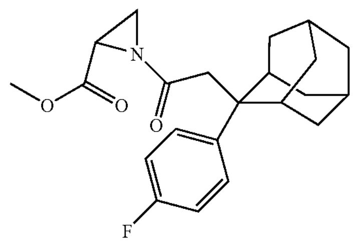 | 81 |
| 98 | 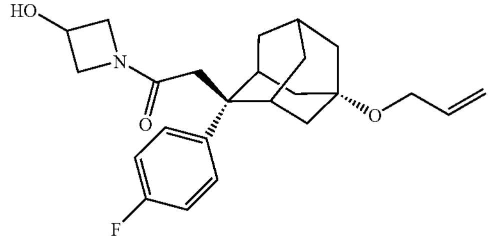 | 1.6 |
| 103 | 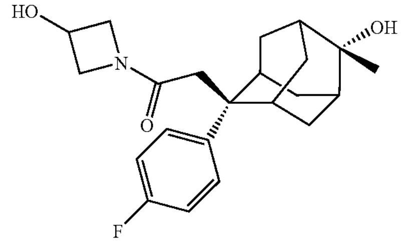 | 10 |
| 106 | 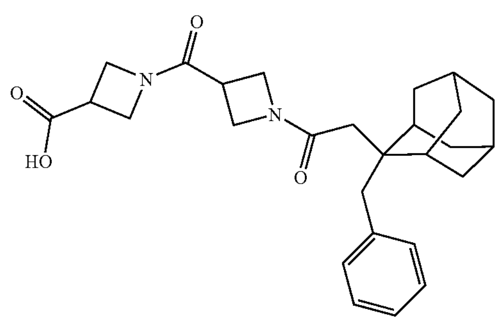 | 457 |
| 117 | 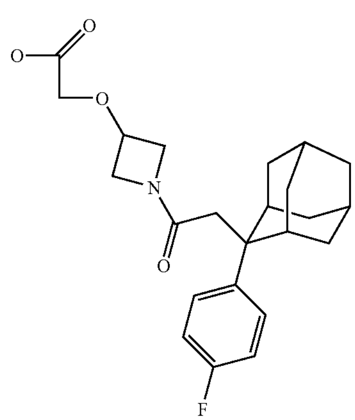 | 90 |

TABLE 2-continued

| Example | Structure | h HSD1 IC50 (nM) |
|---------|-----------|------------------|
| 122 | 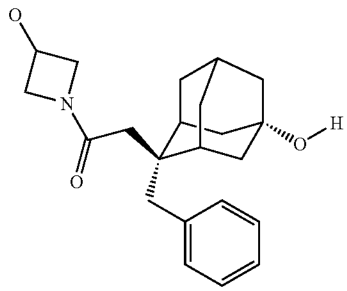 | 253 |
| 124 | 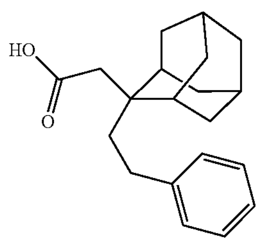 | 2.2 |
| 126 | 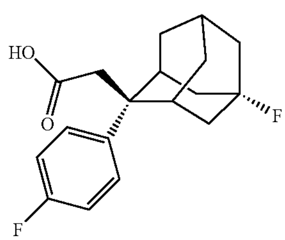 | 13 |
| 127 | 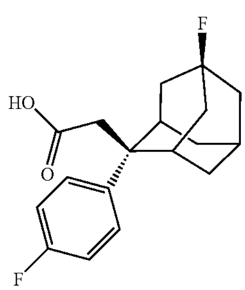 | 14 |
| 132 | 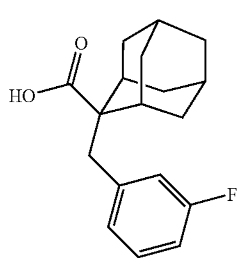 | 15 |

TABLE 2-continued

| Example | Structure | h HSD1 IC50 (nM) |
|---|---|---|
| 134 | 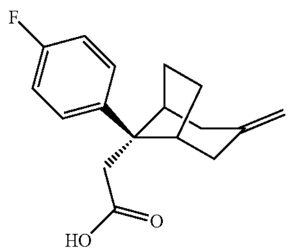 | 30 |
| 136 | 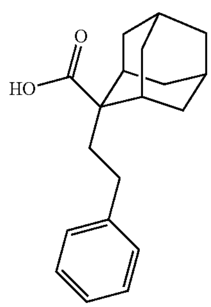 | 1152 |
| 140 | 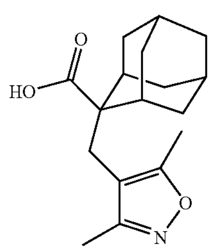 | 651 |
| 164 | 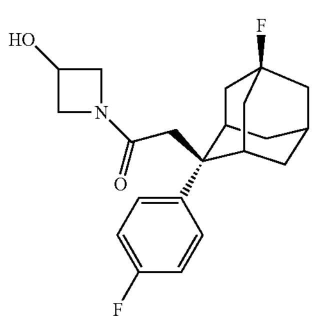 | 2.3 |
| 167 | 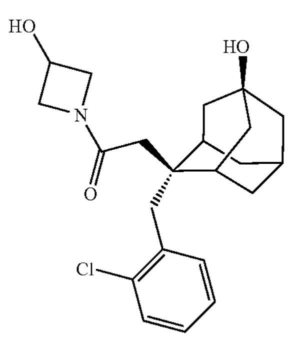 | 20 |

TABLE 2-continued
| Example | Structure | h HSD1 IC50 (nM) |
|---|---|---|
| 174 | 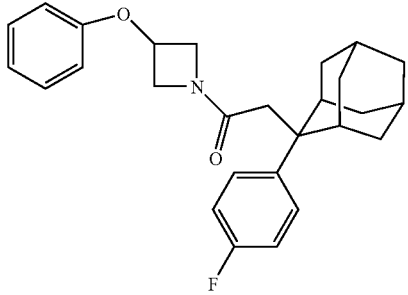 | 1.0 |
| 181 | 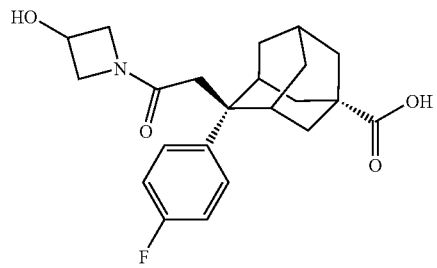 | 128 |
| 182 | 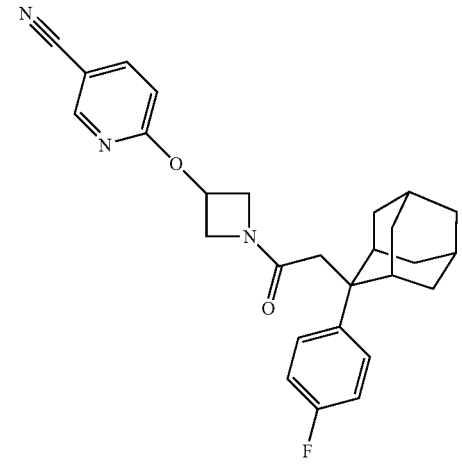 | 2.4 |
| 183 | 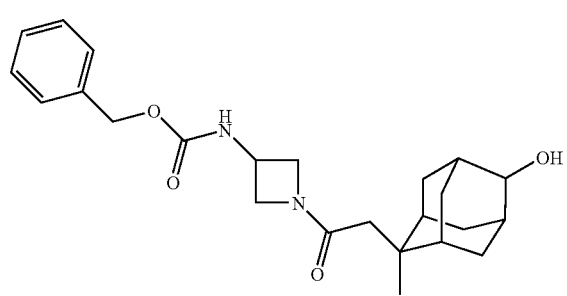 | 182 |

TABLE 2-continued

| Example | Structure | h HSD1 IC50 (nM) |
|---|---|---|
| 188 | 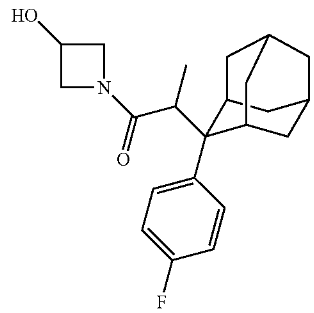 | 121 |
| 190 | 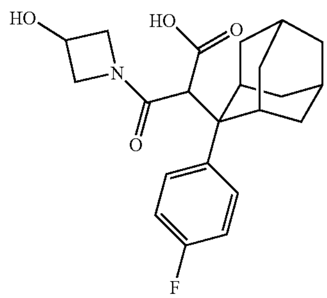 | 9121 |
| 195 | 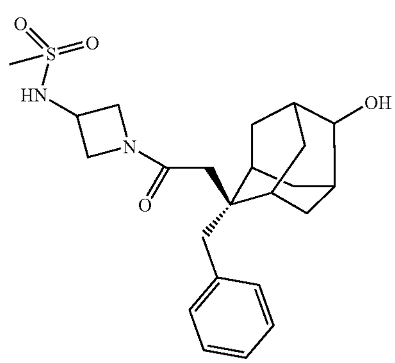 | 105 |
| 199 | 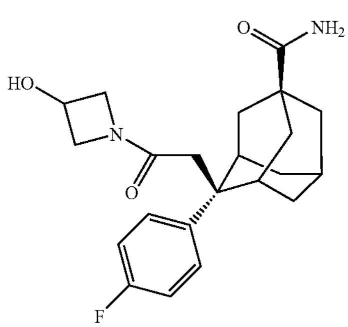 | 6.9 |

TABLE 2-continued

| Example | Structure | h HSD1 IC50 (nM) |
|---|---|---|
| 210 | 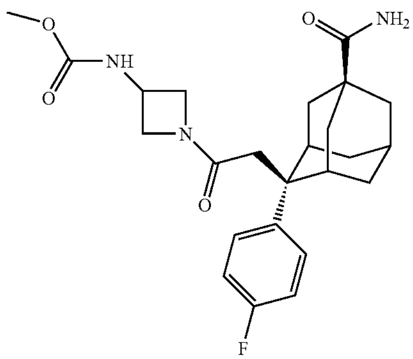 | 316 |
| 212 | 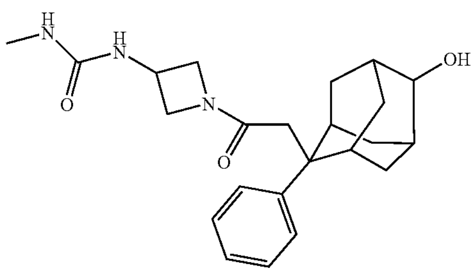 | 127 |
| 213 | 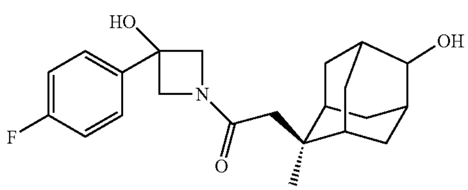 | 44 |
| 216 | 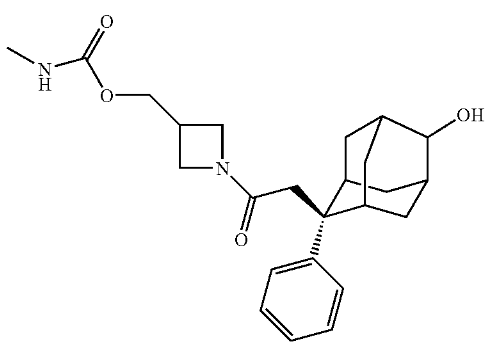 | 5.1 |
| 235 | 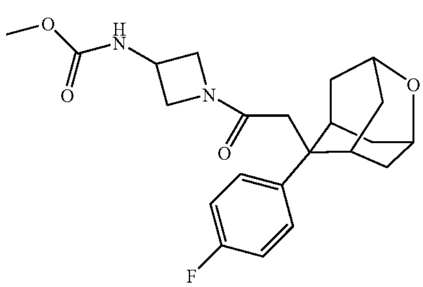 | 520 |

TABLE 2-continued

| Example | Structure | h HSD1 IC50 (nM) |
|---|---|---|
| 236 | 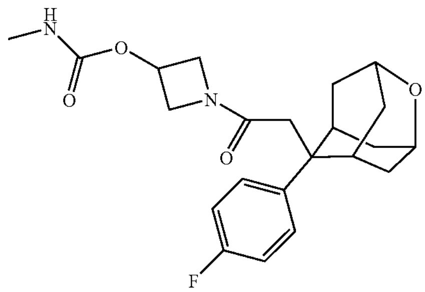 | 274 |
| 240 | 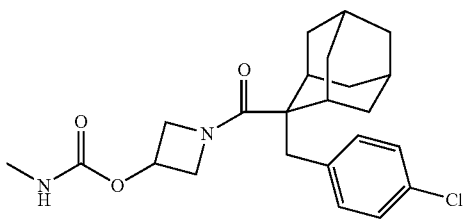 | 67 |
| 242 | 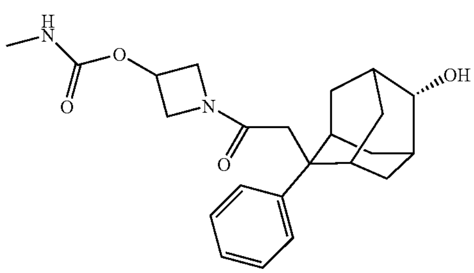 | 8.8 |
| 243 | 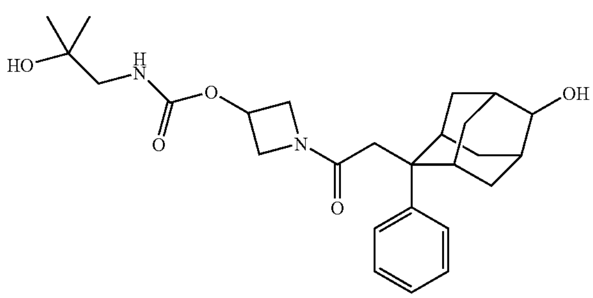 | 16 |
| 247 | 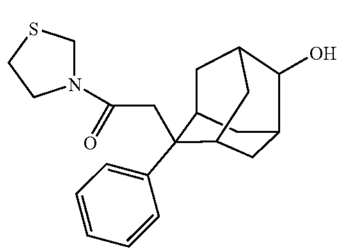 | 3.0 |

TABLE 2-continued

| Example | Structure | h HSD1 IC50 (nM) |
|---------|-----------|------------------|
| 250 | 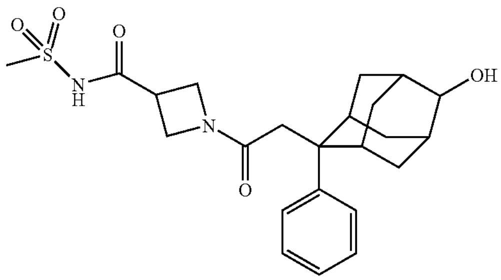 | 1724 |
| 259 | 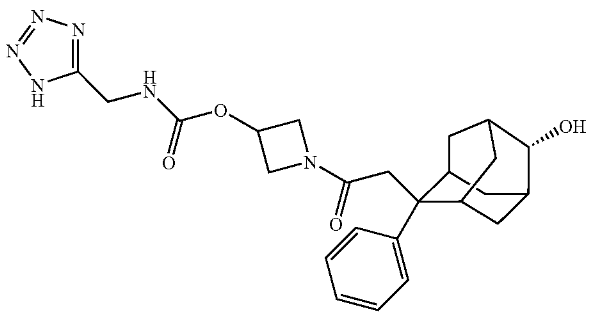 | 75 |
| 265 | 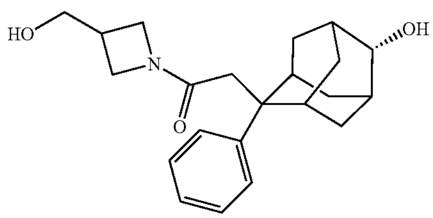 | 6.1 |
| 270 | 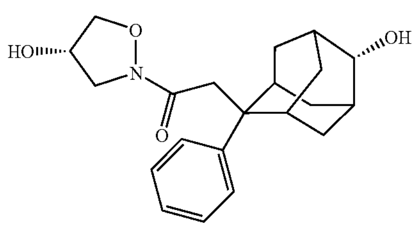 | 16 |
| 277 | 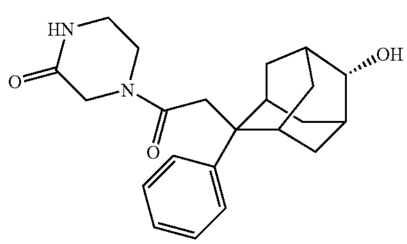 | 10000 |
| 279 | 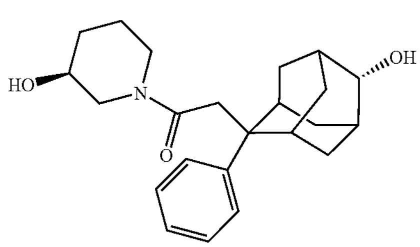 | 260 |

TABLE 2-continued

| Example | Structure | h HSD1 IC50 (nM) |
|---|---|---|
| 281 | 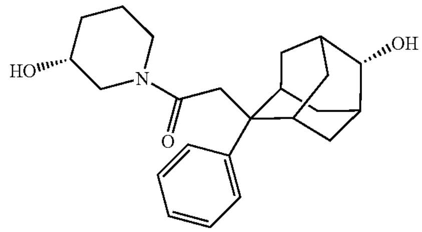 | 175 |
| 292 | 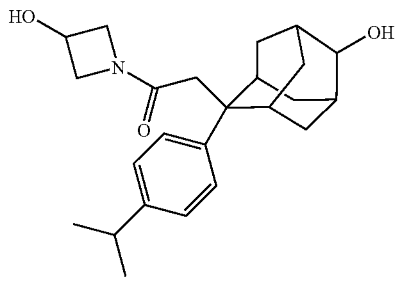 | 2.8 |
| 301 | 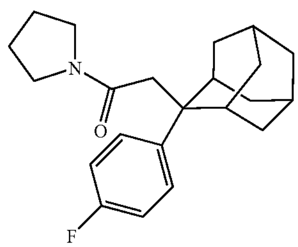 | 0.3 |
| 302 | 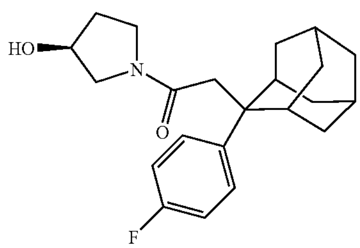 | 2.4 |
| 303 | 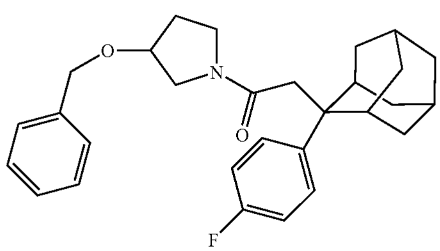 | 4.7 |
| 304 | 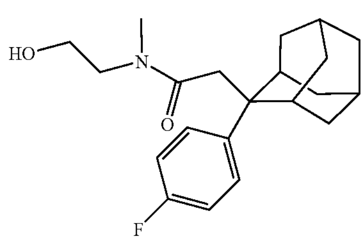 | 25 |

TABLE 2-continued

| Example | Structure | h HSD1 IC50 (nM) |
|---|---|---|
| 305 | 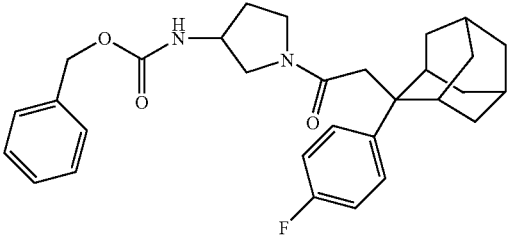 | 28 |
| 306 | 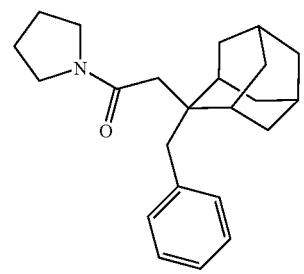 | 30 |
| 307 | 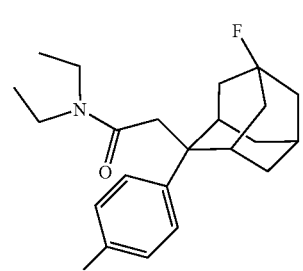 | 383 |
| 308 | 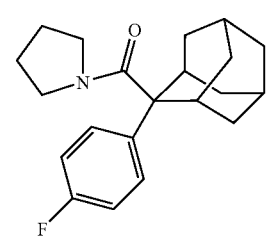 | 10000 |

The in vivo inhibition of recombinant human 11beta-HSD1 was determined as follows.

Studies were conducted utilizing diet induced obese (DIO) mice obtained from Jackson Laboratory (ME, USA). These mice were fed a 60% fat diet (Research Diets D12492) soon after weaning and kept on this diet for 24 weeks. These mice were individually housed. All mice were housed under controlled temperature (23° C.) and lighting (12 hours of light between 6 am to 6 pm, 12 hours of dark) with free access to water. The animals continued on this diet and were utilized for experimentation at 30 to 32 weeks of age, at which time these mice weighed 45 to 55 grams.

The basic model of 11-dehydrocorticosterone (DHC) administration to mice to produce corticosterone has been reported in the literature for clinical and preclinical evaluation of the activity of 11 β HSD. Essentially DHC (Steraloids INC, Newport R.I.), was suspended in the vehicle at a concentration of 10 mg/kg in a volume of 7.5 ml/kg of mouse body weight. For a typical study, non-fasting mice were weighed and separated into groups (n=6) where body weights are not statistically different from each other. Animals were bled via a tail knick, for a 0 time sample and then dosed orally (7.5 ml/kg) with vehicle or drug. At 60 minutes post administration of vehicle or compound, mice were bled again via the tail tip and dosed orally (7.5 ml/kg) with DHC 10 mg/kg. All animals were subsequently bled at 30, 60 and 120 minutes post DHC dosing. Thirty-five microliters of whole blood are collected per time point in microvette tubes coated with EDTA (Sarstedt Tubes Microvette CB 300/Haematology Potassium EDTA # 16.444.300) and kept on ice. Samples were centrifuged at 4° C. in a Beckman Coulter centrifuge for 10 minutes at 2500 RPM. Plasma was separated and collected and immediately frozen at −20° C. until corticosterone analysis could be assessed.

Plasma Corticosterone was measured using an EIA (IDS AC-14F1). Samples were measured at (1:2) for the −30 (or −60 minute) and 0 time point and (1:10) for the 30, 60 and 120 minutes time points. AUC was calculated using Graphpad and the zero timepoint was used as the baseline. One way ANOVA was calculated using Sigmastat. A p value of less that 0.05 via post hoc analysis with Dunnett's was used to determine statistical significance.

The vehicle utilized for the suspension of the compounds was 0.5% methocel; 0.1% tween 80 in water. Methocel Cellulose (M-0262) was purchased from Sigma-Aldrich, St Louis, Mo. 6. Tween 80 (274364) was purchased from Sigma-Aldrich, St Louis, Mo. Compounds were administered in 7.5 ml/kg volumes at final dosages of 0.1 to 300 mg/kg depending on the study and compound evaluated.

Compounds of the present invention were tested in the assay described immediately above and the results shown in the Table 3 below were obtained.

TABLE 3

| Example | Dose | % inhibition |
|---------|------|--------------|
| 25 | 30 mpK | 74 |
| 26 | 30 mpK | 57 |
| 217 | 30 mpK | 67 |
| 242 | 30 mpK | 65 |

Utilities and Combinations

A. Utilities

The compounds of the present invention possess activity as inhibitors of the enzyme 11-beta-hydroxysteroid dehydrogenase type I, and, therefore, may be used in the treatment of diseases associated with 11-beta-hydroxysteroid dehydrogenase type I activity. Via the inhibition of 11-beta-hydroxysteroid dehydrogenase type I, the compounds of the present invention may preferably be employed to inhibit or modulate glucocorticoid production, thereby interrupting or modulating cortisone or cortisol production.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, delayed wound healing, atherosclerosis and its sequelae (acute coronary syndrome, myocardial infarction, angina pectoris, peripheral vascular disease, intermittent claudication), abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma and inflammatory diseases, such as, rheumatoid arthritis, Cushing's Disease, Alzheimer's Disease and osteoarthritis.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other 11-beta-hydroxysteroid dehydrogenase type I inhibitors or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dislipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, memory enhancing agents, cognition promoting agents and anti-inflammatory agents.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones: ciglitazone, pioglitazone, troglitazone, rosiglitazone; PPAR-gamma agonists; PPAR-alpha agonists; PPAR alpha/gamma dual agonists; SGLT2 inhibitors; dipeptidyl peptidase-IV (DPP4) inhibitors; glucagon-like peptide-1 (GLP-1) receptor agonists; aldose reductase inhibitors; RXR agonists: JTT-501, MCC-555, MX-6054, DRF2593, GI-262570, KRP-297, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; beta-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023; and galanin receptor agonists.

Other suitable thiazolidinediones include Mitsubishi's MCC-555 (disclosed in U.S. Pat. No. 5,594,016), Glaxo-Wellcome's GL-262570, englitazone (CP-68722, Pfizer), or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi).

Suitable PPAR alpha/gamma dual agonists include AR-HO39242 (Astra/Zeneca), GW-409544 (Glaxo-Wellcome), KRP297 (Kyorin Merck), as well as those disclosed by Murakami et al., "A Novel Insulin Sensitizer Acts As a Coligand for Peroxisome Proliferation—Activated Receptor Alpha (PPAR alpha) and PPAR gamma; Effect of PPAR alpha Activation on Abnormal Lipid Metabolism in Liver of Zucker Fatty Rats", *Diabetes,* 47:1841-1847 (1998), and WO 01/21602, the disclosure of which is incorporated herein by reference, employing dosages as set out therein, which compounds designated as preferred are preferred for use herein.

Suitable alpha2 antagonists also include those disclosed in WO 00/59506, employing dosages as set out herein.

Suitable SGLT2 inhibitors include T-1095, phlorizin, WAY-123783, and those described in WO 01/27128.

Suitable DPP4 inhibitors include saxagliptan, sitagliptan, vildagliptan, and denagliptan.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) receptor agonists include Exenatide (Byetta™), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DAC™).

Other anti-diabetic agents that can be used in combination with compounds of the invention include ergoset and D-chiroinositol.

Suitable anti-ischemic agents include, but are not limited to, those described in the Physician's Desk Reference and NHE inhibitors, including those disclosed in WO 99/43663.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, cholesterol ester transfer protein inhibitors (e.g., CP-529414 (Pfizer)), and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983, and U.S. Pat. No. 5,962,440.

The HMG CoA reductase inhibitors which may be employed in combination with one or more compounds of formula I include mevastatin and related compounds, as disclosed in U.S. Pat. No. 3,983,140, lovastatin, (mevinolin) and related compounds, as disclosed in U.S. Pat. No. 4,231,938, pravastatin, and related compounds, such as disclosed in U.S. Pat. No. 4,346,227, simvastatin, and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772; cerivastatin, as disclosed in U.S. Pat. Nos. 5,006,530 and 5,177,080; atorvastatin, as disclosed in U.S. Pat. Nos. 4,681,893, 5,273,995, 5,385,929 and 5,686,104; atavastatin (Nissan/Sankyo's nisvastatin (NK-104)), as disclosed in U.S. Pat. No. 5,011,930; visastatin (Shionogi-Astra/Zeneca (ZD-4522)) as disclosed in U.S. Pat. No. 5,260,440.

Preferred hypolipidemic agents are pravastatin, lovastatin, simvastatin, atorvastatin, fluvastatin, cerivastatin, atavastatin, and ZD-4522.

The fibric acid derivatives which may be employed in combination with one or more compounds of formula I include fenofibrate, gemfibrozil, clofibrate, bezafibrate, ciprofibrate, clinofibrate, and the like, probucol, and related compounds, as disclosed in U.S. Pat. No. 3,674,836, fenofibrate and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in *Drugs of the Future* 24:9-15 (1999), (Avasimibe); "The ACAT inhibitor, Cl-1011 is effective in the prevention and regression of aortic fatty streak area in hamsters", Nicolosi et al., *Atherosclerosis* (Shannon, Irel)., 137 (1):77-85 (1998); "The pharmacological profile of FCE 27677: a novel ACAT inhibitor with potent hypolipidemic activity mediated by selective suppression of the hepatic secretion of ApoB 100-containing lipoprotein", Ghiselli, Giancarlo, *Cardiovasc. Drug Rev.,* 16(1):16-30 (1998); "RP 73163: a bioavailable alkylsulfinyl-diphenylimidazole ACAT inhibitor", Smith, C. et al., *Bioorg. Med. Chem. Lett.,* 6(1): 47-50 (1996); "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al., *Curr. Med. Chem.,* 1(3), 204-25 (1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al., *Chemtracts: Org. Chem.,* 8(6): 359-62 (1995), or TS-962 (Taisho Pharmaceutical Co. Ltd.).

The hypolipidemic agent may be an upregulator of LDL receptor activity, such as MD-700 (Taisho Pharmaceutical Co. Ltd) and LY295427 (Eli Lilly).

Examples of suitable cholesterol absorption inhibitors for use in combination with the compounds of the invention include ezetimibe (Zetia®).

Examples of suitable ileal $Na^+$/bile acid cotransporter inhibitors for use in combination with the compounds of the invention include compounds as disclosed in *Drugs of the Future,* 24:425-430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology,* 120:1199-1206 (1997), and Cornicelli et al., "15-Lipoxygenase and its Inhibition: A Novel Therapeutic Target for Vascular Disease", *Current Pharmaceutical Design,* 5:11-20 (1999).

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a cannabinoid receptor 1 antagonist or inverse agonist, a beta 3 adrenergic agonist, a lipase inhibitor, a serotonin (and dopamine) reuptake inhibitor, a thyroid receptor beta drug, and/or an anorectic agent.

Cannabinoid receptor 1 antagonists and inverse agonists which may be optionally employed in combination with compounds of the present invention include rimonabant, SLV 319, CP-945598 (Pfizer), SR-147778 (Sanofi-Aventis), MK0364 (Merck) and those discussed in D. L. Hertzog, *Expert Opin. Ther. Patents*, 14:1435-1452 (2004).

The beta 3 adrenergic agonists which may be optionally employed in combination with compounds of the present invention include AJ9677 (Takeda/Dainippon), L750355 (Merck), or CP331648 (Pfizer) or other known beta 3 agonists, as disclosed in U.S. Pat. Nos. 5,541,204, 5,770,615, 5,491,134, 5,776,983, and 5,488,064, with AJ9677, L750,355, and CP331648 being preferred.

Examples of lipase inhibitors which may be optionally employed in combination with compounds of the present invention include orlistat or ATL-962 (Alizyme), with orlistat being preferred.

The serotonin (and dopamine) reuptake inhibitor and/or modulator which may be optionally employed in combination with a compound of formula I may be sibutramine, topiramate (Johnson & Johnson), APD-356 (Arena) or axokine (Regeneron), with sibutramine and APD-356 being preferred.

Examples of thyroid receptor beta compounds which may be optionally employed in combination with compounds of the present invention include thyroid receptor ligands, such as those disclosed in WO 97/21993 (U. Cal SF), WO 99/00353 (KaroBio), and WO 00/039077 (KaroBio), with compounds of the KaroBio applications being preferred.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); MCHR1 antagonist (e.g., GSK 856464); galanin receptor antagonists; MCR-4 antagonists (e.g., HP-228); leptin or mimetics; urocortin mimetics, CRF antagonists, and CRF binding proteins (e.g., RU-486, urocortin).

Further, the compounds of the present invention may be used in combination with HIV protease inhibitors, including but not limited to Reyataz® and Kaletra®.

Examples of suitable memory enhancing agents, anti-dementia agents, or cognition promoting agents for use in combination with the compounds of the present invention include, but are not limited to, donepezil, rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, prednisone, acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha, prednisolone, methylprednisolone, dexamethazone, flucatisone, betamethasone, hydrocortisone and beclomethasone.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

The compounds of formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of structure I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

What is claimed is:

1. A compound of formula (I)

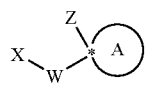
(I)

enantiomers, diastereomers, solvates, or salts thereof wherein:

A is

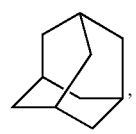

which is substituted with at least one $R_4$ other than hydrogen; or

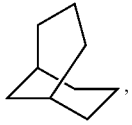

which may be optionally substituted with one or more $R_4$'s;

X is —C(=O)OH, —C(=O)C(=O)OH, —C(=O)NR$_9$R$_9$, tetrazolyl, or —C(=O)NHS(O)$_2$R$_9$;

W is absent, (—CR$_{8a}$R$_{8b}$—)$_m$, (—CR$_{8a}$R$_{8b}$)$_m$—O—, (—CR$_{8a}$R$_{8b}$—)$_m$—N(R$_{14}$)—, $C_{3-6}$ cycloalkyl, alkenyl or alkynyl, wherein the cycloalkyl or alkenyl may be optionally substituted with one or more $R_{8a}$'s;

m is 1-3;

Z is —CN, $C_{3-10}$ alkyl, cycloalkyl, aryl or arylalkyl, all of which may be optionally substituted with one or more $R_4$'s;

provided that W and Z, or when W is absent, X and Z, are attached to the same carbon on Ring A;

$R_4$, at each occurrence, is independently selected from hydrogen, alkyl, aryl, alkenyl, alkynyl, cycloalkyl, halo, =O, —NH$_2$, —CN, —NO$_2$, —C(=O)OH, —C(=O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$, wherein the alkyl, aryl, alkenyl, alkynyl or cycloalkyl may be optionally substituted with one or more $R_5$'s;

$R_5$, at each occurrence, is independently selected from hydrogen, alkyl, haloalkyl, aryl, alkenyl, alkynyl, cycloalkyl, cycloalkylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

$R_8$, at each occurrence, is independently alkyl, aryl or heterocyclyl;

$R_{8a}$, at each occurrence, is independently hydrogen, alkyl or aryl;

$R_{8b}$, at each occurrence, is independently hydrogen, —C(=O)OH, alkyl, —OH, halo, —CN, —OR$_{10}$, —C(=O)R$_{10}$ or —C(=O)NR$_9$R$_9$, wherein the alkyl may be optionally substituted with one or more $R_{9a}$'s; or $R_{8a}$ and $R_{8b}$ are taken together with the carbon to which both are attached to form a 3- to 7-membered ring, which may optionally contain 1-4 heteroatoms selected from N, O, and S and be optionally substituted with 0-3 $R_{9a}$;

$R_9$, at each occurrence, is independently hydrogen, alkyl, alkoxy, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-5 $R_{9a}$, and the heterocyclyl or heterocyclylalkyl contain 1-4 heteroatoms selected from N, O, and S; or two $R_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more $R_{9a}$'s;

$R_{9a}$, at each occurrence, is independently selected from alkyl, haloalkyl, aryl, alkenyl, alkynyl, cycloalkyl, cycloalkylalkyl, heterocyclyl, heterocyclylalkyl, halo, =O, —NH$_2$, —CN, —NO$_2$, —C(=O)OH, —C(=O)OR$_{14}$, —OCF$_3$, —OR$_{10}$, —OH, —OCF$_3$, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —C(=O)R$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_{10}$, at each occurrence, is independently selected from alkyl, cycloalkyl, alkenyl, alkynyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —C(=NR$_{14}$)NR$_{14}$R$_{14}$, —NHC(NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —C(=NR$_{15}$)NR$_{15}$R$_{15}$, —NHC(NR$_{15}$)NR$_{15}$R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and $R_{15}$, at each occurrence, is independently selected from hydrogen, alkyl, cycloalkyl, aryl or arylalkyl.

2. The compound of claim 1, wherein the

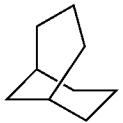

is substituted with at least one $R_4$ other than hydrogen.

3. The compound of claim 1, wherein:

X is —C(=O)OH, —C(=O)C(=O)OH, —C(=O)NR$_9$R$_9$, or tetrazolyl;

W is absent, (—CR$_{8a}$R$_{8b}$—)$_m$, (—CR$_{8a}$R$_{8b}$)$_m$—O—, (—CR$_{8a}$R$_{8b}$)$_m$N(R$_{14}$)—, or alkenyl, wherein the alkenyl may be optionally substituted with one or more R$_{8a}$'s;

m is 1-3;

Z is CN, $C_{3-10}$ alkyl, cycloalkyl, aryl or arylalkyl, all of which may be optionally substituted with one or more $R_4$'s;

provided that W and Z, or when W is absent, X and Z, are attached to the same carbon on Ring A;

$R_4$, at each occurrence, is independently selected from hydrogen, alkyl, aryl, alkenyl, alkynyl, cycloalkyl, halo, =O, —NH$_2$, —CN, —NO$_2$, —C(=O)OH, —C(=O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$, wherein the alkyl, aryl, alkenyl, alkynyl or cycloalkyl may be optionally substituted with one or more $R_5$, at each occurrence, is independently selected from hydrogen, alkyl, haloalkyl, aryl, alkenyl, alkynyl, cycloalkyl, cycloalkylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

$R_8$, at each occurrence, is independently alkyl, aryl or heterocyclyl;

$R_{8a}$, at each occurrence, is independently hydrogen, alkyl or aryl;

$R_{8b}$, at each occurrence, is independently hydrogen, —C(=O)OH, alkyl, —OH, halo, —CN, —OR$_{10}$, —C(=O)R$_{10}$ or —C(=O)NR$_9$R$_9$, wherein the alkyl may be optionally substituted with one or more R$_{9a}$'s; or $R_{8a}$ and $R_{8b}$ are taken together with the carbon to which both are attached to form a 3- to 7-membered ring, which may optionally contain 1-4 heteroatoms selected from N, O, and S and be optionally substituted with 0-3 R$_{9a}$;

$R_9$, at each occurrence, is independently hydrogen, alkyl, alkoxy, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-5 R$_{9a}$, and the heterocyclyl or heterocyclylalkyl contain 1-4 heteroatoms selected from N, O, and S; or two R$_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more R$_{9a}$'s;

$R_{9a}$, at each occurrence, is independently selected from alkyl, haloalkyl, aryl, alkenyl, alkynyl, cycloalkyl, cycloalkylalkyl, heterocyclyl, heterocyclylalkyl, halo, =O, —NH$_2$, —CN, —NO$_2$, —C(=O)OH, —C(=O)OR$_{14}$, —OCF$_3$, —OR$_{10}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —C(=O)R$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

$R_{10}$, at each occurrence, is independently selected from alkyl, cycloalkyl, alkenyl, alkynyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and $R_{15}$, at each occurrence, is independently selected from hydrogen, alkyl, cycloalkyl, aryl or arylalkyl.

4. The compound of claim 1, wherein:

X is —C(O)OH, —C(=O)NR$_9$R$_9$, or tetrazolyl;

W is absent, (—CR$_{8a}$R$_{8b}$—)$_m$, (—CR$_{8a}$R$_{8b}$)$_m$—O— or alkenyl, wherein the alkenyl may be optionally substituted with one or more R$_{8a}$'s;

m is 1-2;

Z is CN, $C_{3-10}$ alkyl, cycloalkyl, aryl or arylalkyl, all of which may be optionally substituted with one or more $R_4$'s;

provided that W and Z, or when W is absent, X and Z, are attached to the same carbon on Ring A;

$R_4$, at each occurrence, is independently selected from hydrogen, alkyl, aryl, alkenyl, alkynyl, cycloalkyl, halo, =O, —$NH_2$, —CN, —$NO_2$, —C(O)OH, —C(O)$R_{10}$, —O$R_{10}$, —OH, —OCF$_3$, —SH, —S$R_{10}$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(O)$R_{10}$, —N$R_9$C(O)$R_{10}$, —OC(=O)$R_{10}$, —S(=O)$R_{10}$, —S(O)$_2R_{10}$, —O—S(O)$_2R_{10}$, —N$R_9$C(=O)O$R_8$ or —N$R_9$S(O$_2$)$R_8$, wherein the alkyl, aryl, alkenyl, alkynyl or cycloalkyl may be optionally substituted with one or more $R_5$, at each occurrence, is independently selected from hydrogen, alkyl, haloalkyl, aryl, alkenyl, alkynyl, cycloalkyl, cycloalkylalkyl, halo, —$NH_2$, —CN, —$NO_2$, —C(=O)OH, —C(=O)$R_{10}$, —OCF$_3$, —O$R_{10}$, —OH, —SH, —S$R_{10}$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(=O)$R_{10}$, —N$R_9$C(=O)$R_{10}$, —OC(=O)$R_{10}$, —S(=O)$R_{10}$, —S(O)$_2R_{10}$, —O—S(O)$_2R_{10}$, —N$R_9$C(=O)O$R_8$ or —N$R_9$S(O$_2$)$R_8$;

$R_8$, at each occurrence, is independently alkyl, aryl or heterocyclyl;

$R_{8a}$, at each occurrence, is independently hydrogen, alkyl or aryl;

$R_{8b}$, at each occurrence, is independently hydrogen, —C(=O)OH, alkyl, —OH, halo, —CN, —O$R_{10}$, —C(=O)$R_{10}$ or —C(=O)N$R_9R_9$, wherein the alkyl may be optionally substituted with one or more $R_{9a}$'s; or $R_{8a}$ and $R_{8b}$ are taken together with the carbon to which both are attached to form a 3- to 7-membered ring, which may optionally contain 1-4 heteroatoms selected from N, O, and S and be optionally substituted with 0-3 $R_{9a}$;

$R_9$, at each occurrence, is independently hydrogen, alkyl, alkoxy, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-5 $R_{9a}$, and the heterocyclyl or heterocyclylalkyl contain 1-4 heteroatoms selected from N, O, and S; or two $R_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more $R_{9a}$'s;

$R_{9a}$, at each occurrence, is independently selected from alkyl, haloalkyl, aryl, alkenyl, alkynyl, cycloalkyl, cycloalkylalkyl, heterocyclyl, heterocyclylalkyl, halo, O, —$NH_2$, —CN, —$NO_2$, —C(=O)OH, —C(=O)O$R_{14}$, —OCF$_3$, —O$R_{10}$, —OH, —SH, —S$R_{14}$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)$_2R_{10}$, —S(O)$_2$N$R_{14}$C(=O)O$R_{10}$, —S(O)$_2$N$R_{14}$C(=O)N$R_{14}R_{14}$, —C(=O)N$R_{14}$S(O)$_2R_{14}$, —C(=O)$R_{14}$, —N$R_{14}$C(=O)$R_{14}$, —OC(=O)$R_{14}$, —S(=O)$R_{14}$, —S(O)$_2R_{14}$, —OS(O)$_2R_{14}$, —N$R_{14}$C(O)O$R_{10}$, —N$R_{14}$S(O$_2$)$R_8$, —C(=O)$R_{10}$, —OC(=O)N$R_{14}R_{14}$, —N$R_{14}$C(=O)N$R_{14}R_{14}$ or arylalkyl, wherein the alkyl, aryl, cycloalkyl, cycloalkylalkyl, heterocyclyl, and heterocyclylalkyl may optionally substituted with 0-3 $R_{10a}$;

$R_{10}$, at each occurrence, is independently selected from alkyl, cycloalkyl, alkenyl, alkynyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)O$R_{14}$, —OCF$_3$, —O$R_{14}$, —OH, —SH, —S$R_{14}$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)$_2R_{14}$, —S(O)$_2$N$R_{14}$C(=O)O$R_{14}$, —S(O)$_2$N$R_{14}$C(=O)N$R_{14}R_{14}$, —C(=O)N$R_{14}$S(O)$_2$CF$_3$, —C(=O)$R_{14}$, —N$R_{14}$C(=O)$R_{14}$, —OC(=O)$R_{14}$, —S(=O)$R_{14}$, —S(O)$_2R_{14}$, —N$R_{14}$C(=O)O$R_8$, —N$R_{14}$S(O$_2$)$R_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)O$R_{15}$, —OCF$_3$, —O$R_{15}$, —OH, —SH, —S$R_{15}$, —C(=O)N$R_{15}R_{15}$, —N$R_{15}R_{15}$, —S(O)$_2$N$R_{15}R_{15}$, —N$R_{15}$S(O)$_2$CF$_3$, —C(=O)N$R_{15}$S(O)$_2R_{15}$, —S(O)$_2$N$R_{15}$C(=O)O$R_{15}$, —S(O)$_2$N$R_{15}$C(=O)N$R_{15}R_{15}$, —C(=O)N$R_{15}$S(O)$_2$CF$_3$, —C(=O)$R_{15}$, —N$R_{15}$C(=O)$R_{15}$, —OC(=O)$R_{15}$, —S(=O)$R_{15}$, —S(O)$_2R_{15}$, —N$R_{15}$C(=O)O$R_8$, —N$R_{15}$S(O$_2$)$R_8$ or arylalkyl; and $R_{15}$, at each occurrence, is independently selected from hydrogen, alkyl, cycloalkyl, aryl or arylalkyl.

5. The compound of claim 1, wherein:

X is —C(O)OH, —C(=O)N$R_9R_9$, or tetrazolyl;

W is absent, (—C$R_{8a}R_{8b}$—)$_m$, (—C$R_{8a}R_{8b}$)$_m$—O— or alkenyl, wherein the alkenyl may be optionally substituted with one or more $R_{8a}$'s;

m is 1-2;

Z is cycloalkyl, aryl or arylalkyl, all of which may be optionally substituted with one or more $R_4$'s;

provided that W and Z, or when W is absent, X and Z, are attached to the same carbon on Ring A;

$R_4$, at each occurrence, is independently selected from hydrogen, alkyl, aryl, alkenyl, alkynyl, cycloalkyl, halo, =O, —$NH_2$, —CN, —$NO_2$, —C(O)OH, —C(O)$R_{10}$, —O$R_{10}$, —OH, —OCF$_3$, —SH, —S$R_{10}$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(O)$R_{10}$, —N$R_9$C(O)$R_{10}$, —OC(=O)$R_{10}$, —S(=O)$R_{10}$, —S(O)$_2R_{10}$, —O—S(O)$_2R_{10}$, —N$R_9$C(=O)O$R_8$ or —N$R_9$S(O$_2$)$R_8$, wherein the alkyl, aryl, alkenyl, alkynyl or cycloalkyl may be optionally substituted with one or more $R_5$'s;

$R_5$, at each occurrence, is independently selected from hydrogen, alkyl, haloalkyl, aryl, alkenyl, alkynyl, cycloalkyl, cycloalkylalkyl, halo, —$NH_2$, —CN, —$NO_2$, —C(=O)OH, —C(=O)$R_{10}$, —OCF$_3$, —O$R_{10}$, —OH, —SH, —S$R_{10}$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(=O)$R_{10}$, —N$R_9$C(=O)$R_{10}$, —OC(=O)$R_{10}$, —S(=O)$R_{10}$, —S(O)$_2R_{10}$, —O—S(O)$_2R_{10}$, —N$R_9$C(=O)O$R_8$ or —N$R_9$S(O$_2$)$R_8$;

$R_8$, at each occurrence, is independently alkyl, aryl or heterocyclyl;

$R_{8a}$, at each occurrence, is independently hydrogen, alkyl or aryl;

$R_{8b}$, at each occurrence, is independently hydrogen, —C(=O)OH, alkyl, —OH, halo, —CN, —OR$_{10}$, —C(=O)R$_{10}$ or —C(=O)NR$_9$R$_9$, wherein the alkyl may be optionally substituted with one or more R$_{9a}$'s; or $R_{8a}$ and $R_{8b}$ are taken together with the carbon to which both are attached to form a 3- to 7-membered ring, which may optionally contain 1-4 heteroatoms selected from N, O, and S and be optionally substituted with 0-3 R$_{9a}$;

$R_9$, at each occurrence, is independently hydrogen, alkyl, alkoxy, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-5 R$_{9a}$, and the heterocyclyl or heterocyclylalkyl contain 1-4 heteroatoms selected from N, O, and S; or two R$_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more R$_{9a}$'s;

$R_{9a}$, at each occurrence, is independently selected from alkyl, haloalkyl, aryl, alkenyl, alkynyl, cycloalkyl, cycloalkylalkyl, heterocyclyl, heterocyclylalkyl, halo, =O, —NH$_2$, —CN, —NO$_2$, —C(=O)OH, —C(=O)OR$_{14}$, —OCF$_3$, —OR$_{10}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(O)OR$_{10}$, —NR$_{14}$S(O$_2$)R$_8$, —C(=O)R$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

$R_{10}$, at each occurrence, is independently selected from alkyl, cycloalkyl, alkenyl, alkynyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and $R_{15}$, at each occurrence, is independently selected from hydrogen, alkyl, cycloalkyl, aryl or arylalkyl.

6. The compound of claim 1, wherein:

X is —C(O)OH, —C(=O)NR$_9$R$_9$, or tetrazolyl;

W is absent, (—CR$_{8a}$R$_{8b}$—)$_m$, (—CR$_{8a}$R$_{8b}$)$_m$—O— or alkenyl, wherein the alkenyl may be optionally substituted with one or more R$_{8a}$'s;

m is 1-2;

Z is aryl or arylalkyl, all of which may be optionally substituted with one or more R$_4$'s;

provided that W and Z, or when W is absent, X and Z, are attached to the same carbon on Ring A;

$R_4$, at each occurrence, is independently selected from hydrogen, alkyl, aryl, alkenyl, alkynyl, cycloalkyl, halo, =O, —NH$_2$, —CN, —NO$_2$, —C(O)OH, —C(O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(O)R$_{10}$, —NR$_9$C(O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$, wherein the alkyl, aryl, alkenyl, alkynyl or cycloalkyl may be optionally substituted with one or more R$_5$'s;

$R_5$, at each occurrence, is independently selected from hydrogen, alkyl, haloalkyl, aryl, alkenyl, alkynyl, cycloalkyl, cycloalkylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O) NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

$R_8$, at each occurrence, is independently alkyl, aryl or heterocyclyl;

$R_{8a}$, at each occurrence, is independently hydrogen, alkyl or aryl;

$R_{8b}$, at each occurrence, is independently hydrogen, —C(=O)OH, alkyl, —OH, halo, —CN, —OR$_{10}$, —C(=O)R$_{10}$ or —C(=O)NR$_9$R$_9$, wherein the alkyl may be optionally substituted with one or more R$_{9a}$'s; or $R_{8a}$ and $R_{8b}$ are taken together with the carbon to which both are attached to form a 3- to 7-membered ring, which may optionally contain 1-4 heteroatoms selected from N, O, and S and be optionally substituted with 0-3 R$_{9a}$;

$R_9$, at each occurrence, is independently hydrogen, alkyl, alkoxy, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-5 R$_{9a}$, and the heterocyclyl or heterocyclylalkyl contain 1-4 heteroatoms selected from N, O, and S; or two R$_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more R$_{9a}$'s;

$R_{9a}$, at each occurrence, is independently selected from alkyl, haloalkyl, aryl, alkenyl, alkynyl, cycloalkyl, cycloalkylalkyl, heterocyclyl, heterocyclylalkyl, halo, =O, —NH$_2$, —CN, —NO$_2$, —C(=O)OH, —C(=O)OR$_{14}$, —OCF$_3$, —OR$_{10}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(O)OR$_{10}$, —NR$_{14}$S(O$_2$)R$_8$, —C(=O)R$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_{10}$, at each occurrence, is independently selected from alkyl, cycloalkyl, alkenyl, alkynyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_2$S(O$_2$)R$_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and $R_{15}$, at each occurrence, is independently selected from hydrogen, alkyl, cycloalkyl, aryl or arylalkyl.

7. The compound of claim 1, wherein:

X is —C(O)OH, —C(=O)NR$_9$R$_9$, or tetrazolyl;

W is absent, —(CR$_{8a}$R$_{8b}$—)$_m$, —(CR$_{8a}$R$_{8b}$)$_m$—O— or alkenyl, wherein the alkenyl may be optionally substituted with one or more $R_{8a}$'s;

m is 1-2;

Z is aryl or arylalkyl, all of which may be optionally substituted with one or more $R_4$'s;

provided that W and Z, or when W is absent, X and Z, are attached to the same carbon on Ring A;

$R_4$, at each occurrence, is independently selected from hydrogen, alkyl, aryl, alkenyl, cycloalkyl, halo, =O, —NH$_2$, —CN, —NO$_2$, —C(=O)OH, —C(=O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$, wherein the alkyl, aryl, alkenyl or cycloalkyl may be optionally substituted with one or more $R_5$'s;

$R_5$, at each occurrence, is independently selected from hydrogen, alkyl, haloalkyl, aryl, alkenyl, cycloalkyl, cycloalkylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

$R_8$, at each occurrence, is independently alkyl, aryl or heterocyclyl;

$R_{8a}$, at each occurrence, is independently hydrogen, alkyl or aryl;

$R_{8b}$, at each occurrence, is independently hydrogen, —C(=O)OH, alkyl, —OH, halo, —CN, —OR$_{10}$, —C(=O)R$_{10}$ or —C(=O)NR$_9$R$_9$, wherein the alkyl may be optionally substituted with one or more $R_{9a}$'s; or $R_{8a}$ and $R_{8b}$ are taken together with the carbon to which both are attached to form a 3- to 7-membered ring, which may optionally contain 1-4 heteroatoms selected from N, O, and S and be optionally substituted with 0-3 $R_{9a}$;

$R_9$, at each occurrence, is independently hydrogen, alkyl, alkoxy, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-5 $R_{9a}$, and the heterocyclyl or heterocyclylalkyl contain 1-4 heteroatoms selected from N, O, and S; or two $R_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more $R_{9a}$'s;

$R_{9a}$, at each occurrence, is independently selected from alkyl, haloalkyl, aryl, alkenyl, cycloalkyl, cycloalkylalkyl, heterocyclyl, heterocyclylalkyl, halo, =O, —NH$_2$, —CN, —NO$_2$, —C(=O)OH, —C(=O)OR$_{14}$, —OCF$_3$, —OR$_{10}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(O)OR$_{10}$, —NR$_{14}$S(O$_2$)R$_8$, —C(=O)R$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_{10}$, at each occurrence, is independently selected from alkyl, cycloalkyl, alkenyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

R$_{14a}$, at each occurrence, is independently selected from alkyl, haloalkyl, aryl, alkenyl, cycloalkyl, cycloalkylalkyl, heterocyclyl, heterocyclylalkyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl, aryl or arylalkyl.

8. The compound of claim 1, wherein:

X is —C(=O)OH, or —C(=O)NR$_9$R$_9$;

W is absent, (—CR$_{8a}$R$_{8b}$—)$_m$, (—CR$_{8a}$R$_{8b}$)$_m$—O— or alkenyl, wherein the alkenyl may be optionally substituted with one or more R$_{8a}$'s;

m is 1-2;

Z is aryl or arylalkyl all of which may be optionally substituted with one or more R$_4$'s;

provided that W and Z, or when W is absent, X and Z, are attached to the same carbon on Ring A;

R$_4$, at each occurrence, is independently selected from hydrogen, alkyl, aryl, cycloalkyl, halo, =O, —NH$_2$, —CN, —NO$_2$, —C(O)OH, —C(O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$, wherein the alkyl, aryl or cycloalkyl may be optionally substituted with one or more R$_5$'s;

R$_5$, at each occurrence, is independently selected from hydrogen, alkyl, haloalkyl, aryl, cycloalkyl, cycloalkylalkyl, halo, —NH$_2$, —CN, —NO$_2$, —C(O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

R$_8$, at each occurrence, is independently alkyl, aryl or heterocyclyl;

R$_{8a}$, at each occurrence, is independently hydrogen, alkyl or aryl;

R$_{8b}$, at each occurrence, is independently hydrogen, —C(=O)OH, alkyl, —OH, halo, —CN, —OR$_{10}$, —C(=O)R$_{10}$ or —C(=O)NR$_9$R$_9$, wherein the alkyl may be optionally substituted with one or more R$_{9a}$'s; or R$_{8a}$ and R$_{8b}$ are taken together with the carbon to which both are attached to form a 3- to 7-membered ring, which may optionally contain 1-4 heteroatoms selected from N, O, and S and be optionally substituted with 0-3 R$_{9a}$;

R$_9$, at each occurrence, is independently hydrogen, alkyl, alkoxy, cycloalkyl, aryl, arylalkyl, or heterocyclyl, wherein the alkyl, cycloalkyl, aryl, arylalkyl or heterocyclyl may be optionally substituted with 0-5 R$_{9a}$, and the heterocyclyl contains 1-4 heteroatoms selected from N, O, and S; or two R$_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more R$_{9a}$'s;

R$_{9a}$, at each occurrence, is independently selected from alkyl, haloalkyl, aryl, cycloalkyl, cycloalkylalkyl, heterocyclyl, heterocyclylalkyl, halo, =O, —NH$_2$, —CN, —NO$_2$, —C(=O)OH, —C(=O)OR$_{14}$, —OCF$_3$, —OR$_{10}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(O)OR$_{10}$, —NR$_{14}$S(O)$_2$R$_8$, —C(=O)R$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_{10}$, at each occurrence, is independently selected from alkyl, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

R$_{14a}$, at each occurrence, is independently selected from alkyl, haloalkyl, aryl, cycloalkyl, cycloalkylalkyl, heterocyclyl, heterocyclylalkyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(O)R$_{15}$, —S(O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl, aryl or arylalkyl.

9. The compound of claim 1, wherein:

X is —C(=O)OH, or —C(=O)NR$_9$R$_9$;

W is absent, (—CR$_{8a}$R$_{8b}$)$_m$ or (—CR$_{8a}$R$_{8b}$)$_m$—O—;

m is 1-2;

Z is aryl or arylalkyl, all of which may be optionally substituted with one or more R$_4$'s provided that W and Z, or when W is absent, X and Z, are attached to the same carbon on Ring A;

R$_4$, at each occurrence, is independently selected from hydrogen, alkyl, aryl, cycloalkyl, halo, =O, —NH$_2$, —CN, —NO$_2$, —C(O)OH, —C(O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$, wherein the alkyl, aryl or cycloalkyl halo may be optionally substituted with one or more R$_5$'s;

R$_5$, at each occurrence, is independently selected from hydrogen, alkyl, haloalkyl, aryl, cycloalkyl, cycloalkylalkyl, halo, —NH$_2$, —CN, —NO$_2$, —C(O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

R$_8$, at each occurrence, is independently alkyl, aryl or heterocyclyl;

R$_{8a}$, at each occurrence, is independently hydrogen, alkyl or aryl;

R$_{8b}$, at each occurrence, is independently hydrogen, —C(=O)OH, alkyl, —OH, halo, —CN, —OR$_{10}$ or —C(O)NR$_9$R$_9$, wherein the alkyl may be optionally substituted with one or more R$_{9a}$'s; or R$_9$, at each occurrence, is independently hydrogen, alkyl, alkoxy, cycloalkyl, aryl, arylalkyl, or heterocyclyl, wherein the alkyl, cycloalkyl, aryl, arylalkyl or heterocyclyl may be optionally substituted with 0-5 R$_{9a}$, and the heterocyclyl contains 1-4 heteroatoms selected from N, O, and S; or two R$_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more R$_{9a}$'s;

R$_{9a}$, at each occurrence, is independently selected from alkyl, haloalkyl, aryl, cycloalkyl, cycloalkylalkyl, heterocyclyl, heterocyclylalkyl, halo, =O, —NH$_2$, —CN, —NO$_2$, —C(=O)OH, —C(=O)OR$_{14}$, —OCF$_3$, —OR$_{10}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —C(=O)R$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl and heterocyclylalkyl may be optionally substituted with 0-3 R$_{10a}$;

R$_{10}$, at each occurrence, is independently selected from alkyl, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(O)R$_{14}$, —S(O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, or aryl, wherein the alkyl, cycloalkyl or aryl may be optionally substituted with 0-3 R$_{14a}$;

R$_{14a}$, at each occurrence, is independently selected from alkyl, haloalkyl, aryl, cycloalkyl, cycloalkylalkyl, heterocyclyl, heterocyclylalkyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(O)R$_{15}$, —S(O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl or aryl.

10. The compound of claim 1, wherein:

X is —C(=O)OH, or —C(=O)NR$_9$R$_9$;

W is absent, (—CR$_{8a}$R$_{8b}$)$_m$ or (—CR$_{8a}$R$_{8b}$)$_m$—O—;

m is 1-2;

Z is aryl or arylalkyl, both of which may be optionally substituted with one or more R$_4$'s;

provided that W and Z, or when W is absent, X and Z, are attached to the same carbon on Ring A;

R$_4$, at each occurrence, is independently selected from hydrogen, alkyl, aryl, cycloalkyl, halo, =O, —NH$_2$, —CN, —NO$_2$, —C(O)OH, —C(O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$, wherein the alkyl, aryl or cycloalkyl may be optionally substituted with one or more R$_5$'s;

R$_5$, at each occurrence, is independently selected from hydrogen, alkyl, haloalkyl, aryl, cycloalkyl, cycloalkylalkyl, halo, —NH$_2$, —CN, —NO$_2$, —C(O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(O)R$_{10}$, —NR$_9$C(O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

R$_8$, at each occurrence, is independently alkyl, aryl or heterocyclyl;

$R_{8a}$, at each occurrence, is independently hydrogen, alkyl or aryl;

$R_{8b}$, at each occurrence, is independently hydrogen, —C(=O)OH, alkyl, —OH, halo, —CN, —OR$_{10}$ or —C(O)NR$_9$R$_9$, wherein the alkyl may be optionally substituted with one or more $R_{9a}$'s; or $R_9$, at each occurrence, is independently hydrogen, alkyl, alkoxy, cycloalkyl, aryl or heterocyclyl, wherein the alkyl, cycloalkyl, aryl or heterocyclyl may be optionally substituted with 0-5 $R_{9a}$, and the heterocyclyl contains 1-4 heteroatoms selected from N, O, and S; or two $R_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more $R_{9a}$'s;

$R_{9a}$, at each occurrence, is independently selected from alkyl, haloalkyl, aryl, cycloalkyl, cycloalkylalkyl, heterocyclyl, halo, =O, —NH$_2$, —CN, —NO$_2$, —C(=O)OH, —C(=O)OR$_{14}$, —OCF$_3$, —OR$_{10}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —C(=O)R$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl and heterocyclyl may be optionally substituted with 0-3 $R_{10a}$;

$R_{10}$, at each occurrence, is independently selected from alkyl, cycloalkyl, aryl, arylalkyl, heterocyclyl or heterocyclylalkyl, wherein the alkyl, cycloalkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, cycloalkyl, cycloalkylalkyl, heterocyclyl, halo, —NH$_2$, —CN, —NO$_2$, —C(=O)OH, —C(=O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(O)R$_{14}$, —S(O)R$_{14}$, —S(O)$_2$R$_{14}$, —NR$_{14}$C(=O)OR$_8$, —NR$_{14}$S(O$_2$)R$_8$ or arylalkyl;

$R_{14}$, at each occurrence, is independently selected from hydrogen, alkyl, cycloalkyl, or aryl, wherein the alkyl, cycloalkyl or aryl may be optionally substituted with 0-3 $R_{14}$;

$R_{14a}$, at each occurrence, is independently selected from alkyl, haloalkyl, aryl, cycloalkyl, cycloalkylalkyl, heterocyclyl, halo, —NH$_2$, —CN, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(O)R$_{15}$, —S(O)R$_{15}$, —S(O)$_2$R$_{15}$, —NR$_{15}$C(=O)OR$_8$, —NR$_{15}$S(O$_2$)R$_8$ or arylalkyl; and $R_{15}$, at each occurrence, is independently selected from hydrogen, alkyl, cycloalkyl or aryl.

11. The compound of claim 1, wherein:

X is —C(=O)NR$_9$R$_9$;

W is absent, (—CR$_{8a}$R$_{8b}$)$_m$ or (—CR$_{8a}$R$_{8b}$)$_m$—O—;

m is 1-2;

Z is aryl or arylalkyl, both of which may be optionally substituted with one or more $R_4$'s;

provided that W and Z, or when W is absent, X and Z, are attached to the same carbon on Ring A;

$R_4$, at each occurrence, is independently selected from hydrogen, alkyl, aryl, cycloalkyl, halo, =O, —NH$_2$, —CN, —NO$_2$, —C(O)OH, —C(O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$, wherein the alkyl, aryl or cycloalkyl may be optionally substituted with one or more $R_5$'s;

$R_5$, at each occurrence, is independently selected from hydrogen, alkyl, haloalkyl, aryl, cycloalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

$R_8$, at each occurrence, is independently alkyl, aryl or heterocyclyl;

$R_{8a}$, at each occurrence, is independently hydrogen, alkyl or aryl;

$R_{8b}$, at each occurrence, is independently hydrogen, —C(=O)OH, alkyl, —OH, halo, —CN, —OR$_{10}$ or —C(O)NR$_9$R$_9$, wherein the alkyl may be optionally substituted with one or more $R_{9a}$'s; or $R_9$, at each occurrence, is independently hydrogen, alkyl, alkoxy, cycloalkyl, aryl or heterocyclyl, wherein the alkyl, cycloalkyl, aryl or heterocyclyl may be optionally substituted with 0-5 $R_{9a}$, and the heterocyclyl contains 1-4 heteroatoms selected from N, O, and S; or two $R_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more $R_{9a}$'s;

$R_{9a}$, at each occurrence, is independently selected from alkyl, haloalkyl, aryl, cycloalkyl, heterocyclyl, halo, =O, —NH$_2$, —CN, —NO$_2$, —C(O)OH, —C(O)OR$_{14}$, —OCF$_3$, —OR$_{10}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —C(=O)R$_{10}$, —OC(=O)NR$_{14}$R$_{14}$, —NR$_{14}$C(=O)NR$_{14}$R$_{14}$ or arylalkyl, wherein the alkyl, aryl, cycloalkyl and heterocyclyl may be optionally substituted with 0-3 $R_{10a}$;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, cycloalkyl, heterocyclyl, halo, —NH$_2$, —CN, —NO$_2$, —C(O)OH, —C(O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

$R_{14}$, at each occurrence, is independently selected from hydrogen, alkyl, cycloalkyl or aryl, wherein the alkyl, cycloalkyl or aryl may be optionally substituted with 0-3 $R_{14a}$;

$R_{14a}$, at each occurrence, is independently selected from alkyl, haloalkyl, aryl, cycloalkyl, heterocyclyl, halo, —NH$_2$, —CN, —NO$_2$, —C(O)OH, —C(O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and $R_{15}$, at each occurrence, is independently selected from hydrogen, alkyl, cycloalkyl or aryl.

12. The compound of claim 1, wherein:

A is

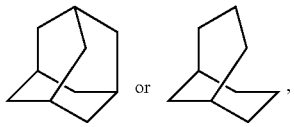

both of which are substituted with at least one $R_4$ other than hydrogen;

X is —C(=O)NR$_9$R$_9$;

W is absent or (—CR$_{8a}$R$_{8b}$)$_m$;

m is 1-2;

Z is aryl or arylalkyl, both of which may be optionally substituted with one or more provided that W and Z, or when W is absent, X and Z, are attached to the same carbon on Ring A;

$R_4$, at each occurrence, is independently selected from hydrogen, alkyl, aryl, cycloalkyl, halo, =O, —NH$_2$, —CN, —NO$_2$, —C(O)OH, —C(O)OR$_{10}$, —OR$_{10}$, —OH, —OCF$_3$, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$, wherein the alkyl, aryl or cycloalkyl may be optionally substituted with one or more $R_5$'s;

$R_5$, at each occurrence, is independently selected from hydrogen, alkyl, haloalkyl, aryl, cycloalkyl, halo, —NH$_2$, —CN, —NO$_2$, —C(O)OH, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

$R_8$, at each occurrence, is independently alkyl, aryl or heterocyclyl;

$R_{8a}$, at each occurrence, is independently hydrogen or alkyl;

$R_{8b}$, at each occurrence, is independently hydrogen, —C(=O)OH, alkyl, —OH, halo, —CN, —OR$_{10}$ or —C(O)NR$_9$R$_9$, wherein the alkyl may be optionally substituted with one or more $R_{9a}$'s; or $R_9$, at each occurrence, is independently hydrogen, alkyl, alkoxy, cycloalkyl, aryl or heterocyclyl, wherein the alkyl, cycloalkyl, aryl or heterocyclyl may be optionally substituted with 0-5 $R_{9a}$, and the heterocyclyl contains 1-4 heteroatoms selected from N, O, and S; or two $R_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more $R_{9a}$'s;

$R_{9a}$, at each occurrence, is independently selected from alkyl, haloalkyl, aryl, cycloalkyl, heterocyclyl, halo, =O, —NH$_2$, —CN, —NO$_2$, —C(O)OH, —C(O)OR$_{14}$, —OCF$_3$, —OR$_{10}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —C(=O)R$_{10}$, —OC(=O)NR$_{14}$R$_{14}$, —NR$_{14}$C(=O)NR$_{14}$R$_{14}$ or arylalkyl, wherein the alkyl, aryl, cycloalkyl and heterocyclyl may be optionally substituted with 0-3 $R_{10a}$;

$R_{10}$, at each occurrence, is independently selected from alkyl, aryl, arylalkyl or heterocyclyl, wherein the alkyl, aryl, arylalkyl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, cycloalkyl, heterocyclyl, halo, —NH$_2$, —CN, —NO$_2$, —C(O)OH, —C(O)OR$_{14}$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

$R_{14}$, at each occurrence, is independently selected from hydrogen, alkyl, cycloalkyl or aryl, wherein the alkyl, cycloalkyl or aryl may be optionally substituted with 0-3 $R_{14a}$;

$R_{14a}$, at each occurrence, is independently selected from alkyl, haloalkyl, aryl, cycloalkyl, heterocyclyl, halo, —NH$_2$, —CN, —NO$_2$, —C(O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and $R_{15}$, at each occurrence, is independently selected from hydrogen, alkyl, cycloalkyl or aryl.

13. The compound of claim 1, wherein:
A is

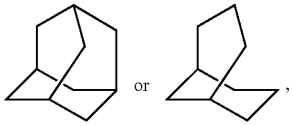

both of which are substituted with at least one $R_4$ other than hydrogen;

X is —C(=O)$NR_9R_9$;

W is absent or (—$CR_{8a}R_{8b}$)$_m$;

m is 1;

Z is aryl or arylalkyl, both of which may be optionally substituted with one or more $R_4$'s;

provided that W and Z, or when W is absent, X and Z, are attached to the same carbon on Ring A;

$R_4$, at each occurrence, is independently selected from hydrogen, alkyl, aryl, cycloalkyl, halo, =O, —$NH_2$, —CN, —$NO_2$, —C(O)OH, —C(O)$OR_{10}$, —$OR_{10}$, —OH, —$OCF_3$, —SH, —$SR_{10}$, —C(=O)$NR_9R_9$, —$NR_9R_9$, —S(O)$_2NR_9R_9$, —$NR_9S(O)_2CF_3$, —C(=O)$NR_9S(O)_2R_9$, —S(O)$_2NR_9C(=O)OR_9$, —S(O)$_2NR_9C(=O)NR_9R_9$, —C(=O)$NR_9S(O)_2CF_3$, —C(=O)$R_{10}$, —$NR_9C(=O)R_{10}$, —OC(=O)$R_{10}$, —S(=O)$R_{10}$, —S(O)$_2R_{10}$, —O—S(O)$_2R_{10}$, —$NR_9C(=O)OR_8$ or —$NR_9S(O_2)R_8$, wherein the alkyl, aryl or cycloalkyl may be optionally substituted with one or more $R_5$'s;

$R_5$, at each occurrence, is independently selected from hydrogen, alkyl, haloalkyl, aryl, cycloalkyl, halo, —$NH_2$, —CN, —$NO_2$, —C(=O)OH, —C(=O)$OR_{10}$, —$OCF_3$, —$OR_{10}$, —OH, —SH, —$SR_{10}$, —C(=O)$NR_9R_9$, —$NR_9R_9$, —S(O)$_2NR_9R_9$, —$NR_9S(O)_2CF_3$, —C(=O)$NR_9S(O)_2R_9$, —S(O)$_2NR_9C(=O)OR_9$, —S(O)$_2NR_9C(=O)NR_9R_9$, —C(=O)$NR_9S(O)_2CF_3$, —C(=O)$R_{10}$, —$NR_9C(=O)R_{10}$, —OC(=O)$R_{10}$, —S(=O)$R_{10}$, —S(O)$_2R_{10}$, —O—S(O)$_2R_{10}$, —$NR_9C(=O)OR_8$ or —$NR_9S(O_2)R_8$;

$R_8$, at each occurrence, is independently alkyl or aryl;

$R_{8a}$, at each occurrence, is independently hydrogen or alkyl;

$R_{8b}$, at each occurrence, is independently hydrogen, —C(=O)OH, alkyl, —OH, halo, —CN or —$OR_{10}$, wherein the alkyl may be optionally substituted with one or more $R_{9a}$'s; or $R_9$, at each occurrence, is independently hydrogen, alkyl, alkoxy, aryl or heterocyclyl, wherein the alkyl, aryl or heterocyclyl may be optionally substituted with 0-5 $R_{9a}$, and the heterocyclyl contains 1-4 heteroatoms selected from N, O, and S; or two $R_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more $R_{9a}$'s;

$R_{9a}$, at each occurrence, is independently selected from alkyl, haloalkyl, aryl, cycloalkyl, heterocyclyl, halo, =O, —$NH_2$, —CN, —$NO_2$, —C(O)OH, —C(O)$OR_{14}$, —$OCF_3$, —$OR_{10}$, —OH, —SH, —$SR_{14}$, —C(=O)$NR_{14}R_{14}$, —$NR_{14}R_{14}$, —S(O)$_2NR_{14}R_{14}$, —$NR_{14}S(O)_2CF_3$, —C(=O)$NR_{14}S(O)_2R_{10}$, —S(O)$_2NR_{14}C(=O)OR_{10}$, —S(O)$_2NR_{14}C(=O)NR_{14}R_{14}$, —C(=O)$NR_{14}S(O)_2R_{14}$, —C(=O)$R_{14}$, —$NR_{14}C(=O)R_{14}$, —OC(=O)$R_{14}$, —S(=O)$R_{14}$, —S(O)$_2R_{14}$, —OS(O)$_2R_{14}$, —$NR_{14}C(=O)OR_{10}$, —$NR_{14}S(O_2)R_8$, —C(=O)$R_{10}$, —OC(=O)$NR_{14}R_{14}$, or —$NR_{14}C(=O)NR_{14}R_{14}$, wherein the alkyl, aryl, cycloalkyl and heterocyclyl may be optionally substituted with 0-3 $R_{10a}$;

$R_{10}$, at each occurrence, is independently selected from alkyl, aryl or heterocyclyl, wherein the alkyl, aryl or heterocyclyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, cycloalkyl, heterocyclyl, halo, —$NH_2$, —CN, —$NO_2$, —C(O)OH, —C(O)$OR_{14}$, —$OCF_3$, —$OR_{14}$, —OH, —SH, —$SR_{14}$, —C(=O)$NR_{14}R_{14}$, —$NR_{14}R_{14}$, —S(O)$_2NR_{14}R_{14}$, —$NR_{14}S(O)_2CF_3$, —C(=O)$NR_{14}S(O)_2R_{14}$, —S(O)$_2NR_{14}C(=O)OR_{14}$, —S(O)$_2NR_{14}C(=O)NR_{14}R_{14}$, —C(=O)$NR_{14}S(O)_2CF_3$, —C(=O)$R_{14}$, —$NR_{14}C(=O)R_{14}$, —OC(=O)$R_{14}$, —S(=O)$R_{14}$, —S(O)$_2R_{14}$, —$NR_{14}C(=O)OR_8$, or —$NR_{14}S(O_2)R_8$;

$R_{14}$, at each occurrence, is independently selected from hydrogen, alkyl or aryl, wherein the alkyl or aryl may be optionally substituted with 0-3 $R_{14a}$;

$R_{14a}$, at each occurrence, is independently selected from alkyl, haloalkyl, aryl, cycloalkyl, heterocyclyl, halo, —$NH_2$, —CN, —$NO_2$, —C(O)OH, —C(O)$OR_{15}$, —$OCF_3$, —$OR_{15}$, —OH, —SH, —$SR_{15}$, —C(=O)$NR_{15}R_{15}$, —$NR_{15}R_{15}$, —S(O)$_2NR_{15}R_{15}$, —$NR_{15}S(O)_2CF_3$, —C(=O)$NR_{15}S(O)_2R_{15}$, —S(O)$_2NR_{15}C(=O)OR_{15}$, —S(O)$_2NR_{15}C(=O)NR_{15}R_{15}$, —C(=O)$NR_{15}S(O)_2CF_3$, —C(=O)$R_{15}$, —$NR_{15}C(=O)R_{15}$, —OC(=O)$R_{15}$, —S(=O)$R_{15}$, —S(O)$_2R_{15}$, —$NR_{15}C(=O)OR_8$, or —$NR_{15}S(O_2)R_8$; and $R_{15}$, at each occurrence, is independently selected from hydrogen, alkyl or aryl.

14. The compound of claim 1, wherein:
A is

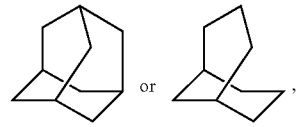

both of which are substituted with at least one $R_4$ other than hydrogen;

X is —C(=O)$NR_9R_9$;

W is absent or (—$CR_{8a}R_{8b}$)$_m$;

m is 1;

Z is aryl or arylalkyl, both of which may be optionally substituted with one or more $R_4$'s;

provided that W and Z, or when W is absent, X and Z, are attached to the same carbon on Ring A;

$R_4$, at each occurrence, is independently selected from hydrogen, alkyl, aryl, cycloalkyl, halo, =O, —$NH_2$, —CN, —$NO_2$, —C(O)OH, —C(O)$OR_{10}$, —$OR_{10}$, —OH, —$OCF_3$, —SH, —$SR_{10}$, —C(=O)$NR_9R_9$, —$NR_9R_9$, —S(O)$_2NR_9R_9$, —$NR_9S(O)_2CF_3$, —C(=O)$NR_9S(O)_2R_9$, —S(O)$_2NR_9C(=O)OR_9$, —S(O)$_2NR_9C(=O)NR_9R_9$, —C(=O)$NR_9S(O)_2CF_3$, —C(=O)$R_{10}$, —$NR_9C(=O)R_{10}$, —OC(=O)$R_{10}$, —S(=O)$R_{10}$, —S(O)$_2R_{10}$, —O—S(O)$_2R_{10}$, —$NR_9C(=O)OR_8$ or —$NR_9S(O_2)R_8$, wherein the alkyl, aryl or cycloalkyl may be optionally substituted with one or more $R_5$'s;

R$_5$, at each occurrence, is independently selected from hydrogen, alkyl, haloalkyl, aryl, cycloalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —C(=O) NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)R$_{10}$, —OC(=O)R$_{10}$, —S(=O)R$_{10}$, —S(O)$_2$R$_{10}$, —O—S(O)$_2$R$_{10}$, —NR$_9$C(=O)OR$_8$ or —NR$_9$S(O$_2$)R$_8$;

R$_8$, at each occurrence, is independently alkyl or aryl;

R$_{8a}$, at each occurrence, is independently hydrogen or alkyl;

R$_{8b}$, at each occurrence, is independently hydrogen, —C(=O)OH, alkyl, —OH, halo, —CN, or —OR$_{10}$;

R$_9$, at each occurrence, is independently hydrogen, alkyl, alkoxy or aryl, wherein the alkyl or aryl may be optionally substituted with 0-5 R$_{9a}$; or two R$_9$'s together with the nitrogen to which they are attached form a unsaturated, saturated or partially saturated cyclic ring system containing from 2-10 carbon atoms and from 0-4 additional heteroatoms selected from N, O, S, S(O) and S(O)$_2$, wherein said ring system may be optionally substituted or fused with one or more R$_{9a}$'s;

R$_{9a}$, at each occurrence, is independently selected from alkyl, haloalkyl, aryl, cycloalkyl, heterocyclyl, halo, =O, —NH$_2$, —CN, —NO$_2$, —C(O)OH, —C(O)OR$_{14}$, —OCF$_3$, —OR$_{10}$, —OH, —SH, —SR$_{14}$, —C(=O) NR$_{14}$R$_{14}$, —NR$_{14}$R$_{14}$, —S(O)$_2$NR$_{14}$R$_{14}$, —NR$_{14}$S (O)$_2$CF$_3$, —C(=O)NR$_{14}$S(O)$_2$R$_{10}$, —S(O)$_2$NR$_{14}$C (=O)OR$_{10}$, —S(O)$_2$NR$_{14}$C(=O)NR$_{14}$R$_{14}$, —C(=O) NR$_{14}$S(O)$_2$R$_{14}$, —C(=O)R$_{14}$, —NR$_{14}$C(=O)R$_{14}$, —OC(=O)R$_{14}$, —S(=O)R$_{14}$, —S(O)$_2$R$_{14}$, —OS (O)$_2$R$_{14}$, —NR$_{14}$C(=O)OR$_{10}$, —NR$_{14}$S(O)$_2$R$_8$, —C(=O)R$_{10}$, —OC(=O)NR$_{14}$R$_{14}$, or —NR$_{14}$C(=O) NR$_{14}$R$_{14}$, wherein the alkyl, aryl, cycloalkyl and heterocyclyl may be optionally substituted with 0-3 R$_{10a}$;

R$_{10}$, at each occurrence, is independently selected from alkyl or aryl, wherein the alkyl or aryl may be optionally substituted with 0-3 R$_{10a}$;

R$_{10a}$, at each occurrence, is independently selected from alkyl, haloalkyl, aryl, cycloalkyl, heterocyclyl, halo, —NH$_2$, —CN, —NO$_2$, —C(O)OH, —C(O)OR$_{14}$, —OCF$_3$, —OR$_{14}$, —OH, —SH, —SR$_{14}$, —C(=O) NR$_{14}$R$_{14}$, —NR$_{14}$R$_{14}$, —S(O)$_2$NR$_{14}$R$_{14}$, —NR$_{14}$S (O)$_2$CF$_3$, —C(=O)NR$_{14}$S(O)$_2$R$_{14}$, —S(O)$_2$NR$_{14}$C (=O)OR$_{14}$, —S(O)$_2$NR$_{14}$C(=O)NR$_{14}$R$_{14}$, —C(=O) NR$_{14}$S(O)$_2$CF$_3$, —C(=O)R$_{14}$, —NR$_{14}$C(=O)R$_{14}$, —OC(=O)R$_{14}$, —S(=O)R$_{14}$, —S(O)$_2$R$_{14}$, —NR$_{14}$C (=O)OR$_8$, or —NR$_{14}$S(O$_2$)R$_8$;

R$_{14}$, at each occurrence, is independently selected from hydrogen, alkyl or aryl, wherein the alkyl or aryl may be optionally substituted with 0-3 R$_{14a}$;

R$_{14a}$, at each occurrence, is independently selected from alkyl, haloalkyl, aryl, cycloalkyl, heterocyclyl, halo, —NH$_2$, —CN, —NO$_2$, —C(O)OH, —C(O)OR$_{15}$, —OCF$_3$, —OR$_{15}$, —OH, —SH, —SR$_{15}$, —C(=O) NR$_{15}$R$_{15}$, —NR$_{15}$R$_{15}$, —S(O)$_2$NR$_{15}$R$_{15}$, —NR$_{15}$S (O)$_2$CF$_3$, —C(=O)NR$_{15}$S(O)$_2$R$_{15}$, —S(O)$_2$NR$_{15}$C (=O)OR$_{15}$, —S(O)$_2$NR$_{15}$C(=O)NR$_{15}$R$_{15}$, —C(=O) NR$_{15}$S(O)$_2$CF$_3$, —C(=O)R$_{15}$, —NR$_{15}$C(=O)R$_{15}$, —OC(=O)R$_{15}$, —S(=O)R$_{15}$, —S(O)$_2$R$_{15}$, —NR$_{15}$C (=O)OR$_8$, or —NR$_{15}$S(O$_2$)R$_8$; and R$_{15}$, at each occurrence, is independently selected from hydrogen or alkyl.

15. The compound of claim 1, wherein the compound is selected from the group consisting of:

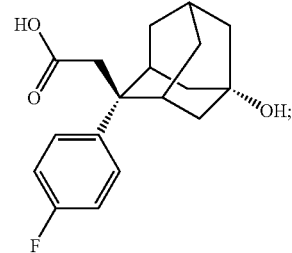

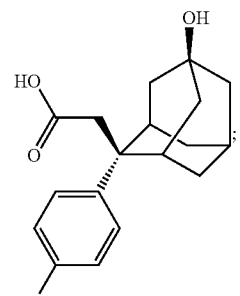

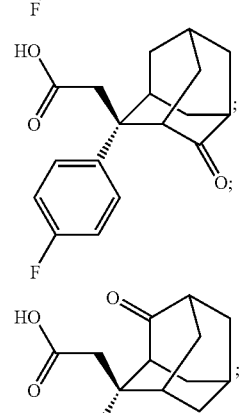

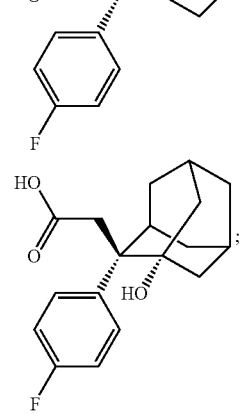

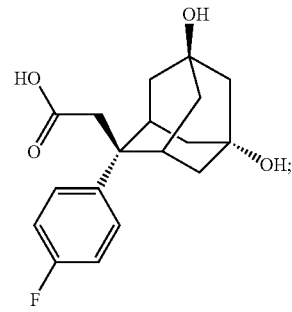

-continued
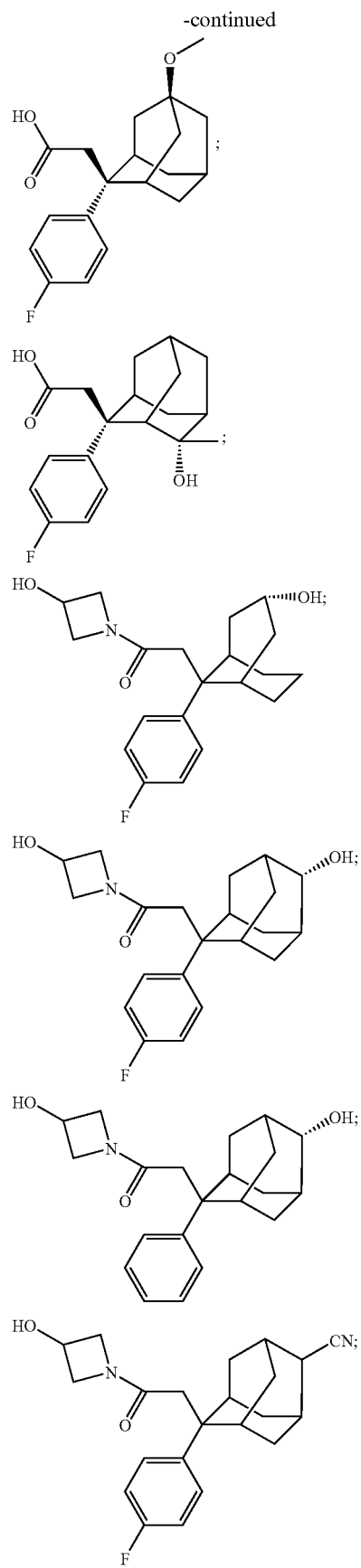
-continued
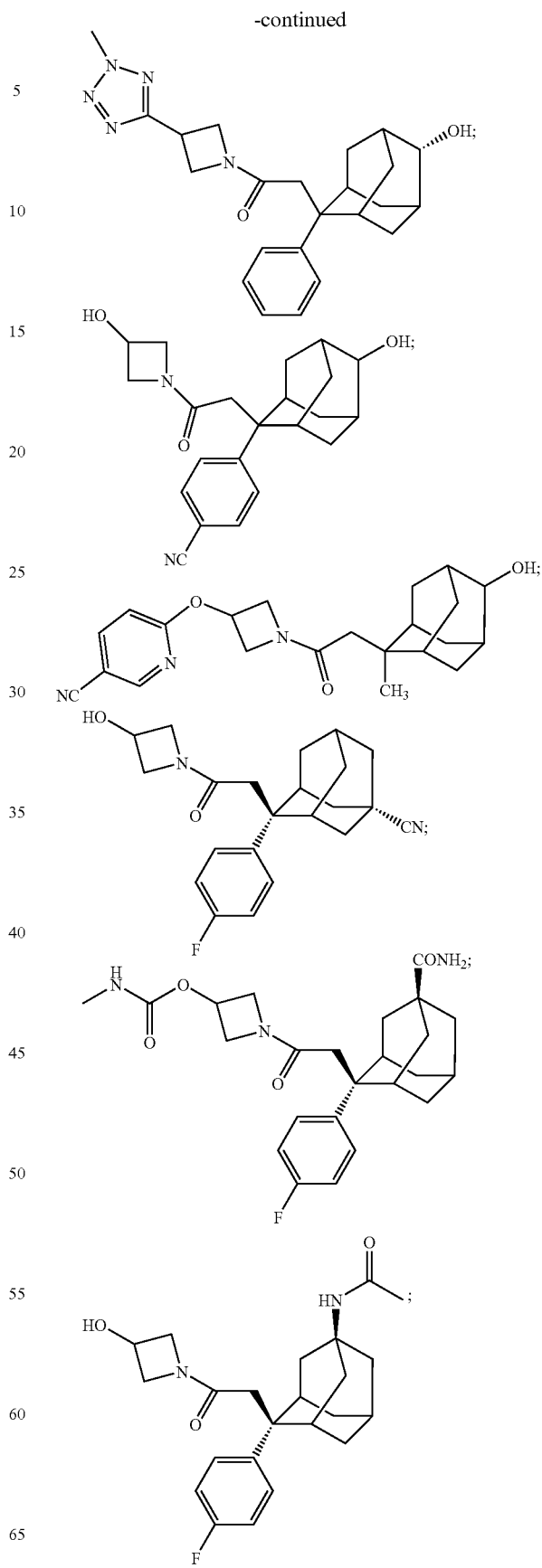

307
-continued
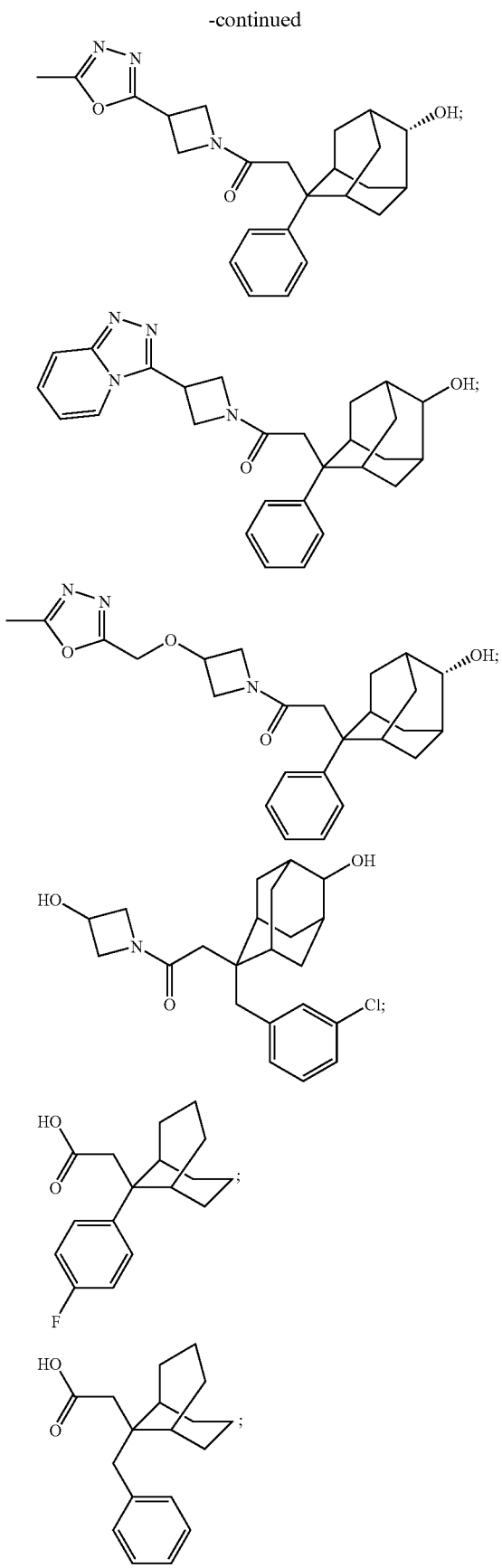
308
-continued
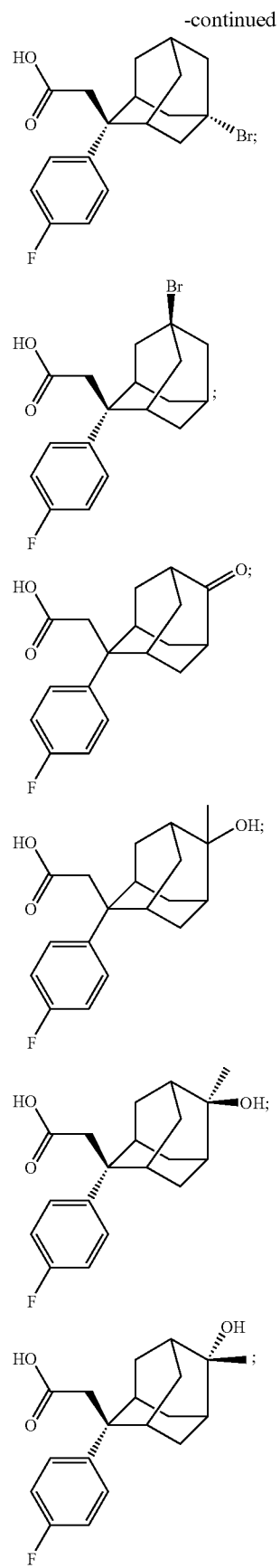

-continued
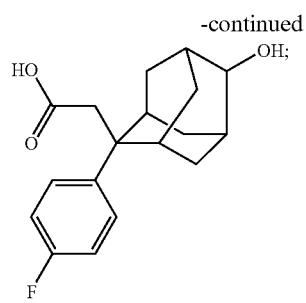
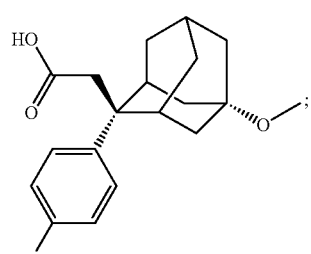
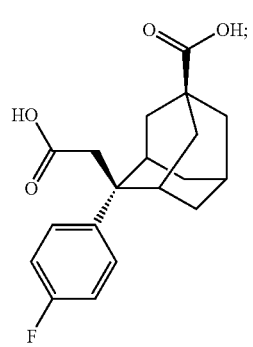
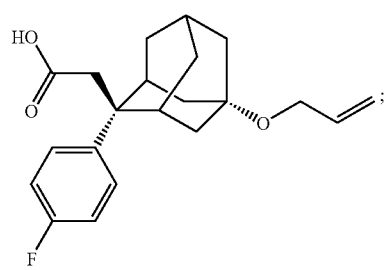
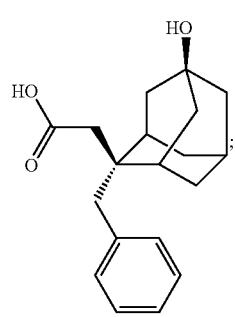
-continued
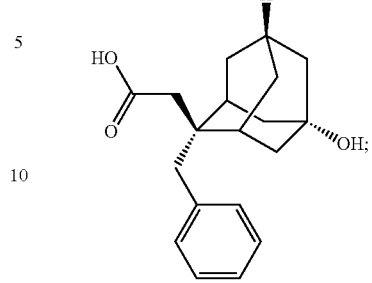
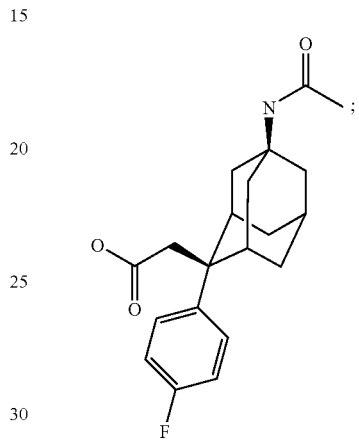
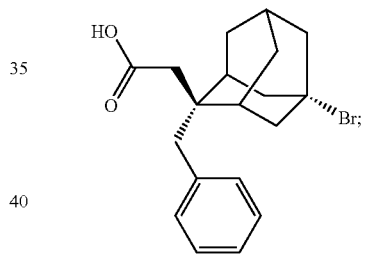
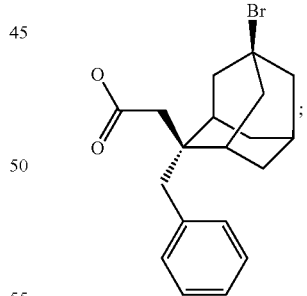
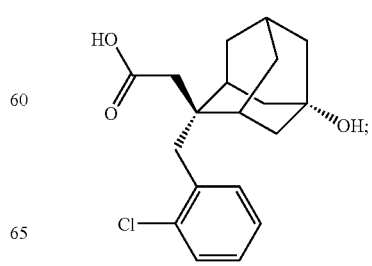

311
-continued
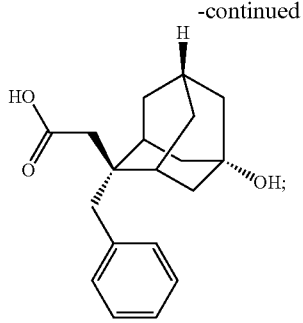
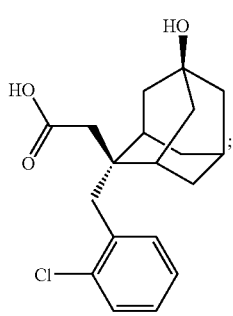
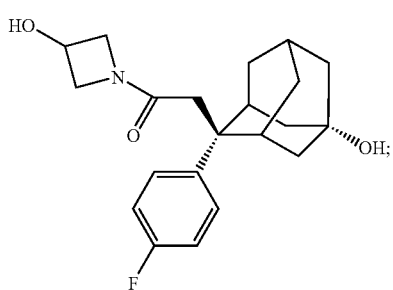
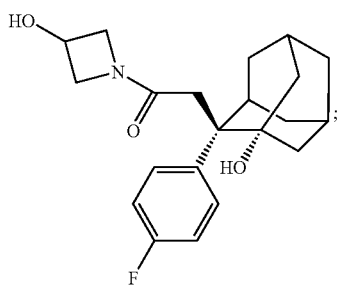
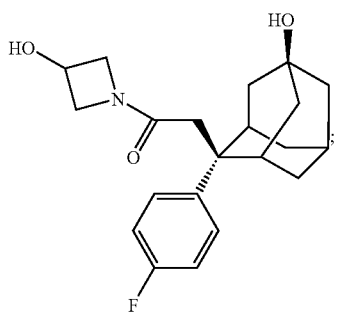
312
-continued
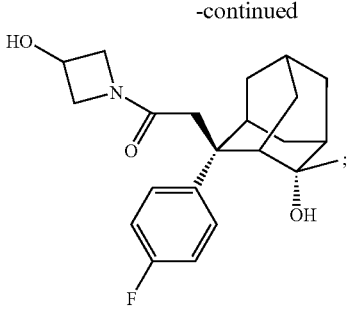
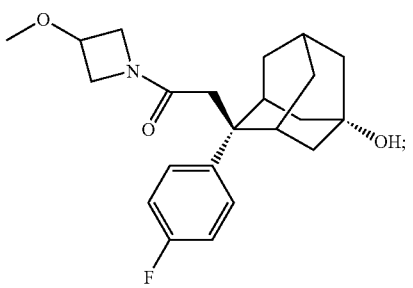
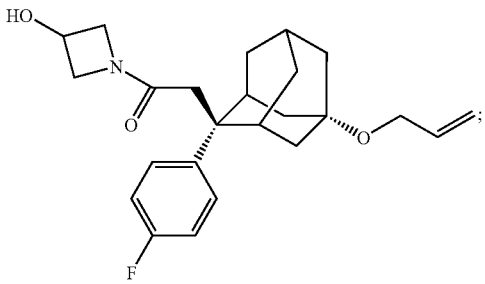
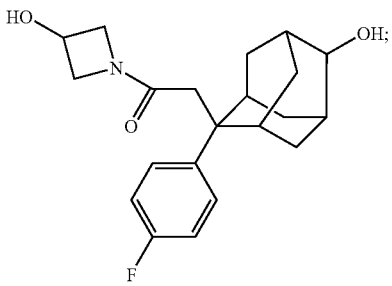
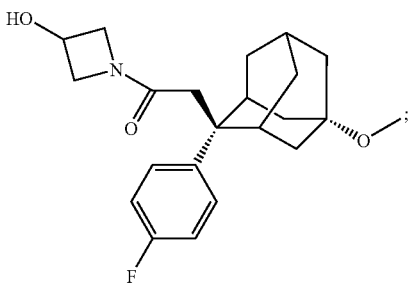

313
-continued
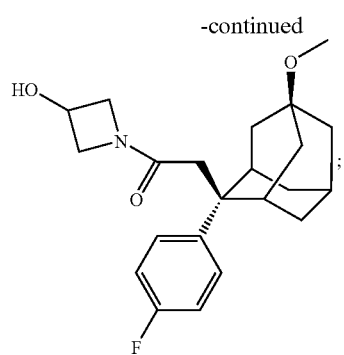
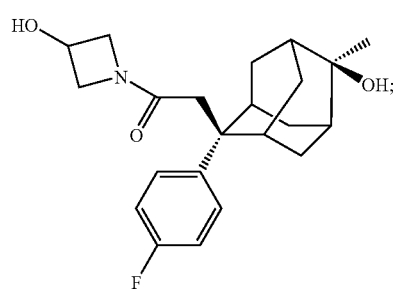
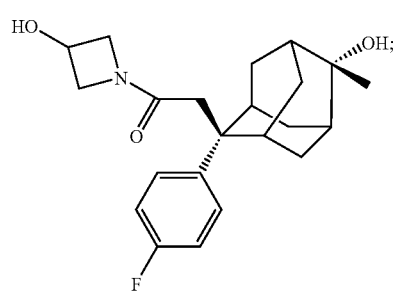
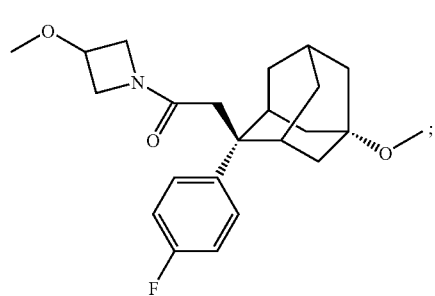
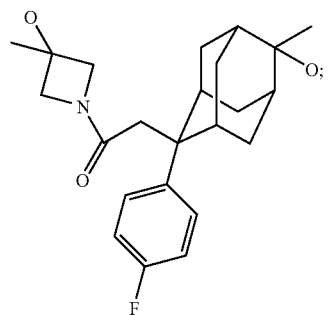
314
-continued
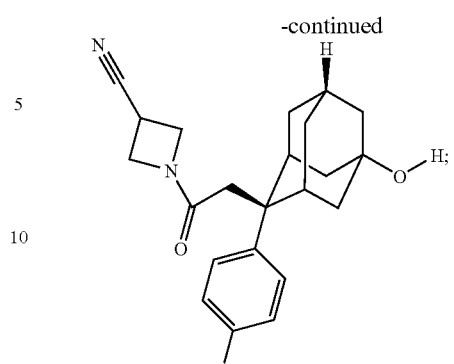
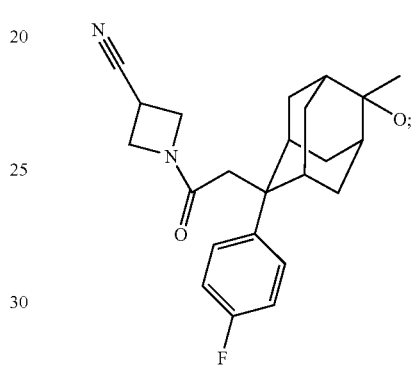
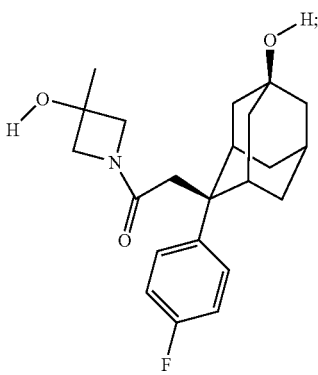

315
-continued
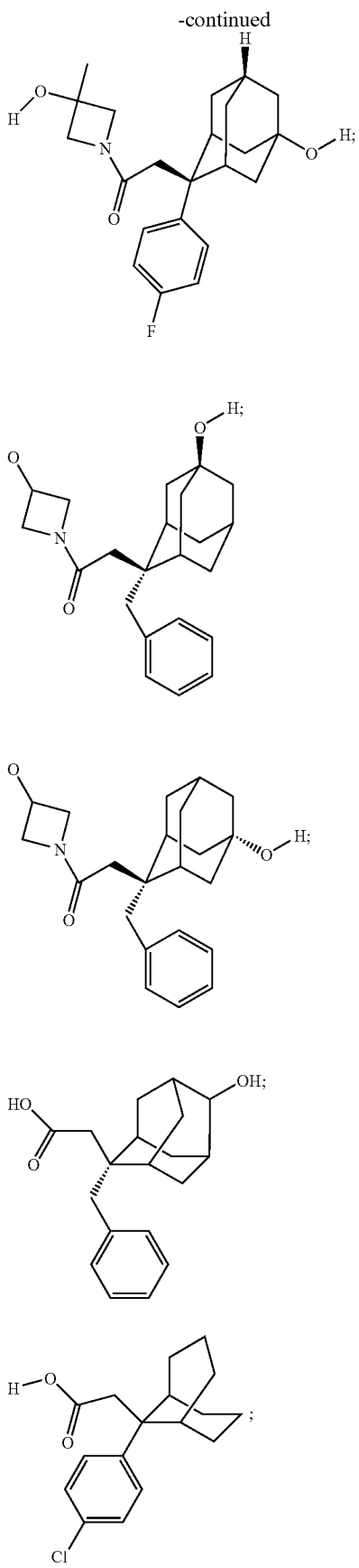
316
-continued
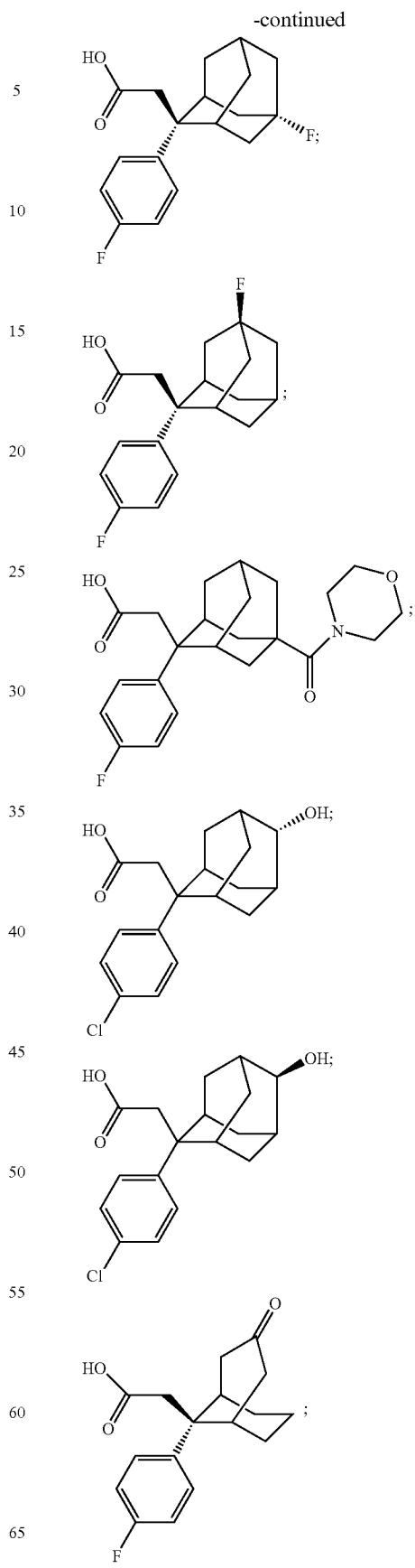

-continued
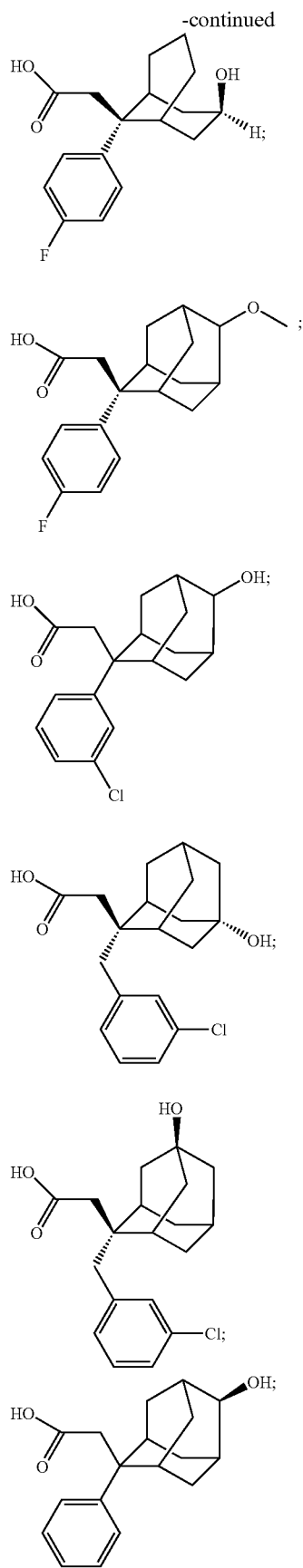
-continued
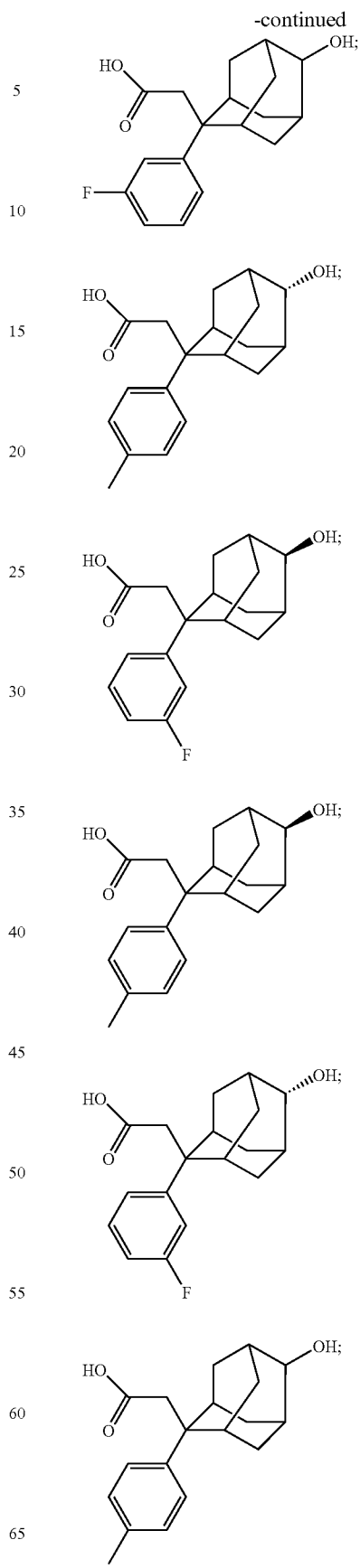

-continued
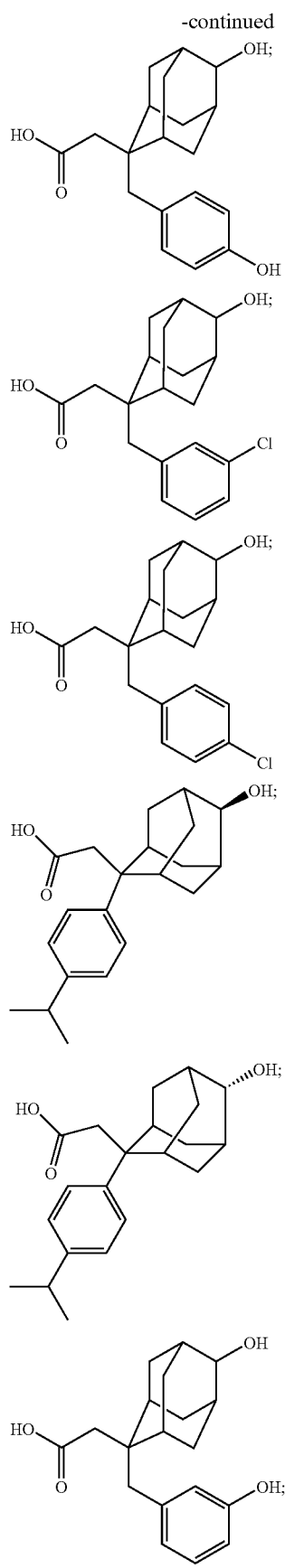
-continued
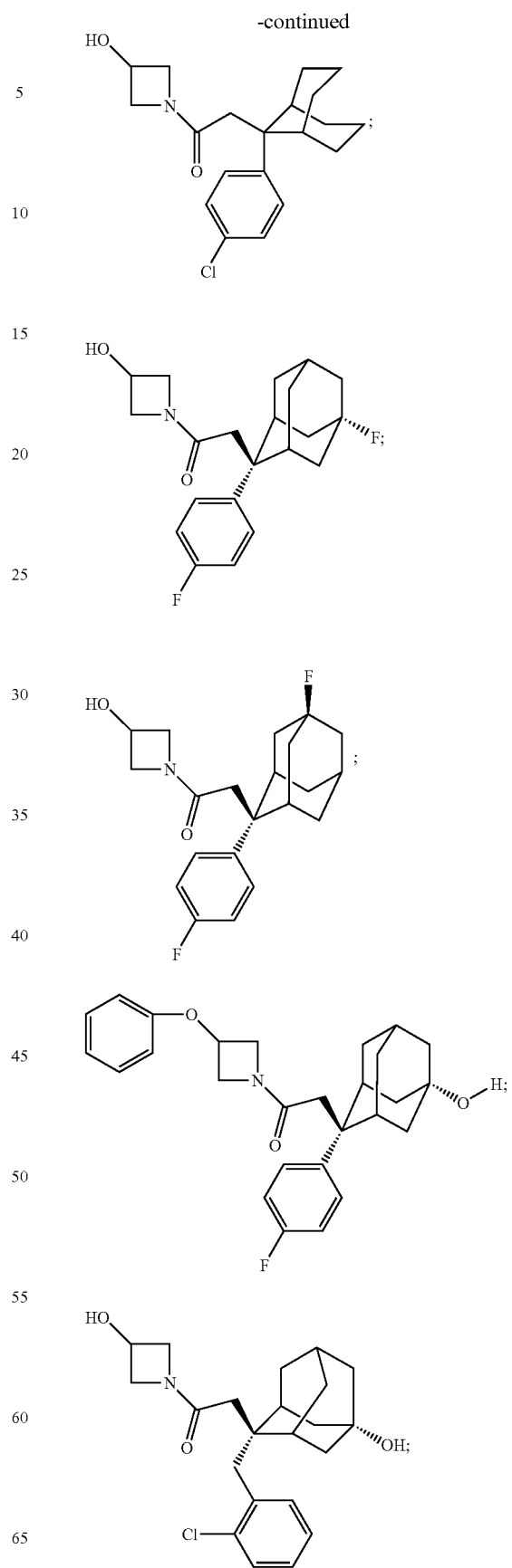

-continued
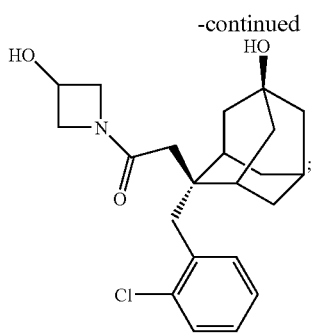
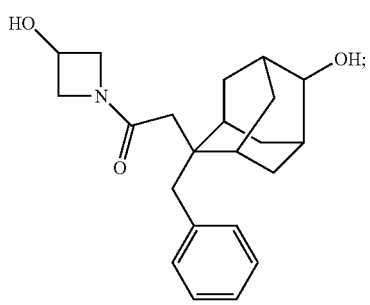
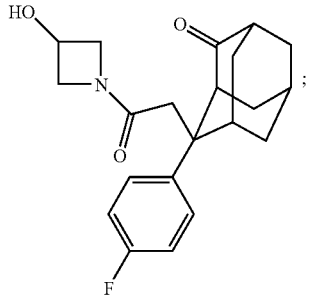
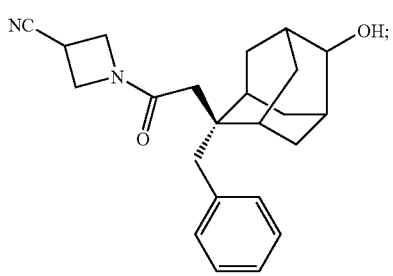
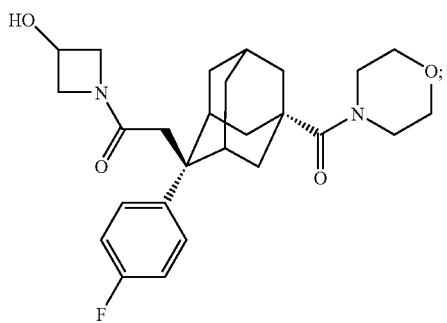
-continued
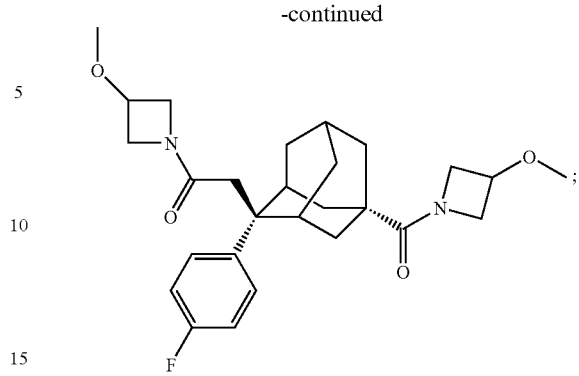
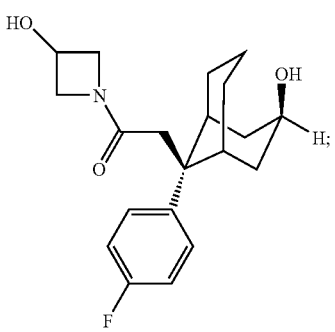
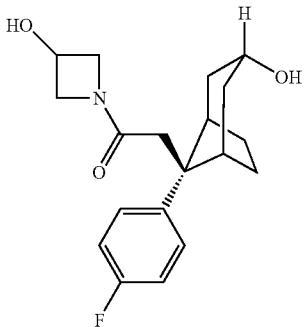
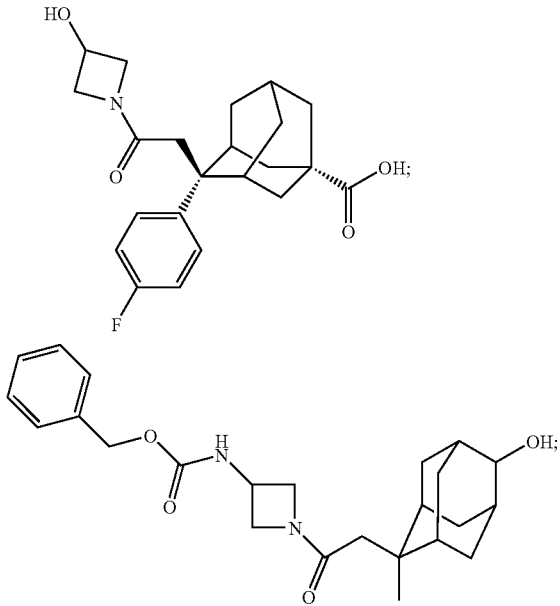

323
-continued
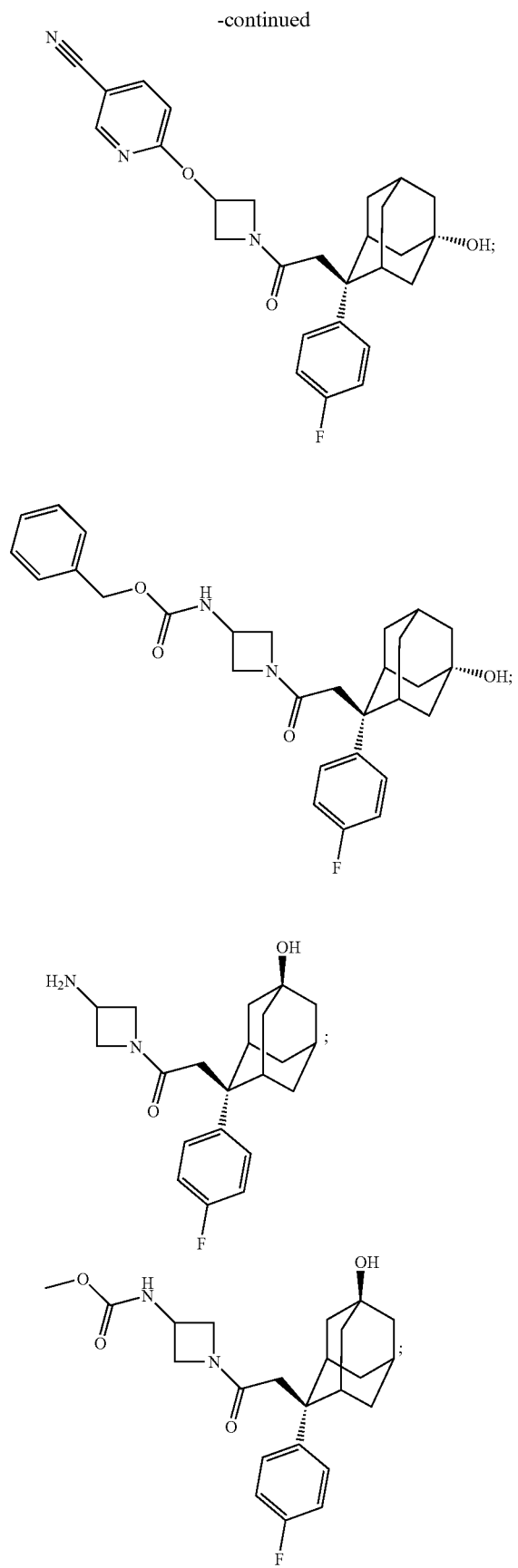
324
-continued
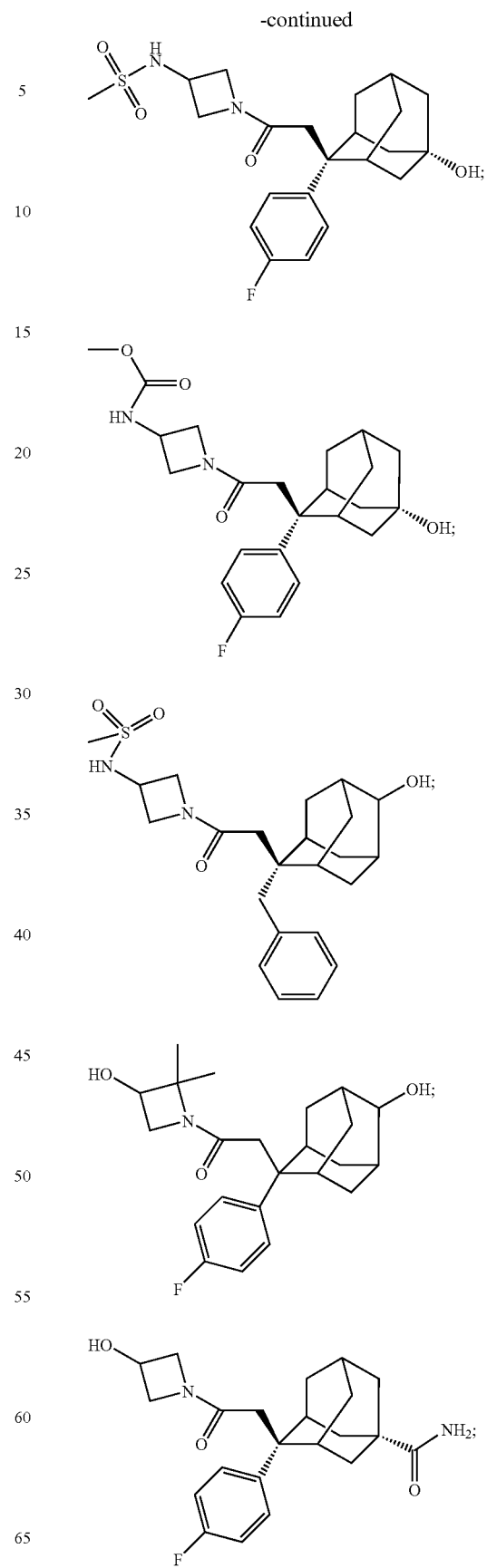

-continued
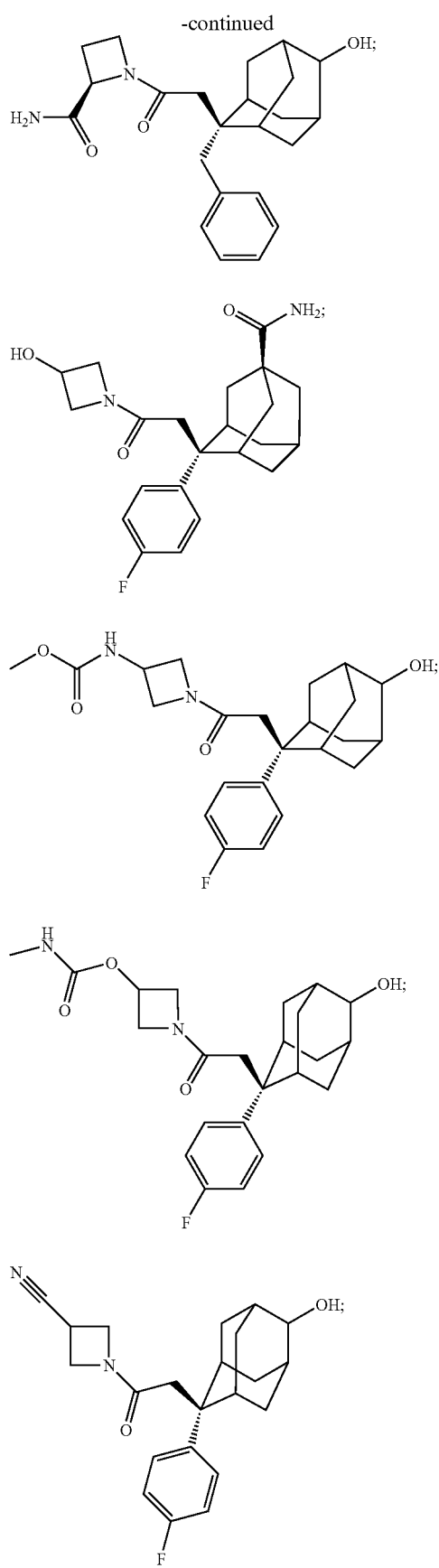
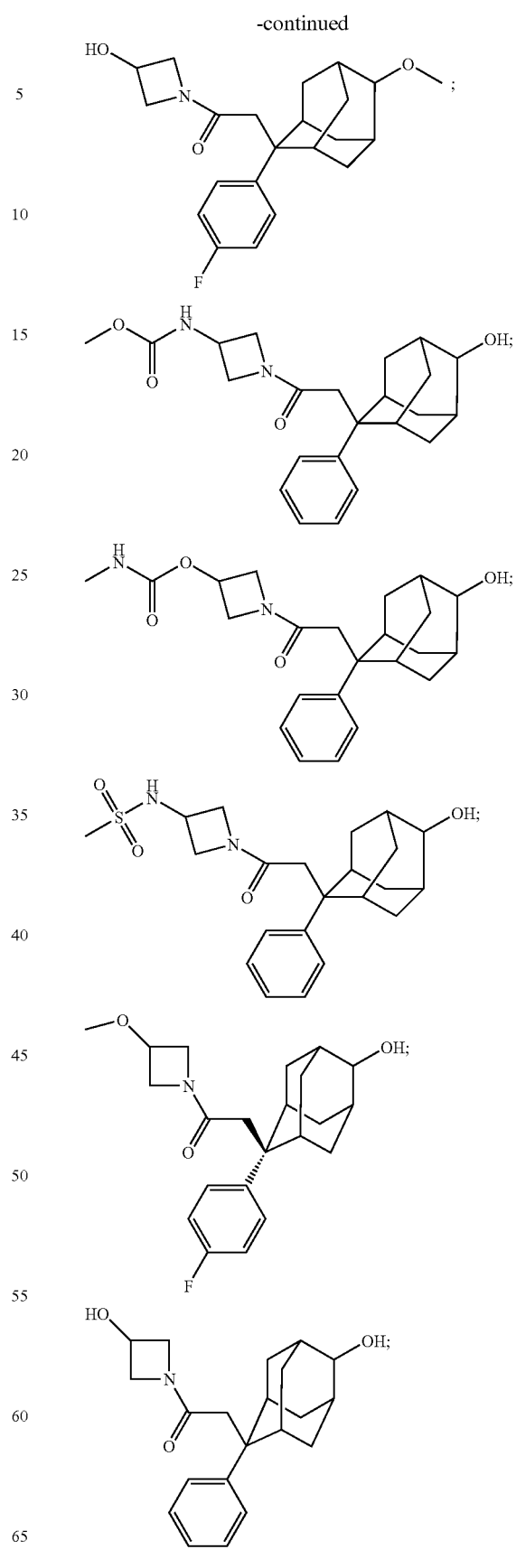

327
-continued
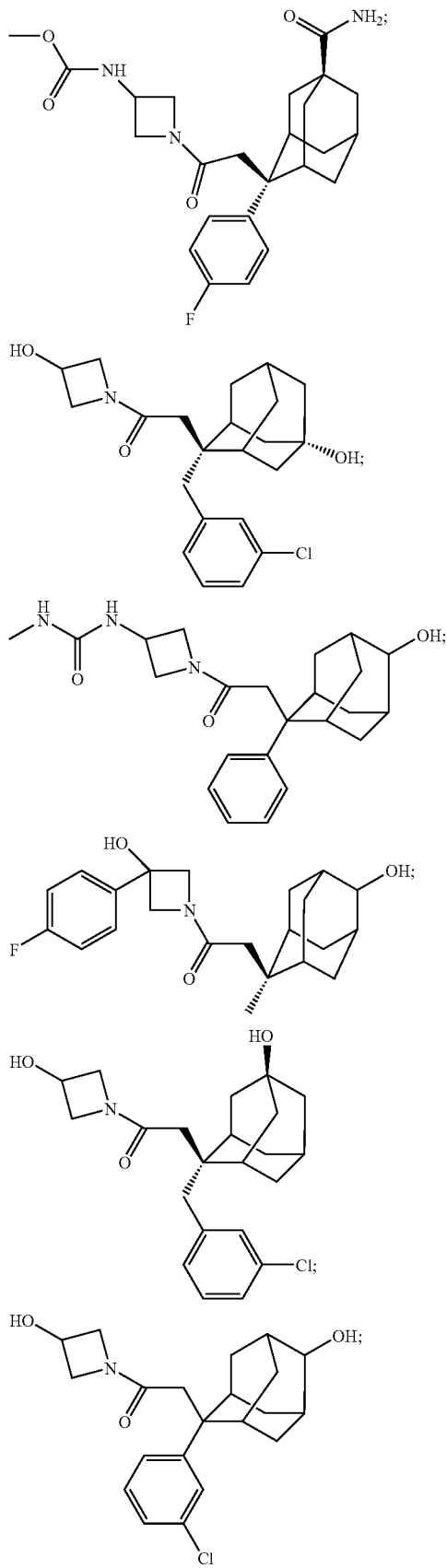
328
-continued
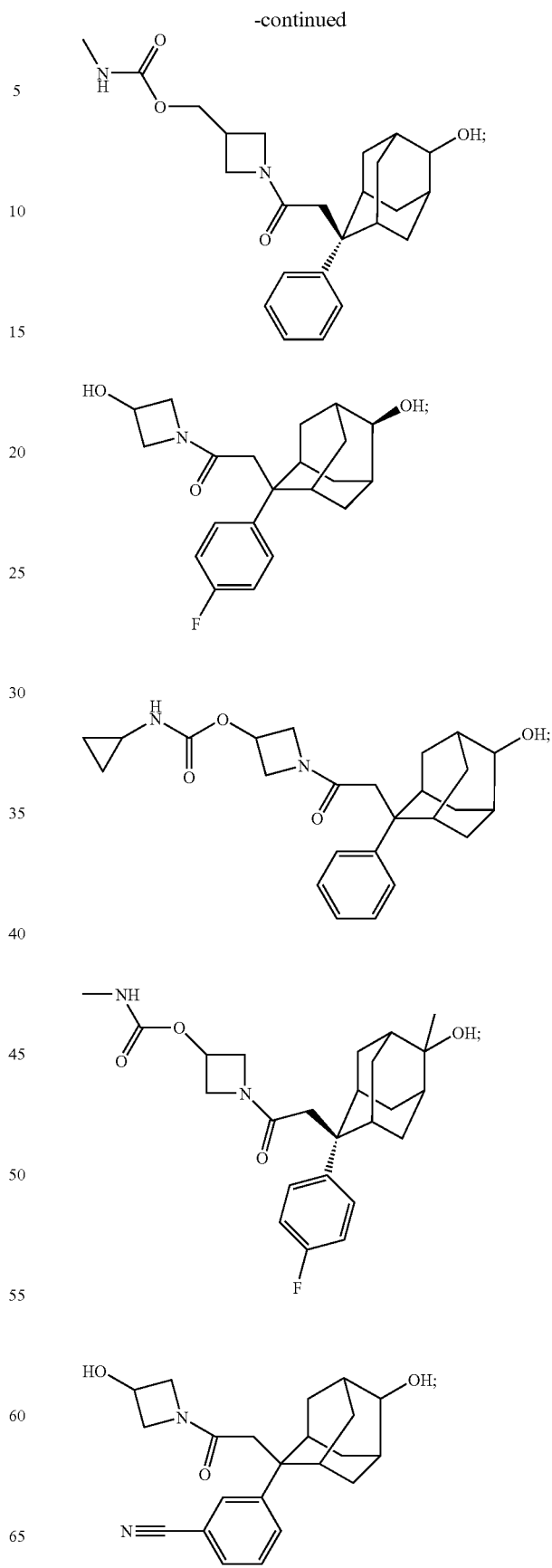

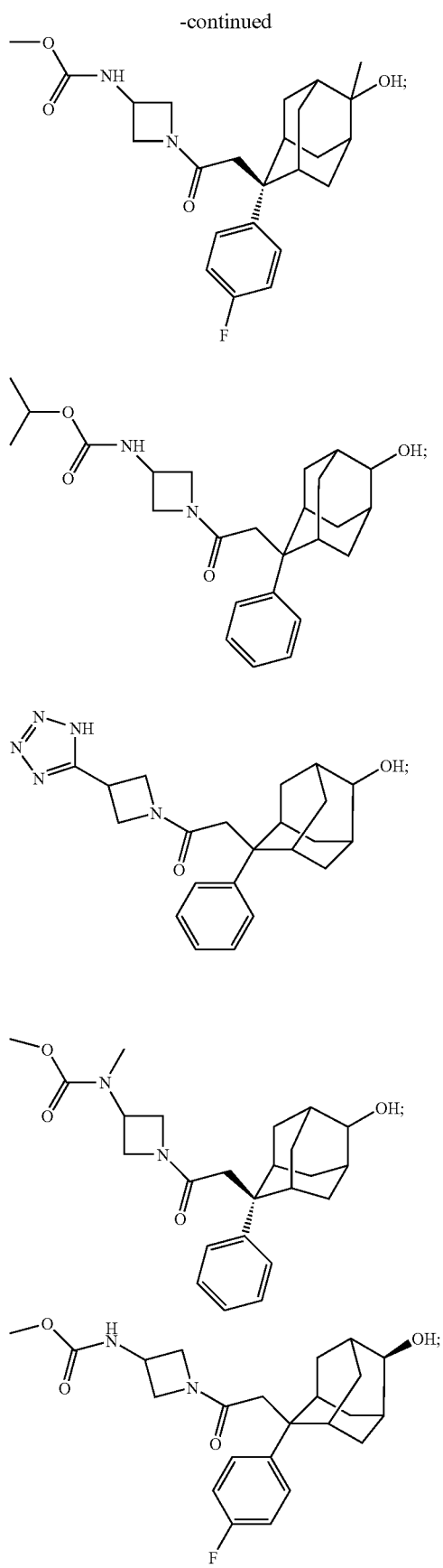

331
-continued
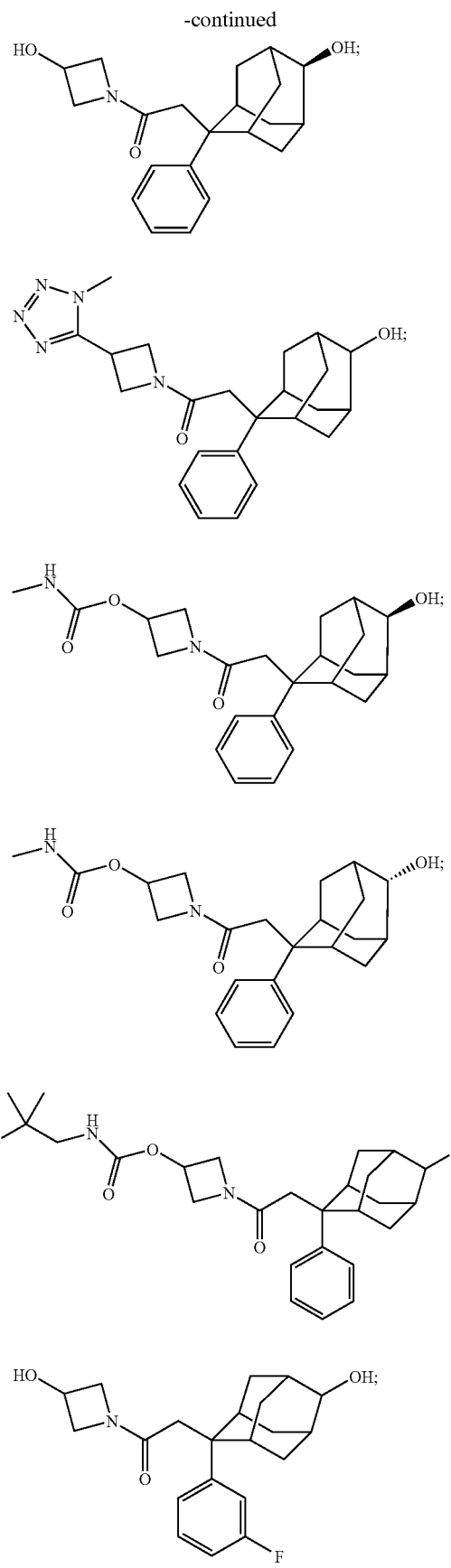
332
-continued
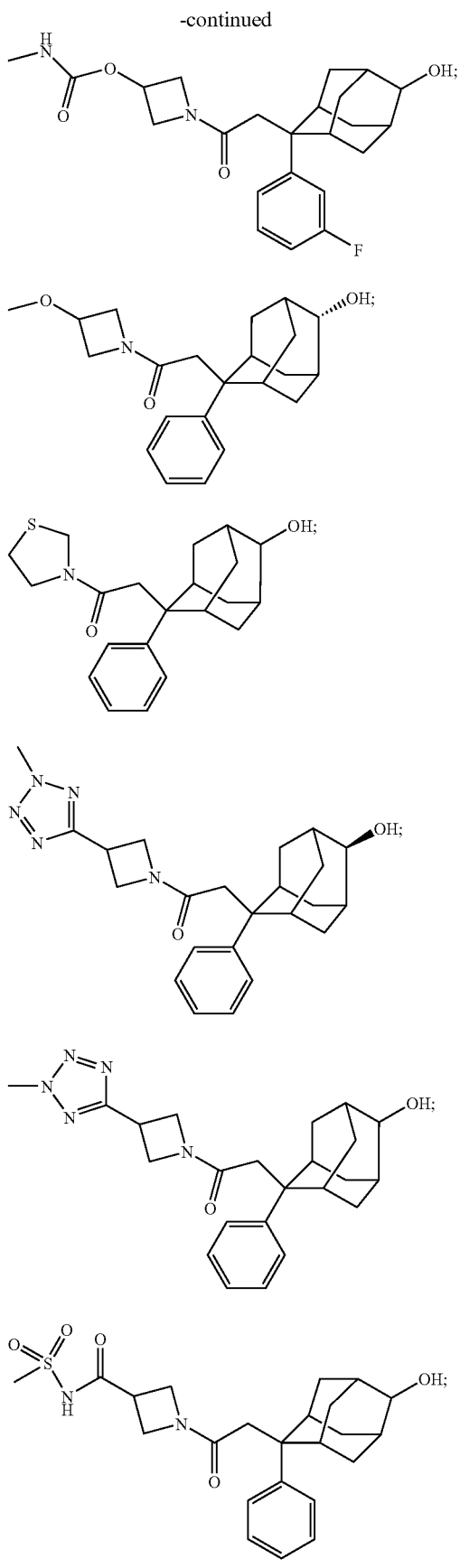

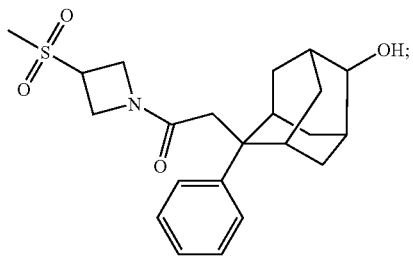

-continued
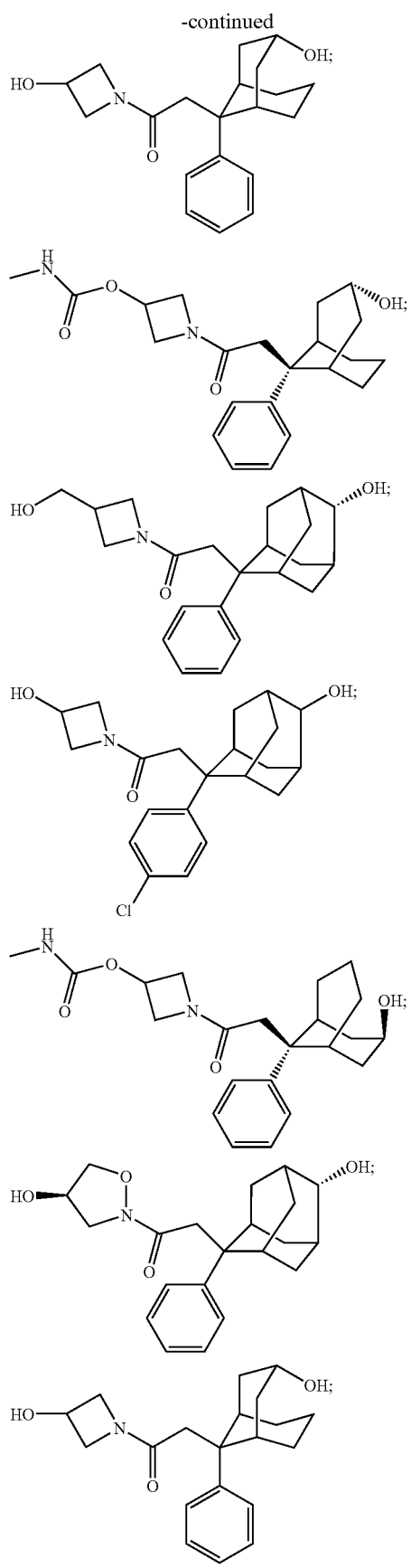
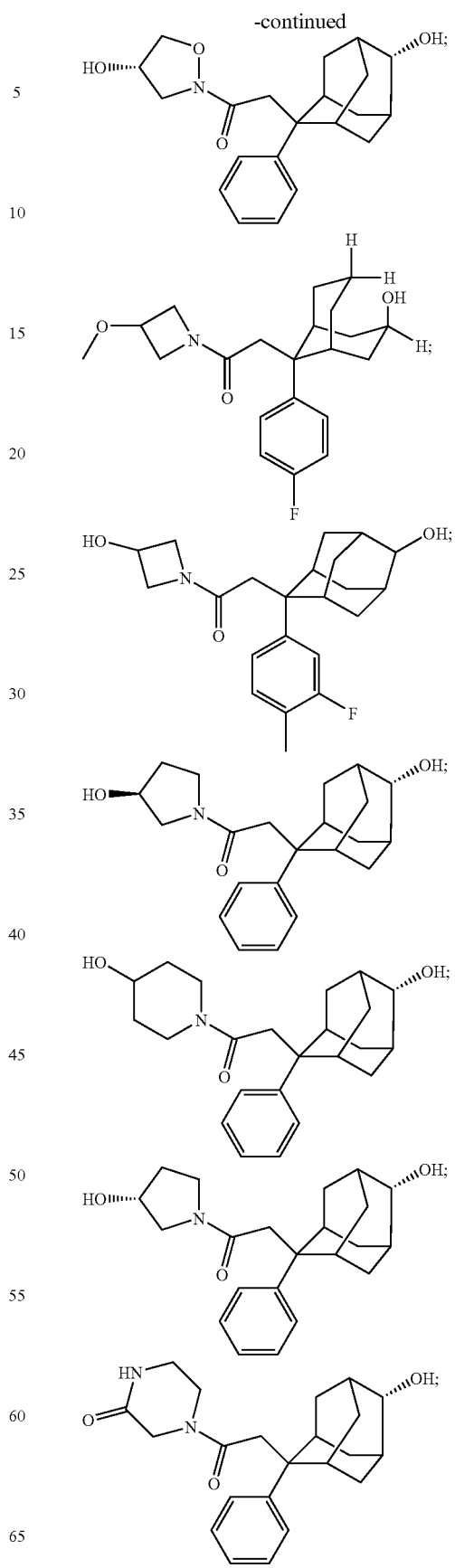

-continued
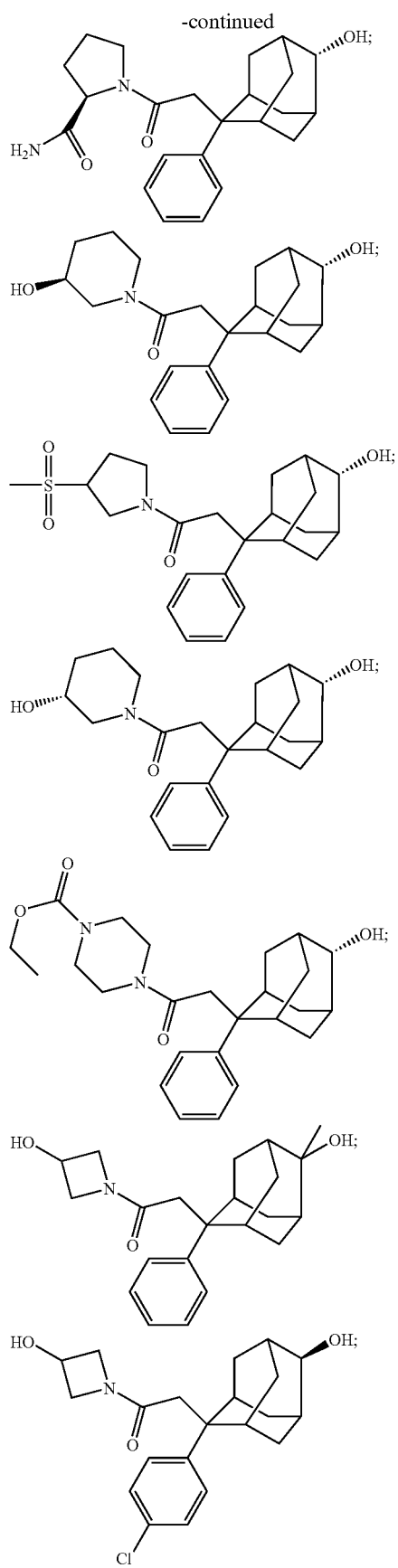
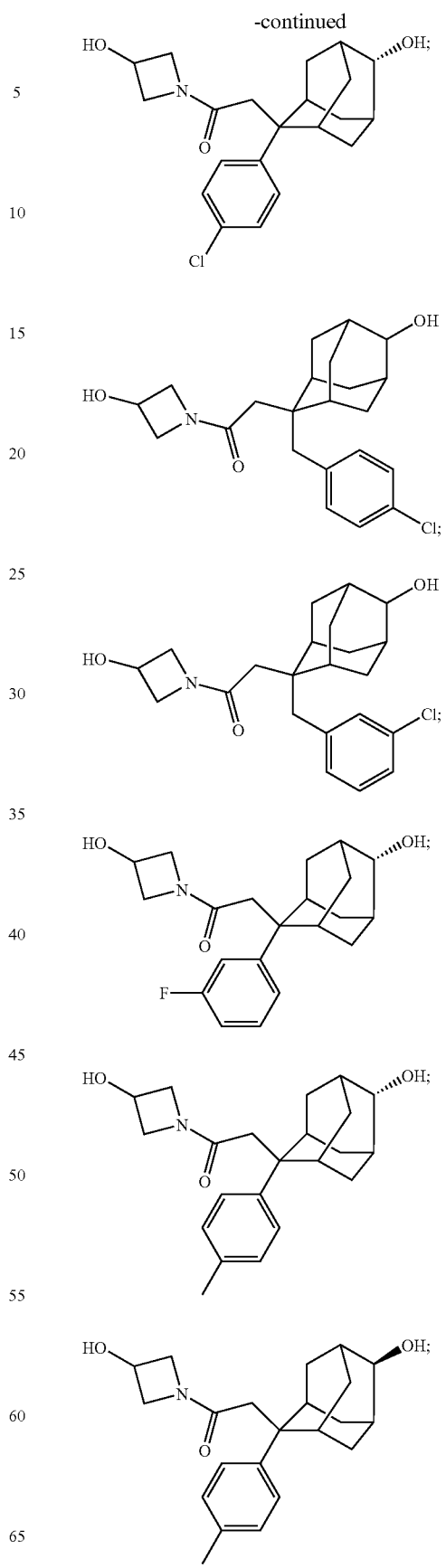

-continued
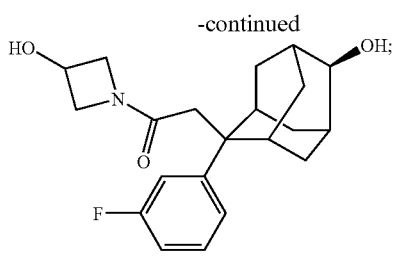
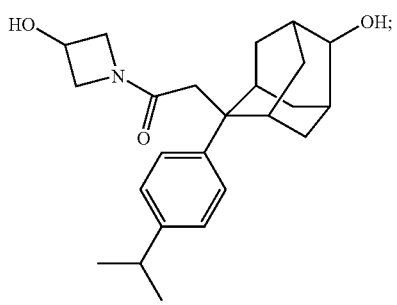
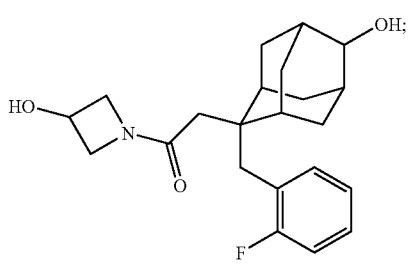
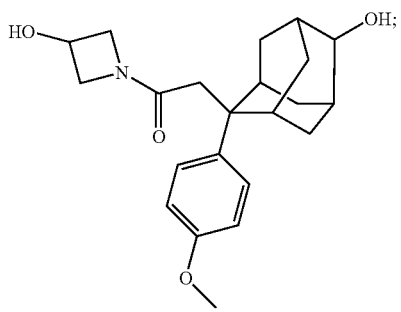
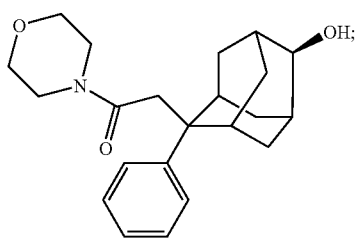
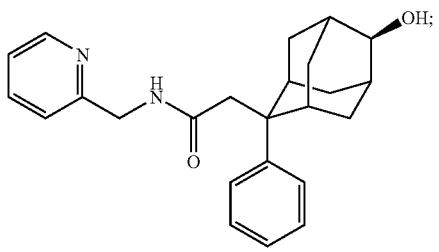
-continued
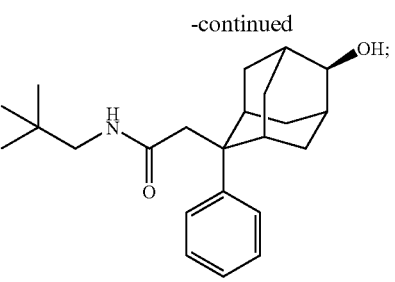
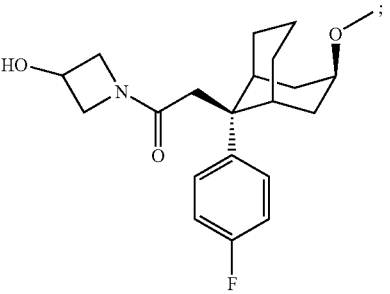
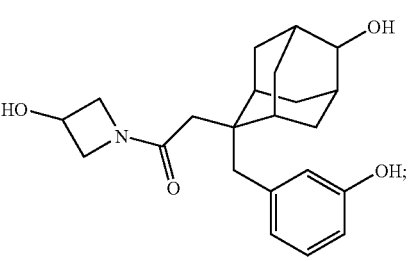
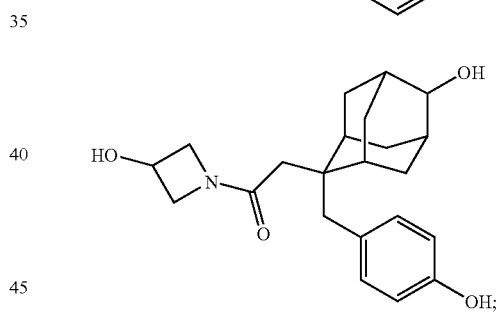
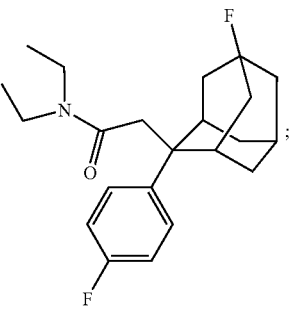
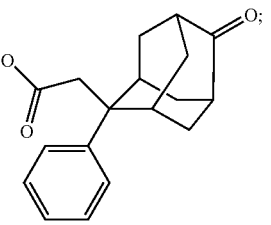

341
-continued
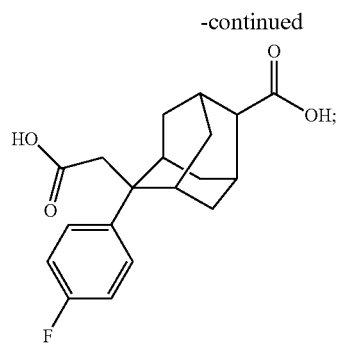
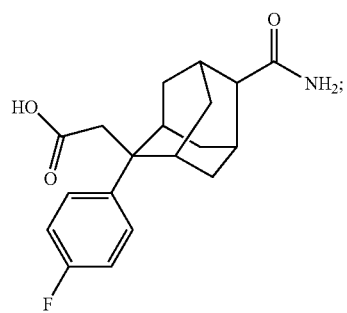
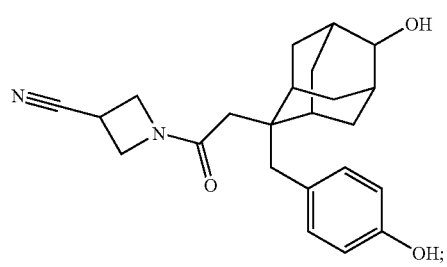
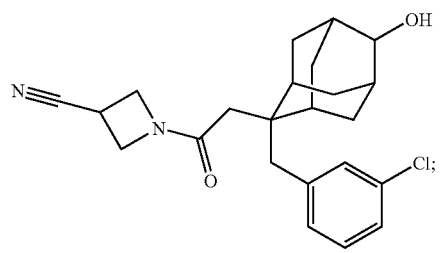
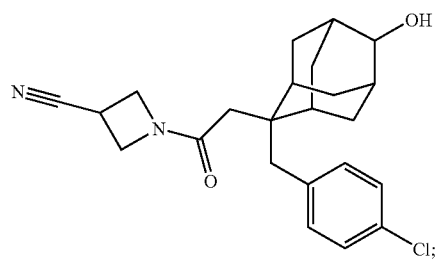
342
-continued
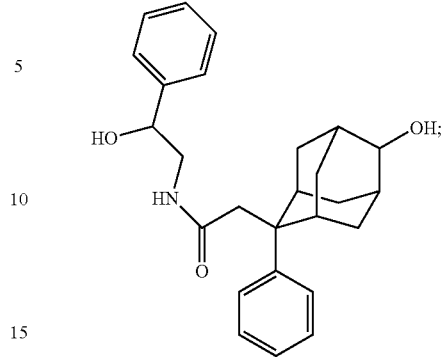
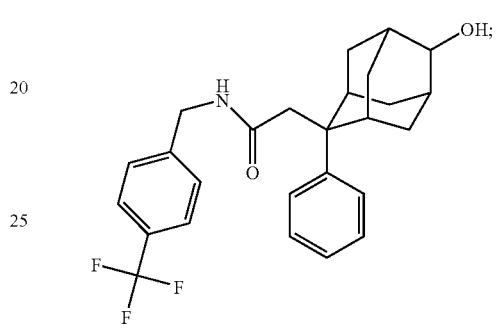
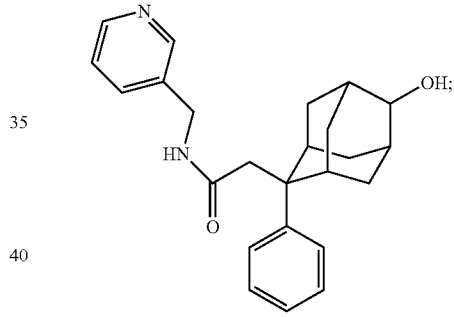
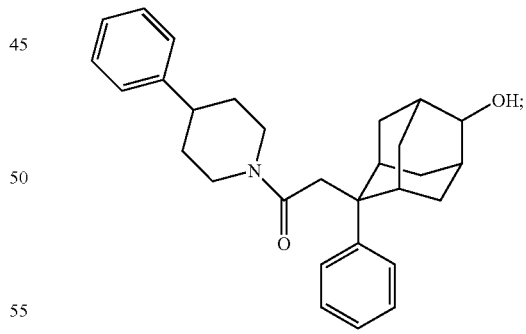
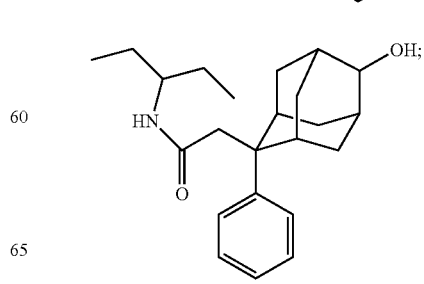

343 344
-continued
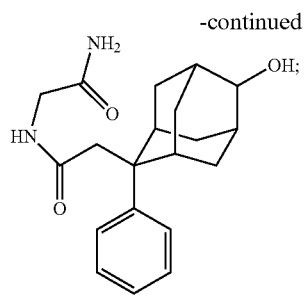
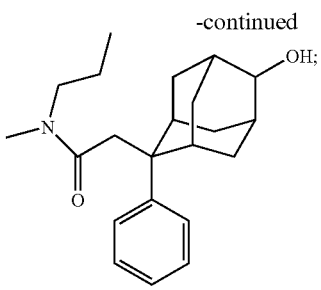
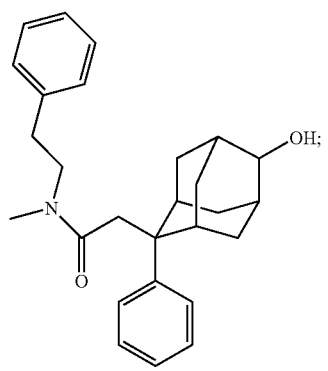
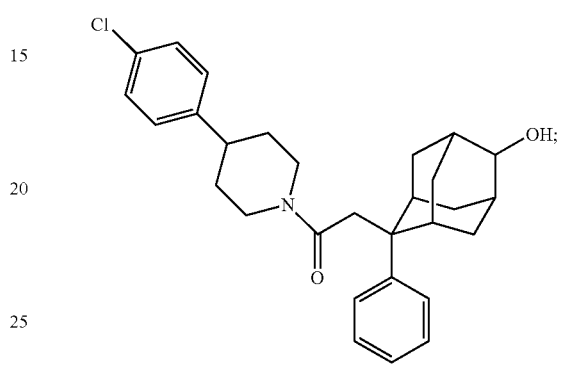
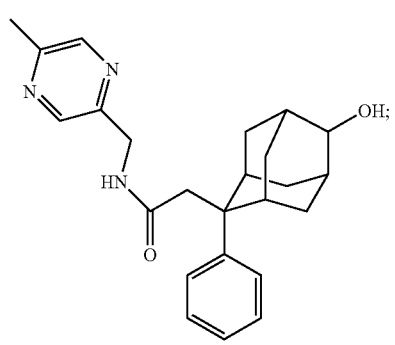
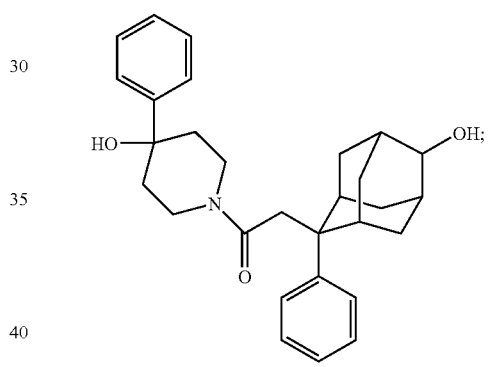
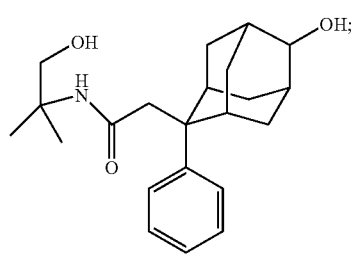
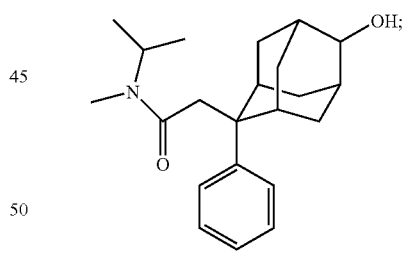
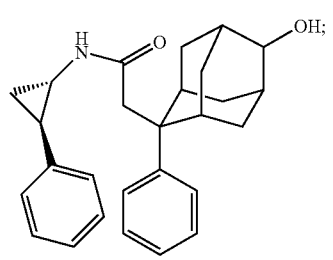
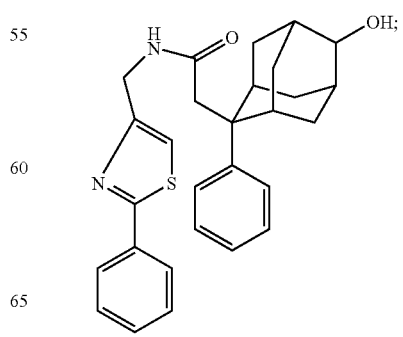

345
-continued
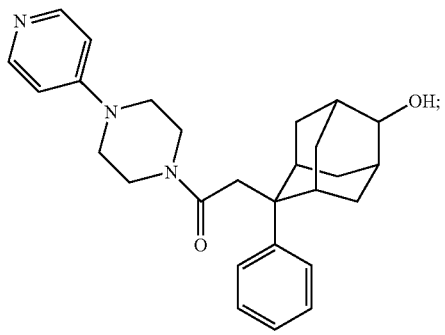
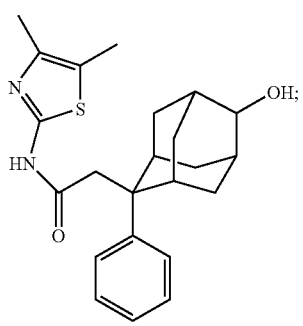
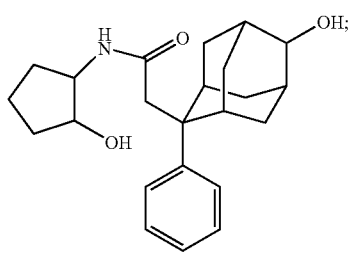
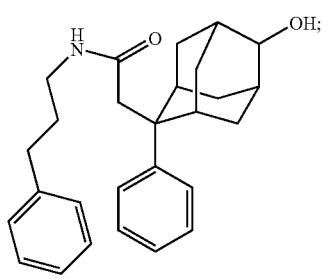
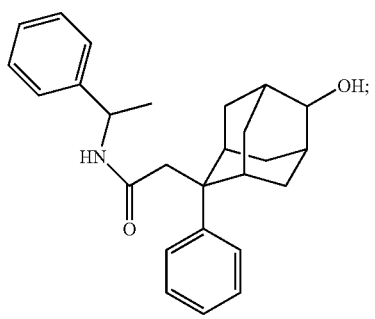
346
-continued
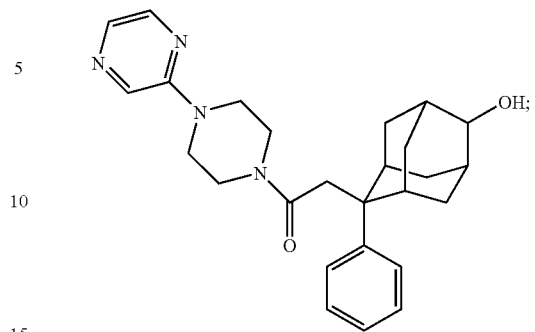
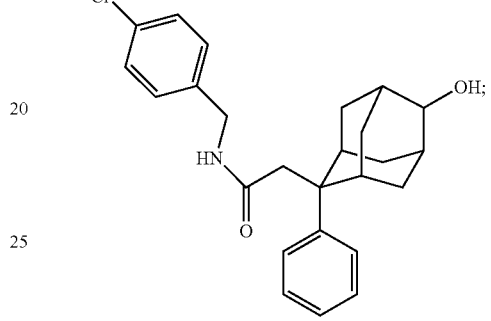
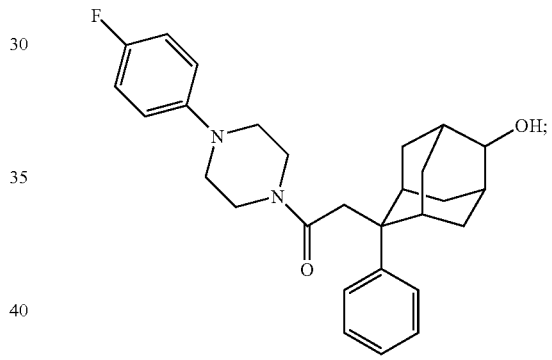
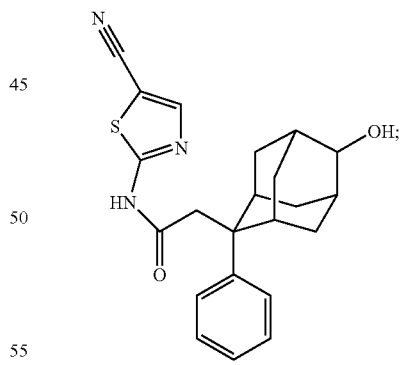
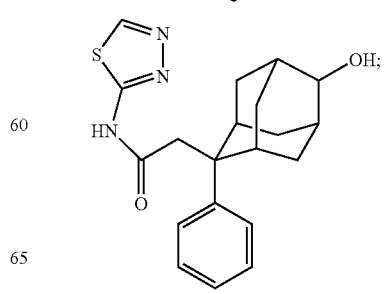

347
-continued
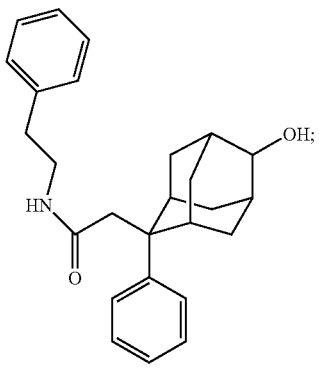
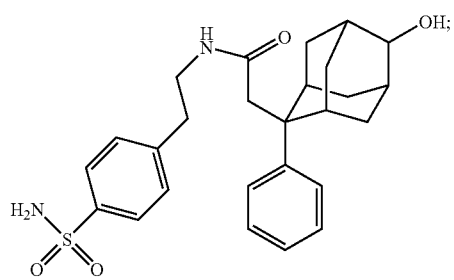
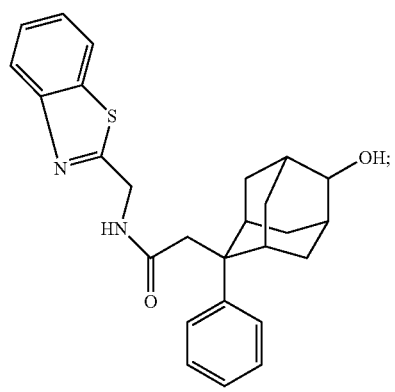
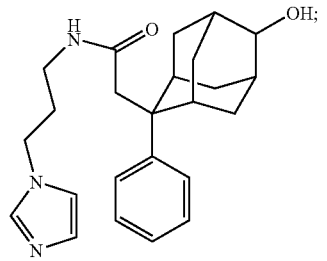
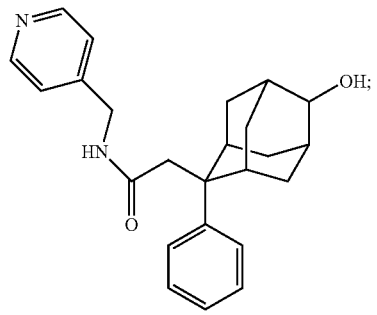
348
-continued
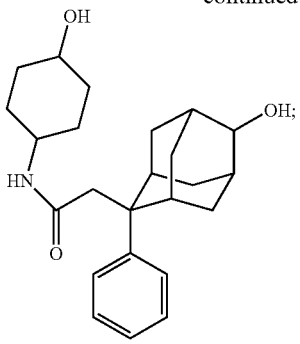
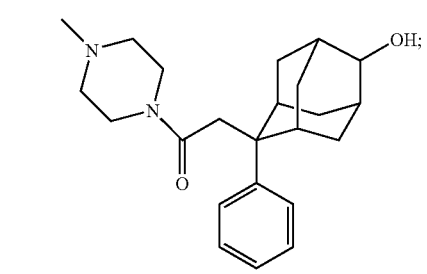
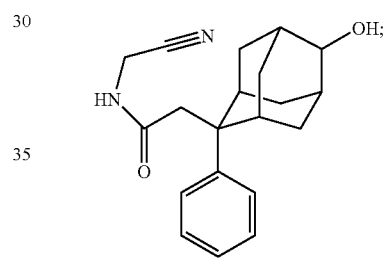
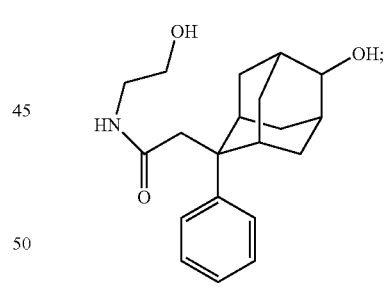
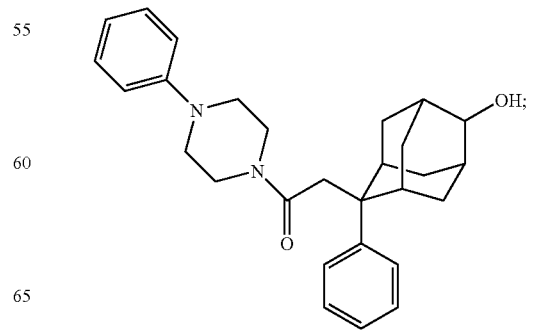

349
-continued
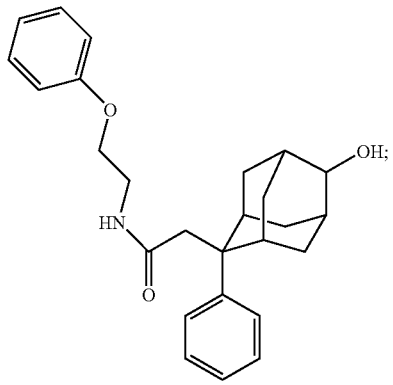
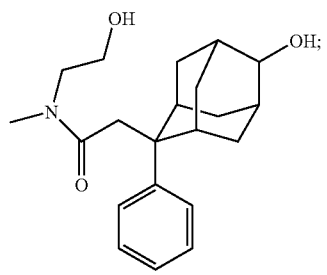
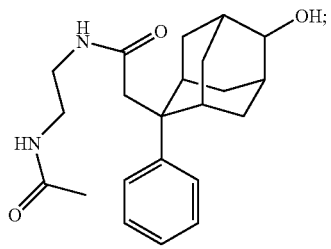
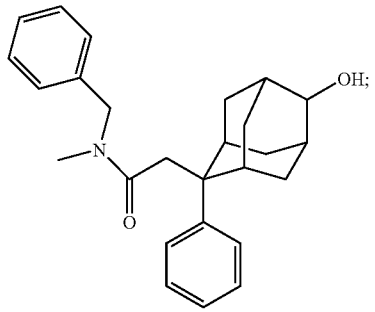
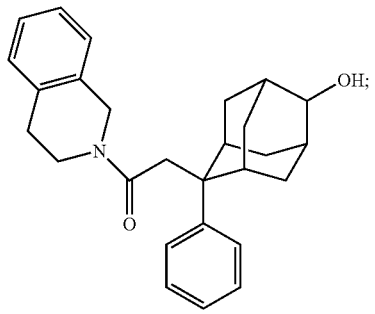
350
-continued
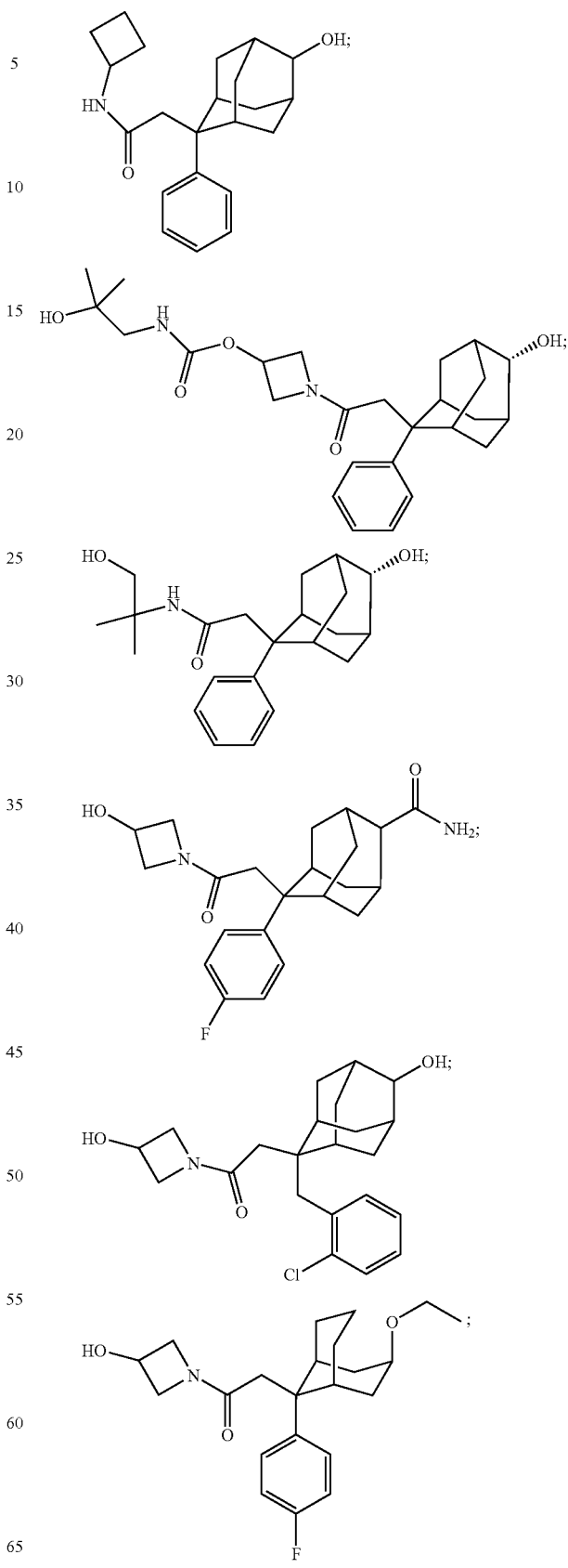

351 352
-continued                        -continued
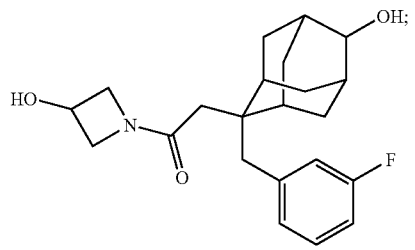
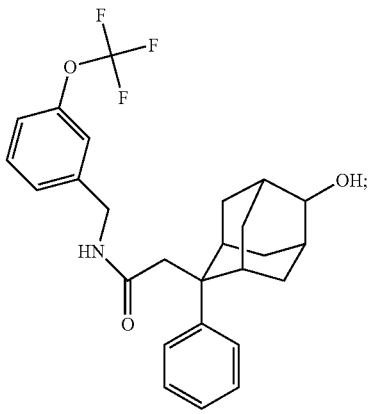
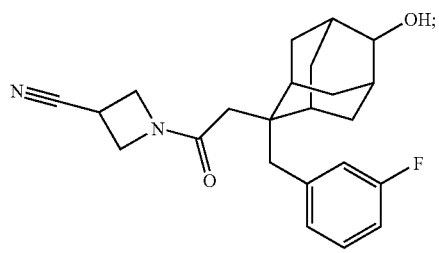
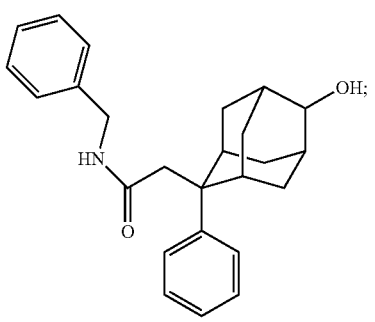
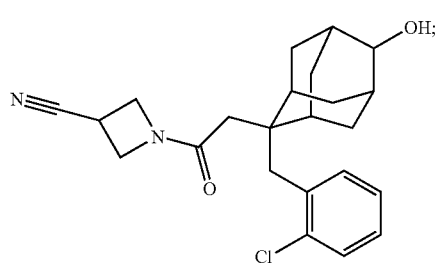
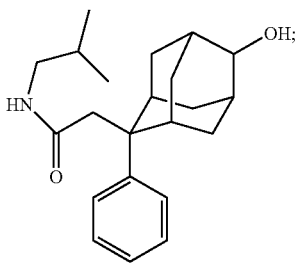
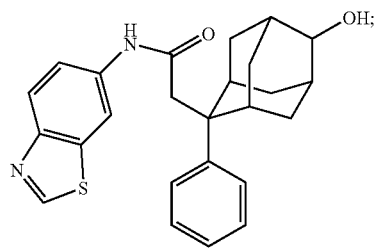
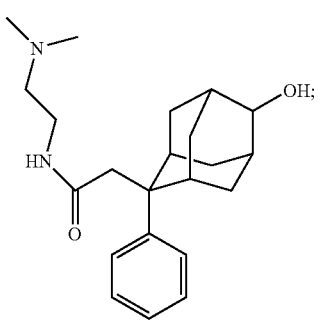
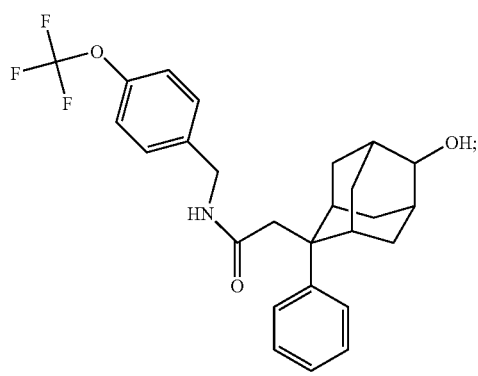
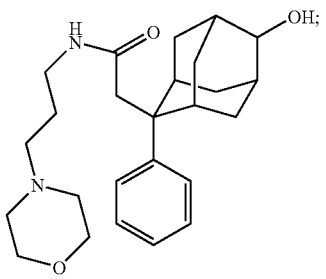

-continued
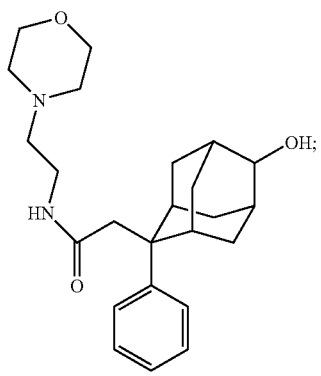
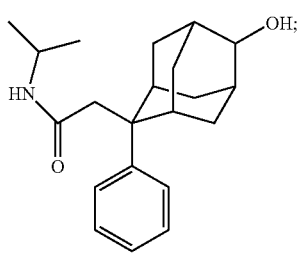
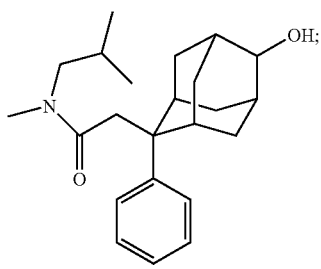
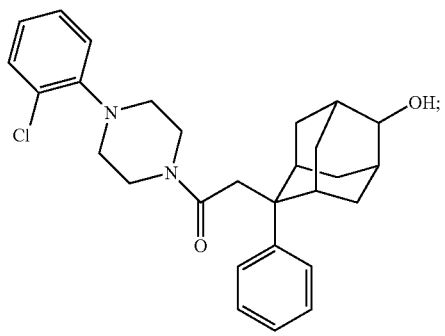
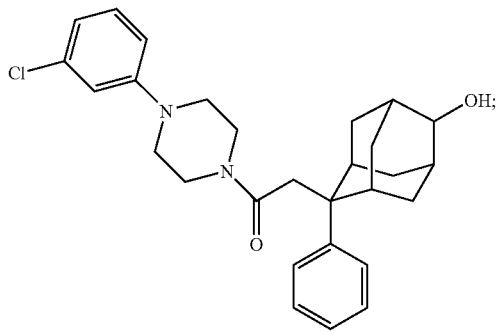
-continued
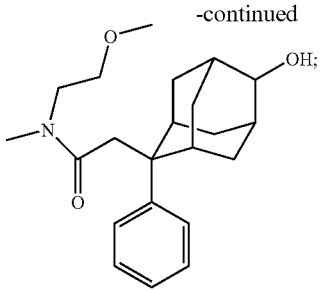
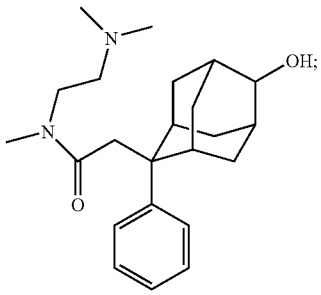
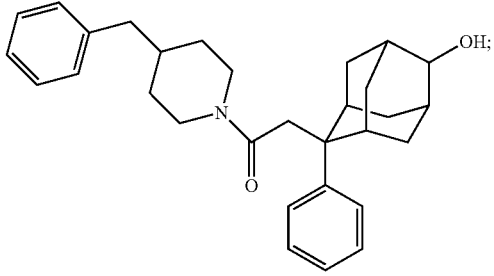
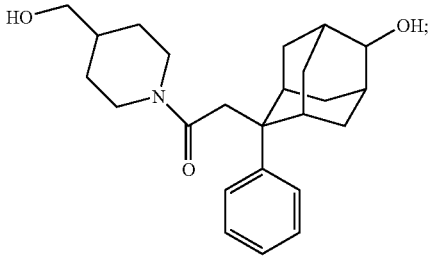
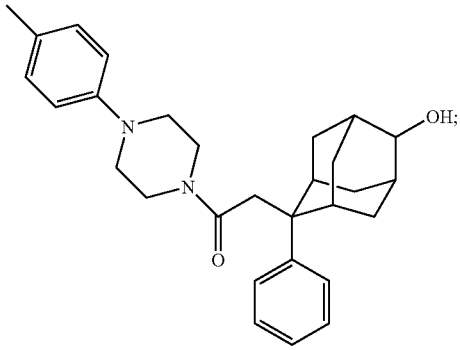

-continued

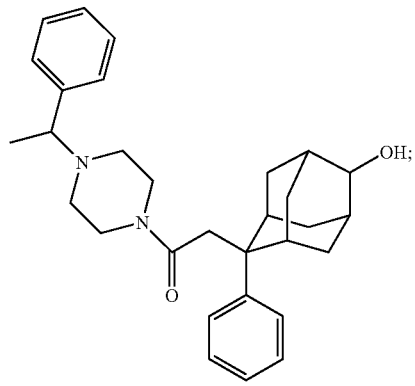

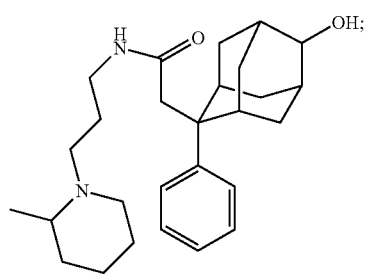

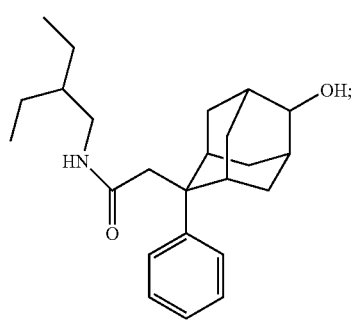

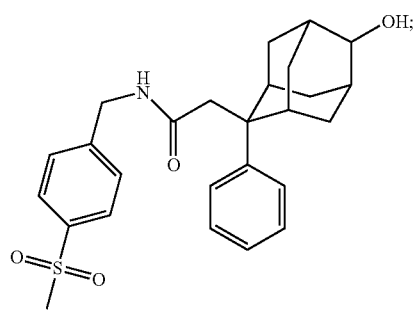

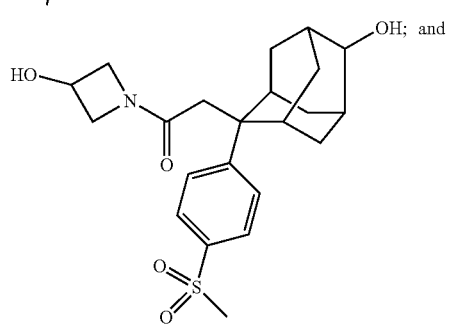

-continued

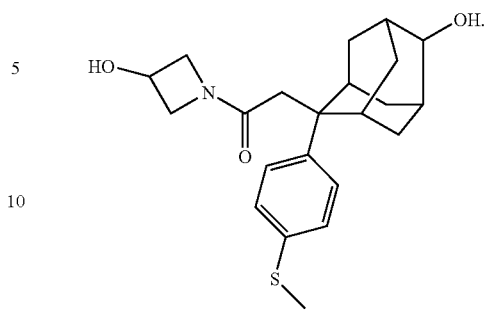

16. A pharmaceutical composition comprising a compound of claim 1.

17. The pharmaceutical composition of claim 16 further comprising a pharmaceutically acceptable carrier.

18. The pharmaceutical composition of claim 16 further comprising at least one additional therapeutic agent.

19. The compound of claim 1, wherein the compound is selected from the group consisting of:

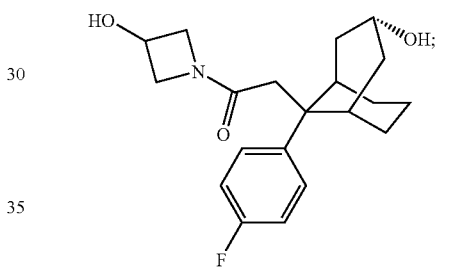

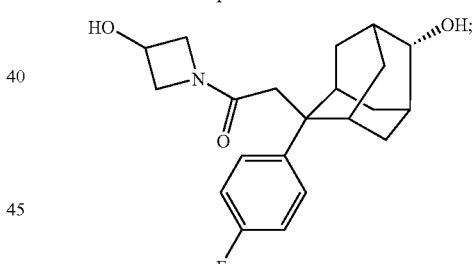

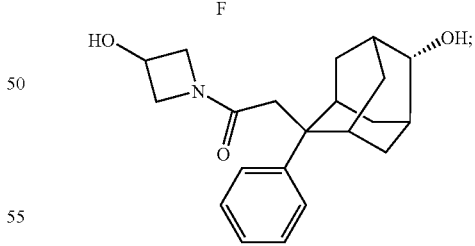

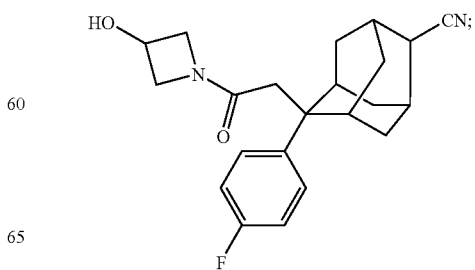

357
-continued
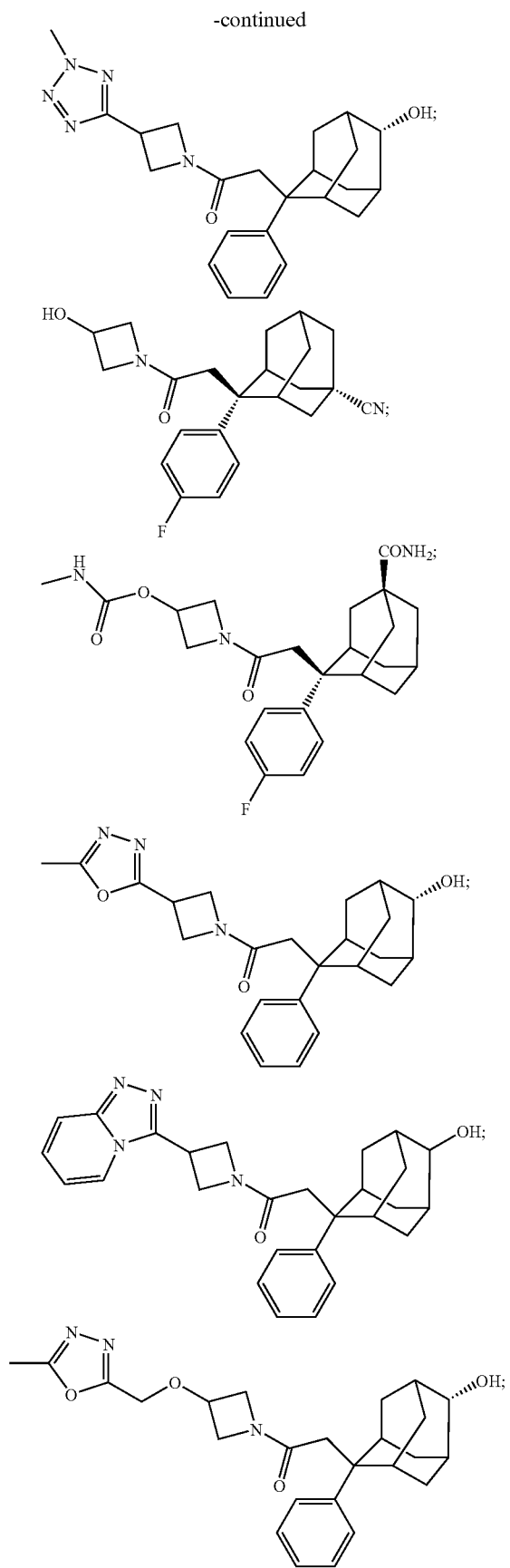
358
-continued
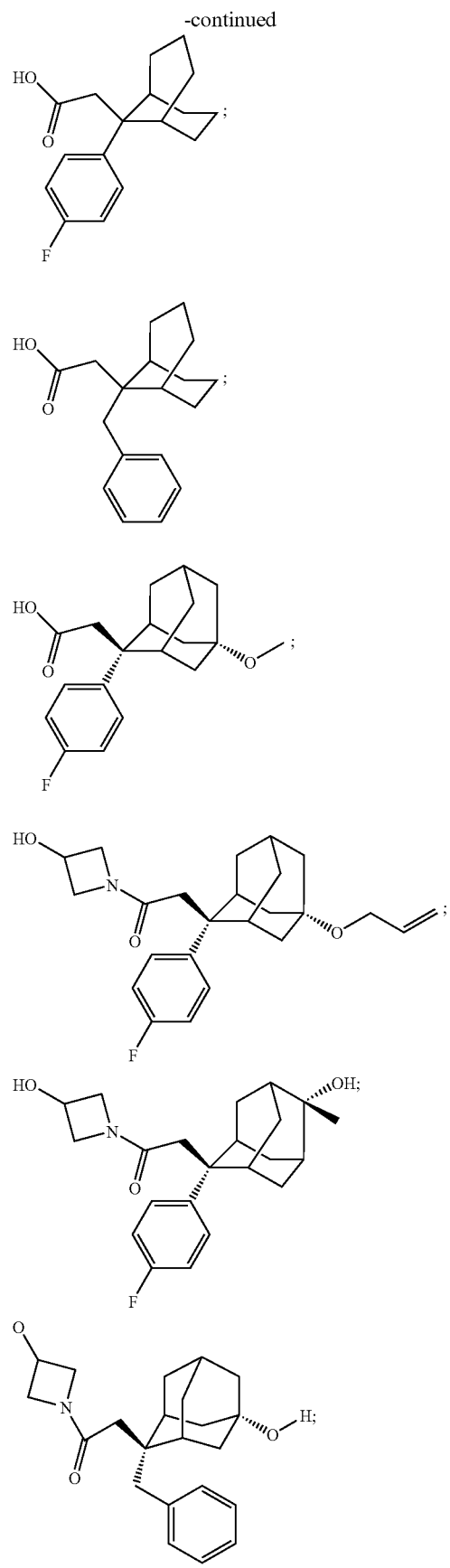

-continued
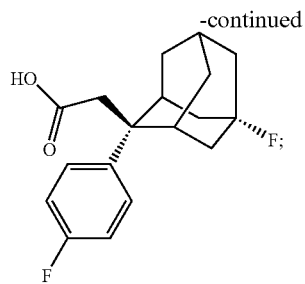
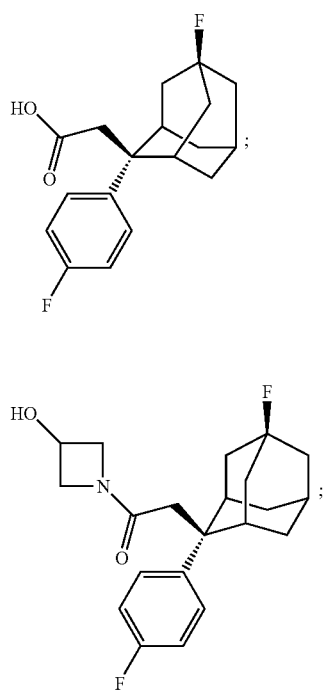
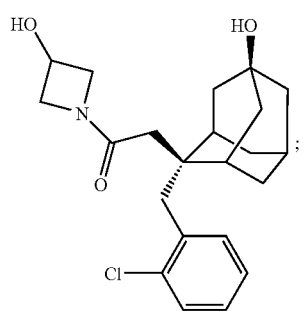
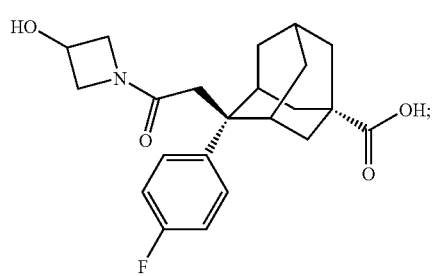
-continued
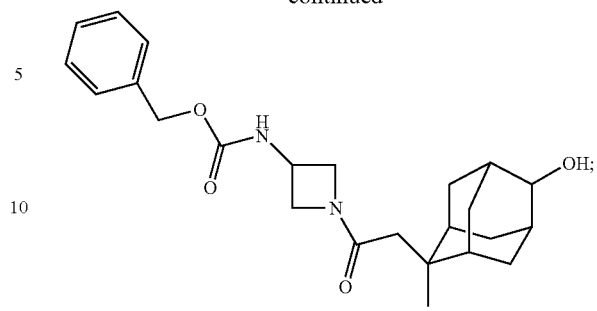
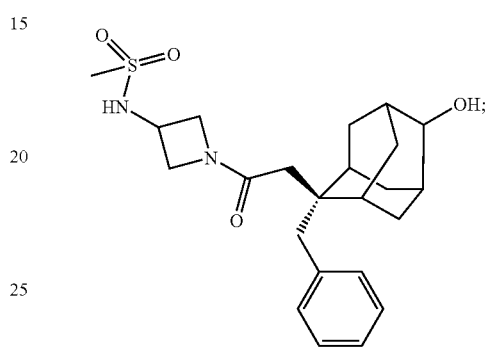
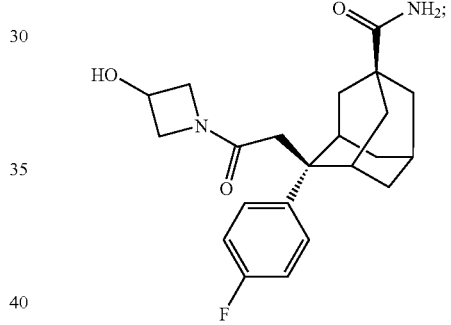
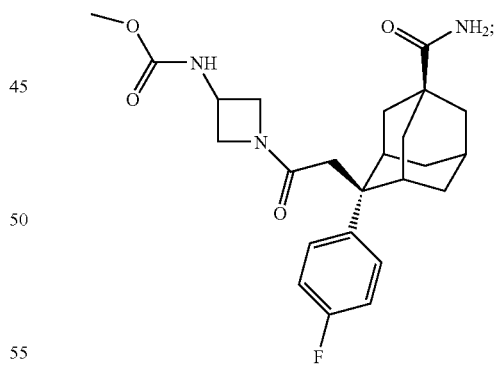
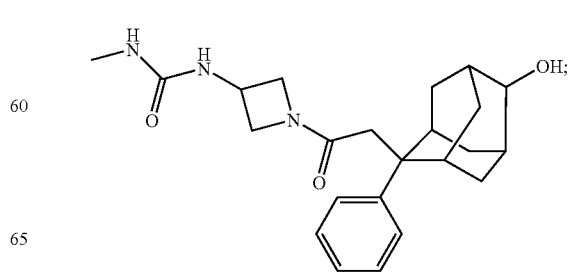

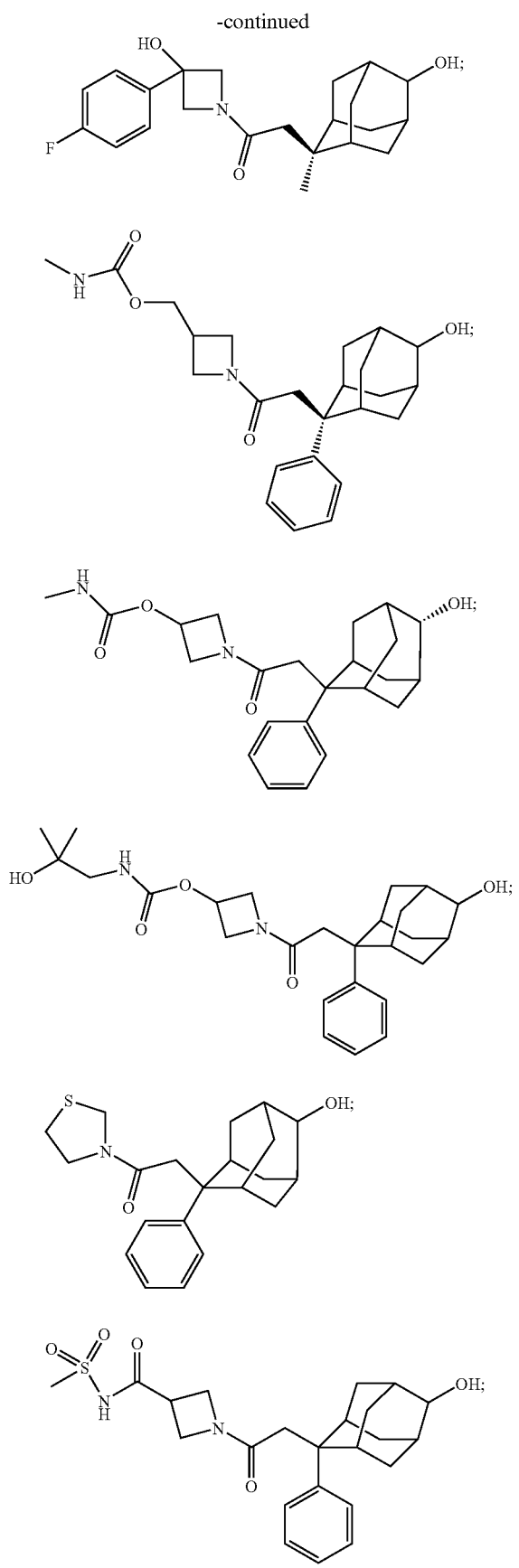
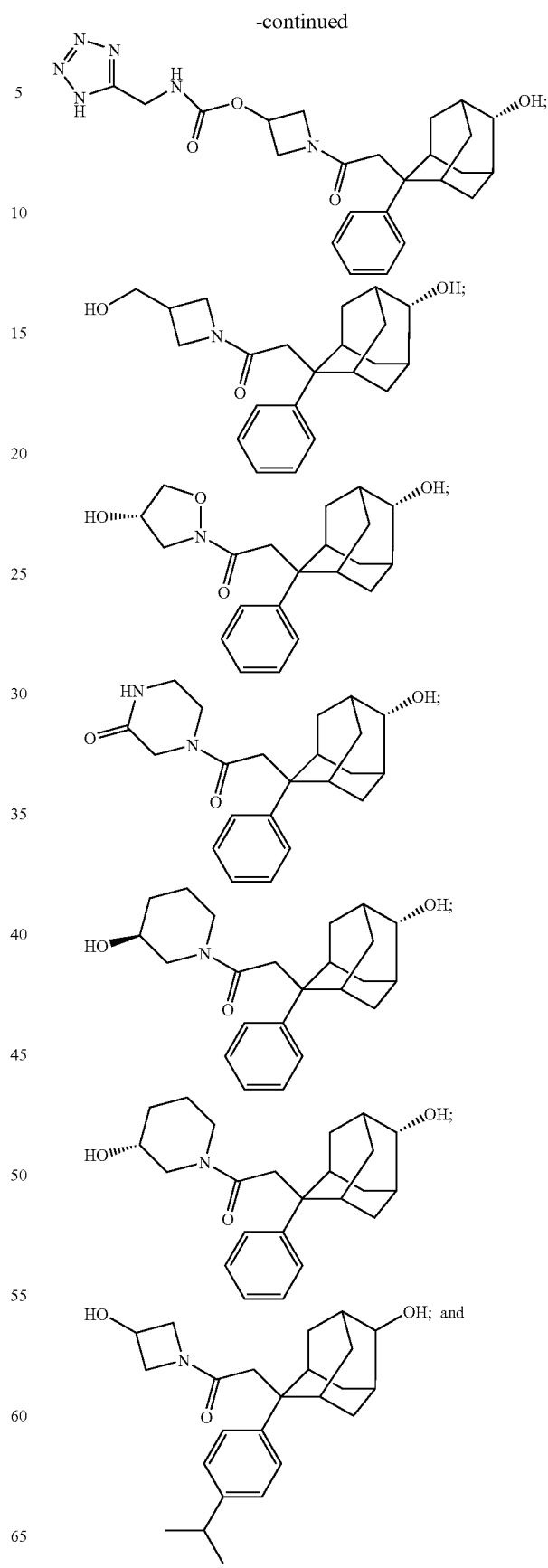

-continued

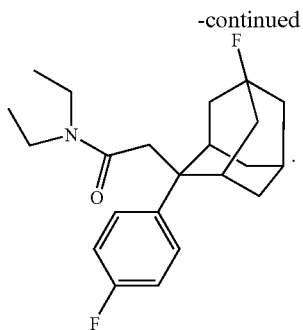

20. A compound having the formula:

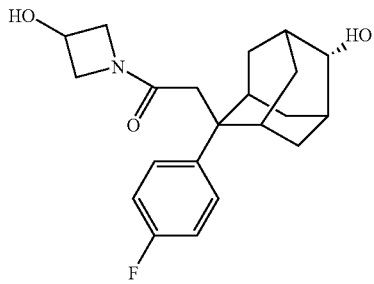

enantiomers, diastereomers, solvates, or salts thereof.

21. A pharmaceutical composition comprising the compound of claim 20.

22. The pharmaceutical composition of claim 21 further comprising a pharmaceutically acceptable carrier.

23. The pharmaceutical composition of claim 21 further comprising at least one additional therapeutic agent.

24. A compound having the formula:

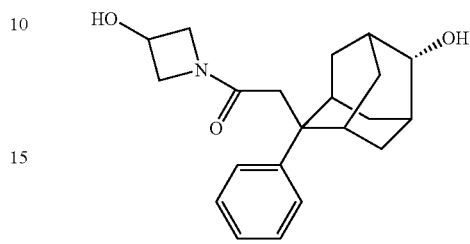

enantiomers, diastereomers, solvates, or salts thereof.

25. A pharmaceutical composition comprising the compound of claim 24.

26. The pharmaceutical composition of claim 25 further comprising a pharmaceutically acceptable carrier.

27. The pharmaceutical composition of claim 25 further comprising at least one additional therapeutic agent.

* * * * *

UNITED STATES PATENT AND TRADEMARK OFFICE
CERTIFICATE OF CORRECTION

PATENT NO. : 7,727,978 B2
APPLICATION NO. : 11/843015
DATED : June 1, 2010
INVENTOR(S) : Xiang-Yang Yu and Jeffrey A Robl It is certified that error appears in the above-identified patent and that said Letters Patent is hereby corrected as shown below:

Column 283
Line 32, "C(O)" should read -- C(=O) --.

Column 284
Line 46, "(NR$_{14}$)" should read -- (=NR$_{14}$) --;
Line 64, "(NR$_{15}$)" should read -- (=NR$_{15}$) --.

Column 285
Line 35, "more" should read -- more R$_5$'s; --.

Column 286
Line 58, "C(O)" should read -- C(=O) --.

Column 287
Line 3, "C(O)" should read -- C(=O) --;
Line 3, "C(O)" should read -- C(=O) --;
Line 8, "C(O)" should read -- C(=O) --;
Line 8, "C(O)" should read -- C(=O) --;
Line 12, "more" should read -- more R$_5$'s; --;
Line 53, "O" should read -- =O --;
Line 60, "C(O)" should read -- C(=O) --.

Column 288
Line 34, "C(O)" should read -- C(=O) --;
Line 45, "C(O)" should read -- C(=O) --;
Line 45, "C(O)" should read -- C(=O) --;
Line 50, "C(O)" should read -- C(=O) --;
Line 50, "C(O)" should read -- C(=O) --.

Column 289
Line 35, "C(O)" should read -- C(=O) --.

Signed and Sealed this

Thirtieth Day of November, 2010

David J. Kappos
*Director of the United States Patent and Trademark Office*

Column 290
Line 9, "C(O)" should read -- C(=O) --;
Line 20, "C(O)" should read -- C(=O) --;
Line 20, "C(O)" should read -- C(=O) --;
Line 25, "C(O)" should read -- C(=O) --;
Line 25, "C(O)" should read -- C(=O) --.

Column 291
Line 11, "C(O)" should read -- C(=O) --;
Line 33, "NR$_2$S" should read -- NR$_{14}$S --;
Line 52, "C(O)" should read -- C(=O) --.

Column 292
Line 53, "C(O)" should read -- C(=O) --.

Column 293
Line 38, "C(O)" should read -- C(=O) --;
Line 38, "C(O)" should read -- C(=O) --;
Line 49, "C(O)" should read -- C(=O) --.

Column 294
Line 27, "C(O)" should read -- C(=O) --;
Line 63, "C(O)" should read -- C(=O) --.

Column 295
Line 11, "C(O)" should read -- C(=O) --;
Line 11, "C(O)" should read -- C(=O) --;
Line 23, "C(O)" should read -- C(=O) --;
Line 38, "C(O)" should read -- C(=O) --.

Column 296
Line 16, "C(O)" should read -- C(=O) --;
Line 17, "S(O)" should read -- S(=O) --;
Line 31, "C(O)" should read -- C(=O) --;
Line 32, "S(O)" should read -- S(=O) --;
Line 47, "C(O)" should read -- C(=O) --;
Line 47, "C(O)" should read -- C(=O) --;
Line 63, "C(O)" should read -- C(=O) --;
Line 63, "C(O)" should read -- C(=O) --.

Column 297
Line 5, "C(O)" should read -- C(=O) --;
Line 48, "C(O)" should read -- C(=O) --;
Line 48, "S(O)" should read -- S(=O) --;
Line 63, "C(O)" should read -- C(=O) --;
Line 63, "S(O)" should read -- S(=O) --.

Column 298
Line 11, "C(O)" should read -- C(=O) --;
Line 11, "C(O)" should read -- C(=O) --;
Line 36, "C(O)" should read -- C(=O) --;
Line 52, "C(O)" should read -- C(=O) --;
Line 52, "C(O)" should read -- C(=O) --.

Column 299
Line 5, "C(O)" should read -- C(=O) --;
Line 5, "C(O)" should read -- C(=O) --;
Line 19, "C(O)" should read -- C(=O) --;
Line 19, "C(O)" should read -- C(=O) --;
Line 46, "more" should read -- more $R_4$'s; --;
Line 51, "C(O)" should read -- C(=O) --;
Line 51, "C(O)" should read -- C(=O) --.

Column 300
Line 9, "C(O)" should read -- C(=O) --;
Line 25, "C(O)" should read -- C(=O) --;
Line 25, "C(O)" should read -- C(=O) --;
Line 44, "C(O)" should read -- C(=O) --;
Line 44, "C(O)" should read -- C(=O) --;
Line 58, "C(O)" should read -- C(=O) --.

Column 301
Line 23, "C(O)" should read -- C(=O) --;
Line 23, "C(O)" should read -- C(=O) --;
Line 63, "C(O)" should read -- C(=O) --;
Line 63, "C(O)" should read -- C(=O) --.

Column 302
Line 14, "C(O)" should read -- C(=O) --;
Line 14, "C(O)" should read -- C(=O) --;
Line 27, "C(O)" should read -- C(=O) --;
Line 27, "C(O)" should read -- C(=O) --;
Line 59, "C(O)" should read -- C(=O) --;
Line 59, "C(O)" should read -- C(=O) --.

Column 303
Line 28, "C(O)" should read -- C(=O) --;
Line 28, "C(O)" should read -- C(=O) --;
Line 45, "C(O)" should read -- C(=O) --;
Line 45, "C(O)" should read -- C(=O) --;
Line 58, "C(O)" should read -- C(=O) --;
Line 58, "C(O)" should read -- C(=O) --.

Column 322
Line 35, after
" 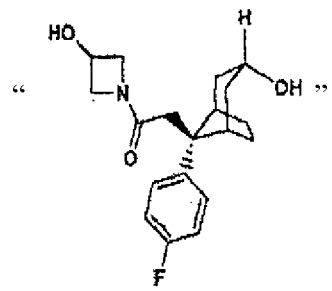 "
insert -- ; --.